United States Patent
Li et al.

(10) Patent No.: US 7,368,551 B2
(45) Date of Patent: May 6, 2008

(54) DE NOVO DNA CYTOSINE METHYLTRANSFERASE GENES, POLYPEPTIDES AND USES THEREOF

(75) Inventors: En Li, Newton, MA (US); Masaki Okano, Kobe (JP); Shaoping Xie, East Brunswick, NJ (US); Taiping Chen, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 574 days.

(21) Appl. No.: 10/623,813

(22) Filed: Jul. 22, 2003

(65) Prior Publication Data

US 2004/0234997 A1 Nov. 25, 2004

Related U.S. Application Data

(63) Continuation-in-part of application No. 09/720,086, filed as application No. PCT/US99/14373 on Jun. 25, 1999.

(60) Provisional application No. 60/093,993, filed on Jul. 24, 1998, provisional application No. 60/090,906, filed on Jun. 25, 1998.

(51) Int. Cl.
| | |
|---|---|
| C07H 21/02 | (2006.01) |
| C07H 5/00 | (2006.01) |
| C07H 19/00 | (2006.01) |
| C07H 21/00 | (2006.01) |
| C08B 37/00 | (2006.01) |
| A61K 38/00 | (2006.01) |

(52) U.S. Cl. .................. 536/23.2; 536/1; 536/18.7; 536/22.1; 536/23.1; 536/23.5; 530/300; 530/350; 435/4; 435/6; 435/7.21; 435/69.1; 435/69.2; 435/183; 435/325

(58) Field of Classification Search ............ 536/1, 536/18.7, 22.1, 23.1, 23.2, 23.5; 530/300, 530/350; 435/4, 6, 7.21, 69.1, 69.2, 183, 435/325

See application file for complete search history.

(56) References Cited

U.S. PATENT DOCUMENTS

| 5,578,716 | A | 11/1996 | Szyf et al. |
|---|---|---|---|
| 6,183,968 | B1 | 2/2001 | Bandman et al. |
| 6,492,168 | B1 | 12/2002 | Kladde et al. |
| 2003/0083292 | A1* | 5/2003 | MacLeod .............. 514/44 |

FOREIGN PATENT DOCUMENTS

| WO | WO 92/06985 | 4/1992 |
|---|---|---|
| WO | WO 95/14772 | 6/1995 |

OTHER PUBLICATIONS

GenCore database. Polynucleotide encoding polypeptides, four sheets. Gene 236(1): 87-95, 1999.*

GenCore database. Polynucleotide encoding polypeptides, four sheets. Nat. Genet. 19(3): 219-220, 1998.*

Okano, M., et al., "Dnmt2 is not required for *de novo* and maintenance methylation of viral DNA in embryonic stem cells," *Nucl. Acids Res. 26*:2536-2540, Oxford University Press (Jun. 1998).

Pradhan, S., et al., "Baculovirus-mediated expression and characterization of the full-length murine DNA methyltransferase," *Nucl. Acids Res. 25*:4666-4673, Oxford University Press (Nov. 1997).

Aoki, A., et al., "Enzymatic properties of *de novo*-type mouse DNA (cytosine-5) methyltransferases," *Nucl. Acids Res. 29*:3506-3512, Oxford University Press (Sep. 2001).

Ariel, M., et al., "Gamete-specific methylation correlates with imprinting of the murine *Xist* gene," *Nat. Genet. 9*:312-315, Nature Publishing Group (1995).

Ausubel, F.M., et al., eds., "Expression of Proteins in Insect Cells Using Baculoviral Vectors," in *Current Protocols in Molecular Biology*, Greene Publishing Associates and Wiley-Interscience, New York, NY, pp. 16.8.1-16.11.7 (1990).

Bachman, K.E., et al., "Dnmt3a and Dnmt3b Are Transcriptional Repressors That Exhibit Unique Localization Properties to Heterochromatin," *J. Biol. Chem. 276*:32282-32287, The American Society for Biochemistry and Molecular Biology, Inc. (Aug. 2001).

Baylin, S.B., et al., "Alterations in DNA Methylation: A Fundamental Aspect of Neoplasia," *Adv. Cancer Res. 72*:141-196, Academic Press (Feb. 1998).

Bestor, T., et al., "Cloning and Sequencing of a cDNA Encoding DNA Methyltransferase of Mouse Cells," *J. Mol. Biol. 203*:971-983, Academic Press (1988).

Bestor, T.H., "Activation of mammalian DNA methyltransferase by cleavage of a Zn binding regulatory domain," *EMBO J. 11*:2611-2617, Oxford University Press (1992).

Brandeis, M., et al., "The ontogeny of allele-specific methylation associated with imprinted genes in the mouse," *EMBO J.* 12:3669-3677, Oxford University Press (1993).

Brockdorff, N., "Convergent themes in X chromosome inactivation and autosomal imprinting," in *Genomic Imprinting*, Reik, W., and Surani, A., eds., Oxford University Press, Oxford, UK, pp. 191-210 (Dec. 1997).

Jones, P.A., and Gonzalgo, M.L., "Altered DNA methylation and genome instability: A new pathway to cancer?," *Proc. Natl. Acad. Sci. USA 94*:2103-2105, National Academy of Sciences (Mar. 1997).

Klimašauskas, S., et al., "The sequence specificity domain of cytosine-C5 methlases," *Nucl. Acids Res. 19*:6183-6190, IRL Press at Oxford University Press (1991).

Kumar, S., et al., "The DNA (cytosine-5) methyltransferase," *Nucl. Acids Res. 22*:1-10, Oxford University Press (1994).

(Continued)

*Primary Examiner*—Alana M. Harris
(74) *Attorney, Agent, or Firm*—Sterne, Kessler, Goldstein & Fox P.L.L.C.

(57) ABSTRACT

De novo DNA cytosine methyltransferase polynucleotides and polypeptides and methods for producing said polypeptides are disclosed. Also disclosed are methods for utilizing de novo DNA cytosine methyltransferase polynucleotides and polypeptides in diagnostic assays, in vitro DNA methylation assays for screening agonists and antagonists, and therapeutic applications such as the treatment of neoplastic disorders.

17 Claims, 65 Drawing Sheets

OTHER PUBLICATIONS

Laird, P.W., and Jaenisch, R., "The Role of DNA Methylation in Cancer Genetics and Epigenetics," *Annu. Rev. Genet.* 30:441-464, Annual Reviews Inc. (1996).

Lauster, R., et al., "Cytosine-specific Type II DNA Methyltransferases. A Conserved Enzyme Core with Variable Target-recognizing Domains," *J. Mol. Biol.* 206:305-312, Academic Press Ltd. (1989).

Lazar, E., et al., "Transforming Growth Factor α: Mutation of Aspartic Acid 47 and Leucine 48 Results in Different Biological Activities," *Mol. Cell. Biol.* 8:1247-1252, American Society for Microbiology (1988).

Lei, H., et al., "De novo DNA cytosine methyltransferase activities in mouse embryonic stem cells," *Development* 122:3195-3205, The Company of Biologists Ltd. (1996).

Leonhardt, H., et al., "A Targeting Sequence Directs DNA Methyltransferase to Sites of DNA Replication in Mammalian Nuclei," *Cell* 71:865-873, Cell Press (1992).

Li, E., et al., "Targeted Mutation of the DNA Methyltransferase Gene Results in Embryonic Lethality," *Cell* 69:915-926 Cell Press (1992).

Li, E., "Role of DNA methylation in mammalian development," in *Genomic Imprinting*, Reik, W., and Surani, A., eds., Oxford University Press, Oxford, UK, pp. 1-20 (Dec. 1997).

Malagnac, F., et al., "A Gene Essential for De Novo Methylation and Development in Ascobolus Reveals a Novel Type of Eukaryotic DNA Methyltransferase Structure," *Cell* 91:281-290, Cell Press (Oct. 1997).

Narayan, A., et al., "Hypomethylation of Pericentromeric DNA in Breast Adenocarcinomas," *Int. J. Cancer* 77:833-838, Wiley-Liss, Inc. (Sep. 1998).

Okano, M., et al., "Cloning and characterization of a family of novel mammalian DNA (cytosine-5) methyltransferases," *Nat. Genet.* 19:219-220, Nature Publishing Group (Jul. 1998).

Okano, M., et al., "DNA Methyltransferases Dnmt3a and Dnmt3b Are Essential for De Novo Methylation and Mammalian Development," *Cell* 99:247-257, Cell Press (Oct. 1999).

Okano, M., and Li, E., "Genetic Analyses of DNA Methyltransferase Genes in Mouse Model System," *J. Nutr.* 132:2462S-2465S, American Institute of Nutrition (Aug. 2002).

Pradhan, S., et al., "Baculovirus-mediated expression and characterization of the full-length murine DNA methyltransferase," *Nucl. Acids Res.* 25:4666-4673, Oxford University Press (Nov. 1997).

Qu, G.-Z., et al., "Satellite DNA hypomethylation vs. overall genomic hypomethylation in ovarian epithelial tumors of different malignant potential," *Mutat. Res.* 423:91-101, Elsevier Science (Jan. 1999).

Razin, A., and Cedar, H., "DNA methylation and embryogensis," in *DNA Methylation: Molecular Biology and Biological Significance*, Jost, J.P., and Saluz, H.P., eds., Birkhäuser Verlag, Basel, Switzerland, pp. 343-357 (1993).

Reid, G.K., et al., "Selective inhibition of DNA methyltransferase enzymes as a novel strategy for cancer treatment," *Curr. Opin. Mol. Ther.* 4:130-137, Current Drugs (Apr. 2002).

Robertson, K.D., et al., "The human DNA methyltransferases (DNMTs) 1, 3a and 3b: coordinate mRNA expression in normal tissues and overexpression in tumors," *Nucl. Acids. Res.* 27:2291-2298, Oxford University Press (Jun. 1999).

Stöger, R., et al., "Maternal-Specific Methylation of the Imprinted Mouse *Igf2r* Locus Identifies the Expressed Locus as Carrying the Imprinting Signal," *Cell* 73:61-71, Cell Press (1993).

Szyf, M., et al., "Induction of Myogenic Differentiation by an Expression Vector Encoding the DNA Methyltransferase cDNA Sequence in the Antisense Orientation," *J. Biol. Chem.* 267:12831-12836, The American Society for Biochemistry and Molecular Biology, Inc. (1992).

Szyf, M., and Detich, N., "Regulation of the DNA Methylation Machinery and Its Role in Cellular Transformation," in *Progress in Nucleic Acid Research and Molecular Biology*, Moldave, K., ed., Academic Press, San Diego, CA, pp. 47-79 (Aug. 2001).

Trasler, J.M., et al., "DNA Methyltransferase in Normal and Dnmt$^n$/Dnmt$^n$ Mouse Embryos," *Dev. Dyn.* 206:239-247, Wiley-Liss, Inc. (1996).

Tremblay, K.D., et al., "A paternal-specific methylation imprint marks the alleles of the mouse *H19* gene," *Nat. Genet.* 9:407-413, Nature Publishing Group (1995).

Tucker, K.L., et al., "Germ-line passage is required for establishment of methylation and expression patterns of imprinted but not of nonimprinted genes," *Genes & Develop.* 10:1008-1020, Cold Spring Harbor Laboratory Press (1996).

Xie, S., et al., "Cloning, expression and chromosome locations of the human *DNMT3* gene family," *Gene* 236:87-95, Elsevier Science B.V. (Aug. 1999).

Yen, R.-W. C., et al., "Isolation and Characterization of the cDNA encoding human DNA methyltransferase," *Nucl. Acids Res.* 20:2287-2291, Oxford University Press (1992).

Yoder, J.A., and Bestor, T.H., "A candidate mammalian DNA methyltransferase related to pmt1p of fission yeast," *Hum. Mol. Genet.* 7:279-284, Oxford University Press (Feb. 1998).

Zuccotti, M., and Monk, M., "Methylation of the mouse *Xist* gene in sperm and eggs correlates with imprinted *Xist* expression and paternal X-inactivation," *Nat. Genet.* 9:316-320, Nature Publishing Group (1995).

International Search Report for International Application No. PCT/US99/14373, mailed Dec. 10, 1999, European Patent Office, Netherlands.

Dialog File 351, Accession No. 10305671, Derwent WPI English language abstract for WO 95/14772.

GenCore database. Sequence alignment between SEQ ID No. 2 and Accession No. AF067972 of Xie et al. Gene 236(1): 87-95, 1999, 3 sheets.

GenCore database. Sequence alignment between SEQ ID No. 2 and Accession No. AF068626 and AF068627 of Okano et al. Nat. Genet. 19(3): 219 and 220, 1998, 8 sheets.

GenCore nucleic acid amino acid database. Sequence comparison between accession No. AF067972 from Gene 1999 paper and Applicants' SEQ ID No. 7 and 8, Feb. 12, 2001.

GenCore nucleic acid database. Sequence comparison between accession No. AAT21884 from WO document 9514772-A1 and Applicants' SEQ ID No. 1 and 3, Jun. 1, 1995.

GenCore nucleic acid and amino acid database. Sequence comparison between sequence 47 of U.S. Patent 6,183,968 and Applicants' SEQ ID No. 2 and 5-8, Mar. 27, 1998.

GenCore nucleic acid and amino acid database. Sequence comparison between sequence accession No. AF069625 from Nature Genetics 1998 paper and Applicants' SEQ ID No. 5 and 6, Dec. 6, 1999.

Chaillet, J.R., et al., "Parental-Specific Methylation of an Imprinted Transgene in Established during Gametogenesis and Progressively Changes during Embryogenesis," *Cell* 66:77-83, Cell Press (1991).

Chen, T., et al., "A Novel Dnmt3a Isoform Produced from an Alternative Promoter Localizes to Euchromatin and Its Expression Correlates with Active *de Novo* Methylation," *J. Biol. Chem.* 277:38746-38754, The American Society for Biochemistry and Molecular Biology, Inc. (Oct. 2002).

Cheng, X., "Structure and function of DNA methyltransferases," *Annu. Rev. Biophys. Biomol. Struct.* 24:293-318, Annual Reviews, Inc. (1995).

Finnegan, E.J., and Dennis, E.S., "Isolation and identification by sequence homology of a putative cytosine methyltransferase from *Arabidopsis thaliana*," *Nucl. Acids. Res.* 21:2383-2388, Oxford University Press (1993).

Flynn, J., et al., "Murine DNA Cytosine-$C^5$ Methyltransferase: Pre-Steady- and Steady-State Kinetic Analysis with Regulatory DNA Sequences," *Biochem.* 35:7308-7315, American Chemical Society (1996).

Flynn, J., et al., "DNA Binding Discrimination of the Murine DNA Cytosine-$C^5$ Methyltransferase," *J. Mol. Biol.* 279:101-116, Academic Press (May 1998).

Hata, K., et al. "Dnmt3L cooperates with the Dnmt3 family of de novo DNA methyltransferases to establish maternal imprints in mice," *Develop.* 129:1983-1993, Company of Biologists Ltd. (Apr. 2002).

Jähner, D., and Jaenisch, R., "DNA Methylation in Early Mammalian Development," in *DNA Methylation. Biochemistry and Biological Significance*, Razin, A., eds., Springer-Verlag, New York, NY, pp. 189-219 (1984).

Jentsch, S., et al., "DNA methyltransferases affecting the sequence 5'CCGG," *Nucl. Acids Res.* 9:2753-2759, IRL Press (1981).

* cited by examiner

Mouse Dnmt3a DNA sequence

```
   1 GAATTCCGGC CTGCTGCCGG GCCGCCCGAC CCGCCGGGCC ACACGGCAGA
  51 GCCGCCTGAA GCCCAGCGCT GAGGCTGCAC TTTTCCGAGG GCTTGACATC
 101 AGGGTCTATG TTTAAGTCTT AGCTCTTGCT TACAAAGACC ACGGCAATTC
 151 CTTCTCTGAA GCCCTCGCAG CCCCACAGCG CCCTCGCAGC CCCAGCCTGC
 201 CGCCTACTGC CCAGCAATGC CCTCCAGCGG CCCCGGGGAC ACCAGCAGCT
 251 CCTCTCTGGA GCGGGAGGAT GATCGAAAGG AAGGAGAGGA ACAGGAGGAG
 301 AACCGTGGCA AGGAAGAGCG CCAGGAGCCC AGCGCCACGG CCCGGAAGGT
 351 GGGGAGGCCT GGCCGGAAGC GCAAGCACCC ACCGGTGGAA AGCAGTGACA
 401 CCCCCAAGGA CCCAGCAGTG ACCACCAAGT CTCAGCCCAT GGCCCAGGAC
 451 TCTGGCCCCT CAGATCTGCT ACCCAATGGA GACTTGGAGA GCGGAGTGA
 501 ACCCCAACCT GAGGAGGGGA GCCCAGCTGC AGGGCAGAAG GGTGGGGCCC
 551 CAGCTGAAGG AGAGGGAACT GAGACCCCAC CAGAAGCCTC CAGAGCTGTG
 601 GAGAATGGCT GCTGTGTGAC CAAGGAAGGC CGTGGAGCCT CTGCAGGAGA
 651 GGGCAAAGAA CAGAAGCAGA CCAACATCGA ATCCATGAAA ATGGAGGGCT
 701 CCCGGGGCCG ACTGCCAGGT GGCTTGGGCT GGGAGTCCAG CCTCCGTCAG
 751 CGACCCATGC CAAGACTCAC CTTCCAGGCA GGGGACCCCT ACTACATCAG
 801 CAAACGGAAA CGGGATGAGT GGCTGGCACG TTGGAAAAGG GAGGCTGAGA
 851 AGAAAGCCAA GGTAATTGCA GTAATGAATG CTGTGGAAGA GAACCAGGCC
 901 TCTGGAGAGT CTCAGAAGGT GGAGGAGGCC AGCCCTCCTG CTGTGCAGCA
 951 GCCCACGGAC CCTGCTTCTC CGACTGTGGC CACCACCCCT GAGCCAGTAG
1001 GAGGGGATGC TGGGGACAAG AATGCTACCA AGCAGCCGA CGATGAGCCT
1051 GAGTATGAGG ATGGCCGGGG CTTTGGCATT GGAGAGCTGG TGTGGGGGAA
1101 ACTTCGGGGC TTCTCCTGGT GGCCAGGCCG AATTGTGTCT TGGTGGATGA
```

FIG. 1A-1

```
1151  CAGGCCGGAG CCGAGCAGCT GAAGGCACTC GCTGGGTCAT GTGGTTCGGA
1201  GATGGCAAGT TCTCAGTGGT GTGTGTGGAG AAGCTCATGC CGCTGAGCTC
1251  CTTCTGCAGT GCATTCCACC AGGCCACCTA CAACAAGCAG CCCATGTACC
1301  GCAAAGCCAT CTACGAAGTC CTCCAGGTGG CCAGCAGCCG TGCCGGGAAG
1351  CTGTTTCCAG CTTGCCATGA CAGTGATGAA AGTGACAGTG CAAGGCTGT
1401  GGAAGTGCAG AACAAGCAGA TGATTGAATG GGCCCTCGGT GGCTTCCAGC
1451  CCTCGGGTCC TAAGGGCCTG GAGCCACCAG AAGAAGAGAA GAATCCTTAC
1501  AAGGAAGTTT ACACCGACAT GTGGGTGGAG CCTGAAGCAG CTGCTTACGC
1551  CCCACCCCCA CCAGCCAAGA AACCCAGAAA GAGCACAACA GAGAAACCTA
1601  AGGTCAAGGA GATCATTGAT GAGCGCACAA GGGAGCGGCT GGTGTATGAG
1651  GTGCGCCAGA AGTGCAGAAA CATCGAGGAC ATTTGTATCT CATGTGGGAG
1701  CCTCAATGTC ACCCTGGAGC ACCCACTCTT CATTGGAGGC ATGTGCCAGA
1751  ACTGTAAGAA CTGCTTCTTG GAGTGTGCTT ACCAGTATGA CGACGATGGG
1801  TACCAGTCCT ATTGCACCAT CTGCTGTGGG GGGCGTGAAG TGCTCATGTG
1851  TGGGAACAAC AACTGCTGCA GGTGCTTTTG TGTCGAGTGT GTGGATCTCT
1901  TGGTGGGGCC AGGAGCTGCT CAGGCAGCCA TTAAGGAAGA CCCCTGGAAC
1951  TGCTACATGT GCGGGCATAA GGGCACCTAT GGGCTGCTGC GAAGACGGGA
2001  AGACTGGCCT TCTCGACTCC AGATGTTCTT TGCCAATAAC CATGACCAGG
2051  AATTTGACCC CCCAAAGGTT TACCCACCTG TGCCAGCTGA AAGAGGAAG
2101  CCCATCCGCG TGCTGTCTCT CTTTGATGGG ATTGCTACAG GGCTCCTGGT
2151  GCTGAAGGAC CTGGGCATCC AAGTGGACCG CTACATTGCC TCCGAGGTGT
2201  GTGAGGACTC CATCACGGTG GGCATGGTGC GGCACCAGGG AAAGATCATG
2251  TACGTCGGGG ACGTCCGCAG CGTCACACAG AAGCATATCC AGGAGTGGGG
2301  CCCATTCGAC CTGGTGATTG GAGGCAGTCC CTGCAATGAC CTCTCCATTG
```

FIG. 1A-2

```
2351  TCAACCCTGC CCGCAAGGGA CTTTATGAGG GTACTGGCCG CCTCTTCTTT
2401  GAGTTCTACC GCCTCCTGCA TGATGCGCGG CCCAAGGAGG GAGATGATCG
2451  CCCCTTCTTC TGGCTCTTTG AGAATGTGGT GGCCATGGGC GTTAGTGACA
2501  AGAGGGACAT CTCGCGATTT CTTGAGTCTA ACCCCGTGAT GATTGACGCC
2551  AAAGAAGTGT CTGCTGCACA CAGGGCCCGT TACTTCTGGG GTAACCTTCC
2601  TGGCATCAAC AGGCCTTTGG CATCCACTGT GAATGATAAG CTGGAGCTGC
2651  AAGAGTGTCT GGAGCACGGC AGAATAGCCA AGTTCAGCAA AGTGAGGACC
2701  ATTACCACCA GGTCAAACTC TATAAAGCAG GGCAAAGACC AGCATTTCCC
2751  CGTCTTCATG AACGAGAAGG AGGACATCCT GTGGTGCACT GAAATGGAAA
2801  GGGTGTTTGG CTTCCCCGTC CACTACACAG ACGTCTCCAA CATGAGCCGC
2851  TTGGCGAGGC AGAGACTGCT GGGCCGATCG TGGAGCGTGC CGGTCATCCG
2901  CCACCTCTTC GCTCCGCTGA AGGAATATTT TGCTTGTGTG TAAGGGACAT
2951  GGGGGCAAAC TGAAGTAGTG ATGATAAAAA AGTTAAACAA ACAAACAAAC
3001  AAAAAACAAA ACAAAACAAT AAAACACCAA GAACGAGAGG ACGGAGAAAA
3051  GTTCAGCACC CAGAAGAGAA AAAGGAATTT AAAGCAAACC ACAGAGGAGG
3101  AAAACGCCGG AGGGCTTGGC CTTGCAAAAG GGTTGGACAT CATCTCCTGA
3151  GTTTTCAATG TTAACCTTCA GTCCTATCTA AAAAGCAAAA TAGGCCCCTC
3201  CCCTTCTTCC CCTCCGGTCC TAGGAGGCGA ACTTTTTGTT TTCTACTCTT
3251  TTTCAGAGGG GTTTTCTGTT TGTTTGGGTT TTTGTTTCTT GCTGTGACTG
3301  AAACAAGAGA GTTATTGCAG CAAAATCAGT AACAACAAAA AGTAGAAATG
3351  CCTTGGAGAG GAAAGGGAGA GAGGGAAAAT TCTATAAAAA CTTAAAATAT
3401  TGGTTTTTTT TTTTTTTCCT TTTCTATATA TCTCTTTGGT TGTCTCTAGC
3451  CTGATCAGAT AGGAGCACAA ACAGGAAGAG AATAGAGACC CTCGGAGGCA
3501  GAGTCTCCTC TCCCACCCCC CGAGCAGTCT CAACAGCACC ATTCCTGGTC
```

FIG. 1A-3

```
3551  ATGCAAAACA GAACCCAACT AGCAGCAGGG CGCTGAGAGA ACACCACACC

3601  AGACACTTTC TACAGTATTT CAGGTGCCTA CCACACAGGA AACCTTGAAG

3651  AAAACCAGTT TCTAGAAGCC GCTGTTACCT CTTGTTTACA GTTTATATAT

3701  ATATGATAGA TATGAGATAT ATATATATAA AAGGTACTGT TAACTACTGT

3751  ACATCCCGAC TTCATAATGG TGCTTTCAAA ACAGCGAGAT GAGCAAAGAC

3801  ATCAGCTTCC GCCTGGCCCT CTGTGCAAAG GGTTTCAGCC CAGGATGGGG

3851  AGAGGGGAGC AGCTGGAGGG GGTTTTAACA AACTGAAGGA TGACCCATAT

3901  CACCCCCCAC CCCTGCCCCA TGCCTAGCTT CACCTGCCAA AAAGGGGCTC

3951  AGCTGAGGTG GTCGGACCCT GGGGAAGCTG AGTGTGGAAT TTATCCAGAC

4001  TCGCGTGCAA TAACCTTAGA ATATGAATCT AAAATGACTG CCTCAGAAAA

4051  ATGGCTTGAG AAAACATTGT CCCTGATTTT GAATTCGTCA GCCACGTTGA

4101  AGGCCCCTTG TGGGATCAGA AATATTCCAG AGTGAGGGAA AGTGACCCGC

4151  CATTAACCCC NCCTGGAGCA AATAAAAAAA CATACAAAAT GT
```

FIG. 1A-4

Mouse Dnmt3b1 DNA Sequence

```
   1  GAATTCCGGG CGCCGGGGTT AAGCGGCCCA AGTAAACGTA GCGCAGCGAT
  51  CGGCGCCGGA GATTCGCGAA CCCGACACTC CGCGCCGCCC GCCGGCCAGG
 101  ACCCGCGGCG CGATCGCGGC GCCGCGCTAC AGCCAGCCTC ACGACAGGCC
 151  CGCTGAGGCT TGTGCCAGAC CTTGGAAACC TCAGGTATAT ACCTTTCCAG
 201  ACGCGGGATC TCCCCTCCCC CATCCATAGT GCCTTGGGAC CAAATCCAGG
 251  GCCTTCTTTC AGGAAACAAT GAAGGGAGAC AGCAGACATC TGAATGAAGA
 301  AGAGGGTGCC AGCGGGTATG AGGAGTGCAT TATCGTTAAT GGGAACTTCA
 351  GTGACCAGTC CTCAGACACG AAGGATGCTC CCTCACCCCC AGTCTTGGAG
 401  GCAATCTGCA CAGAGCCAGT CTGCACACCA GAGACCAGAG GCCGCAGGTC
 451  AAGCTCCCGG CTGTCTAAGA GGGAGGTCTC CAGCCTTCTG AATTACACGC
 501  AGGACATGAC AGGAGATGGA GACAGAGATG ATGAAGTAGA TGATGGGAAT
 551  GGCTCTGATA TTCTAATGCC AAAGCTCACC CGTGAGACCA AGGACACCAG
 601  GACGCGCTCT GAAAGCCCGG CTGTCCGAAC CCGACATAGC AATGGGACCT
 651  CCAGCTTGGA GAGGCAAAGA GCCTCCCCCA GAATCACCCG AGGTCGGCAG
 701  GGCCGCCACC ATGTGCAGGA GTACCCTGTG GAGTTTCCGG CTACCAGGTC
 751  TCGGAGACGT CGAGCATCGT CTTCAGCAAG CACGCCATGG TCATCCCCTG
 801  CCAGCGTCGA CTTCATGGAA GAAGTGACAC CTAAGAGCGT CAGTACCCCA
 851  TCAGTTGACT TGAGCCAGGA TGGAGATCAG GAGGGTATGG ATACCACACA
 901  GGTGGATGCA GAGAGCAGAG ATGGAGACAG CACAGAGTAT CAGGATGATA
 951  AAGAGTTTGG AATAGGTGAC CTCGTGTGGG GAAAGATCAA GGGCTTCTCC
1001  TGGTGGCCTG CCATGGTGGT GTCCTGGAAA GCCACCTCCA AGCGACAGGC
```

FIG. 1B-1

```
1051  CATGCCCGGA ATGCGCTGGG TACAGTGGTT TGGTGATGGC AAGTTTTCTG
1101  AGATCTCTGC TGACAAACTG GTGGCTCTGG GGCTGTTCAG CCAGCACTTT
1151  AATCTGGCTA CCTTCAATAA GCTGGTTTCT TATAGGAAGG CCATGTACCA
1201  CACTCTGGAG AAAGCCAGGG TTCGAGCTGG CAAGACCTTC TCCAGCAGTC
1251  CTGGAGAGTC ACTGGAGGAC CAGCTGAAGC CCATGCTGGA GTGGGCCCAC
1301  GGTGGCTTCA AGCCTACTGG GATCGAGGGC CTCAAACCCA ACAAGAAGCA
1351  ACCAGTGGTT AATAAGTCGA AGGTGCGTCG TTCAGACAGT AGGAACTTAG
1401  AACCCAGGAG ACGCGAGAAC AAAAGTCGAA GACGCACAAC CAATGACTCT
1451  GCTGCTTCTG AGTCCCCCCC ACCCAAGCGC CTCAAGACAA ATAGCTATGG
1501  CGGGAAGGAC CGAGGGGAGG ATGAGGAGAG CCGAGAACGG ATGGCTTCTG
1551  AAGTCACCAA CAACAAGGGC AATCTGGAAG ACCGCTGTTT GTCCTGTGGA
1601  AAGAAGAACC CTGTGTCCTT CCACCCCCTC TTTGAGGGTG GGCTCTGTCA
1651  GAGTTGCCGG GATCGCTTCC TAGAGCTCTT CTACATGTAT GATGAGGACG
1701  GCTATCAGTC CTACTGCACC GTGTGCTGTG AGGGCCGTGA ACTGCTGCTG
1751  TGCAGTAACA CAAGCTGCTG CAGATGCTTC TGTGTGGAGT GTCTGGAGGT
1801  GCTGGTGGGC GCAGGCACAG CTGAGGATGC CAAGCTGCAG GAACCCTGGA
1851  GCTGCTATAT GTGCCTCCCT CAGCGCTGCC ATGGGGTCCT CCGACGCAGG
1901  AAAGATTGGA ACATGCGCCT GCAAGACTTC TTCACTACTG ATCCTGACCT
1951  GGAAGAATTT GAGCCACCCA AGTTGTACCC AGCAATTCCT GCAGCCAAAA
2001  GGAGGCCCAT TAGAGTCCTG TCTCTGTTTG ATGGAATTGC AACGGGGTAC
2051  TTGGTGCTCA AGGAGTTGGG TATTAAAGTG GAAAAGTACA TTGCCTCCGA
2101  AGTCTGTGCA GAGTCCATCG CTGTGGGAAC TGTTAAGCAT GAAGGCCAGA
2151  TCAAATATGT CAATGACGTC CGGAAAATCA CCAAGAAAAA TATTGAAGAG
2201  TGGGGCCCGT TCGACTTGGT GATTGGTGGA AGCCCATGCA ATGATCTCTC
```

FIG. 1B-2

```
2251  TAACGTCAAT CCTGCCCGCA AAGGTTTATA TGAGGGCACA GGAAGGCTCT

2301  TCTTCGAGTT TTACCACTTG CTGAATTATA CCCGCCCCAA GGAGGGCGAC

2351  AACCGTCCAT TCTTCTGGAT GTTCGAGAAT GTTGTGGCCA TGAAAGTGAA

2401  TGACAAGAAA GACATCTCAA GATTCCTGGC ATGTAACCCA GTGATGATCG

2451  ATGCCATCAA GGTGTCTGCT GCTCACAGGG CCCGGTACTT CTGGGGTAAC

2501  CTACCCGGAA TGAACAGGCC CGTGATGGCT TCAAAGAATG ATAAGCTCGA

2551  GCTGCAGGAC TGCCTGGAGT TCAGTAGGAC AGCAAAGTTA AGAAAGTGC

2601  AGACAATAAC CACCAAGTCG AACTCCATCA GACAGGGCAA AAACCAGCTT

2651  TTCCCTGTAG TCATGAATGG CAAGGACGAC GTTTTGTGGT GCACTGAGCT

2701  CGAAAGGATC TTCGGCTTCC CTGCTCACTA CACGGACGTG TCCAACATGG

2751  GCCGCGGCGC CCGTCAGAAG CTGCTGGGCA GGTCCTGGAG TGTACCGGTC

2801  ATCAGACACC TGTTTGCCCC CTTGAAGGAC TACTTTGCCT GTGAATAGTT

2851  CTACCCAGGA CTGGGGAGCT CTCGGTCAGA GCCAGTGCCC AGAGTCACCC

2901  CTCCCTGAAG GCACCTCACC TGTCCCCTTT TTAGCTCACC TGTGTGGGGC

2951  CTCACATCAC TGTACCTCAG CTTTCTCCTG CTCAGTGGGA GCAGAGCCTC

3001  CTGGCCCTTG CAGGGGAGCC CCGGTGCTCC CTCCGTGTGC ACAGCTCAGA

3051  CCTGGCTGCT TAGAGTAGCC CGGCATGGTG CTCATGTTCT CTTACCCTGA

3101  AACTTTAAAA CTTGAAGTAG GTAGTAAGAT GGCTTTCTTT TACCCTCCTG

3151  AGTTTATCAC TCAGAAGTGA TGGCTAAGAT ACCAAAAAAA CAAACAAAAA

3201  CAGAAACAAA AAACAAAAAA AAACCTCAAC AGCTCTCTTA GTACTCAGGT

3251  TCATGCTGCA AAATCACTTG AGATTTTGTT TTTAAGTAAC CCGTGCTCCA

3301  CATTTGCTGG AGGATGCTAT TGTGAATGTG GGCTCAGATG AGCAAGGTCA

3351  AGGGGCCAAA AAAAATTCCC CCTCTCCCCC CAGGAGTATT TGAAGATGAT

3401  GTTTATGGTT TAAGTCTTCC TGGCACCTTC CCCTTGCTTT GGTACAAGGG
```

FIG. 1B-3

3451 CTGAAGTCCT GTTGGTCTTG TAGCATTTCC CAGGATGATG ATGTCAGCAG

3501 GGATGACATC ACCACCTTTA GGGCTTTTCC CTGGCAGGGG CCCATGTGGC

3551 TAGTCCTCAC GAAGACTGGA GTAGAATGTT TGGAGCTCAG GAAGGGTGGG

3601 TGGAGTGGCC CTCTTCCAGG TGTGAGGGAT ACGAAGGAGG AAGCTTAGGG

3651 AAATCCATTC CCCACTCCCT CTTGCCAAAT GAGGGGCCCA GTCCCCAACA

3701 GCTCAGGTCC CCAGAACCCC CTAGTTCCTC ATGAGAAGCT AGGACCAGAA

3751 GCACATCGTT CCCCTTATCT GAGCAGTGTT TGGGGAACTA CAGTGAAAAC

3801 CTTCTGGAGA TGTTAAAAGC TTTTTACCCC ACGATAGATT GTGTTTTTAA

3851 GGGGTGCTTT TTTTAGGGGC ATCACTGGAG ATAAGAAAGC TGCATTTCAG

3901 AAATGCCATC GTAATGGTTT TTAAACACCT TTTACCTAAT TACAGGTGCT

3951 ATTTTATAGA AGCAGACAAC ACTTCTTTTT ATGACTCTCA GACTTCTATT

4001 TTCATGTTAC CATTTTTTTT GTAACTCGCA AGGTGTGGGC TTTTGTAACT

4051 TCACAGGTGT GGGGAGAGAC TGCCTTGTTT CAACAGTTTG TCTCCACTGG

4101 TTTCTAATTT TTAGGTGCAA AGATGACAGA TGCCCAGAGT TTACCTTTCT

4151 GGTTGATTAA AGTTCTATTT CTCTAAAAAA AAAAAAAAAA AAAAA

FIG. 1B-4

Human DNMT3A DNA Sequence

```
   1                       GCCGCGG CACCAGGGCG CGCAGCCGGG
  28 CCGGCCCGAC CCCACCGGCC ATACGGTGGA GCCATCGAAG CCCCCACCCA
  78 CAGGCTGACA GAGGCACCGT TCACCAGAGG GCTCAACACC GGGATCTATG
 128 TTTAAGTTTT AACTCTCGCC TCCAAAGACC ACGATAATTC CTTCCCCAAA
 178 GCCCAGCAGC CCCCCAGCCC CGCGCAGCCC CAGCCTGCCT CCCGGCGCCC
 228 AGATGCCCGC CATGCCCTCC AGCGGCCCCG GGACACCAG CAGCTCTGCT
 278 GCGGAGCGGG AGGAGGACCG AAAGGACGGA GAGGAGCAGG AGGAGCCGCG
 328 TGGCAAGGAG GAGCGCCAAG AGCCCAGCAC CACGGCACGG AAGGTGGGGC
 378 GGCCTGGGAG GAAGCGCAAG CACCCCCCGG TGGAAAGCGG TGACACGCCA
 428 AAGGACCCTG CGGTGATCTC CAAGTCCCCA TCCATGGCCC AGGACTCAGG
 478 CGCCTCAGAG CTATTACCCA ATGGGGACTT GGAGAAGCGG AGTGAGCCCC
 528 AGCCAGAGGA GGGGAGCCCT GCTGGGGGGC AGAAGGGCGG GGCCCCAGCA
 578 GAGGGAGAGG GTGCAGCTGA GACCCTGCCT GAAGCCTCAA GAGCAGTGGA
 628 AAATGGCTGC TGCACCCCCA AGGAGGGCCG AGGAGCCCCT GCAGAAGCGG
 678 GCAAAGAACA GAAGGAGACC AACATCGAAT CCATGAAAAT GGAGGGCTCC
 728 CGGGGCCGGC TGCGGGGTGG CTTGGGCTGG GAGTCCAGCC TCCGTCAGCG
 778 GCCCATGCCG AGGCTCACCT TCCAGGCGGG GGACCCCTAC TACATCAGCA
 828 AGCGCAAGCG GGACGAGTGG CTGGCACGCT GGAAAAGGGA GGCTGAGAAG
 878 AAAGCCAAGG TCAGTGCAGG AATGAATGCT GTGGAAGAAA ACCAGGGGCC
 928 CGGGGAGTCT CAGAAGGTGG AGGAGGCCAG CCCTCCTGCT GTGCAGCAGC
 978 CCACTGACCC CGCATCCCCC ACTGTGGCTA CCACGCCTGA GCCCGTGGGG
1028 TCCGATGCTG GGGACAAGAA TGCCACCAAA GCAGGCGATG ACGAGCCAGA
```

FIG. 1C-1

```
1078  GTACGAGGAC GGCCGGGGCT TTGGCATTGG GGAGCTGGTG TGGGGGAAAC
1128  TGCGGGGCTT CTCCTGGTGG CCAGGCCGCA TTGTGTCTTG GTGGATGACG
1178  GGCCGGAGCC GAGCAGCTGA AGGCACCCGC TGGGTCATGT GGTTCGGAGA
1228  CGGCAAATTC TCAGTGGTGT GTGTTGAGAA GCTGATGCCG CTGAGCTCGT
1278  TTTGCAGTGC GTTCCACCAG GCCACGTACA ACAAGCAGCC CATGTACCGC
1328  AAAGCCATCT ACGAGGTCCT GCAGGTGGCC AGCAGCCGCG CGGGGAAGCT
1378  GTTCCCGGTG TGCCACGACA GCGATGAGAG TGACACTGCC AAGGCCGTCG
1428  AGGTGCAGAA CAAGCCCATG ATTGAATGGG CCCTGGGGGG CTTCCAGCCT
1478  TCTGGCCCTA AGGGCCTGGA GCCACCAGAA GAAGAGAAGA ATCCCTACAA
1528  AGAAGTGTAC ACGGACATGT GGGTGGAACC TGAGGCAGCT GCCTACGCAC
1578  CACCTCCACC AGCCAAAAAG CCCCGGAAGA GCACAGCGGA GAAGCCCAAG
1628  GTCAAGGAGA TTATTGATGA GCGCACAAGA GAGCGGCTGG TGTACGAGGT
1678  GCGGCAGAAG TGCCGGAACA TTGAGGACAT CTGCATCTCC TGTGGGAGCC
1728  TCAATGTTAC CCTGGAACAC CCCCTCTTCG TTGGAGGAAT GTGCCAAAAC
1778  TGCAAGAACT GCTTTCTGGA GTGTGCGTAC CAGTACGACG ACGACGGCTA
1828  CCAGTCCTAC TGCACCATCT GCTGTGGGGG CCGTGAGGTG CTCATGTGCG
1878  GAAACAACAA CTGCTGCAGG TGCTTTTGCG TGGAGTGTGT GGACCTCTTG
1928  GTGGGGCCGG GGGCTGCCCA GGCAGCCATT AAGGAAGACC CCTGGAACTG
1978  CTACATGTGC GGGCACAAGG GTACCTACGG GCTGCTGCGG CGGCGAGAGG
2028  ACTGGCCCTC CCGGCTCCAG ATGTTCTTCG CTAATAACCA CGACCAGGAA
2078  TTTGACCCTC CAAAGGTTTA CCCACCTGTC CCAGCTGAGA AGAGGAAGCC
2128  CATCCGGGTG CTGTCTCTCT TTGATGGAAT CGCTACAGGG CTCCTGGTGC
2178  TGAAGGACTT GGGCATTCAG GTGGACCGCT ACATTGCCTC GGAGGTGTGT
```

```
2228  GAGGACTCCA TCACGGTGGG CATGGTGCGG CACCAGGGGA AGATCATGTA
2278  CGTCGGGGAC GTCCGCAGCG TCACACAGAA GCATATCCAG GAGTGGGGCC
2328  CATTCGATCT GGTGATTGGG GGCAGTCCCT GCAATGACCT CTCCATCGTC
2378  AACCCTGCTC GCAAGGGCCT CTACGAGGGC ACTGGCCGGC TCTTCTTTGA
2428  GTTCTACCGC CTCCTGCATG ATGCGCGGCC CAAGGAGGGA GATGATCGCC
2478  CCTTCTTCTG GCTCTTTGAG AATGTGGTGG CCATGGGCGT TAGTGACAAG
2528  AGGGACATCT CGCGATTTCT CGAGTCCAAC CCTGTGATGA TTGATGCCAA
2578  AGAAGTGTCA GCTGCACACA GGGCCCGCTA CTTCTGGGGT AACCTTCCCG
2628  GTATGAACAG GCCGTTGGCA TCCACTGTGA ATGATAAGCT GGAGCTGCAG
2678  GAGTGTCTGG AGCATGGCAG GATAGCCAAG TTCAGCAAAG TGAGGACCAT
2728  TACTACGAGG TCAAACTCCA TAAAGCAGGG CAAAGACCAG CATTTTCCTG
2778  TCTTCATGAA TGAGAAAGAG GACATCTTAT GGTGCACTGA AATGGAAAGG
2828  GTATTTGGTT TCCCAGTCCA CTATACTGAC GTCTCCAACA TGAGCCGCTT
2878  GGCGAGGCAG AGACTGCTGG GCCGGTCATG GAGCGTGCCA GTCATCCGCC
2928  ACCTCTTCGC TCCGCTGAAG GAGTATTTTG CGTGTGTGTA AGGGACATGG
2978  GGGCAAACTG AGGTAGCGAC ACAAAGTTAA ACAAACAAAC AAAAAACACA
3028  AAACATAATA AAACACCAAG AACATGAGGA TGGAGAGAAG TATCAGCACC
3078  CAGAAGAGAA AAAGGAATTT AAAACAAAAA CCACAGAGGC GGAAATACCG
3128  GAGGGCTTTG CCTTGCGAAA AGGGTTGGAC ATCATCTCCT GATTTTTCAA
3178  TGTTATTCTT CAGTCCTATT TAAAAACAAA ACCAAGCTCC CTTCCCTTCC
3228  TCCCCCTTCC CTTTTTTTTC GGTCAGACCT TTTATTTTCT ACTCTTTTCA
3278  GAGGGGTTTT CTGTTTGTTT GGGTTTTGTT TCTTGCTGTG ACTGAAACAA
3328  GAAGGTTATT GCAGCAAAAA TCAGTAACAA AAAATAGTAA CAATACCTTG
3378  CAGAGGAAAG GTGGGAGGAG AGGAAAAAAG GGAAATTTTT AAAGAAATCT
```

FIG. 1C-3

3428 ATATATTGGG TTGTTTTTTT TTTTGTTTTT TGTTTTTTTT TTTTGGGTTT

3478 TTTTTTTTTA CTATATATCT TTTTTTTGTT GTCTCTAGCC TGATCAGATA

3528 GGAGCACAAG CAGGGGACGG AAAGAGAGAG ACACTCAGGC GGCAGCATTC

3578 CCTCCCAGCC ACTGAGCTGT CGTGCCAGCA CCATTCCTGG TCACGCAAAA

3628 CAGAACCCAG TTAGCAGCAG GGAGACGAGA ACACCACACA AGACATTTTT

3678 CTACAGTATT TCAGGTGCCT ACCACACAGG AAACCTTGAA GAAAATCAGT

3728 TTCTAGAAGC CGCTGTTACC TCTTGTTTAC AGTTTATATA TATATGATAG

3778 ATATGAGATA TATATATAAA AGGTACTGTT AACTACTGTA CAACCCGACT

3828 TCATAATGGT GCTTTCAAAC AGCGAGATGA GTAAAAACAT CAGCTTCCAC

3878 GTTGCCTTCT GCGCAAAGGG TTTCACCAAG GATGGAGAAA GGGAGACAGC

3928 TTGCAGATGG CGCGTTCTCA CGGTGGGCTC TTCCCCTTGG TTTGTAACGA

3978 AGTGAAGGAG GAGAACTTGG GAGCCAGGTT CTCCCTGCCA AAAAGGGGGC

4028 TAGATGAGGT GGTCGGGCCC GTGGACAGCT GAGAGTGGGA TTCATCCAGA

4078 CTCATGCAAT AACCCTTTGA TTGTTTTCTA AAAGGAGACT CCCTCGGCAA

4128 GATGGCAGAG GGTACGGAGT CTTCAGGCCC AGTTTCTCAC TTTAGCCAAT

4178 TCGAGGGCTC CTTGTGGTGG GATCAGAACT AATCCAGAGT GTGGGAAAGT

4228 GACAGTCAAA ACCCCACCTG GAGCAAATAA AAAAACATAC AAAACGTAAA

4278 AAAAAAAAAA AAAAAA

FIG. 1C-4

Human DNMT3B1 DNA Sequence:

```
   1  GGCCGCGAAT TCGGCACGAG CCCTGCACGG CCGCCAGCCG GCCTCCCGCC
  51  AGCCAGCCCC GACCCGCGGC TCCGCCGCCC AGCCGCGCCC CAGCCAGCCC
 101  TGCGGCAGGA AAGCATGAAG GGAGACACCA GGCATCTCAA TGGAGAGGAG
 151  GACGCCGGCG GGAGGGAAGA CTCGATCCTC GTCAACGGGG CCTGCAGCGA
 201  CCAGTCCTCC GACTCGCCCC CAATCCTGGA GGCTATCCGC ACCCCGGAGA
 251  TCAGAGGCCG AAGATCAAGC TCGCGACTCT CCAAGAGGGA GGTGTCCAGT
 301  CTGCTAAGCT ACACACAGGA CTTGACAGGC GATGGCGACG GGAAGATGG
 351  GGATGGCTCT GACACCCCAG TCATGCCAAA GCTCTTCCGG GAAACCAGGA
 401  CTCGTTCAGA AAGCCCAGCT GTCCGAACTC GAAATAACAA CAGTGTCTCC
 451  AGCCGGGAGA GGCACAGGCC TTCCCCACGT TCCACCCGAG GCCGGCAGGG
 501  CCGCAACCAT GTGGACGAGT CCCCCGTGGA GTTCCCGGCT ACCAGGTCCC
 551  TGAGACGGCG GCAACAGCA TCGGCAGGAA CGCCATGGCC GTCCCCTCCC
 601  AGCTCTTACC TTACCATCGA CCTCACAGAC GACACAGAGG ACACACATGG
 651  GACGCCCCAG AGCAGCAGTA CCCCCTACGC CCGCCTAGCC CAGGACAGCC
 701  AGCAGGGGGG CATGGAGTCC CCGCAGGTGG AGGCAGACAG TGGAGATGGA
 751  GACAGTTCAG AGTATCAGGA TGGGAAGGAG TTTGGAATAG GGACCTCGT
 801  GTGGGGAAAG ATCAAGGGCT TCTCCTGGTG GCCCGCCATG GTGGTGTCTT
 851  GGAAGGCCAC CTCCAAGCGA CAGGCTATGT CTGGCATGCG GTGGGTCCAG
 901  TGGTTTGGCG ATGGCAAGTT CTCCGAGGTC TCTGCAGACA AACTGGTGGC
 951  ACTGGGGCTG TTCAGCCAGC ACTTTAATTT GGCCACCTTC AATAAGCTCG
1001  TCTCCTATCG AAAAGCCATG TACCATGCTC TGGAGAAAGC TAGGGTGCGA
1051  GCTGGCAAGA CCTTCCCCAG CAGCCCTGGA GACTCATTGG AGGACCAGCT
1101  GAAGCCCATG TTGGAGTGGG CCCACGGGGG CTTCAAGCCC ACTGGGATCG
1151  AGGGCCTCAA ACCCAACAAC ACGCAACCAG TGGTTAATAA GTCGAAGGTG
```

FIG. 1D-1

```
1201  CGTCGTGCAG GCAGTAGGAA ATTAGAATCA AGGAAATACG AGAACAAGAC
1251  TCGAAGACGC ACAGCTGACG ACTCAGCCAC CTCTGACTAC TGCCCCGCAC
1301  CCAAGCGCCT CAAGACAAAT TGCTATAACA ACGGCAAAGA CCGAGGGGAT
1351  GAAGATCAGA GCCGAGAACA AATGGCTTCA GATGTTGCCA ACAACAAGAG
1401  CAGCCTGGAA GATGGCTGTT TGTCTTGTGG CAGGAAAAAC CCCGTGTCCT
1451  TCCACCCTCT CTTTGAGGGG GGGCTCTGTC AGACATGCCG GGATCGCTTC
1501  CTTGAGCTGT TTTACATGTA TGATGACGAT GGCTATCAGT CTTACTGCAC
1551  TGTGTGCTGC GAGGGCCGAG AGCTGCTGCT TGCAGCAAC ACGAGCTGCT
1601  GCCGGTGTTT CTGTGTGGAG TGCCTGGAGG TGCTGGTGGG CACAGGCACA
1651  GCGGCCGAGG CCAAGCTTCA GGAGCCCTGG AGCTGCTACA TGTGTCTCCC
1701  GCAGCGCTGT CATGGCGTCC TGCGGCGCCG GAAGGACTGG AACGTGCGCC
1751  TGCAGGCCTT CTTCACCAGT GACACGGGGC TTGAATACGA AGCCCCCAAG
1801  CTGTACCCTG CCATTCCCGC AGCCCGAAGG CGGCCCATTC GAGTCCTGTC
1851  ATTGTTTGAT GGCATCGCGA CAGGCTACCT AGTCCTCAAA GAGTTGGGCA
1901  TAAAGGTAGG AAAGTACGTC GCTTCTGAAG TGTGTGAGGA GTCCATTGCT
1951  GTTGGAACCG TGAAGCACGA GGGGAATATC AAATACGTGA ACGACGTGAG
2001  GAACATCACA AAGAAAAATA TTGAAGAATG GGGCCCATTT GACTTGGTGA
2051  TTGGCGGAAG CCCATGCAAC GATCTCTCAA ATGTGAATCC AGCCAGGAAA
2101  GGCCTGTATG AGGGTACAGG CCGGCTCTTC TTCGAATTTT ACCACCTGCT
2151  GAATTACTCA CGCCCCAAGG AGGGTGATGA CCGGCCGTTC TTCTGGATGT
2201  TTGAGAATGT TGTAGCCATG AAGGTTGGCG ACAAGAGGGA CATCTCACGG
2251  TTCCTGGAGT GTAATCCAGT GATGATTGAT GCCATCAAAG TTTCTGCTGC
2301  TCACAGGGCC CGATACTTCT GGGGCAACCT ACCCGGGATG AACAGGCCCG
2351  TGATAGCATC AAAGAATGAT AAACTCGAGC TGCAGGACTG CTTGGAATAC
2401  AATAGGATAG CCAAGTTAAA GAAAGTACAG ACAATAACCA CCAAGTCGAA
```

2451 CTCGATCAAA CAGGGGAAAA ACCAACTTTT CCCTGTTGTC ATGAATGGCA

2501 AAGAAGATGT TTTGTGGTGC ACTGAGCTCG AAAGGATCTT TGGCTTTCCT

2551 GTGCACTACA CAGACGTGTC CAACATGGGC CGTGGTGCCC GCCAGAAGCT

2601 GCTGGGAAGG TCCTGGAGCG TGCCTGTCAT CCGACACCTC TTCGCCCCTC

2651 TGAAGGACTA CTTTGCATGT GAATAGTTCC AGCCAGGCCC CAAGCCCACT

2701 GGGGTGTGTG GCAGAGCCAG GACCCAGGAG GTGTGATTCC TGAAGGCATC

2751 CCCAGGCCCT GCTCTTCCTC AGCTGTGTGG GTCATACCGT GTACCTCAGT

2801 TCCCTCTTGC TCAGTGGGGG CAGAGCCACC TGACTCTTGC AGGGGTAGCC

2851 TGAGGTGCCG CCTCCTTGTG CACAAATCAG ACCTGGCTGC TTGGAGCAGC

2901 CTAACACGGT GCTCATTTTT TCTTCTCCTA AAACTTTAAA ACTTGAAGTA

2951 GGTAGCAACG TGGCTTTTTT TTTTTCCCTT CCTGGGTCTA CCACTCAGAG

3001 AAACAATGGC TAAGATACCA AAACCACAGT GCCGACAGCT CTCCAATACT

3051 CAGGTTAATG CTGAAAAATC ATCCAAGACA GTTATTGCAA GAGTTTAATT

3101 TTTGAAAACT GGGTACTGCT ATGTGTTTAC AGACGTGTGC AGTTGTAGGC

3151 ATGTAGCTAC AGGACATTTT TAAGGGCCCA GGATCGTTTT TTCCCAGGGC

3201 AAGCAGAAGA GAAAATGTTG TATATGTCTT TTACCCGGCA CATTCCCCTT

3251 GCCTAAATAC AAGGGCTGGA GTCTGCACGG GACCTATTAG AGTATTTTCC

3301 ACAATGATGA TGATTTCAGC AGGGATGACG TCATCATCAC ATTCAGGGCT

3351 ATTTTTTCCC CCACAAACCC AAGGGCAGGG GCCACTCTTA GCTAAATCCC

3401 TCCCCGTGAC TGCAATAGAA CCCTCTGGGG AGCTCAGGAA GGGGTGTGCT

3451 GAGTTCTATA ATATAAGCTG CCATATATTT TGTAGACAAG TATGGCTCCT

3501 CCATATCTCC CTCTTCCCTA GGAGAGGAGT GTGAAGCAAG GAGCTTAGAT

3551 AAGACACCCC CTCAAACCCA TTCCCTCTCC AGGAGACCTA CCCTCCACAG

3601 GCACAGGTCC CCAGATGAGA AGTCTGCTAC CCTCATTTCT CATCTTTTTA

3651 CTAAACTCAG AGGCAGTGAC AGCAGTCAGG GACAGACATA CATTTCTCAT

FIG. 1D-3

3701 ACCTTCCCCA CATCTGAGAG ATGACAGGGA AAACTGCAAA GCTCGGTGCT

3751 CCCTTTGGAG ATTTTTTAAT CCTTTTTTAT TCCATAAGAA GTCGTTTTTA

3801 GGGAGAACGG GAATTCAGAC AAGCTGCATT TCAGAAATGC TGTCATAATG

3851 GTTTTTAACA CCTTTTACTC TTCTTACTGG TGCTATTTTG TAGAATAAGG

3901 AACAACGTTG ACAAGTTTTG TGGGGCTTTT TATACACTTT TTAAAATCTC

3951 AAACTTCTAT TTTTATGTTT AACGTTTTCA TTAAAATTTT TTTGTAACTG

4001 GAGCCACGAC GTAACAAATA TGGGGAAAAA ACTGTGCCTT GTTTCAACAG

4051 TTTTTGCTAA TTTTTAGGCT GAAAGATGAC GGATGCCTAG AGTTTACCTT

4101 ATGTTTAATT AAAATCAGTA TTTGTCTAAA AAAAAAAAAA AAAAA

FIG. 1D-4

Mouse Dnmt3a Protein

```
  1  MPSSGPGDTS SSSLEREDDR KEGEEQEENR GKEERQEPSA TARKVGRPGR
 51  KRKHPPVESS DTPKDPAVTT KSQPMAQDSG PSDLLPNGDL EKRSEPQPEE
101  GSPAAGQKGG APAEGEGTET PPEASRAVEN GCCVTKEGRG ASAGEGKEQK
151  QTNIESMKME GSRGRLRGGL GWESSLRQRP MPRLTFQAGD PYYISKRKRD
201  EWLARWKREA EKKAKVIAVM NAVEENQASG ESQKVEEASP PAVQQPTDPA
251  SPTVATTPEP VGGDAGDKNA TKAADDEPEY EDGRGFGIGE LVWGKLRGFS
301  WWPGRIVSWW MTGRSRAAEG TRWVMWFGDG KFSVVCVEKL MPLSSFCSAF
351  HQATYNKQPM YRKAIYEVLQ VASSRAGKLF PACHDSDESD SGKAVEVQNK
401  QMIEWALGGF QPSGPKGLEP PEEEKNPYKE VYTDMWVEPE AAAYAPPPPA
451  KKPRKSTTEK PKVKEIIDER TRERLVYEVR QKCRNIEDIC ISCGSLNVTL
501  EHPLFIGGMC QNCKNCFLEC AYQYDDDGYQ SYCTICCGGR EVLMCGNNNC
551  CRCFCVECVD LLVGPGAAQA AIKEDPWNCY MCGHKGTYGL LRRREDWPSR
601  LQMFFANNHD QEFDPPKVYP PVPAEKRKPI RVLSLFDGIA TGLLVLKDLG
651  IQVDRYIASE VCEDSITVGM VRHQGKIMYV GDVRSVTQKH IQEWGPFDLV
701  IGGSPCNDLS IVNPARKGLY EGTGRLFFEF YRLLHDARPK EGDDRPFFWL
751  FENVVAMGVS DKRDISRFLE SNPVMIDAKE VSAAHRARYF WGNLPGMNRP
801  LASTVNDKLE LQECLEHGRI AKFSKVRTIT TRSNSIKQGK DQHFPVFMNE
851  KEDILWCTEM ERVFGFPVHY TDVSNMSRLA RQRLLGRSWS VPVIRHLFAP
901  LKEYFACV*
```

FIG. 2A

Mouse Dnmt3b1 Protein

```
  1  MKGDSRHLNE EEGASGYEEC IIVNGNFSDQ SSDTKDAPSP PVLEAICTEP
 51  VCTPETRGRR SSSRLSKREV SSLLNYTQDM TGDGDRDDEV DDGNGSDILM
101  PKLTRETKDT RTRSESPAVR TRHSNGTSSL ERQRASPRIT RGRQGRHHVQ
151  EYPVEFPATR SRRRRASSSA STPWSSPASV DFMEEVTPKS VSTPSVDLSQ
201  DGDQEGMDTT QVDAESRDGD STEYQDDKEF GIGDLVWGKI KGFSWWPAMV
251  VSWKATSKRQ AMPGMRWVQW FGDGKFSEIS ADKLVALGLF SQHFNLATFN
301  KLVSYRKAMY HTLEKARVRA GKTFSSSPGE SLEDQLKPML EWAHGGFKPT
351  GIEGLKPNKK QPVVNKSKVR RSDSRNLEPR RRENKSRRRT TNDSAASESP
401  PPKRLKTNSY GGKDRGEDEE SRERMASEVT NNKGNLEDRC LSCGKKNPVS
451  FHPLFEGGLC QSCRDRFLEL FYMYDEDGYQ SYCTVCCEGR ELLLCSNTSC
501  CRCFCVECLE VLVGAGTAED AKLQEPWSCY MCLPQRCHGV LRRRKDWNMR
551  LQDFFTTDPD LEEFEPPKLY PAIPAAKRRP IRVLSLFDGI ATGYLVLKEL
601  GIKVEKYIAS EVCAESIAVG TVKHEGQIKY VNDVRKITKK NIEEWGPFDL
651  VIGGSPCNDL SNVNPARKGL YEGTGRLFFE FYHLLNYTRP KEGDNRPFFW
701  MFENVVAMKV NDKKDISRFL ACNPVMIDAI KVSAAHRARY FWGNLPGMNR
751  PVMASKNDKL ELQDCLEFSR TAKLKKVQTI TTKSNSIRQG KNQLFPVVMN
801  GKDDVLWCTE LERIFGFPAH YTDVSNMGRG ARQKLLGRSW SVPVIRHLFA
851  PLKDYFACE*
```

FIG. 2B

Human DNMT3A Protein

```
  1  MPAMPSSGPG DTSSSAAERE EDRKDGEEQE EPRGKEERQE PSTTARKVGR
 51  PGRKRKHPPV ESGDTPKDPA VISKSPSMAQ DSGASELLPN GDLEKRSEPQ
101  PEEGSPAGGQ KGGAPAEGEG AAETLPEASR AVENGCCTPK EGRGAPAEAG
151  KEQKETNIES MKMEGSRGRL RGGLGWESSL RQRPMPRLTF QAGDPYYISK
201  RKRDEWLARW KREAEKKAKV IAGMNAVEEN QGPGESQKVE EASPPAVQQP
251  TDPASPTVAT TPEPVGSDAG DKNATKAGDD EPEYEDGRGF GIGELVWGKL
301  RGFSWWPGRI VSWWMTGRSR AAEGTRWVMW FGDGKFSVVC VEKLMPLSSF
351  CSAFHQATYN KQPMYRKAIY EVLQVASSRA GKLFPVCHDS DESDTAKAVE
401  VQNKPMIEWA LGGFQPSGPK GLEPPEEEKN PYKEVYTDMW VEPEAAAYAP
451  PPPAKKPRKS TAEKPKVKEI IDERTRERLV YEVRQKCRNI EDICISCGSL
501  NVTLEHPLFV GGMCQNCKNC FLECAYQYDD DGYQSYCTIC CGGREVLMCG
551  NNNCCRCFCV ECVDLLVGPG AAQAAIKEDP WNCYMCGHKG TYGLLRRRED
601  WPSRLQMFFA NNHDQEFDPP KVYPPVPAEK RKPIRVLSLF DGIATGLLVL
651  KDLGIQVDRY IASEVCEDSI TVGMVRHQGK IMYVGDVRSV TQKHIQEWGP
701  FDLVIGGSPC NDLSIVNPAR KGLYEGTGRL FFEFYRLLHD ARPKEGDDRP
751  FFWLFENVVA MGVSDKRDIS RFLESNPVMI DAKEVSAAHR ARYFWGNLPG
801  MNRPLASTVN DKLELQECLE HGRIAKFSKV RTITTRSNSI KQGKDQHFPV
851  FMNEKEDILW CTEMERVFGF PVHYTDVSNM SRLARQRLLG RSWSVPVIRH
901  LFAPLKEYFA CV*
```

FIG. 2C

Human DNMT3B1 Protein

```
  1  MKGDTRHLNG EEDAGGREDS ILVNGACSDQ SSDSPPILEA IRTPEIRGRR
 51  SSSRLSKREV SSLLSYTQDL TGDGDGEDGD GSDTPVMPKL FRETRTRSES
101  PAVRTRNNNS VSSRERHRPS PRSTRGRQGR NHVDESPVEF PATRSLRRRA
151  TASAGTPWPS PPSSYLTIDL TDDTEDTHGT PQSSSTPYAR LAQDSQQGGM
201  ESPQVEADSG DGDSSEYQDG KEFGIGDLVW GKIKGFSWWP AMVVSWKATS
251  KRQAMSGMRW VQWFGDGKFS EVSADKLVAL GLFSQHFNLA TFNKLVSYRK
301  AMYHALEKAR VRAGKTFPSS PGDSLEDQLK PMLEWAHGGF KPTGIEGLKP
351  NNTQPVVNKS KVRRAGSRKL ESRKYENKTR RRTADDSATS DYCPAPKRLK
401  TNCYNNGKDR GDEDQSREQM ASDVANNKSS LEDGCLSCGR KNPVSFHPLF
451  EGGLCQTCRD RFLELFYMYD DDGYQSYCTV CCEGRELLLC SNTSCCRCFC
501  VECLEVLVGT GTAAEAKLQE PWSCYMCLPQ RCHGVLRRRK DWNVRLQAFF
551  TSDTGLEYEA PKLYPAIPAA RRRPIRVLSL FDGIATGYLV LKELGIKVGK
601  YVASEVCEES IAVGTVKHEG NIKYVNDVRN ITKKNIEEWG PFDLVIGGSP
651  CNDLSNVNPA RKGLYEGTGR LFFEFYHLLN YSRPKEGDDR PFFWMFENVV
701  AMKVGDKRDI SRFLECNPVM IDAIKVSAAH RARYFWGNLP GMNRPVIASK
751  NDKLELQDCL EYNRIAKLKK VQTITTKSNS IKQGKNQLFP VVMNGKEDVL
801  WCTELERIFG FPVHYTDVSN MGRGARQKLL GRSWSVPVIR HLFAPLKDYF
851  ACE*
```

FIG. 2D

```
Dnmt3a    1  MPSSGPGDTSSSSLEREDDRKEGEEQEENRGKEERQEPSATARKVGRPGR  50

Dnmt3a   51  KRKHPPVESSDTPKDPAVTTKSQPMAQDSGPSD....LLPNGDLEKRSEP  96
                       . |. : :: |   :: ||.   .|
Dnmt3b    1  ................MKGDSRHLNEEEGASGYEECIIVNGNFSDQSSD  33

Dnmt3a   97  QPEEGSP....AAGQKGGAPAEGEGTETPPEAS.RAVENGCCVTKE..GR 139
             : ||    |  .    | |  .  |||.     |.: |
Dnmt3b   34  TKDAPSPPVLEAICTEPVCTPETRGRRSSSRLSKREVSSLLNYTQDMTGD  83

Dnmt3a  140  G.....ASAGEG......KEQKQTNIESMKMEGSRGRLRGGLGWESSLRQ 178
             |     ||       | ::|   :|   ||  |  |  ||
Dnmt3b   84  GDRDDEVDDDGNGSDILMPKLTRETKDTRTRSESPAVRTRHSNGTSSLERQ 133

Dnmt3a  179  RPMPRLTFQAGDPYYISKRKRDEWLARWKREAEKKAKVIAVMNAVEENQA 228
             |  ||:|       :::        |:  .    ::   . . .   .|
Dnmt3b  134  RASPRITRGRQGRHHV.....QEYPVEFPATRSRRRRASSSASTPWSSPA 178

Dnmt3a  229  SGESQKVEEASPPAVQQPTDPASPTVATTPEPVGGDAGDKNATKAADDEP 278
             | :   .|| .| .|    |    | ..   : ||   .|       |
Dnmt3b  179  SVDF..MEEVTPKSVSTP....SVDLSQDGDQEGMDTTQVDAESRDGDST 222

Dnmt3a  279  EYEDGRGFGIGELVWGKLRGFSWWPGRIVSWWMTGRSRAAEGTRWVMWFG 328
             ||:| :  ||||:|||||::|||||| :|||  | : .|  | ||| |||
Dnmt3b  223  EYQDDKEFGIGDLVWGKIKGFSWWPAMVVSWKATSKRQAMPGMRWVQWFG 272

Dnmt3a  329  DGKFSVVCVEKLMPLSSFCSAFHQATYNKQPMYRKAIYEVLQVASSRAGK 378
             |||||  : :||.  |    |.  ||:||    ||||.|  |:  |  ||||
Dnmt3b  273  DGKFSEISADKLVALGLFSQHFNLATFNKLVSYRKAMYHTLEKARVRAGK 322

Dnmt3a  379  LFPACHDSDESDSGKAVEVQNKQMIEWALGGFQPSGPKGLEPPEEEK..N 426
             |        |  |...| | | |:||| |||.|.|  .||.|  ...:   |
Dnmt3b  323  TF.......SSSPGESLEDQLKPMLEWAHGGFKPTGIEGLKPNKKQPVVN 365

Dnmt3a  427  PYKEVYTDMW.VEP.............EAAAYAPPPPAKKPRKSTTEKPK 462
             |   .|    .||              :.||   |||   :    |   | :
Dnmt3b  366  KSKVRRSDSRNLEPRRRENKSRRRTTNDSAASESPPPKRLKTNSYGGKDR 415
```

FIG.3A-1

```
Dnmt3a  463  VKEIIDERTRERLVYEVRQKCRNIEDICISCGSLNVTLEHPFFIGGMCQN  512
             .  ||  .|||:  ||       :||  |:|||   |    ||  |  ||:||.
Dnmt3b  416  GE...DEESRERMASEVTNNKGNLEDRCLSCGKKNPVSFHPLFEGGLCQS  462

Dnmt3a  513  CKNCFLECAYQYDDDGYQSYCTICCGGREVLMCGNNNCCRCFCVECVDLL  562
             |:..  |||    |  ||:|||||||||:||   |||.|:|   |.|||||||||.:.|
Dnmt3b  463  CRDRFLELFYMYDEDGYQSYCTVCCEGRELLLCSNTSCCRCFCVECLEVL  512

Dnmt3a  563  VGPGAAQAAIKEDPWNCYMCGHKGTYGLLRRREDWPSRLQMFFANNHD.Q  611
             ||  |  |:  |    ::||.||||     .  :|.||||.||   |||  ||   .  |  :
Dnmt3b  513  VGAGTAEDAKLQEPWSCYMCLPQRCHGVLRRRKDWNMRLQDFFTTDPDLE  562

Dnmt3a  612  EFDPPKVYPPVPAEKRKPIRVLSLFDGIATGLLVLKDLGIQVDRYIASEV  661
             ||:|||.||   :||   ||:||||||||||||||||   ||||:|||.|:::||||||
Dnmt3b  563  EFEPPKLYPAIPAAKRRPIRVLSLFDGIATGYLVLKELGIKVEKYIASEV  612

Dnmt3a  662  CEDSITVGMVRHQGKIMYVGDVRSVTQKHIQEWGPFDLVIGGSPCNDLSI  711
             |  :||  ||  |:|:|.|  ||  |||   :|.|.|:||||||||||||||||||||
Dnmt3b  613  CAESIAVGTVKHEGQIKYVNDVRKITKKNIEEWGPFDLVIGGSPCNDLSN  662

Dnmt3a  712  VNPARKGLYEGTGRLFFEFYRLLHDARPKEGDDRPFFWLFENVVAMGVSD  761
             ||||||||||||||||||||||||  ||.   ||||||.||||:||||||||  |.|
Dnmt3b  663  VNPARKGLYEGTGRLFFEFYHLLNYTRPKEGDNRPFFWMFENVVAMKVND  712

Dnmt3a  762  KRDISRFLESNPVMIDAKEVSAAHRARYFWGNLPGMNRPLASTVNDKLEL  811
             |:||||||   ||||||||  .||||||||||||||||||||||.  ..  ||||||
Dnmt3b  713  KKDISRFLACNPVMIDAIKVSAAHRARYFWGNLPGMNRPVMASKNDKLEL  762

Dnmt3a  812  QECLEHGRIAKFSKVRTITTRSNSIKQGKDQHFPVFMNEKEDILWCTEME  861
             |:|||   |  ||   ||.|||||:|||:|||.|  |||  ||  |:|:||||:|
Dnmt3b  763  QDCLEFSRTAKLKKVQTITTKSNSIRQGKNQLFPVVMNGKDDVLWCTELE  812

Dnmt3a  862  RVFGFPVHYTDVSNMSRLARQRLLGRSWSVPVIRHLFAPLKEYFACV*   909
             |:||||  ||||||||  |   |||:|||||||||||||||||||||:||||  |
Dnmt3b  813  RIFGFPAHYTDVSNMGRGARQKLLGRSWSVPVIRHLFAPLKDYFACE*   860
```

FIG.3A-2

```
DNMT3A    1  MPAMPSSGPGDTSSSAAEREEDRKDGEEQEEPRGKEERQEPSTTARKVGR

DNMT3A   51  PGRKRKHPPVESGDTPKDPAVISKSPSMAQDSGASELLPNGDLEKRSEPQ
                 |            |      |   |.     :. |:
DNMT3B    1  ..............MKGDTRHLNGEEDAGGREDSILVNGACSDQSSDSP

DNMT3A  101  PEEGSPAGGQKGGAPAEGEGAAETLPEASRAVENGCCTPKEGRGAPAEAG
             | .    :  |  |   . .           :.         |   .:
DNMT3B   36  PILEAIRTPEIRGGWASSRLSKREVSSLLSYTQDLTGDGDGEDGDGSDTP

DNMT3A  151  KEQKETNIESMKMEGSRGRLRGGLGWESSLRQRPMPRLTFQAGDPYYISK
             |      :|    ||      |   | ||  ||               :: .
DNMT3B   86  VMPKLFRETRTRSESPAVRTRNNNSVSSRERHRPSPRSTRGRQGRNHVDE

DNMT3A  201  RKRDEWLARWKREAEKKAKVIAGMNAVEENQGPGESQKVEEASPPAVQQP
              :   | |      .        .            .  |:          |
DNMT3B  136  SPVEFPATRSLRRRATASAGTPWPSPPSSYLTIDLTDDTEDTH..GTPQS

DNMT3A  251  TDPASPTVATTPEPVGSDAGDKNATKAGDDEPEYEDGRGFGIGELVWGKL
             .    .|   :  | :.     |        |   ||:||:  ||||:|||||:
DNMT3B  184  SSTPYARLAQDSQQGGMESPQVEADSGDGDSSEYQDGKEFGIGDLVWGKI

DNMT3A  301  RGFSWWPGRIVSWWMTGRSRAAEGTRWVMWFGDGKFSVVCVEKLMPLSSF
             :||||||  :|||   | :  .|   |  ||| ||||||||| |   :||.  | |
DNMT3B  234  KGFSWWPAMVVSWKATSKRQAMSGMRWVQWFGDGKFSEVSADKLVALGLF

DNMT3A  351  CSAFHQATYNKQPMYRKAIYEVLQVASSRAGKLFPVCHDSDESDTAKAVE
             |. ||:||    ||||.|  |:  |      ||||  ||              |  ..|
DNMT3B  284  SQHFNLATFNKLVSYRKAMYHALEKARVRAGKTFP.......SSPGDSLE

DNMT3A  401  VQNKPMIEWALGGFQPSGPKGLEP....PEEEKNPYKEVYTDMWVE....
             | |||:|||  |||.   | .||.|     |    |.   :   .
DNMT3B  327  DQLKPMLEWAHGGFKPTGIEGLKPNNTQPVVNKSKVRRAGSRKLESRKYE

DNMT3A  443  .......PEAAAYAPPPPAKKPRKSTAEKPKVKEIIDERTRERLVYEVRQ
                    :.|.    || |   |.              :::..||.:   :|
DNMT3B  377  NKTRRRTADDSATSDYCPAPKRLKTNCYNNGKDRGDEDQSREQMASDVAN
```

FIG.3B-1

```
DNMT3A  486  KCRNIEDICISCGSLNVTLEHPLFVGGMCQNCKNCFLECAYQYDDDGYQS
              .:||  |:|||   |      ||||  ||:|| |:.  |||   |||||||||
DNMT3B  427  NKSSLEDGCLSCGRKNPVSFHPLFEGGLCQTCRDRFLELFYMYDDDGYQS

DNMT3A  536  YCTICCGGREVLMCGNNNCCRCFCVECVDLLVGPGAAQAAIKEDPWNCYM
             |||:|| |||.|:| | .||||||||.:.||| | |   ::||.|||
DNMT3B  477  YCTVCCEGRELLLCSNTSCCRCFCVECLEVLVGTGTAAEAKLQEPWSCYM

DNMT3A  586  CGHKGTYGLLRRREDWPSRLQMFFANNHDQEFDPPKVYPPVPAEKRKPIR
             |  . :|.||||||| ||| ||  ..  |::  ||.|| :|| :|:|||
DNMT3B  527  CLPQRCHGVLRRRKDWNVRLQAFFTSDTGLEYEAPKLYPAIPAARRRPIR

DNMT3A  636  VLSLFDGIATGLLVLKDLGIQVDRYIASEVCEDSITVGMVRHQGKIMYVG
             |||||||||||| ||||:|||.|  :|:|||||||:|| || |:|:| | ||
DNMT3B  577  VLSLFDGIATGYLVLKELGIKVGKYVASEVCEESIAVGTVKHEGNIKYVN

DNMT3A  686  DVRSVTQKHIQEWGPFDLVIGGSPCNDLSIVNPARKGLYEGTGRLFFEFY
             |||.:|.|.|:|||||||||||||||||| ||||||||||||||||||||
DNMT3B  627  DVRNITKKNIEEWGPFDLVIGGSPCNDLSNVNPARKGLYEGTGRLFFEFY

DNMT3A  736  RLLHDARPKEGDDRPFFWLFENVVAMGVSDKRDISRFLESNPVMIDAKEV
             ||. .|||||||||||||:||||||| |  |||||||||||  ||||||| .|
DNMT3B  677  HLLNYSRPKEGDDRPFFWMFENVVAMKVGDKRDISRFLECNPVMIDAIKV

DNMT3A  786  SAAHRARYFWGNLPGMNRPLASTVNDKLELQECLEHGRIAKFSKVRTITT
             ||||||||||||||||||||. ..  |||||||:|||: ||||  ||.||||
DNMT3B  727  SAAHRARYFWGNLPGMNRPVIASKNDKLELQDCLEYNRIAKLKKVQTITT

DNMT3A  836  RSNSIKQGKDQHFPVFMNEKEDILWCTEMERVFGFPVHYTDVSNMSRLAR
             :||||||||.| |||  || |||:||||:||:|||||||||||||  | ||
DNMT3B  777  KSNSIKQGKNQLFPVVMNGKEDVLWCTELERIFGFPVHYTDVSNMGRGAR

DNMT3A  886  QRLLGRSWSVPVIRHLFAPLKEYFACV*
             |:||||||||||||||||||||||:||||
DNMT3B  827  QKLLGRSWSVPVIRHLFAPLKDYFACE*
```

FIG.3B-2

```
Exon1   (>=90bp) CGGCAGgtgagcgccccggggg.intron(17618bp) .tggcttctcccacagGAAAGC
Exon2   ( 148bp) TCAGAGgtggctgggcagtgg.intron(  887bp) .CTGTTTCCTCTACAGGCCGAA
Exon3   (  62bp) ACACAGgtatgtctctgctc.intron( 3343bp) .tgtttccttataaagGACTTG
Exon4   ( 102bp) CCAGCTgtaagtagccacacc.intron( 1642bp) .ctctcttgcttctagGTCCGA
Exon5   ( 125bp) ACCAGGgttgttcccagatg.intron(  602bp) .tccttctgtccacagTCCCTG
Exon6   ( 222bp) TATCAGgtatgccgagaggg.intron( 1403bp) .tgggttttcttccagGATGGG
Exon7   ( 159bp) TCCGAGgtgagtccggggaag.intron( 2588bp) .gtcttttctctttagGTCTCT
Exon8   ( 108bp) CTGGAGgtaacatgggatgag.intron(  917bp) .actctgccttgcagAAAGCT
Exon9   ( 145bp) AACCAGgtgggaatgagtccc.intron(  765bp) .ttttccctcaaaagTGGTTA
Exon10  (  60bp) AATACGgtatttccttcctgt.intron( 1813bp) .aattaccttcacagAGAACA
Exon11  ( 126bp) GCCGAGgtgattgttgggtac.intron(  115bp) .ttcttttctcaatagAACAAA
Exon12  (  45bp) TGGAAGgtaacgttctctccc.intron( 1095bp) .ctgttttttcttacagATGGCT
Exon13  (  80bp) TGCCGGgtaagtcctcctact.intron(  417bp) .ctctctgctgcagGATCGC
Exon14  ( 113bp) CTGCCGgtgagcactggccctc.intron( 1160bp) .tgccactgggtccagGTGTTT
Exon15  ( 184bp) GAATACgtaagcacaggctc.intron(  600bp) .ttccttacctgcagGAAGCC
Exon16  (  85bp) CGACAGgtgagttcgggaac.intron(  824bp) .ctctgccccacagGCTACC
Exon17  ( 146bp) AAAAATgtgagggcagtctgt.intron(  536bp) .gtctctctcttcagATTGAA
Exon18  (  91bp) TGTATGgtgagcatcctctc.intron(  352bp) .cttttctgagcacagAGGGTA
Exon19  ( 149bp) CTGGAGgtgagggaatctggg.intron(  958bp) .tctttctcccacagGCCCGT
Exon20  (  86bp) GAACAGgtaacaaagggctct.intron( 2867bp) .tttggctgttcccagTTAAAG
Exon21  (  70bp) GCCAAGgtaaagaaagtacag.intron(  801bp) .catttgttctccagTTAAAG
Exon22  ( 119bp) CGAAAGgtgagcaaggctgca.intron( 1434bp) .ctccggtaccccagGATCTT
Exon23  (1585bp)
```

FIG.4D

|          | I                  | IV              | VI             |
|----------|--------------------|-----------------|----------------|
| DNMT1    | DVFSGCGGLSEGFHQAG  | DVEMLCGGPPCQGFSGMNR | YRPRFLLENVRNFVSFKR |
| Dnmt1    | DVFSGCGGLSEGFHQAG  | DVEMLCGGPPCQGFSGMNR | YRPRFLLENVRNFVSYRR |
| MET1(Ath)| DIFAGCGGLSHGLKKAG  | QVDFINGGPPCQGFSGMNR | FRPRYFLLENVRTFVSFNK |
| Mascl    | DTFCGGGGVSLGAROAG  | HVDILHLSPPCQTFSRAHT | VRPRLFTVEETDGIMDRQS |
| Masc2    | DIFAGCGGLTLGLDLSG  | EVDFIYGCPPCQGFSGVNR | YKPRFVLLENVKGLITTKL |
| Dnmt2    | ELYSGIGGMMHHALRESH | SFNMILMSPPCQPFTRIGL | KLPKYILLENVKGLINHDK |
| M.Spr    | SLFSGIGAFEAALRNIG  | EFDLLVGGSPCQSFSVAGH | KQPKFVFENVMFENVAMGVSDK |
| DNMT3A   | SLFDGIATGLLVLKDLG  | PFDLVIGGSPCNDLSIVNP | DRPFFWMLFENVAMGVSDK |
| Dnmt3a   | SLFDGIATGLLVLKDLG  | PFDLVIGGSPCNDLSIVNP | DRPFFWMLFENVAMGVSDK |
| DNMT3B   | SLFDGIATGYLVLKELG  | PFDLVIGGSPCNDLSNVNP | DRPFFWMFENVAMKVGDK |
| Dnmt3b   | SLFDGIATGYLVLKELG  | PFDLVIGGSPCNDLSNVNP | NRPFFWMFENVAMKVNDK |
| Zmt3     | SLFDGIATGYLVLRDLG  | PFDLLIGGSPCNDLSIVNP | PQPFFWMLFENVTFMQTHVK |
| consensus| --------F-G        | --GG--PC          | --P-F---ENV    |

|          | IX                | X                   |                      |
|----------|-------------------|---------------------|----------------------|
| DNMT1    | RVVSVRECARSQGFP   | LFGNILDKHRQVGNAVPPPLAKAIG |                |
| Dnmt1    | RVVSVRECARSQGFP   | FFGNILDRHRQVGNAVPPPLAKAIG |                |
| MET1(Ath)| RILTVRECARSQGFP   | FAGNINHKHRQIGNAVPPPLAFALG |                |
| Mascl    | RKFTVRELACIQGFP   | FVGTLTDKRRIIGNAVPPPLSAAIM |                |
| Masc2    | RVYTVRELARAQGFP   | GLGVKKWHRNIGNAVPVPLGEQIG  |                |
| Dnmt2    | RYFTPKEIANLQGFP   | EKTTVKQRYRLLGNSLNVHVVAKLL |                |
| M.Spr    | RRLTPLECFRLQAFD   | AGISNSQLYKQTGNSITVTVLESIF |                |
| DNMT3A   | DILWCTEMERVFGFP   | SNMSRLARQRLLGRSWSVPVIRHLF |                |
| Dnmt3a   | DILWCTEMERVFGFP   | SNMSRLARQRLLGRSWSVPVIRHLF |                |
| DNMT3B   | DVLWCTELERIFGFP   | SNMGRGAROKLLGRSWSVPVIRHLF |                |
| Dnmt3b   | DVLWCTELERIFGFP   | SNMGRGAROKLLGRSWSVPVIRHLF |                |
| Zmt3     | DHIWITELEKIFGFP   | KSMGRPORORVLGKSWSVPVIRHLL |                |
| consensus| -----E--R--GFP    | --------R-----------P---  |                |

FIG. 5A

| | |
|---|---|
| DNMT3A | EDICISCG......SLNVTLEHPLFVGGMCQNCKNCFLECAYQYDDDGYQSYCT |
| Dnmt3a | EDICISCG......SLNVTLEHPFFIGGMCQNCKNCFLECAYQYDDDGYQSYCT |
| DNMT3B | EDGCLSCG......RKNPVSFHPLFEGGLCQTCRDRFLELFYMDDDGYQSYCT |
| Dnmt3b | EDRCLSCG......KKNPVSFHPLFEGGLCQSCRDRFLELFYMYDEDGYQSYCT |
| Zmt3 | EDFCLSCG......SMSVDIIHPLFEGKLCTNCKFNFTETLYRYDEDGYQSYCT |
| ATRX_Human | IVSCTACGQQVNHFQKDSIYRHPSLQVLICKNCFKYYMSDDISRDSDGMDEQCR |
| ATRX_Mouse | IVSCTACGQQVNHFQKDSIYRHPSLQVLICKNCFKYYMSDDISRDSDGMDEQCR |
| Consensus | C           C                C  C                  C |

| | |
|---|---|
| DNMT3A | ICCGGREVLMCGNNNCCRCFCVECVDLLVGPGAAQAAIKE.DPWNCYMCGHKGT |
| Dnmt3a | ICCGGREVLMCGNNNCCRCFCVECVDLLVGPGAAQAAIKE.DPWNCYMCGHKGT |
| DNMT3B | VCCEGRELLLCSNTSCCRCFCVECLEVLVGTGTAAEAKLQ.EPWSCYMCLPQRC |
| Dnmt3b | VCCEGRELLLCSNTSCCRCFCVECLEVLVGAGTAEDAKLQ.EPWSCYMCLPQRC |
| Zmt3 | VCCSGMEVILCAHDSCCCRSFCVDCLDILVCQGTFDRLKNV.DPWTCYLCAPETS |
| ATRX_Human | WCAEGGNLICC..DFCHNAFCKKCILRNLGRKELSTIMDENNQWYCYICHPEPL |
| ATRX_Mouse | WCAEGGNLICC..DFCHNAFCKKCILRNLGRKELSTIMDENNQWYCYICHPEPL |
| Consensus | C            C    C  C                        C C    |

FIG. 5B

Mouse Dnmt3a2 cDNA sequence:

```
   1 ccgcccccaaccccaacgcccctgcccctcccccagacgggcagctatttacagagc
  60 ttcgggccggggctcacacctgagctgtactgcagaggggctgcacctggccttatggg
 119 ctgagaagaaagccaaggtaattgcagtaatgaatgctgtggaagagaaccaggcctct
 178 ggagagtctcagaaggtggaggaggccagccctcctgctgtgcagcagcccacggaccc
 237 tgcttctccgactgtggccaccaccctgagccagtaggagggatgctggggacaaga
 296 atgctaccaaagcagccgacgatgagcctgagtatgaggatggccggggcttggcatt
 355 ggagagctggtgtgggggaaacttcggggcttctcctggtggccaggccgaattgtgtc
 414 ttggtggatgacaggccggagccgagcagctgaaggcactcgctgggtcatgtggttcg
 473 gagatggcaagttctcagtggtgtgtgtggagaagctcatgccgctgagctccttctgc
 532 agtgcattccaccaggccacctacaacaagcagcccatgtaccgcaaagccatctacga
 591 agtcctccaggtggccagcagccgtgccgggaagctgtttccagcttgccatgacagtg
 650 atgaaagtgacagtggcaaggctgtggaagtgcagaacaagcagatgattgaatgggcc
 709 ctcggtggcttccagccctcgggtcctaagggcctggagccaccagaagaagagaagaa
 768 tccttacaaggaagtttacaccgacatgtgggtggagcctgaagcagctgcttacgccc
 827 cacccccaccagccaagaaacccagaaagagcacaacagagaaacctaaggtcaaggag
 886 atcattgatgagcgcacaagggagcggctggtgtatgaggtgcgccagaagtgcagaaa
 945 catcgaggacatttgtatctcatgtgggagcctcaatgtcaccctggagcacccactct
1004 tcattggaggcatgtgccagaactgtaagaactgcttcttggagtgtgcttaccagtat
1063 gacgacgatgggtaccagtcctattgcaccatctgctgtgggggcgtgaagtgctcat
1122 gtgtgggaacaacaactgctgcaggtgcttttgtgtcgagtgtgtggatctcttggtgg
1181 ggccaggagctgctcaggcagccattaaggaagacccctggaactgctacatgtgcggg
1240 cataagggcacctatgggctgctgcgaagacgggaagactggccttctcgactccagat
1299 gttctttgccaataaccatgaccaggaatttgaccccccaaaggtttacccacctgtgc
1358 cagctgagaagaggaagcccatccgcgtgctgtctctctttgatgggattgctacaggg
1417 ctcctggtgctgaaggacctgggcatccaagtggaccgctacattgcctccgaggtgtg
1476 tgaggactccatcacggtgggcatggtgcggcaccagggaaagatcatgtacgtcgggg
1535 acgtccgcagcgtcacacagaagcatatccaggagtggggcccattcgacctggtgatt
1594 ggaggcagtccctgcaatgacctctccattgtcaaccctgcccgcaagggactttatga
1653 gggtactggccgcctcttctttgagttctaccgcctcctgcatgatgcgcggcccaagg
1712 agggagatgatcgcccttcttctggctctttgagaatgtggtggccatgggcgttagt
1771 gacaagagggacatctcgcgatttcttgagtctaaccccgtgatgattgacgccaaaga
1830 agtgtctgctgcacacagggcccgttacttctggggtaaccttcctggcatgaacaggc
1889 ctttggcatccactgtgaatgataagctggagctgcaagagtgtctggagcacggcaga
1948 atagccaagttcagcaaagtgaggaccattaccaccaggtcaaactctataaagcaggg
2007 caaagaccagcatttccccgtcttcatgaacgagaaggaggacatcctgtggtgcactg
2066 aaatggaaagggtgtttggcttccccgtccactacacagacgtctccaacatgagccgc
2125 ttggcgaggcagagactgctgggccgatcgtggagcgtgccggtcatccgccacctctt
2184 cgctccgctgaaggaatattttgcttgtgtgtaagggacatgggggcaaactgaagtag
2243 tgatgataaaaaagttaaacaaacaaacaaacaaaaaacaaaacaaaacaataaaacac
2302 caagaacgagaaaaaaa
```

FIG. 13A

Mouse Dnmt3a2 amino acid sequence:

```
  1  MNAVEENQASGESQKVEEASPPAVQQPTDPASPTVATTPEPVGGDAGDKNATKAADDEP
 60  EYEDGRGFGIGELVWGKLRGFSWWPGRIVSWWMTGRSRAAEGTRWVMWFGDGKFSVVCV
119  EKLMPLSSFCSAFHQATYNKQPMYRKAIYEVLQVASSRAGKLFPACHDSDESDSGKAVE
178  VQNKQMIEWALGGFQPSGPKGLEPPEEEKNPYKEVYTDMWVEPEAAAYAPPPPAKKPRK
237  STTEKPKVKEIIDERTRERLVYEVRQKCRNIEDICISCGSLNVTLEHPLFIGGMCQNCK
296  NCFLECAYQYDDDGYQSYCTICCGGREVLMCGNNNCCRCFCVECVDLLVGPGAAQAAIK
355  EDPWNCYMCGHKGTYGLLRRREDWPSRLQMFFANNHDQEFDPPKVYPPVPAEKRKPIRV
414  LSLFDGIATGLLVLKDLGIQVDRYIASEVCEDSITVGMVRHQGKIMYVGDVRSVTQKHI
473  QEWGPFDLVIGGSPCNDLSIVNPARKGLYEGTGRLFFEFYRLLHDARPKEGDDRPFFWL
532  FENVVAMGVSDKRDISRFLESNPVMIDAKEVSAAHRARYFWGNLPGMNRPLASTVNDKL
591  ELQECLEHGRIAKFSKVRTITTRSNSIKQGKDQHFPVFMNEKEDILWCTEMERVFGFPV
650  HYTDVSNMSRLARQRLLGRSWSVPVIRHLFAPLKEYFACV
```

FIG. 13B

Human DNMT3A2 cDNA sequence:

```
   1 ccgccccagccccatcgccccttccctccccaagacgggcagctacttccagagc
  60 ttcagggccgcggctcacacctgagcgcgactgcagaggggctgcacctggccttatgg
 119 ggatcctggagcgggttgtgagaaggaatgggcgcgtggatcgtagcctgaaagacgag
 178 tgtgatacggctgagaagaaagccaaggtcattgcaggaatgaatgctgtggaagaaaa
 237 ccaggggccgggggagtctcagaaggtggaggaggccagccctcctgctgtgcagcagc
 296 ccactgaccccgcatcccccactgtggctaccacgcctgagcccgtggggtccgatgct
 355 ggggacaagaatgccaccaaagcaggcgatgacgagccagagtacgaggacggccgggg
 414 ctttggcattggggagctggtgtgggggaaactgcggggcttctcctggtggccaggcc
 473 gcattgtgtcttggtggatgacgggccggagccgagcagctgaaggcacccgctgggtc
 532 atgtggttcggagacggcaaattctcagtggtgtgtgttgagaagctgatgccgctgag
 591 ctcgttttgcagtgcgttccaccaggccacgtacaacaagcagcccatgtaccgcaaag
 650 ccatctacgaggtcctgcaggtggccagcagccgcgcggggaagctgttcccggtgtgc
 709 cacgacagcgatgagagtgacactgccaaggccgtggaggtgcagaacaagcccatgat
 768 tgaatgggccctgggggggcttccagccttctggccctaagggcctggagccaccagaag
 827 aagagaagaatccctacaaagaagtgtacacggacatgtgggtggaacctgaggcagct
 886 gcctacgcaccacctccaccagccaaaaagccccggaagagcacagcggagaagcccaa
 945 ggtcaaggagattattgatgagcgcacaagagagcggctggtgtacgaggtgcggcaga
1004 agtgccggaacattgaggacatctgcatctcctgtgggagcctcaatgttaccctggaa
1063 caccccctcttcgttggaggaatgtgccaaaactgcaagaactgctttctggagtgtgc
1122 gtaccagtacgacgacgacggctaccagtcctactgcaccatctgctgtggggccgtg
1181 aggtgctcatgtgcggaaacaacaactgctgcaggtgcttttgcgtggagtgtgtggac
1240 ctcttggtggggccgggggctgcccaggcagccattaaggaagacccctggaactgcta
1299 catgtgcgggcacaagggtacctacgggctgctgcggcggcgagaggactggccctccc
1358 ggctccagatgttcttcgctaataaccacgaccaggaatttgaccctccaaaggtttac
1417 ccacctgtcccagctgagaagaggaagcccatccgggtgctgtctctctttgatggaat
1476 cgctacagggctcctggtgctgaaggacttgggcattcaggtggaccgctacattgcct
1535 cggaggtgtgtgaggactccatcacggtgggcatggtgcggcaccaggggaagatcatg
1594 tacgtcggggacgtccgcagcgtcacacagaagcatatccaggagtggggcccattcga
1653 tctggtgattgggggcagtccctgcaatgacctctccatcgtcaaccctgctcgcaagg
1712 gcctctacgagggcactggccggctcttctttgagttctaccgcctcctgcatgatgcg
1771 cggcccaaggagggagatgatcgcccttcttctggctctttgagaatgtggtggccat
1830 ggcgttagtgacaagagggacatctcgcgatttctcgagtccaaccctgtgatgattg
1889 atgccaaagaagtgtcagctgcacacagggcccgctacttctggggtaaccttcccggt
1948 atgaacaggccgttggcatccactgtgaatgataagctggagctgcaggagtgtctgga
2007 gcatggcaggatagccaagttcagcaaagtgaggaccattactacgaggtcaaactcca
2066 taaagcagggcaaagaccagcatttcctgtcttcatgaatgagaaagaggacatctta
2125 tggtgcactgaaatggaagggtatttggtttcccagtccactatactgacgtctccaa
2184 catgagccgcttggcgaggcagagactgctgggccggtcatggagcgtgccagtcatcc
2243 gccacctcttcgctccgctgaaggagtattttgcgtgtgtgtaagggacatgggggcaa
2302 actgaggtagcgacacaaagttaaacaaacaaacaaaaacacaaaacataataaaaca
2361 ccaagaacatg
```

FIG. 13C

Human DNMT3A2 amino acid sequence:

```
  1  MNAVEENQGPGESQKVEEASPPAVQQPTDPASPTVATTPEPVGSDAGDKNATKAGDDEP
 60  EYEDGRGFGIGELVWGKLRGFSWWPGRIVSWWMTGRSRAAEGTRWVMWFGDGKFSVVCV
119  EKLMPLSSFCSAFHQATYNKQPMYRKAIYEVLQVASSRAGKLFPVCHDSDESDTAKAVE
178  VQNKPMIEWALGGFQPSGPKGLEPPEEEKNPYKEVYTDMWVEPEAAAYAPPPPAKKPRK
237  STAEKPKVKEIIDERTRERLVYEVRQKCRNIEDICISCGSLNVTLEHPLFVGGMCQNCK
296  NCFLECAYQYDDDGYQSYCTICCGGREVLMCGNNNCCRCFCVECVDLLVGPGAAQAAIK
355  EDPWNCYMCGHKGTYGLLRRREDWPSRLQMFFANNHDQEFDPPKVYPPVPAEKRKPIRV
414  LSLFDGIATGLLVLKDLGIQVDRYIASEVCEDSITVGMVRHQGKIMYVGDVRSVTQKHI
473  QEWGPFDLVIGGSPCNDLSIVNPARKGLYEGTGRLFFEFYRLLHDARPKEGDDRPFFWL
532  FENVVAMGVSDKRDISRFLESNPVMIDAKEVSAAHRARYFWGNLPGMNRPLASTVNDKL
591  ELQECLEHGRIAKFSKVRTITTRSNSIKQGKDQHFPVFMNEKEDILWCTEMERVFGFPV
650  HYTDVSNMSRLARQRLLGRSWSVPVIRHLFAPLKEYFACV
```

FIG. 13D

```
                    10         20         30         40         50
Dnmt3a2       1 ccgccccaa  ccccaacgcc ccctgcccct cccccagac gggcagctat  50
DNMT3A2       1 ccgccccag  ccccatcgcc cccttcccct ccccaagac gggcagctac  50

60         70         80         90        100
Dnmt3a2      51 ttacagagct tc-gggccgg ggctcacacc tgagctgtac tgcagagggg 100
DNMT3A2      51 ttccagagct tcagggccgc ggctcacacc tgagcgcgac tgcagagggg 100

110        120        130        140        150
Dnmt3a2     101 ctgcacctgg ccttatgg-- ---------- ---------- ---------- 150
DNMT3A2     101 ctgcacctgg ccttatgggg atcctggagc gggttgtgag aaggaatggg 150

160        170        180        190        200
Dnmt3a2     151 ---------- ---------- ---------- ------gctg agaagaaagc 200
DNMT3A2     151 cgcgtggatc gtagcctgaa agacgagtgt gatacggctg agaagaaagc 200

210        220        230        240        250
Dnmt3a2     201 caaggtaatt gcagtaatga atgctgtgga agagaaccag gcctctggag 250
DNMT3A2     201 caaggtcatt gcaggaatga atgctgtgga agaaaaccag gggcccgggg 250

260        270        280        290        300
Dnmt3a2     251 agtctcagaa ggtggaggag gccagccctc ctgctgtgca gcagcccacg 300
DNMT3A2     251 agtctcagaa ggtggaggag gccagccctc ctgctgtgca gcagcccact 300

310        320        330        340        350
Dnmt3a2     301 gaccctgctt ctccgactgt ggccaccacc cctgagccag taggagggga 350
DNMT3A2     301 gaccccgcat cccccactgt ggctaccacg cctgagcccg tggggtccga 350

360        370        380        390        400
Dnmt3a2     351 tgctggggac aagaatgcta ccaaagcagc cgacgatgag cctgagtatg 400
DNMT3A2     351 tgctggggac aagaatgcca ccaaagcagg cgatgacgag ccagagtacg 400

410        420        430        440        450
Dnmt3a2     401 aggatggccg gggctttggc attggagagc tggtgtgggg gaaacttcgg 450
DNMT3A2     401 aggacggccg gggctttggc attggggagc tggtgtgggg gaaactgcgg 450

460        470        480        490        500
Dnmt3a2     451 ggcttctcct ggtggccagg ccgaattgtg tcttggtgga tgacaggccg 500
DNMT3A2     451 ggcttctcct ggtggccagg ccgcattgtg tcttggtgga tgacgggccg 500

510        520        530        540        550
Dnmt3a2     501 gagccgagca gctgaaggca ctcgctgggt catgtggttc ggagatggca 550
DNMT3A2     501 gagccgagca gctgaaggca cccgctgggt catgtggttc ggagacggca 550

560        570        580        590        600
Dnmt3a2     551 agttctcagt ggtgtgtgtg gagaagctca tgccgctgag ctccttctgc 600
DNMT3A2     551 aattctcagt ggtgtgtgtt gagaagctga tgccgctgag ctcgttttgc 600

610        620        630        640        650
Dnmt3a2     601 agtgcattcc accaggccac ctacaacaag cagcccatgt accgcaaagc 650
DNMT3A2     601 agtgcgttcc accaggccac gtacaacaag cagcccatgt accgcaaagc 650

660        670        680        690        700
Dnmt3a2     651 catctacgaa gtcctccagg tggccagcag ccgtgccggg aagctgtttc 700
DNMT3A2     651 catctacgag gtcctgcagg tggccagcag ccgcgcgggg aagctgttcc 700
```

FIG. 13E-1

```
              710        720        730        740        750
Dnmt3a2  701  cagcttgcca tgacagtgat gaaagtgaca gtggcaaggc tgtggaagtg  750
DNMT3A2  701  cggtgtgcca cgacagcgat gagagtgaca ctgccaaggc cgtggaggtg  750

760        770        780        790        800
Dnmt3a2  751  cagaacaagc agatgattga atgggccctc ggtggcttcc agccctcggg  800
DNMT3A2  751  cagaacaagc ccatgattga atgggccctg gggggcttcc agccttctgg  800

810        820        830        840        850
Dnmt3a2  801  tcctaagggc ctggagccac cagaagaaga aagaatcct  tacaaggaag  850
DNMT3A2  801  ccctaagggc ctggagccac cagaagaaga agaatccc   tacaaagaag  850

860        870        880        890        900
Dnmt3a2  851  tttacaccga catgtgggtg gagcctgaag cagctgctta cgccccaccc  900
DNMT3A2  851  tgtacacgga catgtgggtg gaacctgagg cagctgccta cgcaccacct  900

910        920        930        940        950
Dnmt3a2  901  ccaccagcca agaaacccag aaagagcaca acagagaaac ctaaggtcaa  950
DNMT3A2  901  ccaccagcca aaaagcccg  gaagagcaca gcggagaagc ccaaggtcaa  950

960        970        980        990       1000
Dnmt3a2  951  ggagatcatt gatgagcgca caaggggagcg gctggtgtat gaggtgcgcc 1000
DNMT3A2  951  ggagattatt gatgagcgca caagagagcg gctggtgtac gaggtgcggc 1000

1010       1020       1030       1040       1050
Dnmt3a2 1001  agaagtgcag aaacatcgag gacatttgta tctcatgtgg gagcctcaat 1050
DNMT3A2 1001  agaagtgccg gaacattgag gacatctgca tctcctgtgg gagcctcaat 1050

1060       1070       1080       1090       1100
Dnmt3a2 1051  gtcacccctgg agcacccact cttcattgga ggcatgtgcc agaactgtaa 1100
DNMT3A2 1051  gttaccctgg aacaccccct cttcgttgga ggaatgtgcc aaaactgcaa 1100

1110       1120       1130       1140       1150
Dnmt3a2 1101  gaactgcttc ttggagtgtg cttaccagta tgacgacgat gggtaccagt 1150
DNMT3A2 1101  gaactgcttt ctggagtgtg cgtaccagta cgacgacgac ggctaccagt 1150

1160       1170       1180       1190       1200
Dnmt3a2 1151  cctattgcac catctgctgt gggggggcgtg aagtgctcat gtgtgggaac 1200
DNMT3A2 1151  cctactgcac catctgctgt gggggccgtg aggtgctcat gtgcggaaac 1200

1210       1220       1230       1240       1250
Dnmt3a2 1201  aacaactgct gcaggtgctt ttgtgtcgag tgtgtggatc tcttggtggg 1250
DNMT3A2 1201  aacaactgct gcaggtgctt ttgcgtggag tgtgtggacc tcttggtggg 1250

1260       1270       1280       1290       1300
Dnmt3a2 1251  gccaggagct gctcaggcag ccattaagga agacccctgg aactgctaca 1300
DNMT3A2 1251  gccgggggct gcccaggcag ccattaagga agacccctgg aactgctaca 1300

1310       1320       1330       1340       1350
Dnmt3a2 1301  tgtgcgggca taagggcacc tatgggctgc tgcgaagacg gaagactgg  1350
DNMT3A2 1301  tgtgcgggca caagggtacc tacgggctgc tgcggcggcg agaggactgg 1350

1360       1370       1380       1390       1400
Dnmt3a2 1351  ccttctcgac tccagatgtt cttttgccaat aaccatgacc aggaatttga 1400
DNMT3A2 1351  ccctcccggc tccagatgtt cttcgctaat aaccacgacc aggaatttga 1400
```

FIG. 13E-2

```
                   1410       1420       1430       1440       1450
Dnmt3a2    1401 cccccccaaag gtttacccac ctgtgccagc tgagaagagg aagcccatcc 1450
DNMT3A2    1401 ccctccaaag gtttacccac ctgtcccagc tgagaagagg aagcccatcc 1450

1460       1470       1480       1490       1500
Dnmt3a2    1451 gcgtgctgtc tctctttgat gggattgcta cagggctcct ggtgctgaag 1500
DNMT3A2    1451 gggtgctgtc tctctttgat ggaatcgcta cagggctcct ggtgctgaag 1500

1510       1520       1530       1540       1550
Dnmt3a2    1501 gacctgggca tccaagtgga ccgctacatt gcctccgagg tgtgtgagga 1550
DNMT3A2    1501 gacttgggca ttcaggtgga ccgctacatt gcctcggagg tgtgtgagga 1550

1560       1570       1580       1590       1600
Dnmt3a2    1551 ctccatcacg gtgggcatgg tgcggcacca gggaaagatc atgtacgtcg 1600
DNMT3A2    1551 ctccatcacg gtgggcatgg tgcggcacca ggggaagatc atgtacgtcg 1600

1610       1620       1630       1640       1650
Dnmt3a2    1601 gggacgtccg cagcgtcaca cagaagcata tccaggagtg gggcccattc 1650
DNMT3A2    1601 gggacgtccg cagcgtcaca cagaagcata tccaggagtg gggcccattc 1650

1660       1670       1680       1690       1700
Dnmt3a2    1651 gacctggtga ttggaggcag tccctgcaat gacctctcca ttgtcaaccc 1700
DNMT3A2    1651 gatctggtga ttggggcag tccctgcaat gacctctcca tcgtcaaccc 1700

1710       1720       1730       1740       1750
Dnmt3a2    1701 tgcccgcaag ggactttatg agggtactgg ccgcctcttc tttgagttct 1750
DNMT3A2    1701 tgctcgcaag ggcctctacg agggcactgg ccggctcttc tttgagttct 1750

1760       1770       1780       1790       1800
Dnmt3a2    1751 accgcctcct gcatgatgcg cggcccaagg agggagatga tcgccccttc 1800
DNMT3A2    1751 accgcctcct gcatgatgcg cggcccaagg agggagatga tcgccccttc 1800

1810       1820       1830       1840       1850
Dnmt3a2    1801 ttctggctct ttgagaatgt ggtggccatg ggcgttagtg acaagaggga 1850
DNMT3A2    1801 ttctggctct ttgagaatgt ggtggccatg ggcgttagtg acaagaggga 1850

1860       1870       1880       1890       1900
Dnmt3a2    1851 catctcgcga tttcttgagt ctaacccgt gatgattgac gccaaagaag 1900
DNMT3A2    1851 catctcgcga tttctcgagt ccaaccctgt gatgattgat gccaaagaag 1900

1910       1920       1930       1940       1950
Dnmt3a2    1901 tgtctgctgc acacagggcc cgttacttct ggggtaacct tcctggcatg 1950
DNMT3A2    1901 tgtcagctgc acacagggcc cgctacttct ggggtaacct tcccggtatg 1950

1960       1970       1980       1990       2000
Dnmt3a2    1951 aacaggcctt tggcatccac tgtgaatgat aagctggagc tgcaagagtg 2000
DNMT3A2    1951 aacaggccgt tggcatccac tgtgaatgat aagctggagc tgcaggagtg 2000

2010       2020       2030       2040       2050
Dnmt3a2    2001 tctggagcac ggcagaatag ccaagttcag caaagtgagg accattacca 2050
DNMT3A2    2001 tctggagcat ggcaggatag ccaagttcag caaagtgagg accattacta 2050

2060       2070       2080       2090       2100
Dnmt3a2    2051 ccaggtcaaa ctctataaag cagggcaaag accagcattt ccccgtcttc 2100
DNMT3A2    2051 cgaggtcaaa ctccataaag cagggcaaag accagcattt cctgtcttc 2100
```

FIG. 13E-3

```
              2110       2120       2130       2140       2150
Dnmt3a2  2101 atgaacgaga aggaggacat cctgtggtgc actgaaatgg aaagggtgtt 2150
DNMT3A2  2101 atgaatgaga aagaggacat cttatggtgc actgaaatgg aaagggtatt 2150

2160       2170       2180       2190       2200
Dnmt3a2  2151 tggcttcccc gtccactaca cagacgtctc caacatgagc cgcttggcga 2200
DNMT3A2  2151 tggtttccca gtccactata ctgacgtctc caacatgagc cgcttggcga 2200

2210       2220       2230       2240       2250
Dnmt3a2  2201 ggcagagact gctgggccga tcgtggagcg tgccggtcat ccgccacctc 2250
DNMT3A2  2201 ggcagagact gctgggccgg tcatggagcg tgccagtcat ccgccacctc 2250

2260       2270       2280       2290       2300
Dnmt3a2  2251 ttcgctccgc tgaaggaata ttttgcttgt gtgtaaggga catgggggca 2300
DNMT3A2  2251 ttcgctccgc tgaaggagta ttttgcgtgt gtgtaaggga catgggggca 2300

2310       2320       2330       2340       2350
Dnmt3a2  2301 aactgaagta gtgatgataa aaaagttaaa caaacaaaca aacaaaaaac 2350
DNMT3A2  2301 aactgaggta gcgac----a caaagttaaa caaacaaac- ---aaaaaac 2350

2360       2370       2380
Dnmt3a2  2351 aaaacaaaac aataaaacac caagaacgag
DNMT3A2  2351 acaaaacat- aataaaacac caagaacatg
```

FIG. 13E-4

```
Dnmt3a2    1  MNAVEENQASGESQKVEEASPPAVQQPTDPASPTVATTPEPVGGDAGDKN  50
DNMT3A2    1  MNAVEENQGPGESQKVEEASPPAVQQPTDPASPTVATTPEPVGSDAGDKN  50

Dnmt3a2   51  ATKAADDEPEYEDGRGFGIGELVWGKLRGFSWWPGRIVSWWMTGRSRAAE 100
DNMT3A2   51  ATKAGDDEPEYEDGRGFGIGELVWGKLRGFSWWPGRIVSWWMTGRSRAAE 100

Dnmt3a2  101  GTRWVMWFGDGKFSVVCVEKLMPLSSFCSAFHQATYNKQPMYRKAIYEVL 150
DNMT3A2  101  GTRWVMWFGDGKFSVVCVEKLMPLSSFCSAFHQATYNKQPMYRKAIYEVL 150

Dnmt3a2  151  QVASSRAGKLFPACHDSDESDSGKAVEVQNKQMIEWALGGFQPSGPKGLE 200
DNMT3A2  151  QVASSRAGKLFPVCHDSDESDTAKAVEVQNKPMIEWALGGFQPSGPKGLE 200

Dnmt3a2  201  PPEEEKNPYKEVYTDMWVEPEAAAYAPPPPAKKPRKSTTEKPKVKEIIDE 250
DNMT3A2  201  PPEEEKNPYKEVYTDMWVEPEAAAYAPPPPAKKPRKSTAEKPKVKEIIDE 250

Dnmt3a2  251  RTRERLVYEVRQKCRNIEDICISCGSLNVTLEHPLFIGGMCQNCKNCFLE 300
DNMT3A2  251  RTRERLVYEVRQKCRNIEDICISCGSLNVTLEHPLFVGGMCQNCKNCFLE 300

Dnmt3a2  301  CAYQYDDDGYQSYCTICCGGREVLMCGNNNCCRCFCVECVDLLVGPGAAQ 350
DNMT3A2  301  CAYQYDDDGYQSYCTICCGGREVLMCGNNNCCRCFCVECVDLLVGPGAAQ 350

Dnmt3a2  351  AAIKEDPWNCYMCGHKGTYGLLRRREDWPSRLQMFFANNHDQEFDPPKVY 400
DNMT3A2  351  AAIKEDPWNCYMCGHKGTYGLLRRREDWPSRLQMFFANNHDQEFDPPKVY 400

Dnmt3a2  401  PPVPAEKRKPIRVLSLFDGIATGLLVLKDLGIQVDRYIASEVCEDSITVG 450
DNMT3A2  401  PPVPAEKRKPIRVLSLFDGIATGLLVLKDLGIQVDRYIASEVCEDSITVG 450

Dnmt3a2  451  MVRHQGKIMYVGDVRSVTQKHIQEWGPFDLVIGGSPCNDLSIVNPARKGL 500
DNMT3A2  451  MVRHQGKIMYVGDVRSVTQKHIQEWGPFDLVIGGSPCNDLSIVNPARKGL 500

Dnmt3a2  501  YEGTGRLFFEFYRLLHDARPKEGDDRPFFWLFENVVAMGVSDKRDISRFL 550
DNMT3A2  501  YEGTGRLFFEFYRLLHDARPKEGDDRPFFWLFENVVAMGVSDKRDISRFL 550

Dnmt3a2  551  ESNPVMIDAKEVSAAHRARYFWGNLPGMNRPLASTVNDKLELQECLEHGR 600
DNMT3A2  551  ESNPVMIDAKEVSAAHRARYFWGNLPGMNRPLASTVNDKLELQECLEHGR 600

Dnmt3a2  601  IAKFSKVRTITTRSNSIKQGKDQHFPVFMNEKEDILWCTEMERVFGFPVH 650
DNMT3A2  601  IAKFSKVRTITTRSNSIKQGKDQHFPVFMNEKEDILWCTEMERVFGFPVH 650

Dnmt3a2  651  YTDVSNMSRLARQRLLGRSWSVPVIRHLFAPLKEYFACV 689
DNMT3A2  651  YTDVSNMSRLARQRLLGRSWSVPVIRHLFAPLKEYFACV 689
```

FIG. 13F

A
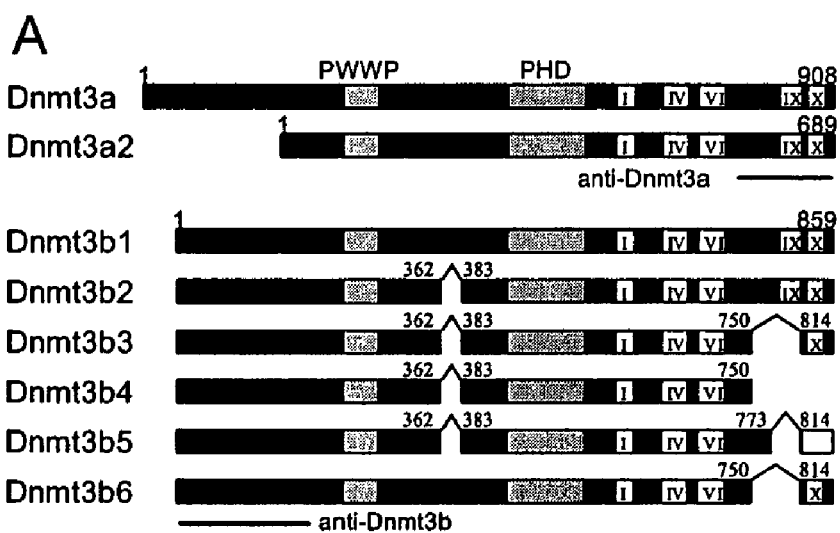
B
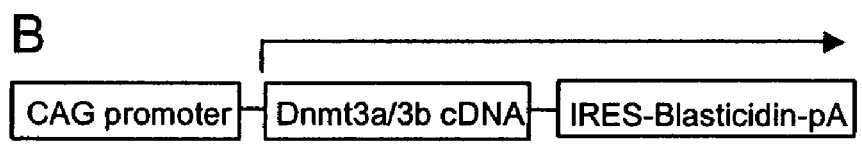
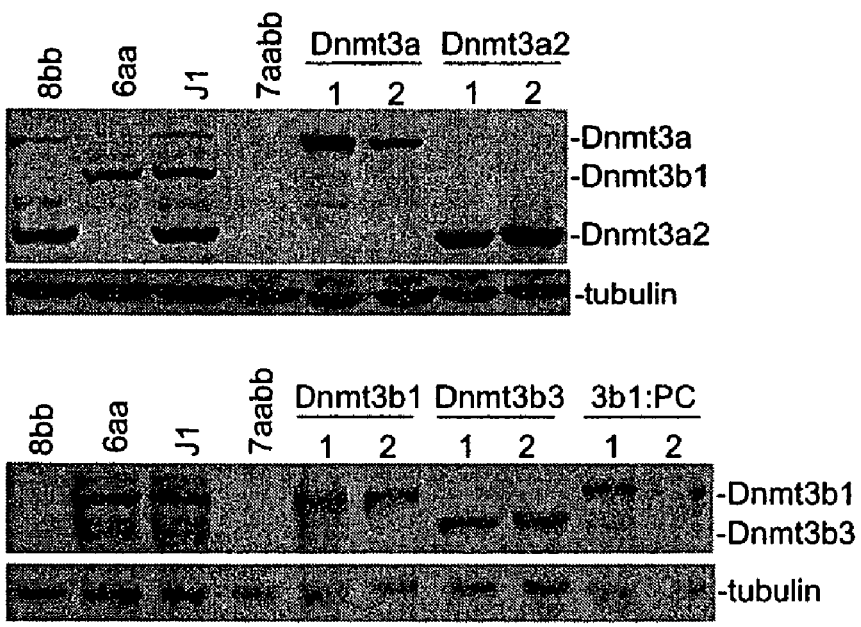
FIG. 20

Mouse Dnmt3a2 Promoter Sequence

```
   1 GGAGCCAGGCACCTGGGGTGTTACCTCAGTGCCTTTAGGATATTGGTTTTCCTAGCTCT
  60 AGAGGGCTGATGTCATCACCCCTATTTTGCAGATGAGAAAACAGACATCTTGGGGTTAA
 119 GTGGTCTGTGTCAAGGTCACCGCAATGGGATCAGGTCTTCCCCAAGCGTTCCAGCCAGA
 178 TAGCGGCGGCTCCCTGCTGGGGCATTCTCCTTCAGTTCTTTGTTCTAATTCATCTTGCA
 237 AACTTAATCCTGGCTAATCTTTGTAAAATACTCATTCACCTTGTTTTTCCAGAACATCT
 296 GCCATGTTACAGAATATCTCCATTCAGTGCTTGACCCCAGTCCCACTACTCAGCCATTT
 355 AGCTTTAGTCAAAATTGAGAGGGTGGGTGGAAGAGTTCTTTCTTCCTTCTACCTGCTTG
 414 CCACCTCCAAATCGTGGTTATCTTCTGATCTCTACTGTCCTATCTCTCACCCACACCCT
 473 TCATTTGATGCAGCCTTCTGCTATCTGCTTGGTGGTTTGGGTAGTTATCCACACAGGAG
 532 TTTGCTTTTCAGTGATTCCCCCTTCCCCCACCCCATCTCCCCAAGTCTAGTGGAATCTA
 591 TCAACTTCCTGAGAGCAGGACCAAGTGTCCATTTCTGTATCCGATGATGCTCCAGTCCT
 650 CTAATGGGGGGGGGGGCGGGGCGCCAGGAGTGGCGTGTGTGCTTCTTCAAACCCAACTT
 709 TAGTCCTCTACTGTNNNNNNNNNNNNNNNNNNNNNNNNNNNNNNNNNNNNNNNNNNNNN
 768 NNNNNNNNNNNNNNNNNNNNNNNNNNNNNNNNNNNNNNNNNNNNNNNNNNNNNNNNNNN
 827 NNNNNNNNNNNNNNNNNNNNNNNNNNNNNNNNNNNNNNNNNNNNNNNNNNNNNNNNNNN
 886 NNNNNNNNNNNNNNNNNNNNNNNNNNNNNNNNNNNNNNNNNNNNNNNNNNNNNNNNNNN
 945 NNNNNNNNNNNNNNNNNNNNNNNNNNNNNNNNNNNNACACACCTTGGGGTACTATGTCTTTGCTCAG
1004 GAATGGCATGAAATGGCCTACACTTTACCTGGTGGTTCTAGGAGAGAGACACTAGCACG
1063 TGCGTGGGAGTGTGTCTATTACTATTACATAATTGCTGAGACAGGGTTTCGTGATGTTC
1122 AGGCTGGCCTTGAACTTGTGTTAGTCAAGAATGATCTTAAATTTCTGATCTCTGGTTTC
1181 CCAAGTTCTAGGATTACAGGTGTACTTCACCACCAAAAGTTTGAACAGCTGCAGATGCC
1240 TTGGCATTGCTCTTAACGAACAGAAAATGAAACAAGCAAGCAAGACCCATTGTGACCCG
1299 GGGGACTCGGGGACTGGACGGGGAAGTTTTCAAAGTCTACTTGTGAACCACGCTTTTA
1358 AAGCACCCCCTCCATTCACCTGTAGCGTGGCGGTGAAGTTATTGTCCTGGGGCGCCCTC
1417 AACCTGCGTGGGACACCTCCTATCCACTCACATCTGTCTTCTGACTTTGCCTAAACTAC
1476 GTTTCCGTAAACTCCGAGCCTCATCTCTAATCTGTAAACTTGCTAGCGCGCTCTCGCAC
1535 GCGCTCTTTTTTTTTTTTTTTCCCGGAAACTCACTTTCTACAACTTTCTCCCCGGAC
1594 TCTCAGGCTGTCTGAAGCCAGCGCTCCTGTCCCACCACCGCTGCTCTGGGTGCCCCGCG
1653 GCCCGCACGCACCCTGCCTCCCTCAAGGTCCCCAACTTCCCTATGTACCCCCCCATCCC
1712 CAGAGTTGGGGAAGGGAGCAGAGCGGGCTGTCCCATAAACCTGGCTGGAGGGCGGGG
1771 CCCTGGGAACGGACTGGCCAGCCTCTCCCCCAGGCCCCCGCGCCCCTCGGGCCCGGGT
1830 GAGGGGCTGGCCCAGCGCCAGCGTAGGAGGCCGGCCCCCTCCCCCCGGCCCGCGCTTAG
1889 CCAACCAGAAACTCCAGTGGGGCCCACGTGACCTGGAGTTCTAGACAAAGAAAATGTTC
1948 CCTCCCTCCCCCCGGCGCCCCCTCCCCCTCCCTCTGGCCCCT*CCGCCCCCAACCCCA*
2007 *ACGCCCCTGCCCCTCCCCCAGACGGGCAGCTATTTACAGAGCTTCGGGCCGGGCTC*
2066 *ACACCTGAGCTGTACTGCAGAGGGGCTGCACCTGGCCTTATGG*
```

FIG. 27

Human DNMT3A2 promoter sequence

```
   1 GGAGCCAGGCACCTAGAGAATTGTCTCATTGTCATTAGGAGATGGTGGCGTTCCATG
  60 GCCAAAGAGGGCTGATGTCATCACTCGTTTTGCAGATGAGACAACAGATTTCTTGGG
 119 GGTTAAGTGACTTGTTTAAGGTCATGGTGGTGGAAACAGAACTGAAGTCCAGATCTT
 178 TTTTTTTTTTTTTTTGAGACGGAGTCTCGCTCTGTTGCCCAGGCTGGAGTGCAGTG
 237 GCATGATCTCGGCTCACTGCAACATCCGCCTCCTAAGTTGAAGCGATTCTCTTGCCT
 296 CAGCCTCCCAAGTAGCTGGGATTACTGGCGCACGCCACCACGCCTGGCTAATTTTTG
 355 TATTTTAGTAGAGACAAGGTTTCACCATGTTAGTCAGGCCGGTCTCAAACTCCTGA
 414 CCTCATGATCCGCCTGCCTCAGCCTTCCAAAGTGCTGGGATTATAGGCGTGAGCCAC
 473 CGCGCTCGGCCAAGTCCAGATCTTCTAACAAGTGCCGCTGCCCAAATAGCCCTCTGC
 532 TGTGGGGTGCATTTTCCTCCATTTCCTCAGTTCTTCCTTCTAATTCATCTTGCCAAC
 591 GGCAACTAGGCTGATTTTCCAAAATACTCATTCATCTTGTCAGAAAACCTGCGGTT
 650 ATTCTTCCTGCTACAGAATATACCCAAGGACGCACCTGAAGGCTTGCCATTACCTT
 709 GCCCTGTCGTGTACTGGGAGGGTGGAGGTGGGCGAGGGTCTCCTCCCTCCCCAGCCC
 768 GGCAGCTCTTGCTCATCCTACCCATCTCACCTCATTCCAAGTCCGATCCAGCCTCCA
 827 GGCCCAGTCGGCTCACCTGGAACTGACCTCTGACCTCTTTTGTCATCCATGCCGCCC
 886 ATTTTTTTCTACTTGGTATTTGTGGCATAGTTACCTTTACATATGTTTGTTTACAG
 945 TGATCCTTTCATATTTCTCCAAGTCTAGTGGAATCTTCAACCCCTCGAGGGCAGAGC
1004 CAACAGGGTCTATTTCTTTATCTGATCCTACAGCCAACGTAATGGAGGGCTGTGGGT
1063 GGGGACTGCGTCTGCCTTGGGGGTAGGTGCCTTTGTTCAGGAGGAGGAAGCTTGAAA
1122 TGGCGGAGGCTGCACCTGGAGGCCGCACCTGGAGGCCCCAGGAGAGGAGTCAGGTCT
1181 TCTCGATCTGCAGATGTTTGAGCCTGGGAATGAAGGAATTGCTGAACTTTCTGAAGG
1240 AGCGCCCTCGCCGCGACCAACCTTGCAAACAGGAAAATGAGAAATCCAGGGAAGGCC
1299 CAGAGTGACGCAGGGGCCCTGGGACTCGAAGCCTGACCTCCTCACGCCGCGCTTTTT
1358 GAGGCCCCCCCGCTTCTCTATTCACCTGTAGTGTGGAGGCGGGAGACCCCCCAAACA
1417 ATCCCCGATCTGGAGCGCTCCCAATGCCTGCGCGCGCCTGCTGTCACTCTCCGTCTG
1476 TGTGCTGAGTTTTCCTACAGCTTCCTGGGCCTCCTATCTGTAAGCTTTTTCTTTTTT
1535 TTTTTTTGGTTGTGCTTCAGAGAAACTCACTTTTCACAACTTTCTCCCGGCTCTCCC
1594 AGGCCGTCCGAAAGCTCCGGCTTGCTTTCGCCCGGACCCCCGGCTCCCTCCGGGCAG
1653 GCGGCTCGGGAGCAGCCCCTTCCCTCCCCTCCCGGCCCCCGGCCCCGCGCTAATCT
1712 CTTCCAGAGCTGGGGGAGGGGCCAGGCGGTCTTCCCGAAGGCGGGGCGCTCCCTGCA
1771 GCCCGGCCTGGGCGGGCCCTGGGAACGGGCGGGGAACGGCCTCGCCCCCCGGCCCCG
1830 CGCCCCTCGGACCGGAGAAGAGGGGCTGGCCCAGCGCCAGCGTCGGAGCGCCGGCCC
1889 CCTCCCCGGGCCGCTCGCAGCCAACCAGGCCCTCCAGCGGGGCCCACGTGACCTGGA
1948 GTCCTAGACAAAGAAAATGTTCCCTCCCTCCCCCCGCCGCCCCCTCCCCTCCCAG
2009 TGGCCCCCT*CCGCCCCCAGCCCCATCGCCCCCTTCCCCTCCCCCAAGACGGGCAGCT*
2066 *ACTTCCAGAGCTTCAGGGCCGCGGCTCACACCTGAGCGCGACTGCAGAGGGGCTGCA*
2125 *CCTGGCCTTATGG*
```

FIG. 28

Mouse and human Dnmt3a2 promoter alignment

Top Sequence = mouse Dnmt3a2 promoter, 1858 bp (gap not counted)
Bottom Sequence = human DNMT3A2 promoter, 2065 bp

```
1-104      (1-105)       77%  ==
1289-1338  (1475-1530)   82%  ==
1518-1858  (1724-2065)   87%
```

```
         0         .         :         .         :         .         :         .         :
         1 GGAGCCAGGCACCTGGGGTGTTACCTCAGTGCCTTTAGGATAT TGGTT
           |||||||||||||| | |  ||  |||| || | ||||||| ||--|||
         1 GGAGCCAGGCACCTAGAGAATTGTCTCATTGTCATTAGGAGATGGTGGCG

50          .         :         .         :         .         :         .         :
        49 TTCC TAGCTCTAGAGGGCTGATGTCATCACCCCTATTTTGCAGATGAGA
           ||||-| ||   |||||||||||||||||||| | |--|||||||||||||
        51 TTCCATGGCCAAAGAGGGCTGATGTCATCACTCGT TTTGCAGATGAGA

100         .
        98 AAACAGA
           ||||||
        99 CAACAGA

0         .         :         .         :         .         :         .         :
      1289 TCTTTTTTTTTTTT TT T TCCCG GAAACTCAC TTTCTACAACT
           ||||||||||||||--||-|---|  | |-|||||||||-||||-||||||
      1475 TCTTTTTTTTTTTTTGGTTGTGCTTCAGAGAAACTCACTTTTC ACAACT

50          .
      1332 TTCTCCC
           |||||||
      1524 TTCTCCC

0         .         :         .         :         .         :         .         :
      1518 GGGCCCTGGGAACGGAC TGG CCAGCCTCTCCCCCAGGCCCCCCGCGCC
           ||||||||||||||| |- ||- | ||||| ||||| ||||||--|||||
      1724 GGGCCCTGGGAACGGGCGGGGAACGGCCTCGCCCCCCGGCCCC GCGCC

50          .         :         .         :         .         :         .         :
      1566 CCTCGGGCCCG GGTGAGGGGCTGGCCCAGCGCCAGCGTAGGAG GCCGG
           |||||| || |-| ||||||||||||||||||||||||| ||||-|||||
      1772 CCTCGGACCGGAGAAGAGGGGCTGGCCCAGCGCCAGCGTCGGAGCGCCGG

100         .         :         .         :         .         :         .         :
      1614 CCCCCTCCCCCCGGCC CGCGCTTAGCCAACCAGAAACTCCAGTGGGGCC
           ||||||||| -||||-| |||--||||||||||    |||||| ||||||
      1822 CCCCCTCCCCG GGCCGCTCGC  AGCCAACCAGGCCCTCCAGCGGGGCC

150         .         :         .         :         .         :         .         :
      1663 CACGTGACCTGGAGTTCTAGACAAAGAAAATGTTCCCTCCCTCCCCCCG
           |||||||||||||| |||||||||||||||||||||||||||||||||||
      1869 CACGTGACCTGGAGTCCTAGACAAAGAAAATGTTCCCTCCCTCCCCCCG

200         .         :         .         :         .         :         .         :
      1713 GCGCCCCC TCCCCCTCCCTCTGGCCCCCTCCGCCCCCAACCCCAACGCC
           |||||||-|||||-||||   ||||||||||||| ||||| ||||
      1919 CCGCCCCCCTCCCC TCCCAGTGGCCCCCTCCGCCCCCAGCCCCATCGCC

250         .         :         .         :         .         :         .         :
      1762 CCCTGCCCCTCCCCCCAGACGGGCAGCTATTTACAGAGCTTC GGGCCGG
           |||| ||||||||||| |||||||||||||||||| |||||||||-||||||
      1968 CCCTTCCCCTCCCCCAAGACGGGCAGCTACTTCCAGAGCTTCAGGGCCGC

300         .         :         .         :         .         :         .
      1811 GGCTCACACCTGAGC TGTACTGCAGAGGGGCTGCACCTGGCCTTATGG
           ||||||||||||||- |-||||||||||||||||||||||||||||||||
      2018 GGCTCACACCTGAGCGCG ACTGCAGAGGGGCTGCACCTGGCCTTATGG
```

FIG. 29

DE NOVO DNA CYTOSINE METHYLTRANSFERASE GENES, POLYPEPTIDES AND USES THEREOF

CROSS-REFERENCE TO RELATED APPLICATIONS

This application is a continuation-in-part of U.S. application Ser. No. 09/720,086, which is the National Stage of International Application No. PCT/US99/14373, filed Jun. 25, 1999 and published in English under PCT Article 21(2)), which claims the benefit of U.S. Application Ser. No. 60/093,993, filed Jul. 24, 1998, and U.S. Application Ser. No. 60/090,906, filed Jun. 25, 1998. The content of all the aforesaid applications are relied upon and incorporated by reference in their entirety.

BACKGROUND OF THE INVENTION

1. Field of the Invention

The present invention relates generally to the fields of molecular biology, developmental biology, cancer biology and medical therapeutics. Specifically, the present invention relates to novel de novo DNA cytosine methyltransferases. More specifically, isolated nucleic acid molecules are provided encoding mouse Dnmt3a, and Dnmt3b and human DNMT3A and DNMT3B de novo DNA cytosine methyltransferase genes. Dnmt3a and Dnmt3b mouse and DNMT3A and DNMT3B human polypeptides are also provided, as are vectors, host cells and recombinant methods for producing the same. Also provided are isolated nucleic acid molecules encoding mouse Dnmt3a2 and human DNMT3A2, which are small forms of the corresponding Dnmt3a mouse and DNMT3A human genes. Dnmt3a2 mouse and DNMT3A2 human polypeptides are also provided, as are vectors, host cells and recombinant methods for producing the same. The invention further relates to an in vitro method for cytosine C5 methylation. Also provided is a diagnostic method for neoplastic disorders, and methods of gene therapy using the polynucleotides of the invention.

2. Related Art

Methylation at the C-5 position of cytosine predominantly in CpG dinucleotides is the major form of DNA modification in vertebrate and invertebrate animals, plants, and fungi. Two distinctive enzymatic activities have been shown to be present in these organisms. The de novo DNA cytosine methyltransferase, whose expression is tightly regulated in development, methylates unmodified CpG sites to establish tissue or gene-specific methylation patterns. The maintenance methyltransferase transfers a methyl group to cytosine in hemi-methylated CpG sites in newly replicated DNA, thus functioning to maintain clonal inheritance of the existing methylation patterns.

De novo methylation of genomic DNA is a developmentally regulated process (Jahaner, D. and Jaenish, R., "DNA Methylation in Early Mammalian Development," In *DNA Methylation: Biochemistry and Biological Significance*, Razin, A. et al., eds., Springer-Verlag (1984) pp. 189-219 and Razin, A., and Cedar, H., "DNA Methylation and Embryogenesis," in *DNA Methylation: Molecular Biology and Biological Significance*, Jost., J. P. et al., eds., Birkhäuser Verlag, Basel, Switzerland (1993) pp. 343-357). It plays a pivotal role in the establishment of parental-specific methylation patterns of imprinted genes (Chaillet, J. R. et al., *Cell* 66:77-83 (1991); Stöger, R. et al., *Cell* 73:61-71 (1993); Brandeis, M. et al., *EMBO J.* 12:3669-3677 (1993); Tremblay, K. D. et al., *Nature Genet.* 9:407-413 (1995); and Tucker, K. L. et al., *Genes Dev.* 10:1008-1020 (1996)), and in the regulation of X chromosome inactivation in mammals (Brockdoff, N. "Convergent Themes in X Chromosome Inactivation and Autosomal Imprinting," in *Genomic Imprinting: Frontiers in Molecular Biology*, Reik, W. and Sorani, A. eds., IRL Press Oxford (1997) pp. 191-210; Ariel, M. et al., *Nature Genet.* 9:312-315 (1995); and Zucotti, M. and Monk, M. *Nature Genet.* 9:316-320 (1995)).

Thus, C5 methylation is a tightly regulated biological process important in the control of gene regulation. Additionally, aberrant de novo methylation can lead to undesirable consequences. For example, de novo methylation of growth regulatory genes in somatic tissues is associated with tumorigenesis in humans (Laird, P. W. and Jaenisch, R. *Ann. Rev. Genet.* 30:441-464 (1996); Baylin, S. B. et al., *Adv. Cancer. Res.* 72:141-196 (1998); and Jones, P. A. and Gonzalgo, M. L. *Proc. Natl. Acad. Sci. USA* 94:2103-2105 (1997)).

The gene encoding the major maintenance methyltransferase, Dnmt1, was first cloned in mice (Bestor, T. H. et al., *J. Mol. Biol.* 203:971-983 (1988), and the homologous genes were subsequently cloned from a number of organisms, including *Arabidoposis*, sea urchin, chick, and human. Dnmt1 is expressed ubiquitously in human and mouse tissues. Targeted disruption of Dnmt1 results in a genome-wide loss of cytosine methylation and embryonic lethality (Li et al., 1992). Interestingly, Dnmt1 is dispensable for the survival and growth of the embryonic stem cells, but appears to be required for the proliferation of differentiated somatic cells (Lei et al., 1996). Although it has been shown that the enzyme encoded by Dnmt1 can methylate DNA de novo in vitro (Bestor, 1992), there is no evidence that Dnmt1 is directly involved in de novo methylation in normal development. Dnmt1 appears to function primarily as a maintenance methyltransferase because of its strong preference for hemi-methylated DNA and direct association with newly replicated DNA (Leonhardt, H. et al., *Cell* 71:865-873 (1992)). Additionally, ES cells homozygous for a null mutation of Dnmt1 can methylate newly integrated retroviral DNA, suggesting that Dnmt1 is not required for de novo methylation and an independently encoded de novo DNA cytosine methyltransferase is present in mammalian cells (Lei et al., 1996).

Various methods of disrupting Dnmt1 protein activity are known to those skilled in the art. For example, see PCT Publication No. WO92/06985, wherein mechanism based inhibitors are discussed. Applications involving antisense technology are also known; U.S. Pat. No. 5,578,716 discloses the use of antisense oligonucleotides to inhibit Dnmt1 activity, and Szyf et al., *J. Biol. Chem.* 267: 12831-12836, 1992, demonstrates that myogenic differentiation can be affected through the antisense inhibition of Dnmt1 protein activity.

Thus, while there is a significant amount of knowledge in the art regarding the maintenance C5 methyltransferase (Dnmt1), there is no information regarding nucleic acid or protein structure and expression or enzymatic properties of the de novo C5 methyltransferase in mammals.

SUMMARY OF THE INVENTION

A first aspect of the invention provides novel de novo DNA cytosine methyltransferase nucleic acids and polypeptides that are not available in the art.

More specifically, isolated nucleic acid molecules are provided encoding mouse Dnmt3a, and Dmnt3b and human DNMT3A and DNMT3B de novo DNA cytosine methyltransferase genes. Dmnt3a and Dnmt3b mouse and DNMT3A and DNMT3B human polypeptides are also provided, as are vectors, host cells and recombinant methods for producing the same. Also provided are isolated nucleic acid molecules encoding mouse Dnmt3a2 and human DNMT3A2, which are small forms of the corresponding Dnmt3a mouse and DNMT3A human genes. Dnmt3a2 mouse and DNMT3A2 human polypeptides are also provided, as are vectors, host cells and recombinant methods for producing the same. Also provided are Dnmt3a2 mouse and human DNMT3A2 promoter sequences.

A second aspect of the invention relates to de novo DNA cytosine methyltransferase recombinant materials and methods for their production.

A third aspect of the invention relates to the production of recombinant de novo DNA cytosine methyltransferase polypeptides.

A fourth aspect of the invention relates to methods for using such de novo DNA cytosine methyltransferase polypeptides and polynucleotides. Such uses include the treatment of neoplastic disorders, among others.

Yet another aspect of the invention relates to diagnostic assays for the detection of diseases associated with inappropriate de novo DNA cytosine methyltransferase activity or levels and mutations in de novo DNA cytosine methyltransferases that might lead to neoplastic disorders.

BRIEF DESCRIPTION OF THE FIGURES

FIGS. 1A-1D shows the nucleotide sequences of mouse Dnmt3a and Dnmt3b and human DNMT3A and DNMT3B genes respectively.

FIGS. 2A-2D shows the deduced amino acid sequence of mouse Dnmt3a and Dnmt3b and human DNMT3A and DNMT3B genes, respectively. Sequences are presented in single letter amino acid code.

FIG. 3A shows a comparison of mouse Dnmt3a and Dnmt3b amino acid sequences, and FIG. 3B presents a comparison of the protein sequences of human DNMT3A and DNMT3B1.

FIGS. 4C and 4D present a schematic of the human DNMT3B gene organization and exon/intron junction sequences.

FIG. 5A presents a comparison of highly conserved protein structural motifs for eukaryotic and prokaryotic C5 methyltransferase. FIG. 5B presents a sequence alignment of the C-rich domain of vertebrate DNMT3 proteins and the X-lined ATRX gene.

FIG. 11A shows a schematic diagram of Dnmt3a and Dnmt3b proteins. The conserved PWWP and PHD domains, the methyltransferase motifs (I, IV, VI, IX, and X), and the sites of alternative splicing are indicated (the C-terminal 45 amino acids of Dnmt3b5 are out of frame and shown as an open bar). The locations of the epitopes for the Dnmt3 antibodies (164, 157, and 64B1446) are also shown. FIG. 11B demonstrates the specificity of the Dnmt3a and Dnmt3b antibodies. Mouse (m) and human (h) Dnmt3a and Dnmt3b were expressed as GFP fusion proteins in Cos-7 cells and analyzed by immunoblotting with the indicated antibodies. FIG. 11C demonstrates that ES cells express Dnmt3b1 and Dnmt3b6. Cell lysates from wt (J1), Dnmt3a$^{-/-}$ (6aa), Dnmt3b$^{-/-}$ (8bb), and [Dnmt3a$^{-/-}$, Dnmt3b$^{-/-}$] double mutant (7aabb) ES cells as well as Cos-7 cells transfected with different Dnmt3b isoforms were immunoblotted with Dnmt3b-specific antibody 157. FIG. 11D demonstrates that ES cells express at least two forms of Dnmt3a proteins, Dnmt3a and Dnmt3a2. The same ES cell lysates as described in FIG. 11C as well as control Dnmt3a protein expressed in Cos-7 cells were immunoblotted with Dnmt3a-specific antibody 164 (lanes 1-5) and the mAb 64B1446 (lanes 6-10). FIG. 11E demonstrates that Dnmt3a2 co-migrates with atruncated Dnmt3a protein lacking the N-terminal 219 amino acid residues. Plasmid constructs encoding N-terminally truncated Dnmt3a proteins or vector alone were transfected into 6aa ES cells. The overexpressed proteins as well as endogenous Dnmt3a2 (from J1 cells) were immunoprecipitated and detected with antibody 64B1446. Note that lysis buffer containing low salt (150 mM NaCl) could not extract Dnmt3a and Dnmt3b1. FIG. 11F illustrates that Dnmt3a2 cannot be derived from Dnmt3a cDNA. Plasmid construct encoding Dnmt3a or vector alone was transfected into 6aa ES cells. The transfected cells as well as J1 cells were lysed and immunoblotted with antibody 64B1446.

FIG. 12A presents the structure of mouse and human Dnmt3a gene, mRNAs and proteins. Exons are shown as black bars. The Dnmt3a2 unique exons are indicated by "*". Dnmt3a and Dnmt3a2 proteins have identical amino acid sequences except that Dnmt3a has 219 (mouse) or 223 (human) extra residues at the N terminus (human DNMT3A amino acid numbering is shown in parenthesis). The primers used for RT-PCR are shown under the corresponding exons (F, forward; R, reverse). The probes (lines under the Dmnt3a protein) that are used for Northern hybridization represent the corresponding cDNA fragments. FIG. 12B presents Northern blots of total RNA (20 μg per lane) from NIH 3T3, J1, and 6aa cells were probed with Probe 1 (lanes 1-3) or Probe 2 (lanes 4-6). As a loading control, ethidium bromide (EB) staining of 28S rRNA was shown (lanes 7-9). FIG. 12C presents RT-PCR results of Dnmt3a expression. Total RNA from J1 cells was reverse transcribed using poly (dT)$_{12-18}$ and the resulting cDNAs were subjected to PCR amplification with the indicated Dnmt3a primers. Dnmt3a cDNA was used as a positive control.

FIGS. 13A-13F present the nucleotide and predicted amino acid sequences of mouse Dnmt3a2 and human DNMT3A2. FIG. 13A presents mouse Dnmt3a2 cDNA sequence. Nucleotides 148-2217 represent coding sequence. FIG. 13B presents mouse Dnmt3a2 predicted amino acid sequence. FIG. 13C presents human DNMT3A2 cDNA sequence. Nucleotides 217-2286 represent coding sequence. FIG. 13D presents human DNMT3A2 predicted amino acid sequence. FIGS. 13E1-E4 present an alignment of the human DNMT3A2 and mouse Dnmt3a2 cDNA sequences. FIG. 13F presents an alignment of the human DNMT3A2 and mouse Dnmt3a2 predicted amino acid sequences.

FIG. 14A presents a schematic representation of the luciferase reporter constructs. The genomic region that contains the Dnmt3a2 unique exon (exon 7, black bar) embedded in a GC-rich region (striped bar) is shown at the top. The putative Dnmt3a2 transcription start site is indicated. In the reporter constructs, a 2.0-kb genomic fragment that contains part of exon 7 and the putative promoter region was inserted in both orientations upstream of the cDNA encoding the firefly luciferase (luc) followed by the SV40 late poly(A) signal (pA). FIG. 14B demonstrates a luciferase activity assay. ES cells and NIH 3T3 cells were transfected with the reporter constructs (P2-luc and P2R-luc) and the empty vector pGL-3-Basic (luc) in the presence of pRL-TK (expresses *Renilla* luciferase), and luciferase activities were measured by luminescence. Firefly luciferase activity was normalized to *Renilla* luciferase activity to minimize transfection efficiency variations. The results were expressed as relative activity using the background activity generated by the empty vector as baseline. Each bar represents the mean+ standard deviation of data from six independent reactions performed in two separate experiments.

FIG. 15A illustrates the targeted disruption of Dnmt3a2. The wild type genomic DNA structure with exons (black bars) and a GC-rich region (striped bar) in the putative Dnmt3a2 promoterregion is shown at the top. The putative transcription and translation start sites for Dnmt3a2 are indicated. In the P2 targeting vector, a 2.1-kb genomic fragment encompassing the Dnmt3a2 unique exon and the putative promoter region was replaced with an hCMV-hygTK cassette in an opposite transcriptional orientation as Dnmt3a. A PGK-DTA cassette was introduced for negative selection to increase the targeting frequency. The location of the probe for Southern hybridization and Sca I (S) sites are also shown. FIG. 15B presents Southern analysis of the genotype of ES cell lines. Genomic DNA was digested with Sca I and hybridized with the indicated probe. The 17 kb untargeted allele (wt/6aa) and the 9 kb targeted allele (P2) are indicated. FIG. 15C presents Northern analysis of total RNA from the ES cell lines. Note the intensity of the 4.0 kb and 4.2 kb bands was reduced by half in Dnmt3a+/− cells and was diminished in 296 cells. The 28S rRNA stained with ethidium bromide is shown as a loading control (bottom panel). FIG. 15D presents immunoprecipitation and immunoblotting analyses of the ES cell lines with antibody 64B1446.

FIG. 16A illustrates the production of recombinant Dnmt3a proteins. His$_6$-tagged Dnmt3a, Dnmt3a:PC→AD, and Dnmt3a2 were expressed in *E. coli* and purified by metal chelation chromatography. The purity of the recombinant proteins was estimated by Coomassie blue staining (lanes 1-3) and their identity was verified by immunoblotting with antibody 64B1446 (lanes 4-6). FIG. 16B illustrates methylation of double-stranded poly (dI-dC) by Dnmt3a and Dnmt3a2. The recombinant proteins were incubated with poly (dI-dC) in the presence of S-adenosyl-L-methionine [methyl-3H] and the methyltransferase activity was measured by the incorporation of $^3$H-methyl group into poly (dI-dC). Each bar represents the mean+ standard deviation of data from three independent reactions. FIG. 16C demonstrates the localization of Dnmt3a and Dnmt3a2. GFP-Dnmt3a and Dnmt3a2 were transfected in NIH3T3 cells and the cells were fixed and analyzed by fluorescence microscopy. The top panel shows the GFP signal and the bottom panel shows the nuclei stained with DAPI. The arrows point to two heterochromatin regions and are used for orientation. FIG. 16D illustrates the subcellular distribution of endogenous Dnmt3 proteins. ES cells were extracted to obtain the cytoplasmic, chromatin, and the nuclear matrix fractions (left). Equal amounts of each fraction were analyzed by immunoblotting with antibody 64B1446 (right, $1^{st}$ panel), anti-histone H1 ($2^{nd}$ panel), and anti-lamin B ($3^{rd}$ panel).

In FIG. 17A undifferentiated ES cells (day 0) or differentiated embryoid bodies (day 2-14) were lysed and equal amount of proteins (30 µg/lane for Dmnt3a and tubulin, 5 µg/lane for Dmnt3a2 and Dnmnt3b) were analyzed by immunoblotting with the indicated antibodies. In FIG. 17B different organs from wild type or Dnmt3a$^{-/-}$ mice (3 weeks old) were homogenized and lysed, and the lysates immunoprecipitated and immunoblotted with Dnmt3a (64B1446) antibody (top panel) or Dnmt3b antibody 157 (bottom panel). ES cells were used as a positive control. Note that 64B1446 cross-reacts with a nonspecific band of ~105 kDa (indicated by *) in some tissues. Br, brain; Li, liver; Mu, muscle; Te, testis; Ht, heart; Sp, spleen; Th, thymus; St, stomach; Si, small intestine. In FIG. 17C total RNA isolated from different tissues was analyzed by RT-PCR using primers either specific to Dnmt3a (F4 and R1) or to Dnmt3a2 (F5 and R1). Lu, lung; Ov, ovary. In FIG. 17D the same RNA samples were analyzed by RT-PCR using Dnmt3b-specific primers flanking exon 10 (top panel) or exons 21-22 (bottom panel) followed by Southern hybridization using Dnmt3b cDNA fragments as probes. Dnmt3b1 and Dnmt3b3 cDNAs were used as controls (lanes 1 and 2). The bands representing the presence (+) or absence (−) of exon 10 or exons 21-22 are indicated on the right and the major Dnmnt3b isoforms present in ES cells and each tissue are indicated at the bottom.

FIGS. 18A-18B present expression of DNMT3A and DNMT3B in human EC cell lines. The indicated EC cell lines were lysed and equal amount of proteins (30 µg/lane) was analyzed by immunoblotting with antibody 64B1446 (A) or antibody 157 (B). Human DNMT3A and DNMT3B isoforms expressed in Cos-7 cells were used as positive controls. FIG. 18C presents expression of DNMT1, DNMT3A, and DNMT3B in breast and ovarian tumor cell lines. For comparison, a human EC cell line, NCCIT, and mouse ES cells (J1) and NIH 3T3 cells were included (lanes 1, 11, 12). Equal amount of proteins (30 µg/lane) from the indicated cell lysates was analyzed by immunoblotting with the indicated antibodies. Note that the anti-DNMT1 antibody does not recognize mouse Dnmt1. FIG. 18D presents De novo methylation activity in human cell lines. The indicated cells were infected with Moloney Murine Leukemia Virus (MMLV). Five or 20 days after infection, genomic DNA was digested with Kpn I alone (K), Kpn I plus Msp I (K/M), or Kpn I plus Hpa II (K/H), and analyzed by Southern hybridization using the pMu3 probe. The MMLV and an enlarged 3' LTR region, two Kpn I (K) and five Hpa II/Msp I sites (vertical lines) and the pMu3 probe are shown at the bottom.

Figure 4A:
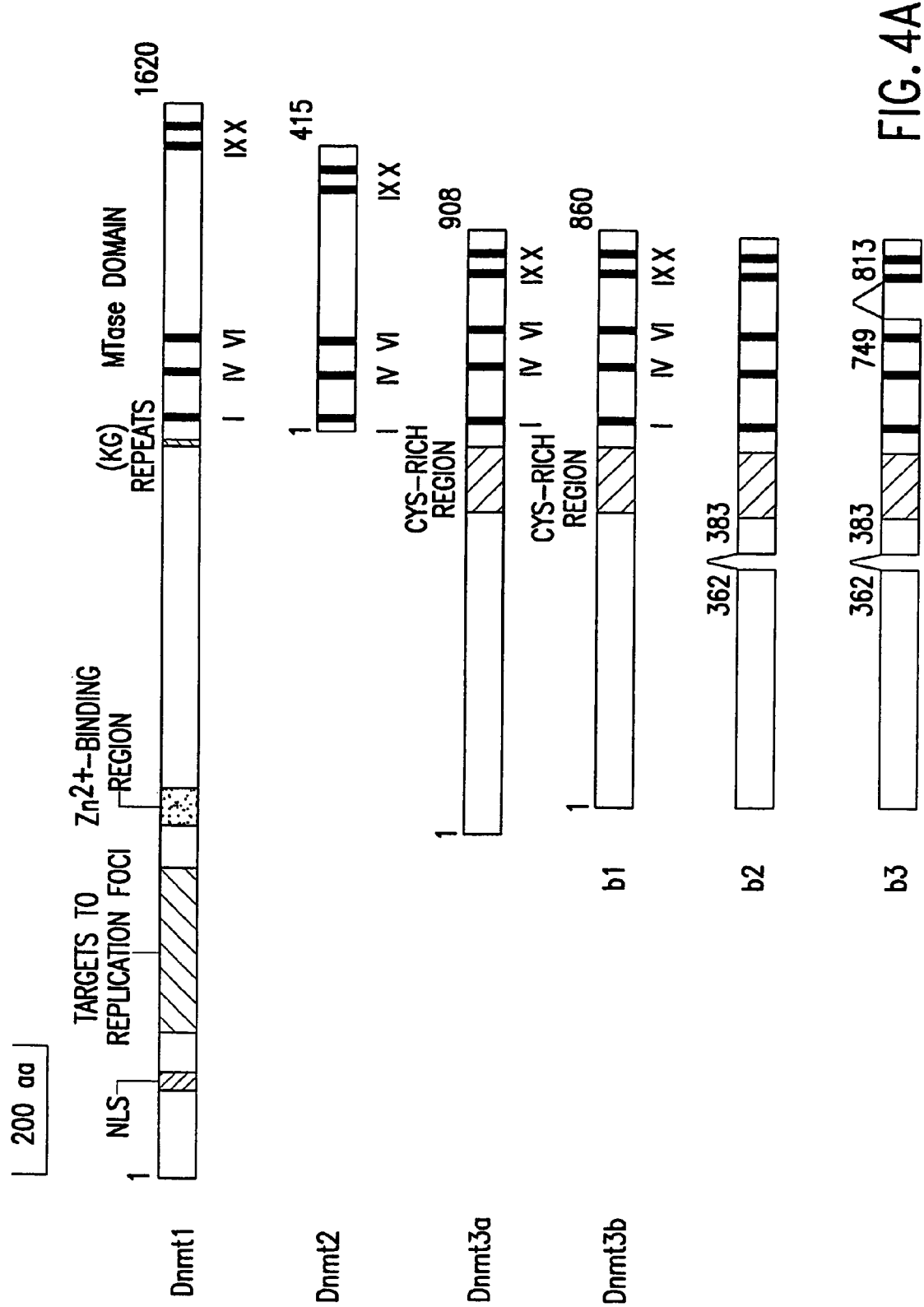
FIG. 4A presents a schematic comparison of mouse Dnmt1, Dnmt2, Dnmt3a and Dnmt3b protein structures.

(A) Genomic DNA from [Dnmt3a−/−, Dnmt3b−/−] ES cells (7aabb and 10aabb) that had been grown in culture for 5-40 passages, as well as wild-type (J1) and Dnmt1 mutant (n/n and c/c) ES cells, was digested with HpaII and hybridized to probes for endogenous C-type retrovirus repeats (pMO), minor satellite repeats, and IAP repeats. As a control for complete digestion, DNA from J1 cells was digested with Msp I. The Dnmt1$^n$ allele (n stands for N-terminal disruption) is a partial loss-of-function mutation (Li, E., et al., Cell 69:915-26 (1992)). and the Dnmt1$^c$ allele (c stands for disruption of the catalytic or C-terminal domain) is a null mutation (Lei, H., et al., Development 122:3195-205 (1996)). (B) Genomic DNA from J1, Dnmt3a−/− (6aa), or Dnmt3b−/− (8bb) ES cells that had been grown in culture for 5-25 passages, as well as 7aabb (P40), was digested with HpaII and hybridized to pMO probe. (C) Lysates from the indicated ES cell lines were immunoblotted with anti-Dnmt1 and anti-tubulin antibodies.

FIGS. 20A-20B present stable expression of Dnmt3a and Dnmt3b isoforms in late-passage 7aabb cells. (A) Schematic diagram of Dnmt3a and Dnmt3b isoforms. The conserved PWWP and PHD domains, the methyltransferase motifs (I, IV, VI, IX, and X), and the sites of alternative splicing are indicated (the C-terminal 45 amino acids of Dnmt3b5 are out of frame and shown as an open bar). The locations of the epitopes for the Dnmt3a and Dnmt3b antibodies are also shown. (B) cDNAs encoding Dnmt3a/3b isoforms were subcloned in an expression vector (schematically shown at the top) and these constructs were individually electroporated into late-passage (P70) 7aabb cells, which were subsequently selected in blasticidin-containing medium for seven days. Blasticidin-resistant clones were analyzed with immunoblotting using anti-Dmnt3a (middle panel) or anti-Dnmt3b (bottom panel) antibodies. As a loading control, the same membranes were immunoblotted with anti-tubulin antibody.

FIGS. 21A-21I demonstrate that expression of Dnmt3a/3b proteins in 7aabb cells restores DNA methylation. (A-D) Methylation of repetitive sequences. Genomic DNA from the indicated ES cell lines was digested with Hpa II (A-C) or Mae II (D) and hybridized to the indicated probes. DNA from J1 cells digested with Msp I was used as a control for complete digestion. (E) Analysis of the methylation status of the major satellite repeating unit by bisulfite sequencing. Genomic DNA from J1 and 7aabb cells as well as stable cell lines expressing Dnmt3a, Dnmt3a2, Dnmt3b1, and Dnmt3b3 was analyzed. The methylation status of six CpG sites from 8-12 individual clones is shown schematically (black circles represent methylated sites), and the percentages of methylated CpG sites are indicated in parenthesis. (F-D) Methylation of unique genes. The same genomic DNA samples described in (A-D) were digested with Bam HI and Hha I (F and H), EcoRI and Hpa II (G), or EcoRV and Hha I (I) and hybridized to probes corresponding to the 3' region of β-globin (F), the 5' region of Pgk-1 (G), an exon of Pgk-2 (H), or the 5' region of Xist (I). DNA from J1 cells digested with Bam HI alone (F and H) or EcoRI alone (G) was used as controls.

FIGS. 22A-22E demonstrate expression of Dnmt3a and Dnmt3b proteins in 7aabb cells fails to restore maternal methylation imprints. The same DNA samples described in FIG. 3 were digested with Sac I and Hha I (A), Bam HI and Hpa II (B), Pvu II and Hpa II (C and D), or Xba I and Hha I (E) and hybridized to probes corresponding to the 5' upstream region of H19 (A), the DMR2 of Igf2 (B), region 2 of Igf2r (C), the DMR of Peg1, or the DMR1 of Snrpn (E). As controls, DNA from J1 cells was digested with the corresponding enzymes without Hha I or Hpa II. The fragments derived from the paternal (p) and maternal (m) alleles are indicated.

FIGS. 23A-23E demonstrate Dnmt3b6 has no enzymatic activity in vivo. (A) Strategy of targeted deletion of Dnmt3b exons 21 and 22. The top line shows the Dnmt3b genomic structure with exons represented by vertical bars. The targeting vector (second line) was constructed by replacing exons 21 and 22 with a PGK-puromycin cassette. A PGK-DTA cassette was introduced for negative selection to increase the targeting frequency. (B) Southern analysis of the genotype of ES cell lines. Genomic DNA was digested with EcoRV and hybridized to a 3' external probe, as shown in (A). The 16-kb wild-type allele, the 5-kb Dnmt3b1 targeted allele, and the 14-kb Dnmt3b null allele (30) are indicated. (C) Lysates from the indicated cell lines were immunoblotted with anti-Dnmt3b (top), anti-Dnmt3a (middle), and anti-tubulin (bottom) antibodies. (D and E) Genomic DNA from the indicated ES cell lines was digested with Hpa II and hybridized to probes for endogenous C-type retrovirus repeats (D) and minor satellite repeats (E).

Figure 24:
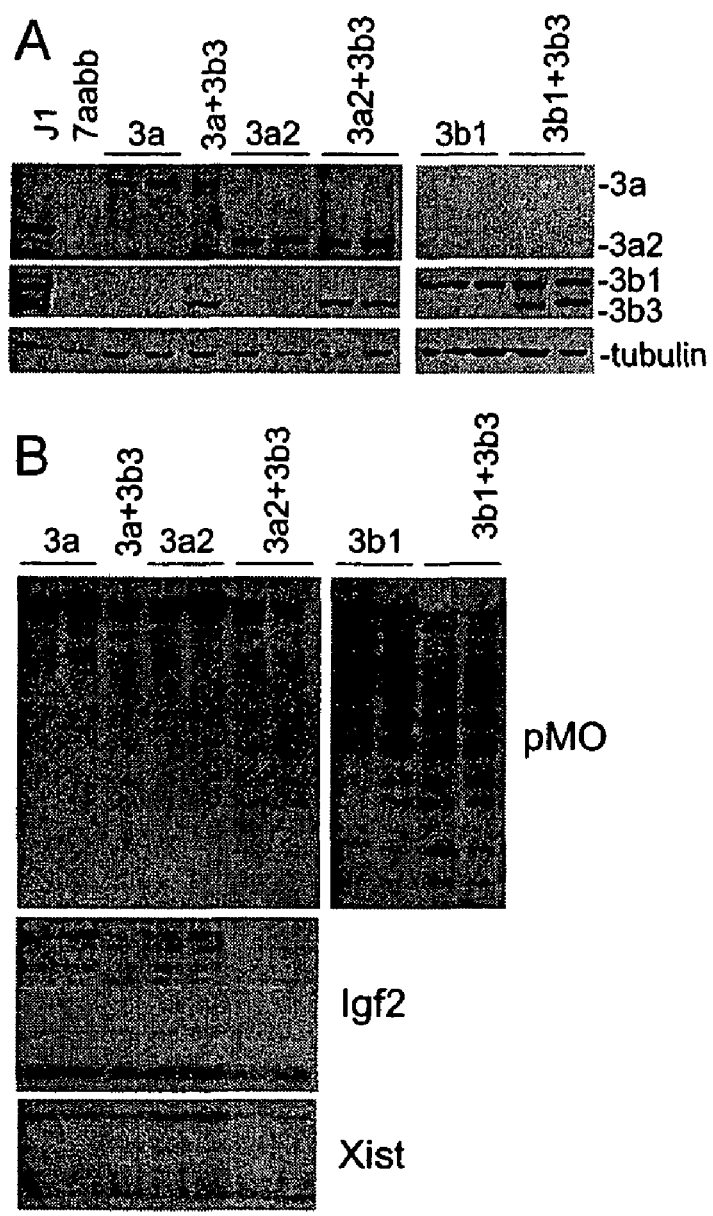

FIGS. 24A-24B demonstrate Dnmt3b3 inhibits de novo methylation by Dnmt3a and Dnmt3b. (A) Dnmt3a, Dnmt3a2, or Dnmt3b1 cDNA was electroporated into late-passage 7aabb cells in the presence or absence of Dnmt3b3 cDNA, and stable clones were analyzed for protein expression by immunoblotting using anti-Dnmt3a (top), anti-Dnmt3b (middle), and anti-tubulin (bottom) antibodies. (B) Genomic DNA from the indicated stable clones was analyzed for methylation using pMO, Igf2, and Xist probes, as indicated.

Figure 25:
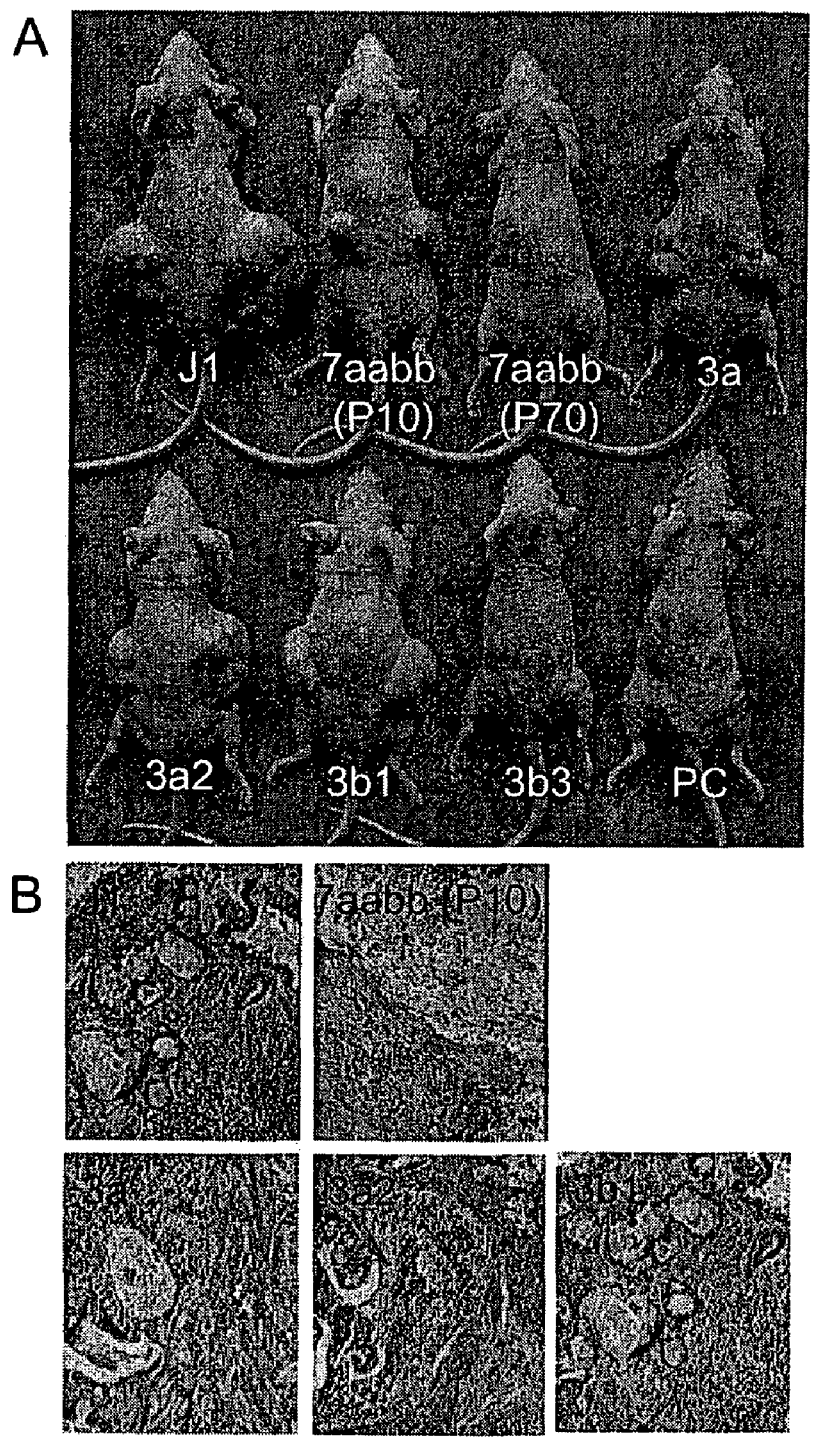

FIGS. 25A-25B demonstrate active Dnmt3a/3b isoforms rescue the capacity of late-passage 7aabb cells to form terotomas in nude mice. (A) The indicated ES cell lines were injected into nude mice subcutaneously on both sides (3-4 mice for each cell line, $5 \times 10^5$ cells per site) and the mice were examined for terotomas after 4 weeks. A typical representation of the size of the terotomas derived from each cell line is shown. (B) Histological sections of teratomas derived from J1, early-passage (P10) 7aabb, and Dnmt3a, Dnmt3a2, and Dnmt3b1 stable clones showing the presence of multiple types of differentiated cells.

Figure 26:
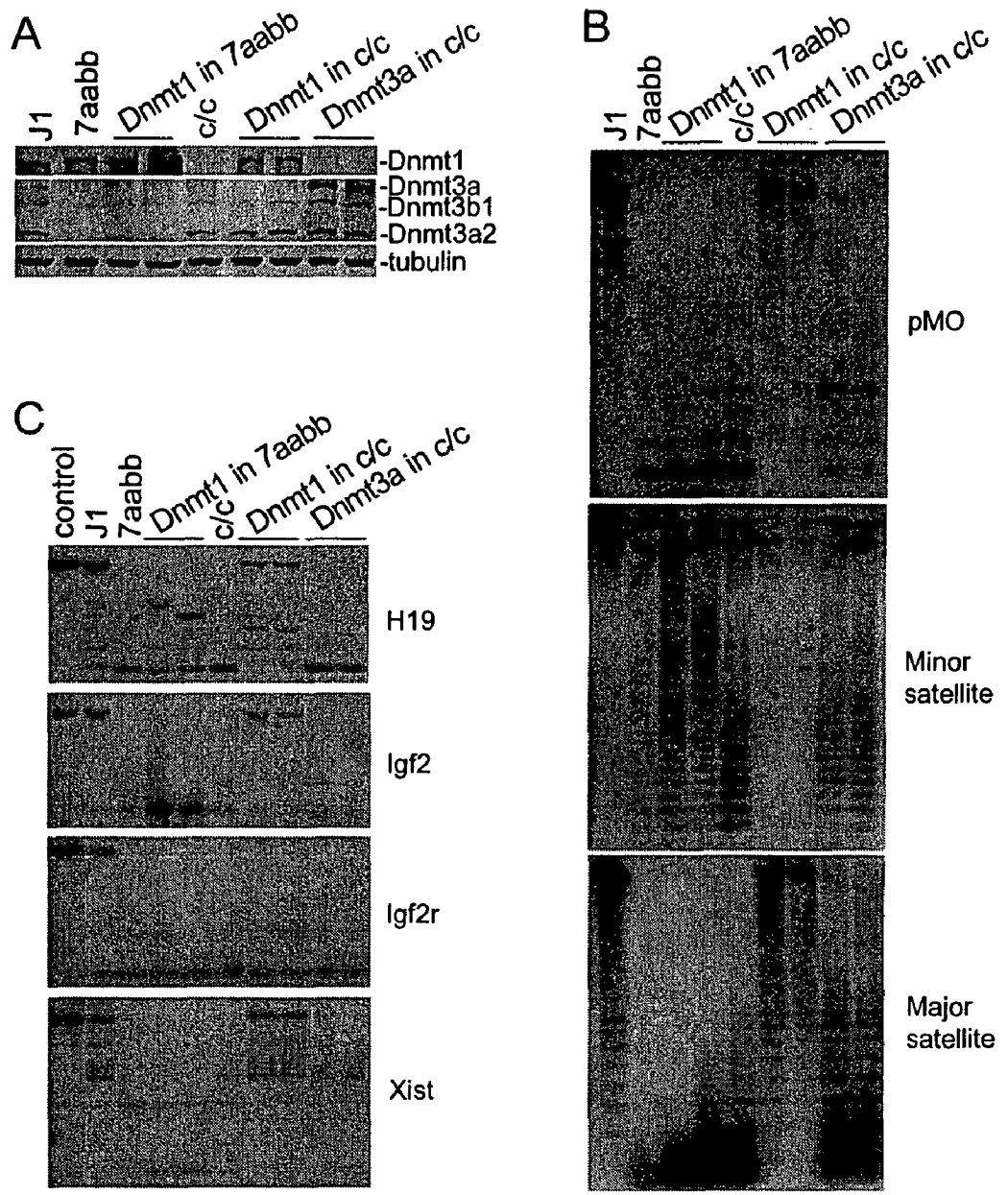

FIGS. 26A-26C demonstrate Dnmt1 and Dnmt3 proteins function cooperatively in maintaining methylation patterns. (A) Dnmt1 or Dnmt3a was overexpressed in 7aabb (P70) or Dnmt1−/− (c/c) ES cells as indicated and stable clones were examined for protein expression by immunoblotting using anti-Dnmt1 (top), anti-Dnmt3a (middle), and anti-tubulin (bottom) antibodies. (B and C) Genomic DNA from the indicated ES cell lines was analyzed for methylation of repetitive sequences (B) and unique genes (C) using the indicated probes.

FIG. 27 presents mouse Dnmt3a2 promoter sequence. Underlined sequences represent GC-rich regions that have high promoter potential as predicted by the computer program PROSCAN. An about 100 to 250 nucleotide region is represented by 250 "N" nucleotides from nucleotide position 723-972. This region could not be sequenced, presumably due to high GC content. The sequence of the first exon of Dnmt3a2 is italicized and bolded.

FIG. 28 presents human DNMT3A2 promoter sequence. The sequence of the first exon of DNMT3A2 is italicized. The promoter sequence was identified by BLAST searching SEQ ID NO:118 against the human genome sequence database available at http://www.ncbi.nlm.nih.gov/BLAST/. The sequence of the first exon of DNMT3A2 is italicized and bolded.

FIG. 29 presents a sequence alignment of mouse Dnmt3a2 and human DNMT3A2 promoter sequence. The about 100 to about 250 nucleotide region in the mouse Dnmt3a2 promoter, denoted by 250 "N" nucleotides in FIG. 27, was not counted in the numbering of the nucleotides.

DETAILED DESCRIPTION OF THE PREFERRED EMBODIMENTS

Definitions

In the description that follows, a number of terms used in recombinant DNA technology are utilized extensively. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Recombinant vector: Any cloning vector or expression vector which contains the desired cloned gene(s).

Host Animal: Transgenic animals, all of whose germ and somatic cells contain the DNA construct of the invention. Such transgenic animals are in general vertebrates. Preferred host animals are mammals such as non-human primates, humans, mice, sheep, pigs, cattle, goats, guinea pigs, rodents, e.g. rats, and the like. The term host animal also includes animals in all stages of development, including embryonic and fetal stages.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. According to the invention, preferred promoters are heterologous to the de novo DNA cytosine methyltransferase genes, that is, the promoters do not drive expression of the gene in a mouse or human. Such promoters include the CMV promoter (In Vitrogen, San Diego, Calif.), the SV40, MMTV, and hMTIIa apromoters (U.S. Pat. No. 5,457,034), the HSV-1 4/5 promoter (U.S. Pat. No. 5,501,979), and the early intermediate HCMV promoter (WO92/17581). In one emdodiment, it is preferred that the promoter is tissue-specific, that is, it is induced selectively in a specific tissue. Also, tissue-specific enhancer elements may be employed. Additionally, such promoters may include tissue and cell-specific promoters of an organism.

Gene: A DNA sequence that contains information needed for expressing a polypeptide or protein.

Structural gene: A DNA sequence that is transcribed into messenger RNA (mRNA) that is then translated into a sequence of amino acids characteristic of a specific polypeptide.

Complementary DNA (cDNA): A "complementary DNA," or "cDNA" gene includes recombinant genes synthesized by reverse transcription of mRNA and from which intervening sequences (introns) have been removed.

Expression: Expression is the process by which a polypeptide is produced from a structural gene. The process involves transcription of the gene into mRNA and the translation of such mRNA into polypeptide(s).

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad. Sci.* 80:726-730 (1983)). Two nucleic acid molecules are considered to be "nonhomologous" if their nucleotide sequences share a similarity of less than 40%.

Polynucleotide: This term generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Isoform: This term refers to a protein or polynucleotide that is produced from an alternatively spliced RNA transcript or from an RNA transcript that is generated by an alternative promoter. As used herein, "isoform" refers to the polypeptides and polynucleotides encoding the polypeptides.

Polypeptide: This term refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties*, 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors", *Methods in Enzymol.* 182:626-646 (1990) and Rattan et al., "Protein Synthesis: Posttranslational Modifications and Aging", *Ann NY Acad Sci* 663:48-62 (1992).

Variant: The term used herein is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCS program package (Devereux, J., et al., *Nucleic Acids Research* 12(I):387 (1984)), BLASTP, BLASTN, FASTA (Atschul, S. F., et al., *J Mol. Biol* 215:403 (1990)).

Therefore, as used herein, the term "identity" represents a comparison between a test and reference polynucleotide. More specifically, reference polynucleotides are identified in this invention as SEQ ID NOS: 1, 2,3,4,83, and 84 and a test polynucleotide is defined as any polynucleotide that is 90% or more identical to a reference polynucleotide. As used herein, the term "90% or more" refers to percent identities from 90 to 99.99 relative to the reference polynucleotide. Identity at a level of 90% or more is indicative of the fact that, assuming for exemplification purposes a test and reference polynucleotide length of 100 nucleotides, that no more than 10% (i.e., 10 out of 100) nucleotides in the test polynucleotide differ from that of the reference polynucleotide. Such differences may be represented as point mutations randomly distributed over the entire length of the sequence or they may be clustered in one or more locations of varying length up to the maximum allowable 10 nucleotide difference. Differences are defined as nucleotide substitutions, deletions or additions of sequence. These differences may be located at any position in the sequence, including but not limited to the 5' end, 3' end, coding and non coding sequences.

Fragment: A "fragment" of a molecule such as de novo DNA cytosine methyltransferases is meant to refer to any polypeptide subset of that molecule.

Functional Derivative: The term "functional derivatives" is intended to include the "variants," "analogues," or "chemical derivatives" of the molecule. A "variant" of a molecule such as de novo DNA cytosine methyltransferases is meant to refer to a naturally occurring molecule substantially similar to either the entire molecule, or a fragment thereof. An "analogue" of a molecule such as de novo DNA cytosine methyltransferases is meant to refer to a non-natural molecule substantially similar to either the entire molecule or a fragment thereof.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Protein Activity or Biological Activity of the Protein: These expressions refer to the metabolic or physiologic function of de novo DNA cytosine methyltransferase protein including similar activities or improved activities or these activities with decreased undesirable side-effects. Also included are antigenic and immunogenic activities of said de novo DNA cytosine methyltransferase protein. Among the physiological or metabolic activities of said protein is the transfer of a methyl group to the cytosine C5 position of duplex DNA. Such DNA may completely lack any methylation of may be hemimethylated. As demonstrated in Examples 4 and 5, de novo DNA cytosine methyltransferases methylate C5 in cytosine moieties in nonmethylated DNA.

De novo DNA Cytosine Methyltransferase Polynucleotides: This term refers to a polynucleotide containing a nucleotide sequence that encodes a de novo DNA cytosine methyltransferase polypeptide or fragment thereof, variant, or isoform or that encodes a de novo DNA cytosine methyltransferase polypeptide or fragment thereof, variant, or isoform, wherein said nucleotide sequence has at least 90% identity to a nucleotide sequence encoding the polypeptide of SEQ ID Nos: 5, 6, 7, 8, 85 or 86 or a corresponding fragment thereof, or which has sufficient identity to a nucleotide sequence contained in SEQ ID NO:1, 2, 3, 4, 83, or 84.

De novo DNA Cytosine Methyltransferase Polypeptides: This term refers to polypeptides with amino acid sequences sufficiently similar to the de novo DNA cytosine methyltransferase protein sequence in SEQ ID NO:5, 6, 7, 8, 85 or 86 and that at least one biological activity of the protein is exhibited.

Antibodies: As used herein includes polyclonal and monoclonal antibodies, chimeric, single chain, and humanized antibodies, as well as Fab fragments, including the products of an Fab or other immunoglobulin expression library.

Substantially pure: As used herein means that the desired purified protein is essentially free from contaminating cellular components, said components being associated with the desired protein in nature, as evidenced by a single band following polyacrylamide-sodium dodecyl sulfate gel electrophoresis. Contaminating cellular components may include, but are not limited to, proteinaceous, carbohydrate, or lipid impurities.

The term "substantially pure" is further meant to describe a molecule which is homogeneous by one or more purity or homogeneity characteristics used by those of skill in the art. For example, a substantially pure de novo DNA cytosine methyltransferases will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the factor with other compounds. In addition, the term is not meant to exclude de novo DNA cytosine methyltransferase fusion proteins isolated from a recombinant host.

Isolated: A term meaning altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of a de novo DNA cytosine methyltransferase polypeptide can be substantially purified by the one-step method described in Smith and Johnson, *Gene* 67:31-40 (1988).

Neoplastic disorder: This term refers to a disease state which is related to the hyperproliferation of cells. Neoplastic disorders include, but are not limited to, carcinomas, sarcomas and leukemia.

Gene Therapy: A means of therapy directed to altering the normal pattern of gene expression of an organism. Generally, a recombinant polynucleotide is introduced into cells or tissues of the organism to effect a change in gene expression.

Antisense RNA gene/Antisense RNA. In eukaryotes, mRNA is transcribed by RNA polymerase II. However, it is also known that one may construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translation stop codons in the antisense RNA sequence.

Antisense oligonucleotide: A DNA or RNA molecule or a derivative of a DNA or RNA molecule containing a nucleotide sequence which is complementary to that of a specific mRNA. An antisense oligonucleotide binds to the complementary sequence in a specific MRNA and inhibits translation of the MRNA. There are many known derivatives of such DNA and RNA molecules. See, for example, U.S. Pat. Nos. 5,602,240, 5,596,091, 5,506,212, 5,521,302, 5,541,307, 5,510,476, 5,514,787, 5,543,507, 5,512,438, 5,510,239, 5,514,577, 5,519,134, 5,554,746, 5,276,019, 5,286,717, 5,264,423, as well as WO96/35706, WO96/32474, WO96/

29337 (thiono triester modified antisense oligodeoxynucleotide phosphorothioates), WO94/17093 (oligonucleotide alkylphosphonates and alkylphosphothioates), WO94/08004 (oligonucleotide phosphothioates, methyl phosphates, phosphoramidates, dithioates, bridged phosphorothioates, bridge phosphoramidates, sulfones, sulfates, ketos, phosphate esters and phosphorobutylamines (van der Krol et al, *Biotech.* 6:958-976 (1988); Uhlmann et al., *Chem. Rev.* 90:542-585 (1990)), WO94/02499 (oligonucleotide alkylphosphonothioates and arylphosphonothioates), and WO92/20697 (3'-end capped oligonucleotides). Particular de novo DNA cytosine methyltransferase antisense oligonucleotides of the present invention include derivatives such as S-oligonucleotides (phosphorothioate derivatives or S-oligos, see, Jack Cohen, *Oligodeoxynucleotides, Antisense Inhibitors of Gene Expression*, CRC Press (1989)). S-oligos (nucleosidephosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1, 1-dioxide which is a sulfur transfer reagent. See Iyer et al., *J. Org. Chem.* 55:4693-4698 (1990); and Iyer etal., *J. Am. Chem. Soc.* 112:1253-1254 (1990).

Antisense Therapy: A method of treatment wherein antisense oligonucleotides are administered to a patient in order to inhibit the expression of the corresponding protein.

I. Deposited Material

The invention relates to polynucleotides encoding and polypeptides of novel de novo DNA cytosine methyltransferase proteins. The invention relates especially to de novo DNA cytosine methyltransferase mouse Dnmt3a, Dnmt3a2 and Dnmt3b cDNAs and the human DNMT3A, DNMT3A2 and DNMT3B cDNAs set out in SEQ ID NOs:1, 83, 2, 3, 84 and 4, respectively. The invention also relates to mouse Dnmt3a, Dnmt3a2 and Dnmt3b and human DNMT3A, DNMT3A2 and DNMT3B de novo DNA cytosine methyltransferase polypeptides set out in SEQ ID NOs:5, 85, 6, 7, 86 and 8, respectively. The invention further relates to the de novo DNA cytosine methyltransferase nucleotide sequences of the mouse Dnmt3a cDNA (plasmid pMT3a), Dnmt3a2 cDNA, and Dnmt3b cDNA (plasmid pMT3b), and the human DNMT3A cDNA (plasmid pMT3A), and DNMT3A2 cDNA in ATCC Deposit Nos.209933, PTA-4611, 209934, 98809, and PTA-4610 respectively, and the amino acid sequences encoded therein.

The nucleotide sequence of the human DNMT3B cDNA identified in SEQ ID NO:4 is available in a clone (ATCC Deposit No. 326637) independently deposited by the I.M.A.G.E. Consortium. The invention relates to the de novo DNA cytosine methyltransferase polypeptide encoded therein.

Clones containing mouse Dnmt3a and Dnmt3b cDNAs were deposited with the American Type Culture Collection (ATCC), 10801 University Boulevard, Manassas, Va. 20110-2209, USA, on Jun. 16, 1998, and assigned ATCC Deposit Nos. 209933 and 209934, respectively. The human DNMT3A cDNA was deposited with the ATCC on Jul. 10, 1998, and assigned ATCC Deposit No. 98809. Clones containing mouse Dnmt3a2 and human DNMT3A2 were deposited with the American Type Culture Collection (ATCC) on Aug. 23, 2002 and assigned ATCC deposit No. PTA-4611 and PTA-4610, respectively.

While the ATCC deposits are believed to contain the de novo DNA cytosine methyltransferase cDNA sequences shown in SEQ ID NOs: 1, 2, 3, 4, 83 and 84, the nucleotide sequences of the polynucleotide contained in the deposited material, as well as the amino acid sequence of the polypeptide encoded thereby, are controlling in the event of any conflict with any description of sequences herein.

The deposits for mouse Dnmt3a, Dnmt3a2 and Dmnt3b cDNAs and the human DNMT3A and DNMT3A2 cDNA were made under the terms of the Budapest Treaty on the international recognition of the deposit of microorganisms for purposes of patent procedure. The deposits are provided merely as a convenience for those of skill in the art and are not an admission that a deposit is required for enablement, such as that required under 35 U.S.C. § 112.

II. Polynucleotides of the Invention

Another aspect of the invention relates to isolated polynucleotides, and polynucleotides closely related thereto, which encode the de novo DNA cytosine methyltransferase polypeptides. As shown by the results presented in FIG. 5, sequencing of the cDNAs contained in the deposited clones encoding mouse and human de novo DNA cytosine methyltransferases confirms that the de novo DNA cytosine methyltransferase proteins of the invention are structurally related to other proteins of the DNA methyltransferase family.

The polynucleotides of the, present invention encoding de novo DNA cytosine methyltransferase proteins may be obtained using standard cloning and screening procedures as described in Examples 1 and 5. Polynucleotides of the invention can also be obtained from natural sources such as genomic DNA libraries or can be synthesized using well known and commercially available techniques.

Among particularly preferred embodiments of the invention are polynucleotides encoding de novo DNA cytosine methyltransferase polypeptides having the amino acid sequence set out in SEQ ID NO:5, SEQ ID NO:6, SEQ ID NO:7, SEQ ID NO:8, SEQ ID NO:85, or SEQ ID NO:86, and variants thereof.

A particular nucleotide sequence encoding a de novo DNA cytosine methyltransferase polypeptide maybe identical over its entire length to the coding sequence in SEQ ID NOs:1, 2, 3, 83, or 84. Alternatively, a particular nucleotide sequence encoding a de novo DNA cytosine methyltransferase polypeptide may be an alternate form of SEQ ID NOs:1, 2, 3, 4, 83, or 84 due to degeneracy in the genetic code or variation in codon usage encoding the polypeptides of SEQ ID NOs:5, 6, 7, 8, 85, or 86. Preferably, the polynucleotides of the invention contain a nucleotide sequence that is highly identical, at least 90% identical, with a nucleotide sequence encoding a de novo DNA cytosine methyltransferase polypeptide or at least 90% identical with the encoding nucleotide sequence set forth in SEQ ID NOs:1, 2, 3, 83, or 84. Polynucleotides of the invention may be 90 to 99% identical to the nucleotides sequence set forth in SEQ ID NO:4.

When a polynucleotide of the invention is used for the recombinant production of a de novo DNA cytosine methyltransferase polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* 86:821-824 (1989), or it may be the HA tag, which corresponds to an epitope derived from the influenza hemagglutinin protein (Wilson, I., et al., *Cell* 37:767, 1984). The polynucleotide may also contain non-coding 5' and 3' sequences, such as transcribed, non-translated sequences, splicing and polyadenylation signals, ribosome binding sites and sequences that stabilize mRNA.

Embodiments of the invention include isolated nucleic acid molecules comprising a polynucleotide having a nucleotide sequence at least 90% identical, and more preferably at least 91%, 92%, 93%, 94%, 95%, 96%, 97%, 98% or 99% identical to (a) a nucleotide sequence encoding a de novo DNA cytosine methyltransferase polypeptide having the amino acid sequence in SEQ ID NO:1, SEQ ID NO:2, SEQ ID NO:3; SEQ ID NO:83, or SEQ ID NO:84; (b) a nucleotide sequence encoding a de novo DNA cytosine methyltransferase polypeptide having the amino acid sequence encoded by the cDNA clone contained in ATCC Deposit No. 209933, ATCC Deposit No. 209934, ATCC Deposit No.98809, ATCC Deposit No. PTA-461 1, or ATCC Deposit No. PTA-4610; or (c) a nucleotide sequence complementary to any of the nucleotide sequences in (a) or (b). Additionally, an isolated nucleic acid of the invention may be a polynucleotide at least 90% but not more than 99% identical to (a) a nucleotide sequence encoding a de novo DNA cytosine methyltransferase polypeptide having the amino acid sequence in SEQ ID NO:4; (b) a nucleotide sequence encoding a de novo DNA cytosine methyltransferase polypeptide having the amino acid sequence encoded by the cDNA clone contained in ATCC Deposit No.326637; or (c) a nucleotide sequence complementary to any of the nucleotide sequences in (a) or (b).

Conventional means utilizing known computer programs such as the BestFit program (Wisconsin Sequence Analysis Package, Version 10 for Unix, Genetics Computer Group, University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to any one of the nucleotide sequences shown in SEQ ID NO:1, SEQ ID NO:2, SEQ ID NO:3, SEQ ID NO:4, SEQ ID NO:83, or SEQ ID NO:84 or to any one of the nucleotide sequences of the deposited cDNA clones contained in ATCC Deposit No. 209933, ATCC Deposit No. 209934, ATCC Deposit No. 98809, ATCC Deposit No. 326637, ATCC Deposit No. PTA-4611, or ATCC Deposit No. PTA-4610, respectively.

Further preferred embodiments are polynucleotides encoding de novo DNA cytosine methyltransferases and de novo DNA cytosine methyltransferase variants that have an amino acid sequence of the de novo DNA cytosine methyltransferase protein of SEQ ID NO:5, SEQ ID NO:6, SEQ ID NO:7, SEQ ID NO:8, SEQ ID NO:85, or SEQ ID NO:86 in which several, 1, 1-2, 1-3, 1-5 or 5-10 amino acid residues are substituted, deleted or added, in any combination.

Further preferred embodiments of the invention are polynucleotides that are at least 90% identical over their entire length to a polynucleotide encoding a de novo DNA cytosine methyltransferase polypeptide having the amino acid sequence set out in SEQ ID NO:5, SEQ ID NO:6, SEQ ID NO:7, SEQ ID NO:8, SEQ ID NO:85, or SEQ ID NO:86, and polynucleotides which are complementary to such polynucleotides. Most highly preferred are polynucleotides that comprise regions that are at least 90% identical over their entire length to a polynucleotide encoding the de novo DNA cytosine methyltransferase polypeptides of the ATCC deposited human DNMT3A and DNMT3A2 cDNA clones and polynucleotides complementary thereto, and 90% to 99% identical over their entire length to a polynucleotide encoding the de novo DNA cytosine methyltransferase polypeptides of the ATCC deposited human DNMT3B cDNA clone and polynucleotides complementary thereto. In this regard, polynucleotides at least 95% identical over their entire length to the same are particularly preferred, and those with at least 97% identity are especially preferred. Furthermore, those with at least 98% identity are highly preferred and with at least 99% identity being the most preferred.

In a more specific embodiment, the nucleic acid molecules of the present invention, e.g., isolated nucleic acids comprising a polynucleotide having a nucleotide sequence encoding a de novo DNA cytosine methyltransferase polypeptide or fragment thereof, are not the sequence of nucleotides, the nucleic acid molecules (e.g., clones), or the nucleic acid inserts identified in one or more of the below cited public EST or STS GenBank Accession Reports.

The following public ESTs were identified that relate to portions of SEQ ID NO:1: AA052791(SEQ ID NO:9); AA111043(SEQ ID NO:10); AA154890(SEQ ID NO:11); AA240794(SEQ ID NO:12); AA756653(SEQ ID NO:13); W58898(SEQ ID NO:14); W59299(SEQ ID NO:15); W91664(SEQ ID NO:16); W91665(SEQ ID NO:17); to portions of SEQ ID NO:2: AA116694 (SEQ ID NO:18); AA119979 (SEQ ID NO:19); AA177277 (SEQ ID NO:20); AA210568 (SEQ ID NO:21); AA399749 (SEQ ID NO:22); AA407106 (SEQ ID NO:23); AA575617 (SEQ ID NO:24); to portions of SEQ ID NO:3: AA004310 (SEQ ID NO:25); AA004399 (SEQ ID NO:26); AA312013 (SEQ ID NO:27); AA355824 (SEQ ID NO:28); AA533619 (SEQ ID NO:29); AA361360 (SEQ ID NO:30); AA364876 (SEQ ID NO:31); AA503090 (SEQ ID NO:32); AA533619 (SEQ ID NO:33); AA706672 (SEQ ID NO:34); AA774277 (SEQ ID NO:35); AA780277 (SEQ ID NO:36); H03349 (SEQ ID NO:37); H04031 (SEQ ID NO:38); H53133 (SEQ ID NO:39); H53239 (SEQ ID NO:40); H64669 (SEQ ID NO:41); N26002 (SEQ ID NO:42); N52936 (SEQ ID NO:43); N88352 (SEQ ID NO:44); N89594 (SEQ ID NO:45); R19795 (SEQ ID NO:46); R47511 (SEQ ID NO:47); T50235 (SEQ ID NO:48); T78023 (SEQ ID NO:49); T78186 (SEQ ID NO:50); W22886 (SEQ ID NO:51); W67657 (SEQ ID NO:52); W68094 (SEQ ID NO:53); W76111 (SEQ ID NO:54); Z38299 (SEQ ID NO:55); Z42012 (SEQ ID NO:56); and that relate to SEQ ID NO:4: AA206103(SEQ ID NO:57); AA206264(SEQ ID NO:58); AA216527(SEQ ID NO:59); AA216697(SEQ ID NO:60); AA305044(SEQ ID NO:61); AA477705(SEQ ID NO:62); AA477706(SEQ ID NO:63); AA565566(SEQ ID NO:64); AA599893(SEQ ID NO:65); AA729418(SEQ ID NO:66); AA887508(SEQ ID NO:67); F09856(SEQ ID NO:68); F12227(SEQ ID NO:69); N39452(SEQ ID NO:70); N48564 (SEQ ID NO:71); T66304(SEQ ID NO:72); and T66356 (SEQ ID NO:73); AA736582(SEQ ID NO:77); AA748883 (SEQ ID NO:78); AA923295(SEQ ID NO:79); AAI000396 (SEQ ID NO:80); AI332472(SEQ ID NO:81); W22473 (SEQ ID NO:82) and the I.M.A.G.E. Consortium clone ID 22089 (ATCC Deposit No. 326637)(SEQ ID NO:76). Additionally, STSs G06200(SEQ ID NO:74) and G15302(SEQ ID NO:75) were identified in a search with SEQ ID NOS.:3 and 4, respectively. All identified public sequences are hereby incorporated by reference.

Polynucleotides of the invention also include isoforms of the mouse Dnmt3a and human DNMT3A sequences disclosed herein which may arise through the use of an alternative promoter of the Dmnt3a or DNMT3A gene. For example, isoforms of mouse Dnmt3a arising through differential promoter usage include but are not limited to a polynucleotide represented by SEQ ID NO:83. Isoforms of human DNMT3A arising through differential promoter usage include but are not limited to the polynucloitde represented by SEQ ID NO:84.

The present invention is further directed to fragments of SEQ ID NO:1, 2, 3, 83 or 84, or to fragments of the cDNA nucleotide sequence found in ATCC Deposit Nos. 209933, 209934, 98809, PTA-4611, or PTA-4610. A fragment may be defined to be at least about 15 nt, and more preferably at least about 20 nt, still more preferably at least about 30 nt, and even more preferably, at least about 40 nt in length. Such fragments are useful as diagnostic probes and primers as discussed herein. Of course larger DNA fragments are also useful according to the present invention, as are fragments corresponding to most, if not all, of the nucleotide sequence of the cDNA clones contained in the plasmids deposited as ATCC Deposit No. 209933, ATCC Deposit No. 209934 ATCC Deposit No. 98809, ATCC Deposit No. PTA-4611, ATCC Deposit No. PTA-4610 or as shown in SEQ ID NO:1, SEQ ID NO:2, SEQ ID NO:3, SEQ ID NO:83, or SEQ ID NO:84. Generally, polynucleotide fragments of the invention may be defined algebraically in the following way: (a) for SEQ ID NO:1, as 15+N, wherein N equals zero or any positive integer up to 4176; (b) for SEQ ID NO:2, as 15+N, wherein N equals zero or any positive integer up to 4180; and (c) for SEQ ID NO:3, as 15+N, wherein N equals zero or any positive integer up to 4401; (d) for SEQ ID NO:83, as 15+N, wherein N equals zero or any positive integer up to 2303; (e) for SEQ ID NO:84, as 15+N, wherein N equals zero or any positive integer up to 2356. By a fragment at least 20 nt in length, for example, is intended fragments which include 20 or more contiguous bases from a nucleotide sequence of the ATCC deposited cDNAs or the nucleotide sequence as shown in SEQ ID NO:1, SEQ ID NO:2, SEQ ID NO:3, SEQ ID NO:83 or SEQ ID NO:84.

In a specific embodiment, the fragments of SEQ ID NO:1 and SEQ ID NO:2 are SEQ ID NO:83 and SEQ ID NO:84, respectively.

In another embodiment, the invention is directed to fragments of SEQ ID NO:4. Such fragments are defined as comprising the nucleotide sequence encoding the specific amino acid residues integral and immediately adjacent to the site where DNMT3B exons are spliced together. The DNMT3B sequence of SEQ ID NO:4 consists of 23 exon sequences defined accordingly: Exon 1 consists of nucleotides 1-108 of SEQ ID NO:4; Exon 2 consists of nucleotides 109-256 of SEQ ID NO:4; Exon 3 consists of nucleotides 257-318 of SEQ ID NO:4; Exon 4 consists of nucleotides 319-420 of SEQ ID NO:4; Exon 5 consists of nucleotides 421-546 of SEQ ID NO:4; Exon 6 consists of nucleotides 547-768 of SEQ ID NO:4; Exon 7 consists of nucleotides 769-927 of SEQ ID NO:4; Exon 8 consists of nucleotides 928-1035 of SEQ ID NO:4; Exon 9 consists of nucleotides 1036-1180 of SEQ ID NO:4; Exon 10 consists of nucleotides 1181-1240 of SEQ ID NO:4; Exon 11 consists of nucleotides 1241-1366 of SEQ ID NO:4; Exon 12 consists of nucleotides 1367-1411 of SEQ ID NO:4; Exon 13 consists of nucleotide 1412-1491 of SEQ ID NO:4; Exon 14 consists of nucleotides 1492-1604 of SEQ ID NO:4; Exon 15 consists of nucleotides 1605-1788 of SEQ ID NO:4; Exon 16 consists of nucleotides 1789-1873 of SEQ ID NO:4; Exon 17 consists of nucleotides 1874-2019 of SEQ ID NO:4; Exon 18 consists of nucleotides 2020-2110 of SEQ ID NO:4; Exon 19 consists of nucleotides 2111-2259 of SEQ ID NO:4; Exon 20 consists of nucleotides 2260-2345 of SEQ ID NO:4; Exon 21 consists of nucleotides 2346-2415 of SEQ ID NO:4; Exon 22 consists of nucleotides 2416-2534 of SEQ ID NO:4; and Exon 23 consists of nucleotides 2535-4145 of SEQ ID NO:4.

It should be understood by those skilled in the art that with regards to SEQ ID NO:4, Exon 1 and Exon 23 are herein defined for the purposes of the invention. The first nucleotide of Exon 1 may or may not be the transcriptional start site for the DNMT3B genomic locus, and the last nucleotide identified for Exon 23 may or may not reflect the last nucleotide transcribed in vivo.

Thus, by way of example, fragments of SEQ ID NO:4 comprise the following exon-exon junctions of 20 nucleotides in length: the exon1/exon 2 junction of nucleotides 98-118 of SEQ ID NO:4; the exon 2/exon 3 junction of nucleotides 246-266 of SEQ ID NO:4; the exon 3/exon 4 junction of nucleotides 308-328 of SEQ ID NO:4; the exon 4/exon 5 junction of nucleotides 410-430 of SEQ ID NO:4; the exon 5/exon 6 junction of nucleotides 536-556 of SEQ ID NO:4; the exon 6/exon 7 junction of nucleotides 758-778 of SEQ ID NO:4; the exon 7/exon 8 junction of nucleotides 917-937 of SEQ ID NO:4; the exon 8/exon 9 junction of nucleotides 1025-1045 of SEQ ID NO:4; the exon 9/exon 10 junction of nucleotides 1170-1190 of SEQ ID NO:4; the exon 10/exon 11 junction of nucleotides 1230-1250 of SEQ ID NO:4; the exon 11/exon 12 junction of nucleotides 1356-1376 of SEQ ID NO:4; the exon 12/exon 13 junction of nucleotides 1401-1421 of SEQ ID NO:4; the exon 13/exon 14 junction of nucleotides 1481-1501 of SEQ ID NO:4; the exon 14/exon 15 junction of nucleotides 1594-1614 of SEQ ID NO:4; the exon 15/exon 16 junction of nucleotides 1778-1798 of SEQ ID NO:4; the exon 16/exon 17 junction of nucleotides 1863-1883 of SEQ ID NO:4; the exon 17/exon 18 junction of nucleotides 2009-2029 of SEQ ID NO:4; the exon 18/exon 19 junction of nucleotides 2100-2120 of SEQ ID NO:4; the exon 19/exon 20 junction of nucleotides 2249-2269 of SEQ ID NO:4; the exon 20/exon 21 junction of nucleotides 2335-2355 of SEQ ID NO:4; the exon 21/exon 22 junction of nucleotides 2405-2425 of SEQ ID NO:4; and the exon 22/exon 23 junction of nucleotides 2524-2544 of SEQ ID NO:4.

As will be clear to those skilled in the art, other exon-exon junction fragments of SEQ ID NO:4 are possible which comprise 30, 40, 50, 60, 70, 80, 90, 100, 200, 300, 400, 500, etc., nucleotides of SEQ ID NO:4. For the purposes of constructing such fragments, the following exon-exon junctions are identified: the exon1/exon 2 junction of nucleotides 108 and 109 of SEQ ID NO:4; the exon 2/exon 3 junction of nucleotides 256 and 257 of SEQ ID NO:4; the exon 3/exon 4 junction of nucleotides 318 and 319 of SEQ ID NO:4; the exon 4/exon 5 junction of nucleotides 420 and 421 of SEQ ID NO:4; the exon 5/exon 6 junction of nucleotides 546 and 547 of SEQ ID NO:4; the exon 6/exon 7 junction of nucleotides 768 and 769 of SEQ ID NO:4; the exon 7/exon 8 junction of nucleotides 927 and 928 of SEQ ID NO:4; the exon 8/exon 9 junction of nucleotides 1035 and 1036 of SEQ ID NO:4; the exon 9/exon 10 junction of nucleotides 1180 and 1181 of SEQ ID NO:4; the exon 10/exon 11 junction of nucleotides 1240 and 1241 of SEQ ID NO:4; the exon 11/exon 12 junction of nucleotides 1366 and 1367 of SEQ ID NO:4; the exon 12/exon 13 junction of nucleotides 1411 and 1412 of SEQ ID NO:4; the exon 13/exon 14 junction of nucleotides 1491 and 1492 of SEQ ID NO:4; the exon 14/exon 15 junction of nucleotides 1604 and 1605 of SEQ ID NO:4; the exon 15/exon 16 junction of nucleotides 1788 and 1789 of SEQ ID NO:4; the exon 16/exon 17 junction of nucleotides 1873 and 1874 of SEQ ID NO:4; the exon 17/exon 18 junction of nucleotides 2019 and 2020 of SEQ ID NO:4; the exon 18/exon 19 junction of nucleotides 2110 and 2111 of SEQ ID NO:4; the exon 19/exon 20 junction of nucleotides 2259 and 2260 of SEQ ID NO:4; the exon 20/exon 21 junction of nucleotides 2345 and 2346 of SEQ ID NO:4; the exon 21/exon 22 junction of nucleotides 2415 and 2416 of SEQ ID NO:4; and the exon 22/exon 23 junction of nucleotides 2534 and 2535 of SEQ ID NO:4. Junction nucleotides may be located at any position of the selected SEQ ID NO:4 fragment.

The present invention further relates to polynucleotides that hybridize to the above-described sequences. In this regard, the present invention especially relates to polynucleotides that hybridize under stringent conditions to the above-described polynucleotides. As herein used, the term "stringent conditions" means hybridization will occur only if there is at least 90% and preferably at least 95% identity and more preferably at least 97% identity between the sequences.

Furthermore, a major consideration associated with hybridization analysis of DNA or RNA sequences is the degree of relatedness the probe has with the sequences present in the specimen under study. This is important with a blotting technique (e.g., Southern or Northern Blot), since a moderate degree of sequence homology under nonstringent conditions of hybridization can yield a strong signal even though the probe and sequences in the sample represent non-homologous genes.

The particular hybridization technique is not essential to the invention, any technique commonly used in the art is within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5 M sodium chloride, 0.15 M sodium citrate, pH 7.0), 5× Denhardt's (1× Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C. Additionally, if hybridization is to an immobilized nucleic acid, a washing step may be utilized wherein probe binding to polynucleotides of low homology, or nonspecific binding of the probe, may be removed. For example, a stringent wash step may involve a buffer of 0.2×SSC and 0.5% SDS at a temperature of 65° C.

Additional information related to hybridization technology and, more particularly, the stringency of hybridization and washing conditions may be found in Sambrook et al., *Molecular Cloning: A Laboratory Manual*, Second Edition, Cold Spring Harbor Laboratory, Cold Spring Harbor, N.Y. (1989), which is incorporated herein by reference.

Polynucleotides of the invention which are sufficiently identical to a nucleotide sequences contained in SEQ ID NO:1, SEQ ID NO:2, SEQ ID NO:3, SEQ ID NO:4, SEQ ID NO:83 or SEQ ID NO:84 or in the cDNA inserts of ATCC Deposit No. 209933, ATCC Deposit No. 209934, ATCC Deposit No. 98809, ATCC Deposit No. 326637, ATCC Deposit No. PTA-4611 or ATCC Deposit No. PTA-4610 may be used as hybridization probes for cDNA and genomic DNA, to isolate full-length cDNAs and genomic clones encoding de novo DNA cytosine methyltransferase proteins and to isolate cDNA and genomic clones of other genes that have a high sequence similarity to the de novo DNA cytosine methyltransferase genes. Such hybridization techniques are known to those of skill in the art. Typically, these nucleotide sequences are at least about 90% identical, preferably at least about 95% identical, more preferably at least about 97%, 98% or 99% identical to that of the reference. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

The present invention also provides isolated polynucleotides encoding a mouse Dnmt3a2 and human DNMT3A2 promoter regions as set forth in SEQ ID NO:118 and SEQ ID NO:119, respectively, that is capable of directing expression of mouse and human de novo cytosine methyltransferases. The present invention further provides a nucleic acid construct or vector, comprising a mouse Dnmt3a2 or human DNMT3A2 promoter having a nucleotide sequence of SEQ ID NO:118 or 119, respectively, or an operative fragment thereof having promoter activity, and host cells harboring the same.

In some embodiments, the promoter sequence can be modified by the addition of sequences, such as enhancers, or deletions of nonessential and/or undesired sequences. The promoter sequences can be sufficiently similar to that of the native promoter to provide for the desired specificity of transcription of a DNA sequence of interest. The promoter sequences can include natural and synthetic sequences as well as sequences which may be a combination of synthetic and natural sequences.

The present invention is further directed to isolated polynucleotides comprising promoter fragments of mouse Dnmt3a2. Such fragments include nucleotides 1-100, 1-80, 1-60, 1-35, 10-100, 20-100 and 40-100 of SEQ ID NO:118. Other fragments include nucleotides 1-722, 449-699, 460-660, 475-640, 485-620, 490-600, 500-590, 525-575, 449-690, 449-670, 449-630, 449-590, 449-550, 449-530, 460-699, 480-699, 510-699, 530-699, 550-699, 590-699, 620-699, 600-1150, 650-1100, 700-1050, 750-1050, 1530-1840, 1550-1800, 1550-1770, 1550-1760, 1550-1700, 1550-1680, 1550-1640, 1550-1600, 1575-1840, 1600-1840, 1620-1840, 1650-1840, 1700-1840, 1730-1840, 1770-1840, 1790-1840, 1500-2095, 1530-2095, 1570-2095, 1620-2095, 1650-2095, 1690-2095, 1720-2095, 1750-2095, 1790-2095, 1820-2095, 1900-2095, 2000-2095, 1500-2070, 1550-2025, 1550-2000, 1550-1975, 1550-1950, 1550-1940, 1550-1900, 1550-1870 and 1550-1830 of SEQ ID NO:118.

The present invention further relates to isolated polynucleotides comprising promoter sequence fragments of human DNMT3A2. Such fragments include nucleotides 1-100, 1-80, 1-60, 1-35, 10-100, 20-100 and 40-100 of SEQ ID NO:119. Other fragments include nucleotides 400-700, 450-690, 475-660, 485-640, 490-620, 500-600, 525-595, 400-690, 450-670, 450-630, 450-590, 450-550, 450-530, 450-699, 450-699, 500-700, 530-700, 550-700, 590-700, 620-700, 600-925, 650-875, 700-800, 750-800, 1280-1586, 1300-1550, 1300-1520, 1300-1490, 1300-1450, 1300-1420, 1300-1390, 1300-1350, 1325-1590, 1350-1580, 1370-1580, 1400-1580, 1440-1580, 1480-1580, 1520-1590, 1540-1580, 1500-1850, 1530-1850, 1570-1850, 1620-1850, 1650-1850, 1690-1850, 1720-1850 1475-1530, 1480-1520, 1490-1520, 1495-1520, 1724-2065, 1740-2055, 1760-2070, 1770-2050, 1790-2035, 1800-2020, 1820-2000, 1825-1990, 1845-1980, 1860-1950, 1870-1920 and 1890-1910.

In some embodiments, the invention provides isolated polynucleotides at least 50% identical, preferably 55%, 65%, 70%, 75%, 80%, 85%, 90%, 91%, 92%, 93%, 94%, 95%, 96%, 97%, 98%, 99%, or 100% identical to polynucleotide sequences encoding the Dnmt3a2 promoter sequence in SEQ ID NO:118 or 119, wherein the polynucleotide sequence has Dnmt3a2 promoter activity in embryonic stem cells.

In other embodiments, the invention provides isolated polynucleotide sequence of SEQ ID NO:118, SEQ ID NO:119, or a fragment thereof that has promoter activity, operatively linked, in a transcriptional unit, to a DNA sequence encoding a protein of interest. In one embodiment, the DNA sequence encodes a protein of interest selected from the group consisting of SEQ ID NO:5, 6, 7, 8, 85, 86 and fragments thereof. In some embodiments, the DNA sequence encodes a polypeptide fragment of SEQ ID NO:5, 6, 7, 8, 85 or 86 that possesses wild-type protein activity. In other embodiments, the DNA sequence encodes a polypeptide fragment of SEQ ID NO:5, 6, 7, 8, 85 or 86 that is a dominant negative mutant that inhibits endogenous de novo cytosine methyltransferase activity. In other embodiments, the DNA sequence operatively linked to the promoter sequences can be a reporter gene. The reporter gene can encode a fluorescent or light-emitting protein such as green fluorescent protein, yellow fluorescent protein, blue fluorescent protein, phycobiliprotein, luciferase, or apoaequorin. In other embodiments, the reporter gene can encode B-galactosidase or chloramphenicol acetyltransferase.

The promoter sequences as described herein are particularly useful for directing expression of operably linked genes in mammalian cells. In a preferred embodiment, the promoter sequences are used to direct expression of transgenes in stem cells. In other embodiments, the cells are embryonic cells. In another embodiment, the cells are cancer cells.

III. Vectors, Host Cells, and Recombinant Expression

The present invention also relates to vectors that comprise a polynucleotide of the present invention, host cells which are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems for polynucleotides of the invention. Introduction of polynucleotides into host cells can be effected by methods described in many standard laboratory manuals, such as Sambrook et al., *Molecular Cloning: A Laboratory Manual*, 2nd Ed., Cold Spring Harbor Laboratory Press, Cold Spring Harbor, N.Y. (1989). For example, calcium phosphate transfection, DEAE-dextran mediated transfection, transvection, microinjection, cationic lipid-mediated transfection, electroporation, transduction, scrape loading, ballistic introduction, infection or any other means known in the art may be utilized.

Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophages, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *Molecular Cloning: A Laboratory Manual* (supra).

RNA vectors may also be utilized for the expression of the de novo DNA cytosine methyltransferases disclosed in this invention. These vectors are based on positive or negative strand RNA viruses that naturally replicate in a wide variety of eukaryotic cells (Bredenbeek, P. J. and Rice, C. M., Virology 3: 297-310, (1992)). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11: 18-22, (1993); Frolov, I., et al., *Proc. Natl. Acad. Sci. (USA)* 93: 11371-11377, (1996)). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

As used herein, the term "operably linked," when used in the context of a linkage between a structural gene and an expression control sequence, e.g., a promoter, refers to the position and orientation of the expression control sequence relative to the structural gene so as to permit expression of the structural gene in any host cell. For example, an operable linkage would maintain proper reading frame and would not introduce any in frame stop codons.

As used herein, the term "heterologous promoter," refers to apromoternot normally and naturally associated with the structural gene to be expressed. For example, in the context of expression of a de novo DNA cytosine methyltransferase polypeptide, a heterologous promoter would be any promoter other than an endogenous promoter associated with the de novo DNA cytosine methyltransferase gene in non-recombinant mouse or human chromosomes. In specific embodiments of this invention, the heterologous promoter is a prokaryotic or bacteriophage promoter, such as the lac promoter, T3 promoter, or T7 promoter. In other embodiments, the heterologous promoter is a eukaryotic promoter.

In other embodiments, this invention provides an isolated nucleic acid molecule comprising a de novo DNA cytosine methyltransferase structural gene operably linked to a heterologous promoter. As used herein, the term "a de novo DNA cytosine methyltransferase structural gene" refers to a nucleotide sequence at least about 90% identical to one of the following nucleotide sequences:

(a) a nucleotide sequence encoding the de novo DNA cytosine methyltransferase polypeptide having the complete amino acid sequence in SEQ ID NO:5, SEQ ID NO:6, SEQ ID NO:7, SEQ ID NO:85 or SEQ ID NO:86;

(b) a nucleotide sequence encoding the de novo DNA cytosine methyltransferase polypeptide having the complete amino acid sequence encoded by the cDNA insert of ATCC Deposit No. 209933, ATCC Deposit No. 209934, ATCC Deposit No.98809, ATCC Deposit No. PTA-4611, or ATCC Deposit No. PTA-4610; or (c) a nucleotide sequence complementary to any of the nucleotide sequences in (a) or (b).

In preferred embodiments, the de novo DNA cytosine methyltransferase structural gene is 90%, and more preferably 91%, 92%, 93%, 94%, 95%, 97%, 98%, 99%, or 100% identical to one or more of nucleotide sequences (a), (b), or (c) supra.

In another embodiment the term "a de novo DNA cytosine methyltransferase structural gene" refers to a nucleotide sequence about 90% to 99% identical to one of the following nucleotide sequences:

(a) a nucleotide sequence encoding the de novo DNA cytosine methyltransferase polypeptide having the complete amino acid sequence in SEQ ID NO:8;

(b) a nucleotide sequence encoding the de novo DNA cytosine methyltransferase polypeptide having the complete amino acid sequence encoded by the cDNA insert of ATCC Deposit No. 326637; or (c) a nucleotide sequence complementary to any of the nucleotide sequences in (a) or (b).

In preferred embodiments, the de novo DNA cytosine methyltransferase structural gene is 90%, and more preferably 91%, 92%, 93%, 94%, 95%, 97%, 98%, or 99% identical to SEQ ID NO:8, ATCC Deposit No. 326637 or polynucleotides complementary thereto.

This invention also provides an isolated nucleic acid molecule comprising a de novo DNA cytosine methyltransferase structural gene operably linked to a heterologous promoter, wherein said isolated nucleic acid molecule does not encode a fusion protein comprising the de novo DNA cytosine methyltransferase structural gene or a fragment thereof.

This invention further provides an isolated nucleic acid molecule comprising a de novo DNA cytosine methyltransferase structural gene operably linked to a heterologous promoter, wherein said isolated nucleic acid molecule is capable of expressing a de novo DNA cytosine methyltransferase polypeptide when used to transform an appropriate host cell.

This invention also provides an isolated nucleic acid molecule comprising a polynucleotide having a nucleotide sequence at least 90%, 91%, 92%, 93%, 94%, 95%, 96%, 97%, 98%, 99%, or 100% identical to a sequence encoding a de novo DNA cytosine methyltransferase, polypeptide having the amino acid sequence of SEQ ID NO:5, SEQ ID NO:6, SEQ ID NO:7, SEQ ID NO:8, SEQ ID NO:85 or SEQ ID NO:86 wherein said isolated nucleic acid molecule does not contain a nucleotide sequence at least 90% identical to the 3' untranslated region of SEQ ID NO:1 (nucleotides 2942-4191), SEQ ID NO:2 (nucleotides 2847-4174), SEQ ID NO:3 (nucleotides 3090-4397), SEQ ID NO:4 (nucleotides 2677-4127), SEQ ID NO:83 (nucleotides 2215-2318) or SEQ ID NO:84 (nucleotides 2274-2371) or a fragment of the 3' untranslated region greater than 25, 50, 75, 100, or 125 bp in length.

This invention further provides an isolated nucleic acid molecule comprising a polynucleotide having a nucleotide sequence at least 90%, 91%, 92%, 93%, 94%, 95%, 96%, 97%, 98%, 99%, or 100% identical to a sequence encoding a de novo DNA cytosine methyltransferase polypeptide having the amino acid sequence of SEQ ID NO:5, SEQ ID NO:6, SEQ ID NO:7 or SEQ ID NO:8, SEQ ID NO:85 or SEQ ID NO:86 wherein said isolated nucleic acid molecule does not contain a nucleotide sequence at least 90% identical to the 5' untranslated region of SEQ ID NO:1 (nucleotides 1-216), SEQ ID NO:2 (nucleotides 1-268), SEQ ID NO:3 (nucleotides 1-352), SEQ ID NO:4 (nucleotides 1-114), SEQ ID NO:83 (nucleotides 1-147) or SEQ ID NO:84 (nucleotides 1-216) or a fragment of the 5' untranslated region greater than 25, 35, 45, 55, 65, 75, 85, or 90 baseband processor/MAC.

Suitable known prokaryotic promoters for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), adenovirus promoter, Herpes virus promoter, and metallothionein promoters, such as the mouse metallothionein-I promoter and tissue and organ-specific promoters known in the art.

If the de novo DNA cytosine methyltransferase polypeptide is to be expressed for use in screening assays, generally, it is preferred that the polypeptide be produced at the surface of the cell. In this event, the cells may be harvested prior to use in the screening assay. If de novo DNA cytosine methyltransferase polypeptide is secreted into the medium, the medium can be recovered in order to recover and purify the polypeptide; if produced intracellularly, the cells must first be lysed before the polypeptide is recovered.

De novo DNA cytosine methyltransferase polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

IV. Polypeptides of the Invention

The de novo DNA cytosine methyltransferase polypeptides of the present invention include the polypeptide of SEQ ID NO:5, SEQ ID NO:6, SEQ ID NO:7, SEQ ID NO:8, SEQ ID NO:85 or SEQ ID NO:86 as well as polypeptides and fragments which have activity and have at least 90% identity to the polypeptide of SEQ ID NO:5, SEQ ID NO:6, SEQ ID NO:7, SEQ ID NO:8, SEQ ID NO:85 or SEQ ID NO:86, or the relevant portion and more preferably at least 96%, 97% or 98% identity to the polypeptide of SEQ ID NO:5, SEQ ID NO:6, SEQ ID NO:7, SEQ ID NO:8, SEQ ID NO:85 or SEQ ID NO:86, and still more preferably at least 91%, 92%, 93%, 94%, 95%, 96%, 97%, 98%, 99%, or 100% identity to the polypeptide of SEQ ID NO:5, SEQ ID NO:6, SEQ ID NO:7, SEQ ID NO:8, SEQ ID NO:85 or SEQ ID NO:86.

The polypeptides of the present invention are preferably provided in an isolated form.

The polypeptides of the present invention include the polypeptide encoded by the deposited cDNAs; a polypeptide comprising amino acids from about 1 to about 908 in SEQ ID NO:5; a polypeptide comprising amino acids from about 1 to about 859 in SEQ ID NO:6; a polypeptide comprising amino acids from about 1 to about 912 in SEQ ID NO:7, a polypeptide comprising amino acids from about 1 to about 853 in SEQ ID NO:8, a polypeptide comprising amino acids from about 1 to about 689 in SEQ ID NO:85, and a polypeptide comprising amino acids from about 1 to about 689 in SEQ ID NO:86 as well as polypeptides which are at least about 90% identical, and more preferably at least about 91%, 92%, 93%, 94%, 95%, 96%, 97%, 98%, 99%, or 100% identical to the polypeptides described above and also include portions of such polypeptides with at least 30 amino acids and more preferably at least 50 amino acids.

Polypeptides of the invention also include alternative splicing variants of the Dnmt3 sequences disclosed herein. For example, alternative variant spliced proteins of mouse Dnmt3b include but are not limited to a polypeptide wherein, except for at least one conservative amino acid substitution, said polypeptide has a sequence selected from the group consisting of: (1) amino acid residues 1 to 362 and 383 to 859 from SEQ ID NO:2; and (2) amino acid residues 1 to 362 and 383 to 749 and 813 to 859 from SEQ ID NO:2; and alternative variant spliced proteins of human DNMT3B include but are not limited to a polypeptide wherein, except for at least one conservative amino acid substitution, said polypeptide has a sequence selected from the group consisting of: (1) amino acid residues 1 to 355 and 376 to 853 from SEQ ID NO:4; and (2) amino acid residues 1 to 355 and 376 to 743 and 807 to 853 from SEQ ID NO:4.

Polypeptides of the invention also include isoforms of mouse Dnmt3a and human DNMT3A disclosed herein which may arise through the use of an alternative promoter of the Dnmt3a or DNMT3A gene. For example, isoforms of mouse Dnmt3a arising through differential promoter usage include but are not limited to a polypeptide wherein, except for at least one conservative amino acid substitution, said polypeptide has the sequence encoded by SEQ ID NO:84. Isoforms of human DNMT3A arising through differential promoter usage include but are not limited to a polypeptide wherein, except for at least one conservative amino acid substitution, said polypeptide has the sequence encoded by SEQ ID NO:85.

The de novo DNA cytosine methyltransferase polypeptides may be a part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

Biologically active fragments of the de novo DNA cytosine methyltransferase polypeptides are also included in the invention. A fragment is a polypeptide having an amino acid sequence that entirely is the same as part but not all of the amino acid sequence of one of the aforementioned de novo DNA cytosine methyltransferase polypeptides. As with de novo DNA cytosine methyltransferase polypeptides, fragments may be "free-standing," or comprised within a larger polypeptide of which they form a part or region, most preferably as a single continuous region. In the context of this invention, a fragment may constitute from about 10 contiguous amino acids identified in SEQ ID NO:5, SEQ ID NO:6, SEQ ID NO:7, SEQ ID NO:8, SEQ ID NO:85, or SEQ ID NO:86. More specifically, polypeptide fragment lengths may be defined algebraically as follows: (a) for SEQ ID NO:5, as 10+N, wherein N equals zero or any positive integer up to 898; (b) for SEQ ID NO:6, as 10+N, wherein N equals zero or any positive integer up to 849; (c) for SEQ ID NO:7, as 10+N, wherein N equals zero or any positive integer up to 902; (d) for SEQ ID NO:8, as 10+N, wherein N equals zero or any positive integer up to 843; (e) for SEQ ID NO:85, as 10+N, wherein N equals zero or any positive integer up to 679; and (f) for SEQ ID NO:86, as 10+N, wherein N equals zero or any positive integer up to 679.

Preferred fragments include, for example, truncation polypeptides having the amino acid sequence of de novo DNA cytosine methyltransferase polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate protein activity, including those with a similar activity or an improved activity, or with a decreased undesirable activity. Also included are those that are antigenic or immunogenic in an animal, especially in a human.

In a specific embodiment, the polypeptide fragments are SEQ ID NO:85 and SEQ ID NO:86.

Thus, the polypeptides of the invention include polypeptides having an amino acid sequence at least 90% identical to that of SEQ ID NO:5, SEQ ID NO:6, SEQ ID NO:7, SEQ ID NO:8, SEQ ID NO:85 or SEQ ID NO:86 or fragments thereof with at least 90% identity to the corresponding fragment of SEQ ID NO:5, SEQ ID NO:6, SEQ ID NO:7 or SEQ ID NO:8, SEQ ID NO:85 or SEQ ID NO:86, all of which retain the biological activity of the de novo DNA cytosine methyltransferase protein, including antigenic activity. Included in this group are variants of the defined sequence and fragment. Preferred variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. Particularlypreferred are variants in which several, 5 to 10, 1 to 5, or 1 to 2 amino acids are substituted, deleted, or added in any combination.

The de novo DNA cytosine methyltransferase polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

V. In Vitro DNA Methylation

One preferred embodiment of the invention enables the in vitro methylation at the C5 position of cytosine in DNA. The starting substrate DNA may be hemimethylated (i.e., one strand of the duplex DNA is methylated) or may lack methylation completely. The polypeptides of the invention, being de novo DNA cytosine methyltransferases, are uniquely suited to the latter function, owing to the fact that, unlike maintenance methyltransferases, their preferred substrate is not hemimethylated DNA.

As exemplified in Examples 4 and 5, isolated polypeptides of the invention function as in vitro DNA methyltransferases when combined in an appropriately buffered solution with the appropriate cofactors and a substrate DNA. The substrate DNA may be selected from any natural source, e.g., genomic DNA, or a recombinant source such as a DNA fragment amplified by the polymerase chain reaction. The substrate DNA maybe prokaryotic or eukaryotic DNA. In a preferred embodiment, the substrate DNA is mammalian DNA, and most preferredly, the substrate DNA is human DNA.

It will be well appreciated by those in the art that in vitro methylation of DNA may be used to direct or regulate the expression of said DNA in a biological system. For example, over-expression, under-expression or lack of expression of a particular native DNA sequence in a host cell or organism may be attributed to the fact that the DNA is under-methylated (hypomethylated) or not methylated. Thus, in vitro methylation of a recombinant form of said DNA, and the subsequent introduction of the methylated, recombinant DNA into the cell or organism, may effect an increase or decrease in the expression of the encoded polypeptide.

Also, it will be readily apparent to the skilled artisan that the in vitro methylation pattern will be maintained after introduction into a biological system by the action of maintenance methyltransferase polypeptides in said system.

In one embodiment of the invention, the biological system selected for the introduction of in vitro methylated DNA may be prokaryotic or eukaryotic. In a preferred embodiment, the biological system is mammalian, and the most preferred embodiment is when the biological system is human.

Methods for introducing the in vitro methylated DNA into the biological system are well known in the art, and the skilled artisan will recognize that the in vitro methylation of DNA may be a preliminary step to any system of gene therapy detailed herein.

VI. Genetic Screening and Diagnostic Assays

To map the human chromosome locations, the GenBank STS database was searched using Dnmt3a and Dnmt3b sequences as queries. The search identified markers WI-6283 (GenBank Accession number G06200) and SHGC-15969 (GenBank Accession number G15302) as matching the cDNA sequence of Dnmt3a and Dnmt3b, respectively. WI-6283 has been mapped to 2p23 between D2S171 and D2S174 (48-50 cM) on the radiation hybrid map by Whitehead Institute/MIT Center for Genome Research. The corresponding mouse chromosome location is at 4.0 cM on chromosome 12. SHGC-15969 has been mapped to 20 pl 1.2 between D20S184 and D20S106 (48-50 cM) by Stanford Human Genome Center. The corresponding mouse chromosome locus is at 84.0 cM on chromosome 2.

These data are valuable as markers to be correlated with genetic map data. Such data are found, for example, in V. McKusick, Mendelian Inheritance in Man (available on-line through Johns Hopkins, University Welch Medical Library). The relationship between genes and diseases that have been mapped to the same chromosomal region are then identified through linkage analysis (coinheritence of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

This invention also relates to the use of de novo DNA cytosine methyltransferase polynucleotides for use as diagnostic reagents. Detection of a mutated form of a de novo DNA cytosine methyltransferase gene associated with a dysfunction will provide a diagnostic tool that can add to or define a diagnosis of a disease or susceptibility to a disease which results from under-expression, over-expression or altered expression of the mutated de novo DNA cytosine methyltransferase. Individuals carrying mutations in one or more de novo DNA cytosine methyltransferase genes may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled de novo DNA cytosine methyltransferase nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers, et al., *Science* 230:1242 (1985)). Sequence changes at specific locations may also be revealed by nuclease protection assays, such as RNase and S1 protection or the chemical cleavage method (see Cotton, et al., *Proc. Natl. Acad. Sci. USA* 85:4397-4401 (1985)).

The diagnostic assays offer a process for diagnosing or determining a susceptibility to neoplastic disorders through detection of mutations in one or more de novo DNA cytosine methyltransferase genes by the methods described.

In addition, neoplastic disorders may be diagnosed by methods that determine an abnormally decreased or increased level of de novo DNA cytosine methyltransferase polypeptide or de novo DNA cytosine methyltransferase mRNA in a sample derived from a subject. Decreased or increased expression may be measured at the RNA level using any of the methods well known in the art for the quantitation of polynucleotides; for example, RT-PCR, RNase protection, Northern blotting and other hybridization methods may be utilized. Assay techniques that may be used to determine the level of a protein, such as an de novo DNA cytosine methyltransferase protein, in a sample derived from a host are well known to those of skill in the art. Such assay methods include radioimmunoassays, competitive-binding assays, Western blot analysis and ELISA assays.

Additionally, methods are provided for diagnosing or determining a susceptibility of an individual to neoplastic disorders, comprising (a) assaying the de novo DNA cytosine methyltransferase protein gene expression level in mammalian cells or body fluid; and (b) comparing said de novo DNA cytosine methyltransferase protein gene expression level with a standard de novo DNA cytosine methyltransferase protein gene expression level whereby an increase or decrease in said de novo DNA cytosine methyltransferase gene expression level over said standard is indicative of an increased or decreased susceptibility to a neoplastic disorder.

VII. De novo DNA Cytosine Methyltransferase Antibodies

The polypeptides of the invention or their fragments or analogs thereof, or cells expressing them may also be used as immunogens to produce antibodies immunospecific for the de novo DNA cytosine methyltransferase polypeptides. By "immunospecific" is meant that the antibodies have affinities for the polypeptides of the invention that are substantially greater in their affinities for related polypeptides such as the analogous proteins of the prior art.

Antibodies generated against the de novo DNA cytosine methyltransferase polypeptides can be obtained by administering the polypeptides or epitope bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature 256:495-497 (1975)), the trioma technique, the human B-cell hybridoma technique (Kozbor, et al., *Immunology Today* 4:72 (1983)) and the EBV-hybridoma technique (Cole, et al., *Monoclonal Antibodies and Cancer Therapy*, pp. 77-96, Alan R. Liss, Inc., (1985)).

Techniques for the production of single chain antibodies (U.S. Pat. No. 4,946,778) may also be adapted to produce single chain antibodies to polypeptides of this invention. Also, transgenic mice, or other organisms including other mammals, may be used to express humanized antibodies.

The above-described antibodies maybe employed to isolate or to identify clones expressing the polypeptide or to purify the polypeptides by affinity chromatography.

Antibodies against de novo DNA cytosine methyltransferase polypeptides may also be employed to treat neoplastic disorders, among others.

VIII. Agonist and Antagonist Screening

The de novo DNA cytosine methyltransferase polypeptides of the present invention maybe employed in a screening process for compounds which bind one of the proteins and which activate (agonists) or inhibit activation of (antagonists) one of the polypeptides of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics (see Coligan, et al., *Current Protocols in Immunology* 1(2):Chapter 5 (1991)).

By "agonist" is intended naturally occurring and synthetic compounds capable of enhancing a de novo DNA cytosine methyltransferase activity (e.g., increasing the rate of DNA methylation). By "antagonist" is intended naturally occurring and synthetic compounds capable of inhibiting a de novo DNA cytosine methyltransferase activity.

DNA methylation is an important, fundamental regulatory mechanism for gene expression, and, therefore, the methylated state of a particular DNA sequence may be associated with many pathologies. Accordingly, it is desirous to find both compounds and drugs which stimulate de novo DNA cytosine methyltransferase activity and which can inhibit the function of de novo DNA cytosine methyltransferase protein. In general, agonists are employed for therapeutic and prophylactic purposes including the treatment of ceratin types of neoplastic disorders. For example, de novo methylation of growth regulatory genes in somatic tissues is associated with tumorigenesis in humans (Laird, P. W. and Jaenisch, R. *Ann. Rev. Genet*. 30:441-464 (1996); Baylin, S. B. et al., *Adv. Cancer. Res*. 72:141-196 (1998); and Jones, P. A. and Gonzalgo, M. L. *Proc. Natl. Acad. Sci. USA* 94:2103-2105 (1997)).

In general, such screening procedures involve producing appropriate cells which express the polypeptide of the present invention. Such cells include cells from mammals, yeast, *Drosophila* or *E. coli*. Cells expressing the protein (or cell membrane containing the expressed protein) are then contacted with a test compound to observe binding, stimulation or inhibition of a functional response.

Alternatively, the screening procedure may be an in vitro procedure in which the activity of isolated DNMT3 protein is tested in the presence of a potential agonist or antagonist of DNMT3 de novo DNA cytosine. methyltransferase activity. Such in vitro assays are known to those skilled in the art, and by way of example are demonstrated in Example 4 and 5.

The assays may simply test binding of a candidate compound wherein adherence to the cells bearing the protein is detected by means of a label directly or indirectly associated with the candidate compound or in an assay involving competition with a labeled competitor. Further, these assays may test whether the candidate compound affects activity of the protein, using detection systems appropriate to the cells bearing the protein at their surfaces. Inhibitors of activation are generally assayed in the presence of a known agonist and the effect on activation by the agonist in the presence of the candidate compound is observed. Standard methods for conducting such screening assays are well understood in the art.

Examples of potential de novo DNA cytosine methyltransferase protein antagonists include antibodies or, in some cases, oligonucleotides or proteins which are closely related to the substrate of the de novo DNA cytosine methyltransferase protein, e.g., small molecules which bind to the protein so that the activity of the protein is prevented.

IX. Gene Therapy Applications

For overview of gene therapy, see Strachan, T. & Read A. P., Chapter 20, "Gene Therapy and Other Molecular Genetic-based Therapeutic Approaches," (and references cited therein) in *Human Molecular Genetics*, BIOS Scientific Publishers Ltd. (1996).

Initial research in the area of gene therapy focused on a few well-characterized and highly publicized disorders: cystic fibrosis (Drumm, M. L. et al., *Cell* 62:1227-1233 (1990); Gregory, R. J. et al., *Nature* 347:358-363 (1990); Rich, D. P. et al., *Nature* 347:358-363 (1990)); and Gaucher disease (Sorge, J. et al., *Proc. Natl. Acad. Sci.* (*USA*) 84:906-909 (1987); Fink, J. K. et al., *Proc. Natl. Acad. Sci.* (*USA*) 87:2334-2338 (1990)); and certain forms of hemophilia-Bontempo, F. A. et al., *Blood* 69:1721-1724 (1987); Palmer, T. D. et al., *Blood* 73:438-445 (1989); Axelrod, J. H. et al., *Proc. Natl. Acad. Sci.* (*USA*) 87:5173-5177 (1990); Armentano, D. et al., *Proc. Natl. Acad. Sci.* (*USA*) 87:6141-6145 (1990)); and muscular dystrophy (Partridge, T. A. et al., *Nature* 337:176-179 (1989); Law, P. K. et al., *Lancet* 336: 114-115 (1990); Morgan, J. E. et al., *J. Cell Biol*. 111:2437-2449 (1990)).

More recently, the application of gene therapy in the treatment of a wider variety of disorders is progressing, for example: cancer (Runnebaum, I. B., *Anticancer Res*. 17(4B): 2887-2890, (1997)), heart disease (Rader, D. J., *Int. J Clin. Lab. Res*. 27(1): 35-43, (1997); Malosky, S., *Curr. Opin. Cardiol*. 11(4): 361-368, (1996)), central nervous system disorders and injuries (Yang, K., et al., *Neurotrauma J*. 14(5): 281-297, (1997); Zlokovic, B. V., et al., *Neurosur-* gery 40(4): 789-803, (1997); Zlokovic, B. V., et al., *Neurosurgery* 40(4): 805-812, (1997)), vascular diseases (Clowes, A. W., *Thromb. Haemost.* 78(1): 605-610, 1997), muscle disorders (Douglas, J. T., et al., *Neuromuscul. Disord.* 7(5): 284-298, (1997); Huard, J., et al., *Neuromuscul. Disord.* 7(5): 299-313, (1997)), rheumatoid arthritis (Evans, C. H., et al., *Curr. Opin. Rheumatol.* 8(3): 230-234, (1996)) and epithelial tissue disorders (Greenhalgh, D.A., et al., *Invest Dermatol. J.* 103(5 Suppl.): 63S-93S, (1994)).

In a preferred approach, one or more isolated nucleic acid molecules of the invention are introduced into or administered to the animal. Such isolated nucleic acid molecules may be incorporated into a vector or virion suitable for introducing the nucleic acid molecules into the cells or tissues of the animal to be treated, to form a transfection vector. Techniques for the formation of vectors or virions comprising the de novo DNA cytosine methyltransferase-encoding nucleic acid molecules are well known in the art and are generally described in "Working Toward Human Gene Therapy," Chapter 28 in *Recombinant DNA*, 2nd Ed., Watson, J. D. et al., eds., New York: Scientific American Books, pp. 567-581 (1992). An overview of suitable vectors or virions is provided in an article by Wilson, J. M. (*Clin. Exp. Immunol.* 107(Suppl. 1): 31-32, (1997)). Such vectors are derived from viruses that contain RNA (Vile, R. G., et al., *Br. Med Bull.* 51(1): 12-30, (1995)) or DNA (Ali M., et al., *Gene Ther.* 1(6): 367-384, (1994)). Example vector systems utilized in the art include the following: retroviruses (Vile, R. G., supra.), adenoviruses (Brody, S. L. et al., *Ann. N.Y Acad. Sci.* 716: 90-101, (1994)), adenoviral/retroviral chimeras (Bilbao, G., et al., *FASEB J.* 11(8): 624-634, (1997)), adeno-associated viruses (Flotte, T. R. and Carter, B. J., *Gene Ther.* 2(6): 357-362, (1995)), herpes simplex virus (Latchman, D. S., *Mol. Biotechnol.* 2(2): 179-195, (1994)), Parvovirus (Shaughnessy, E., et al., *Semin Oncol.* 23(1): 159-171, (1996)) and reticuloendotheliosis virus (Donburg, R., *Gene Therap.* 2(5): 301-310, (1995)). Also of interest in the art, the development of extrachromosomal replicating vectors for gene therapy (Calos, M. P., *Trends Genet.* 12(11): 463-466, (1996)).

Other, nonviral methods for gene transfer known in the art (Abdallah, B. et al., *Biol. Cell* 85(1): 1-7, (1995)) might be utilized for the introduction of de novo DNA cytosine methyltransferase polynucleotides into target cells; for example, receptor-mediated DNA delivery (Philips, S. C., *Biologicals* 23(1): 13-16, (1995)) and lipidic vector systems (Lee, R. J. and Huang, L., *Crit. Rev. Ther. Drug Carrier Syst.* 14(2): 173-206, (1997)) are promising alternatives to viral-based delivery systems.

General methods for construction of gene therapy vectors and the introduction thereof into affected animals for therapeutic purposes may be obtained in the above-referenced publications, the disclosures of which are specifically incorporated herein by reference in their entirety. In one such general method, vectors comprising the isolated polynucleotides of the present invention are directly introduced into target cells or tissues of the affected animal, preferably by injection, inhalation, ingestion or introduction into a mucous membrane via solution; such an approach is generally referred to as "in vivo" gene therapy. Alternatively, cells, tissues or organs may be removed from the affected animal and placed into culture according to methods that are well-known to one of ordinary skill in the art; the vectors comprising the de novo DNA cytosine methyltransferase polynucleotides may then be introduced into these cells or tissues by any of the methods described, generally above for introducing isolated polynucleotides into a cell or tissue, and, after a sufficient amount of time to allow incorporation of the de novo DNA cytosine methyltransferase polynucleotides, the cells or tissues may then be re-inserted into the affected animal. Since the introduction of a de novo DNA cytosine methyltransferase gene is performed outside of the body of the affected animal, this approach is generally referred to as "ex vivo" gene therapy.

For both in vivo and ex vivo gene therapy, the isolated de novo DNA cytosine methyltransferase polynucleotides of the invention may alternatively be operatively linked to a regulatory DNA sequence, which may be a de novo DNA cytosine methyltransferase promoter or an enhancer, or a heterologous regulatory DNA sequence such as a promoter or enhancer derived from a different gene, cell or organism, to form a genetic construct as described above. This genetic construct may then be inserted into a vector, which is then used in a gene therapy protocol. The need for transcriptionally targeted and regulatable vectors providing cell-type specific and inducible promoters is well recognized in the art (Miller, N. and Whelan, J., *Hum. Gene Therap.* 8(7): 803-815, (1997); and Walther, W. and Stein, U., *Mol. Med. J.*, 74(7): 379-392, (1996)), and for the purposes of de novo DNA cytosine methyltransferase gene therapy, is incorporated herein by reference.

The construct/vector maybe introduced into the animal by an in vivo gene therapy approach, e.g., by direct injection into the target tissue, or into the cells or tissues of the affected animal in an ex vivo approach. In another preferred embodiment, the genetic construct of the invention may be introduced into the cells or tissues of the animal, either in vivo or ex vivo, in a molecular conjugate with a virus (e.g., an adenovirus or an adeno-associated virus) or viral components (e.g., viral capsid proteins; see WO 93/07283). Alternatively, transfected host cells, which may be homologous or heterologous, may be encapsulated within a semi-permeable barrier device and implanted into the affected animal, allowing passage of de novo DNA cytosine methyltransferase polypeptides into the tissues and circulation of the animal but preventing contact between the animal's immune system and the transfected cells (see WO 93/09222). These approaches result in increased production of de novo DNA cytosine methyltransferase by the treated animal via (a) random insertion of the de novo DNA cytosine methyltransferase gene into the host cell genome; or (b) incorporation of the de novo DNA cytosine methyltransferase gene into the nucleus of the cells where it may exist as an extrachromosomal genetic element. General descriptions of such methods and approaches to gene therapy may be found, for example, in U.S. Pat. No. 5,578, 461, WO 94/12650 and WO 93/09222.

Antisense oligonucleotides have been described as naturally occurring biological inhibitors of gene expression in both prokaryotes (Mizuno et al., *Proc. Natl. Acad. Sci. USA* 81:1966-1970 (1984)) and eukaryotes (Heywood, *Nucleic Acids Res.* 14:6771-6772 (1986)), and these sequences presumably function by hybridizing to complementary MRNA sequences, resulting in hybridization arrest of translation (Paterson, et al., *Proc. Natl. Acad. Sci. USA*, 74:4370-4374 (1987)).

Thus, another gene therapy approach utilizes antisense technology. Antisense oligonucleotides are short synthetic DNA or RNA nucleotide molecules formulated to be complementary to a specific gene or RNA message. Through the binding of these oligomers to a target DNA or mRNA sequence, transcription or translation of the gene can be selectively blocked and the disease process generated by that gene can be halted (see, for example, Jack Cohen, *Oligode-* oxynucleotides, Antisense Inhibitors of Gene Expression, CRC Press (1989)). The cytoplasmic location of MRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, et al., *J. Natl. Cancer Inst*. 81:1539-1544 (1989)).

Antisense therapy is the administration of exogenous oligonucleotides which bind to a target polynucleotide located within the cells. For example, antisense oligonucleotides may be administered systemically for anticancer therapy (Smith, International Application Publication No. WO 90/09180).

The antisense oligonucleotides of the present invention include derivatives such as S-oligonucleotides (phosphorothioate derivatives or S-oligos, see, Jack Cohen, supra). S-oligos (nucleoside phosphorothioates) are isoelectronic analogs of an oligonucleotide (O-oligo) in which a non-bridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer et al., *J. Org. Chem*. 55:4693-4698 (1990); and Iyer et al., *J. Am. Chem. Soc*. 112:1253-1254 (1990), the disclosures of which are fully incorporated by reference herein.

As described herein, sequence analysis of SEQ ID NO:1, SEQ ID NO:2, SEQ ID NO:3, SEQ ID NO:4, SEQ ID NO:83, or the SEQ ID NO:84 cDNA clone shows that sequence that is nonhomologous to known DNA methyltransferase sequences may be identified (see FIGS. 1 and 4). Thus, the antisense oligonucleotides of the present invention may be RNA or DNA that is complementary to and stably hybridize with such sequences that are specific for a de novo DNA cytosine methyltransferase gene of the invention. Use of an oligonucleotide complementary to such regions allows for selective hybridization to a de novo DNA cytosine methyltransferase MRNA and not to an mRNA encoding a maintenance methyltransferase protein.

Preferably, the antisense oligonucleotides of the present invention are a 15 to 30-mer fragment of the antisense DNA molecule coding for unique sequences of the de novo DNA cytosine methyltransferase cDNAs. Preferred antisense oligonucleotides bind to the 5'-end of the de novo DNA cytosine methyltransferase mRNAs. Such antisense oligonucleotides maybe used to down regulate or inhibit expression of the gene.

Other criteria that are known in the art may be used to select the antisense oligonucleotides, varying the length or the annealing position in the targeted sequence.

Included as well in the present invention are pharmaceutical compositions comprising an effective amount of at least one of the antisense oligonucleotides of the invention in combination with a pharmaceutically acceptable carrier. In one embodiment, a single antisense oligonucleotide is utilized.

In another embodiment, two antisense oligonucleotides are utilized which are complementary to adjacent regions of the genome. Administration of two antisense oligonucleotides that are complementary to adjacent regions of the genome or corresponding mRNA may allow for more efficient inhibition of genomic transcription or MRNA translation, resulting in more effective inhibition of protein or mRNA production.

Preferably, the antisense oligonucleotide is coadministered with an agent which enhances the uptake of the antisense molecule by the cells. For example, the antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448, the disclosures of which are incorporated by reference in their entirety (see also U.S. Pat. Nos. 4,235,871, 4,231,877, 4,224,179, 4,753,788, 4,673,567, 4,247,411, and 4,814,270 for general methods of preparing liposomes comprising biological materials).

Alternatively, the antisense oligonucleotide may be combined with a lipophilic carrier such as any one of a number of sterols including cholesterol, cholate and deoxycholic acid. A preferred sterol is cholesterol.

In addition, the antisense oligonucleotide maybe conjugated to apeptide that is ingested by cells. Examples of useful peptides include peptide hormones, antigens or antibodies, and peptide toxins. By choosing a peptide that is selectively taken up by the targeted tissue or cells, specific delivery of the antisense agent maybe effected. The antisense oligonucleotide maybe covalently bound via the 5'OH group by formation of an activated aminoalkyl derivative. The peptide of choice may then be covalently attached to the activated antisense oligonucleotide via an amino and sulfhydryl reactive hetero bifunctional reagent. The latter is bound to a cysteine residue present in the peptide. Upon exposure of cells to the antisense oligonucleotide bound to the peptide, the peptidyl antisense agent is endocytosed and the antisense oligonucleotide binds to the target mRNA to inhibit translation (Haralambid et al., WO 8903849 and Lebleu et al., EP 0263740).

The antisense oligonucleotides and the pharmaceutical compositions of the present invention may be administered by any means that achieve their intended purpose. For example, administration may be by parenteral, subcutaneous, intravenous, intramuscular, intraperitoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the antisense oligonucleotide is contained in an amount effective to achieve the desired effect, for example, inhibition of proliferation and/or stimulation of differentiation of the subject cancer cells. While individual needs vary, determination of optimal ranges of effective amounts of each component is with the skill of the art.

Alternatively, antisense oligonucleotides can be prepared which are designed to interfere with transcription of the gene by binding transcribed regions of duplex DNA (including introns, exons, or both) and forming triple helices (e.g., see Froehler et al., WO 91/06626 or Toole, WO 92/10590). Preferred oligonucleotides for triple helix formation are oligonucleotides which have inverted polarities for at least two regions of the oligonucleotide (Id.). Such oligonucleotides comprise tandem sequences of opposite polarity such as 3' - - - 5'-L-5' - - - 3', or 5' - - - 3'-L-3' - - - 5', wherein L represents a 0-10 base oligonucleotide linkage between oligonucleotides. The inverted polarity form stabilizes single-stranded oligonucleotides to exonuclease degradation (Froehler et al., supra). The criteria for selecting such inverted polarity oligonucleotides is known in the art, and such preferred triple helix-forming oligonucleotides of the invention are based upon SEQ ID NO:1, SEQ ID NO:2, SEQ ID NO:3, SEQ ID NO:4, SEQ ID NO:83 or SEQ ID NO:84.

In therapeutic application, the triple helix-forming oligonucleotides can be formulated in pharmaceutical preparations for a variety of modes of administration, including systemic or localized administration, as described above.

The antisense oligonucleotides of the present invention may be prepared according to any of the methods that are well known to those of ordinary skill in the art, as described above.

Another gene therapy approach that may be utilized to alter expression of the de novo DNA methyl transferase genes of the invention is RNA interference (RNAi). The ability to specifically inhibit gene function in a variety of organisms utilizing double-stranded RNA (dsRNA)-mediated interference is well known in the fields of molecular biology (see for example C. P. Hunter, Current Biology 9:R440-442 (1999); Hamilton et al., Science, 286:950-952 (1999); and S. W. Ding, Current Opinions in Biotechnology 11:152-156(2000) hereby incorporated by reference in their entireties). Double-stranded RNA (dsRNA) that is homologous to a gene (or fragment therof) of interest is introduced into cells and effectively blocks expression of that gene in cells. The dsRNA molecules are digested in vivo to 21-23 nt fragment small interfering RNAs (siRNAs) which mediate the RNAi effect. In *C. elegans* and *Drosophila*, RNAi is induced by delivery of long dsRNA (up to 1-2 kb) produced by in vitro transcription. In mammalian cells, introduction of long dsRNA elicits a strong antiviral response that blocks any gene-specific silencing. However, introduction of 21 nt siRNAs with 2 nt 3' overhangs into mammalian cells does not stimulate the antiviral response and effectively targets specific mRNAs for gene silencing. The specificity of this gene silencing mechanism is extremely high, blocking expression only of targeted genes, while leaving other genes unaffected. Expression of de novo DNA methyl transferase transcripts of the invention may be turned off, for example, by delivery of siRNAs or vectors encoding the same into gonads or early embryos. In another embodiment, the siRNAs are delivered to cells or tissues to turn off expression of one or more De novo DNA methyl transferases. In a preferred embodiment, the cells are cancer cells. The artisan will appreciate that the siRNAs may be delivered to cells using an in vivo or ex vivo approach. Prefered ex vivo approaches involve transferring siRNAs to blood cells, bone marrow-derived cells, or stem cells.

The siRNAs or vectors encoding the same may be delivered to cells by techniques known in the art as described above. Further, the siRNAs may be prepared by any methods that are known in the art, including, but not limited to, oligonucleotide synthesis, in vitro transcription, ribonuclease digestion, or generation of siRNAs in vivo. In one embodiment, the siRNAs may be produced from vectors that are introduced into cells. The vectors may be introduced by any known methods in the art, including but not limited to transfection, electroporation, or viral delivery systems. Preferred vectors are the pSilencer siRNA expression vectors, pSilencer 2.0-U6 and pSilencer 3.0-H1. In a further embodiment, transcription of the siRNAs is driven by a RNA polymerase III (pol III) promoter. The pol III promoter may be derived from any gene that is under the control of RNA polymerase III, including but not limited to H1 or U6.

The siRNAs of the invention are encoded by nucleotide sequences within SEQ ID NO:1, SEQ ID NO:2, SEQ ID NO:3, SEQ ID NO:4, SEQ ID NO:83 or SEQ ID NO:84. In one embodiment, the siRNAs are about 20-1000 nucleotides in length. In another embodiment, the siRNAs are about 20-500 nucleotides in length. In another embodiment, the siRNAs are about 20-100 nucleotides in length. In another embodiment, the siRNAs are about 20-50 nucleotides in length. In a preferred embodiment, the siRNAs are about 21-23 nucleotides in length. The siRNAs may be produced by PCR amplification of genomic DNA or cDNA, using primers derived from de novo DNA methyl transferase sequence, and cloned into expression vectors for siRNA production. In another embodiment, oligonucleotides that correspond to de novo DNA methyl transferase sequence maybe chemically synthesized and inserted into expression vectors for siRNA production. The siRNAs or vectors encoding the same are introduced into cells to block expression of the de novo methyl transferase polypeptides. siRNA can also be produced by chemical synthesis of oligonucleotide of RNA of 21-23 nucleotides. In one embodiment, the de novo methyl transferase polypeptides are selected from the group consisting of mouse Dnmt3a, Dnmt3a2, Dnmt3b1, Dnmt3b2, Dnmt3b3, Dnmt3b4, Dnmt3b5, Dnmt3b6, and human DNMT3A, DNMT3A2, DNMT3B1, DNMT3B2, DNMT3B3, DNMT3B4, DNMT3B5 and DNMT3B6.

In one embodiment, the siRNAs are composed of nucleotides A, G, T, C, or U. Additionally, the siRNAs may be composed of unusual or modified nucleotides including but not limited to inosinic acid, 1-methyl inosinic acid, 1-methyl guanylic acid, NN-dimethyl guanylic acid, pseudouridylic acid, ribothymidylic acid, 5-hydroxymethylcytosine, and 5-hydroxymethyluridine. RNA may be synthesized either in vivo or in vitro and later introduced into cells. Endogenous RNA polymerase of the cell may mediate transcription in vivo, or cloned RNA polymerase can be used for transcription in vitro. For transcription from a transgene in vivo or an expression construct, a regulatory region (e.g., promoter, enhancer, silencer, splice donor and acceptor, polyadenylation) maybe used to transcribe the RNA strand (or strands); the promoters may be known inducible promoters that respond to infection, stress, temperature, wounding, or chemicals. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or maynot be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA containing nucleotide sequence identical to a fragment of the de novo DNA methyl transferase sequences are preferred for inhibition; however, RNA sequences with insertions, deletions, and point mutations relative to the de novo DNA methyl transferase sequences of the invention can also be used for inhibition. Sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

Ribozymes provide an alternative method to inhibit MRNA function. Ribozymes may be RNA enzymes, self-splicing RNAs, and self-cleaving RNAs (Cech et al., *Journal of Biological Chemistry* 267:17479-17482 (1992)). It is possible to construct de novo ribozymes which have an endonuclease activity directed in trans to a certain target sequence. Since these ribozymes can act on various sequences, ribozymes can be designed for virtually any RNA substrate. Thus, ribozymes are very flexible tools for inhibiting the expression of specific genes and provide an alternative to antisense constructs.

A ribozyme against chloramphenicol acetyltransferase mRNA has been successfully constructed (Haseloff et al., *Nature* 334:585-591 (1988); Uhlenbeck et al., *Nature* 328: 596-600 (1987)). The ribozyme contains three structural domains: 1) a highly conserved region of nucleotides which flank the cleavage site in the 5' direction; 2) the highly conserved sequences contained in naturally occurring cleavage domains of ribozymes, forming a base-paired stem; and 3) the regions which flank the cleavage site on both sides and ensure the exact arrangement of the ribozyme in relation to the cleavage site and the cohesion of the substrate and enzyme. RNA enzymes constructed according to this model have already proved suitable in vitro for the specific cleaving of RNA sequences (Haseloff et al., supra).

Alternatively, hairpin ribozymes may be used in which the active site is derived from the minus strand of the satellite RNA of tobacco ring spot virus (Hampel et al., *Biochemistry* 28:4929-4933 (1989)). Recently, a hairpin ribozyme was designed which cleaves human immunodeficiency virus type 1 RNA (Ojwang et al., *Proc. Natl. Acad. Sci. USA* 89:10802-10806 (1992)). Other self-cleaving RNA activities are associated with hepatitis delta virus (Kuo et al., *J. Virol.* 62:4429-4444 (1988)).

As discussed above, preferred targets for ribozymes are the de novo DNA cytosine methyltransferase nucleotide sequences that are not homologous with maintenance methyltransferase sequences such as Dnmt 1 or Dnmt 2. Preferably, the ribozyme molecule of the present invention is designed based upon the chloramphenicol acetyltransferase ribozyme or hairpin ribozymes, described above. Alternatively, ribozyme molecules are designed as described by Eckstein et al., (International Publication No. WO 92/07065) who disclose catalytically active ribozyme constructions which have increased stability against chemical and enzymatic degradation, and thus are useful as therapeutic agents.

In an alternative approach, an external guide sequence (EGS) can be constructed for directing the endogenous ribozyme, RNase P, to intracellular mRNA, which is subsequently cleaved by the cellular ribozyme (Altman et al., U.S. Pat. No. 5,168,053). Preferably, the EGS comprises a ten to fifteen nucleotide sequence complementary to an mRNA and a 3'-NCCA nucleotide sequence, wherein N is preferably a purine (Id.). After EGS molecules are delivered to cells, as described below, the molecules bind to the targeted mRNA species by forming base pairs between the mRNA and the complementary EGS sequences, thus promoting cleavage of mRNA by RNase P at the nucleotide at the 5' side of the base-paired region (Id.).

Included as well in the present invention are pharmaceutical compositions comprising an effective amount of at least one ribozyme or EGS of the invention in combination with a pharmaceutically acceptable carrier. Preferably, the ribozyme or EGS is coadministered with an agent which enhances the uptake of the ribozyme or EGS molecule by the cells. For example, the ribozyme or EGS may be combined with a lipophilic cationic compound which may be in the form of liposomes, as described above. Alternatively, the ribozyme or EGS may be combined with a lipophilic carrier such as any one of a number of sterols including cholesterol, cholate and deoxycholic acid. A preferred sterol is cholesterol.

The ribozyme or EGS, and the pharmaceutical compositions of the present invention may be administered by any means that achieve their intended purpose. For example, administration may be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired. For example, as much as 700 milligrams of antisense oligodeoxynucleotide has been administered intravenously to a patient over a course of 10 days (i.e., 0.05 mg/kg/hour) without signs of toxicity (Sterling, "Systemic Antisense Treatment Reported," *Genetic Engineering News* 12(12):1, 28 (1992)).

Compositions within the scope of this invention include all compositions wherein the ribozyme or EGS is contained in an amount which is effective to achieve inhibition of proliferation and/or stimulate differentiation of the subject cancer cells, or alleviate AD. While individual needs vary, determination of optimal ranges of effective amounts of each component is with the skill of the art.

In addition to administering the antisense oligonucleotides, ribozymes, or EGS as a raw chemical in solution, the therapeutic molecules may be administered as part of a pharmaceutical preparation containing suitable pharmaceutically acceptable carriers comprising excipients and auxiliaries which facilitate processing of the antisense oligonucleotide, ribozyme, or EGS into preparations which can be used pharmaceutically.

Suitable formulations for parenteral administration include aqueous solutions of the antisense oligonucleotides, dsRNAs, ribozymes, EGS in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Alternatively, antisense RNA molecules, ribozymes, and EGS can be coded by DNA constructs which are administered in the form of virions, which are preferably incapable of replicating in vivo (see, for example, Taylor, WO 92/06693). For example, such DNA constructs may be administered using herpes-based viruses (Gage et al., U.S. Pat. No. 5,082,670). Alternatively, antisense RNA sequences, ribozymes, and EGS can be coded by RNA constructs which are administered in the form of virions, such as retroviruses. The preparation of retroviral vectors is well known in the art (see, for example, Brown et al., "Retroviral Vectors," in *DNA Cloning: A Practical Approach*, Volume 3, IRL Press, Washington, D.C. (1987)).

Specificity for gene expression may be conferred by using appropriate cell-specific regulatory sequences, such as cell-specific enhancers and promoters. Such regulatory elements are known in the art, and their use enables therapies designed to target specific tissues, such as liver, lung, prostate, kidney, pancreas, etc., or cell populations, such as lymphocytes, neurons, mesenchymal, epithelial, muscle, etc.

In addition to the above noted methods for inhibiting the expression of the de novo methyltransferase genes of the invention, gene therapeutic applications may be employed to provide expression of the polypeptides of the invention.

The invention further provides methods of inhibiting de novo methylation in cells comprising expressing Dnmt3b3 and/or Dnmt3b6 in cells.

The present invention is further illustrated by the following Examples. These Examples are provided to aid in the understanding of the invention and are not to be construed as a limitation thereof.

EXAMPLES

Example 1

Cloning and Sequence Analysis of the Mouse Dnmt3a and Dnmt3b and the Human DNMT3A and DNMT3B Genes and Polypeptides In search of a mammalian de novo DNA methyltransferase, two independent approaches were undertaken, based on the assumption that an unknown mammalian DNA methyltransferase must contain the highly conserved cytosine methyltransferase motifs in the catalytic domain of known methyltransferases (Lauster, R. et al., *J. Mol. Biol.* 206:305-312 (1989) and Kumar, S. et al., *Nucl. Acids Res.* 22:1-10 (1994)). Our first approach, an RT/PCR-based screening using oligonucleotide primers corresponding to the conserved motifs of the known cytosine DNA methyltransferases, failed to detect any novel methyltransferase gene from Dnmt1 null ES cells (data not shown). The second approach was a tblastn search of the dbEST database using full length bacterial cytosine methyltransferase sequences as queries.

A search of the dbEST database was performed with the tblastn program (Altschul, S. F. et al., *J. Mol. Biol.* 215: 403-410 (1990)) using bacterial cytosine methyltransferases as queries. Candidate EST sequences were used one by one as queries to search the non-redundant protein sequence database in GenBank with the blastx program. This process would eliminate EST clones corresponding to known genes (including known DNA methyltransferases) and those which show a higher similarity to other sequences than to DNA methyltransferases. Two EST clones (GenBank numbers W76111 and N88352) were found after the initial search. Two more EST sequences (f12227 and T66356) were later found after a blastn search of dbEST with the EST sequence of W76111 as a query. Two of the EST clones (W76111 and T66356) were deposited by the I.M.A.G.E. Consortium (Lawrence Livermore National Laboratory, Livermore, Calif.) and obtained from American Type Culture Collection (Manassas, Va). Sequencing of these two cDNA clones revealed that they were partial cDNA clones with large open reading frames corresponding to two related genes. The translated amino acid sequences revealed the presence of the highly conserved motifs characteristic of DNA cytosine methyltransferases. The EST sequences were then used as probes for screening mouse E7.5 embryo and ES cell cDNA libraries and a human heart cDNA library (Clontech, Calif.).

In a screening of the dbEST database using 35 bacterial cytosine-5 DNA methyltransferase sequences as queries, eight EST clones were found to have the highest similarity but not to be identical to the known cytosine-5-DNA methyltransferase genes. Six of the eight EST sequences were deposited by the I.M.A.G.E. Consortium (Lawrence Livermore National Laboratory, Livermore, Calif.) and obtained from TIGR/ATCC (American Type Culture Collection, Manassas, Va.). Sequencing of these 6 cDNA clones revealed that they were partial cDNA clones with large open reading frames corresponding to three novel genes. The translated amino acid sequences revealed the presence of the highly conserved motifs characteristic of DNA cytosine methyltransferases. The EST sequences were then used as probes for screening a mouse ES cell cDNA library, a mouse E11.5 embryonic cDNA library (Clontech, Calif.) and human heart cDNA library.

Human and mouse cDNA libraries were screened using EST sequences as probes. Sequencing analysis of several independent cDNA clones revealed that two homologous genes were present in both human and mouse. This was further confirmed by Southern analysis of genomic DNA, intron/exon mapping and sequencing of genomic DNA (data not shown). The full length mouse cDNAs for each gene were assembled and complete sequencing revealed that both genes contained the highly conserved cytosine methyltransferase motifs and shared overall 51% of amino acid identity (76% identity in the catalytic domain) (FIG. 3). Since these two genes showed little sequence similarities to Dnmt1 (Bestor, T. H. et al., *J. Mol. Biol.* 203:971-983 (1988) and Yen, R-W. C. et al., *Nucleic Acids Res.* 20:2287-2291 (1992)) and a recently cloned putative DNA methyltransferase gene, Dnmt2 (see Yoder, J. A. and Bestor, T. H. *Hum. Mol. Genet.* 7:279-284 (1998)) and Okano, M., Xie, S. and Li, E., (submitted)), beyond the conserved methyltransferase motifs in the catalytic domain, they were named Dnmt3a and Dnmt3b.

The full length Dnmt3a and Dnmt3b genes encode 908 and 859 amino acid polypeptides, termed Dnmt3a and Dnmt3b1, respectively. Nucleotide and amino acid sequences of each are presented in FIGS. 1A, 1B, 2A, and 2B. The Dnmt3b gene also produces through alternative splicing at least two shorter isoforms of 840 and 777 amino acid residues, termed Dnmt3b2 and Dnmt3b3, respectively, (FIG. 4).

To obtain full length human cDNA, fetal heart and fetal testis cDNA libraries were screened using EST clones as probes. Sequencing analysis of several overlapping DNMT3A cDNA clones indicates that the DNMT3A gene encodes a polypeptide of 912 amino acid residues. DNMT3B cDNA clones were not detected in the fetal heart library, but several DNMT3B cDNA clones were obtained after screening the fetal testis library. PCR screening of large cDNA clones from 24 human tissues was also performed using the Human Rapid-Screen™ cDNA LibraryPanels (OriGene Technologies, MD). The largest cDNA clone contained a 4.2 kb insert from a small intestine cDNA library. Sequencing analysis of overlapping cDNA clones indicated that the deduced full length DNMT3B consists of 853 amino acid residues. Since in-frame stop codons are found upstream of the ATG of both DNMT3A and DNMT3B, it is concluded that these cDNA clones encode full-length DNMT3A and DNMT3B proteins.

The full length human DNMT3A and DNMT3B cDNAs encode 912 and 853 amino acid polypeptides, termed DNMT3A and DNMT3B1, respectively. Nucleotide and polypeptide sequences are presented in FIGS. 1C, 1D, 2C and 2D, respectively. The DNMT3B gene also produces through alternative splicing at least two shorter isoforms, termed DNMT3B2 and DNMT3B3, respectively. DNMT3B2 comprises amino acid residues 1 to 355 and 376 to 853 of SEQ ID NO:4; and DNMT3B3 comprises amino acid residues 1 to 355 and 376 to 743 and 807 to 853 of SEQ ID NO:4.

Also identified through screening was a related zebrafish gene, termed Zmt-3, which from the EST database (GenBank number AF135438).

The GenBank STS database was used to map chromosome localization by using DNMT3A and DNMT3B sequences as queries. The results identified markers WI-6283 (GenBank Accession number G06200) and SHGC-15969 (GenBank Accession number G15302), which matched the cDNA sequence of DNMT3A and DNMT3B, respectively. WI-6283 has been mapped to 2p23 between D2S171 and D2S174 (48-50 cM) on the radiation hybrid map by Whitehead Institute/MIT Center for Genome Research. The corresponding mouse chromosome location is at 4.0 cM on chromosome 12. SHGC-15969 has been mapped to 20p1 1.2 between D20S184 and D20S106 (48-50 cM) by Stanford Human Genome Center. The corresponding mouse chromosome locus is at 84.0 cM on chromosome 2.

Taking the advantage of the newly identified DNMT3A and DNMT3B cDNA sequences, the human genomic sequence database was searched by BLAST. While human DNMT3A cDNA did not match any related genornic sequences in the database, a DNMT3B genomic YAC clone from GenBank (AL035071) was identified when DNMT3B cDNA sequences were used as queries.

The DNMT3B cDNA and the genomic DNA GenBank (AL035071) clone were used to map all exons using BESTFIT of the GCG program. As shown in FIG. 4C, there are total 23 exons, spanning some 48 kb genomic DNA. The putative first exon is located within a CpG island where the promoter is probably located as predicted by the GENSCAN program (Whitehead/MIT Center for Genome Research).

Sequencing of various cDNA clones indicates that the human DNMT3B gene contains three alternatively spliced exons, exons 10, 21 and 22. Similar to the mouse gene, DNMT3B1 contains all 23 exons, whereas DNMT3B2 lacks exon 10 and DNMT3B3 lacks exons 10, 21 and 22. The nucleotide sequences at the exon/intron boundaries are shown in FIG. 4D. The elucidation of human DNMT3B gene structure may facilitate analysis of DNMT3B mutations in certain cancers with characteristic hypomethylation of genomic: DNA (Narayan, A., et al., *Int. J. Cancer* 77:833-838 (1998); Qu, G., et al., *Mutan. Res.* 423:91-101 (1999)).

FIG. 3A presents an alignment of mouse Dnmt3a and Dnmt3b polypeptide sequences that was accomplished using the GCG program. The vertical lines indicate amino acid identity, while the dots and the colons indicate similarities. Dots in amino acid sequences indicate gaps introduced to maximize alignment. The conserved Cys-rich region is shaded. The full length mouse Dnmt3a and Dnmt3b genes encode 908 and 859 amino acid polypeptides. Furthermore, the analysis reveals that both genes contained the highly conserved cytosine methyltransferase motifs and share overall 51% of amino acid identity (76% identity in the catalytic domain). The Dnmt3b gene also produces at least two shorter isoforms of 840 and 777 amino acid residues, termed Dnmt3b2 and Dnmt3b3, respectively, through alternative splicing (FIG. 4).

FIG. 3B presents a GCG program alignment using the of the protein sequences of human DNMT3A and DNMT3B1. Vertical lines represent identical amino acid residues, whereas dots represent conserved changes. Dots in amino acid sequences indicate gaps introduced to maximize alignment.

In FIG. 4A, presents a schematic diagram of the overall protein structures for mouse Dnmt1, mouse Dnmt2, a putative methyltransferase, and the family of Dnmt3a and Dnmt3b(1-3) methyltransferases. Dnmt1, Dnmt3a and Dnmt3bs all have a putative N-terminal regulatory domain. The filled bars represent the five conserved methyltransferase motifs (I, IV, VI, IX, and X). The shaded boxes in Dnmt3a and Dnmt3bs represent the Cys-rich region that shows no sequence homology to the Cys-rich, $Zn^{2+}$-binding region of Dnmt1 polypeptide. Sites of alternative splicing at amino acid residues 362-383 and 749-813 in Dnmt3bs are indicated.

Figure 4B:
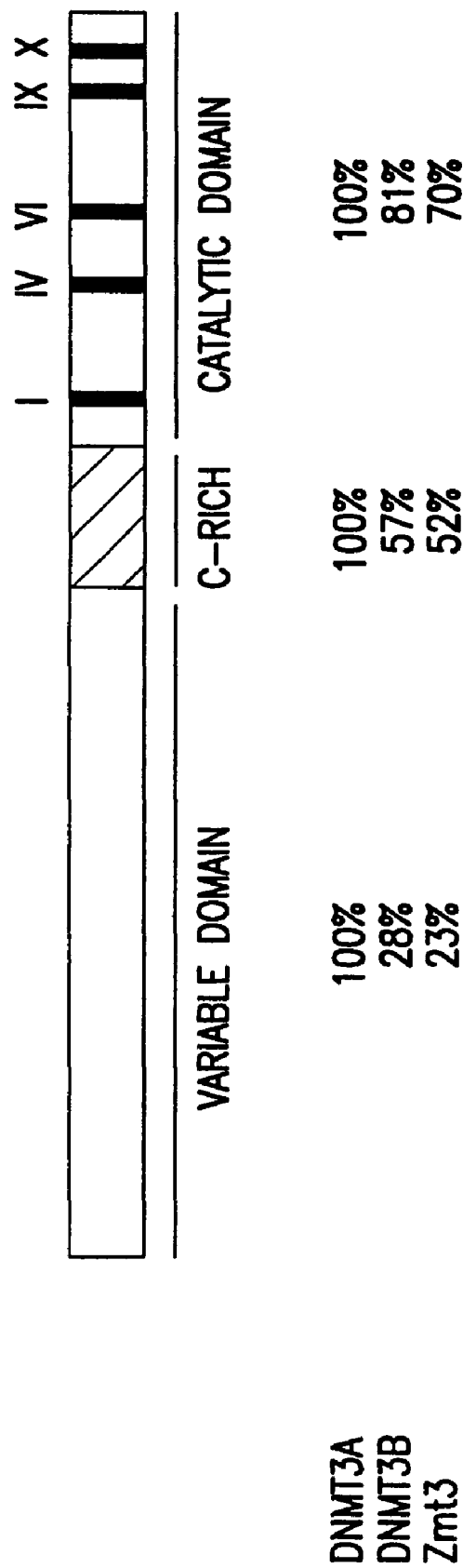
FIG. 4B presents a schematic of the DNMT3A, DNMT3B and zebrafish Zmt3 proteins.
Figure 4C:
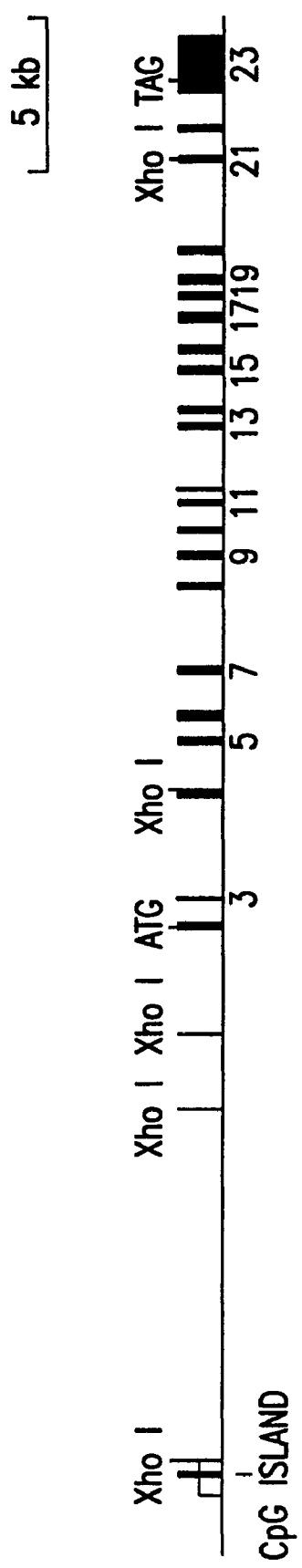

An analysis of the human DNMT3 proteins provides similar results as with the mouse Dnmt proteins. FIG. 4B presents a similar schematic of the human DNMT3 proteins and zebrafish Znmt3 protein. The homology between differences between these DNMT3 proteins is indicated by the percentage of sequence identity when compared to DNMT3A.

In addition, the genomic organization of the human DNMT3B1 locus is presented in FIG. 4C as possessing 23 exons (filled rectangles), a CpG island (dotted rectangle),a translation initiation codon (ATG) and a stop codon (TAG) in exons 2 and 23, respectively. FIG. 4D presents the size of the exons and introns as well as sequences (uppercase for exons and lowercase for introns) at exon/intron boundaries.

In FIG. 5, sequence analysis of the catalytic domain indicates that this new family of DNA methyltransferases contains conserved amino acid residues in each of the five highly conserved motifs, but significant differences are discernible when compared to the known consensus sequences.

FIG. 5A presents an alignment by ClustalW 1.7 of the amino acid sequences of the five highly conserved motifs in eukaryotic methyltransferase genes. Amino acid residues which are conserved in five or more genes are highlighted. The Dnmt3 family methyltransferases are most closely related to a bacterial DNA methyltransferase (M. Spr.). Sequence comparison of the catalytic domain of all known eukaryotic DNA methyltransferases and most of the bacterial cytosine methyltransferases used in the tblastn search indicates that this family of methyltransferases are distantly related to all the known eukaryotic DNA methyltransferases, including the Dnmt 1 polypeptide from vertebrate and plant (Bestor, T. H. et al., *J. Mol. Biol.* 203:971-983 (1988), Yen, R-W. C. et al., *Nucleic Acids Res.* 20:2287-2291 (1992) and Finnegan, E. J. and Dennis, E. S. *Nucleic Acids Res.* 21:2383-2388 (1993)); the human and mouse Dnmt 2 polypeptides (Yoder, J. A. and Bestor, T. H. *Hum. Mol. Genet.* 7:279-284 (1998), Okano, M., Xie, S. & Li, E., (submitted)); and masc1 from Ascobolus (Malagnac, F. et al., *Cell* 91:281-290 (1997)), indicating that the Dnmt3 gene family originated from a unique prokaryotic prototype DNA methyltransferase during evolution.

The cysteine-rich region located upstream of the catalytic domain was found to be conserved among all of the DNMT3 proteins (FIG. 5B). This Cysteine-rich region, however, is unrelated to the Cysteine-rich (or $Zn^{2+}$-binding) region of DNMT1 (Bestor, T. H., et al., *J. Mo. Biol.* 203:971-983 (1998); Bestor, T. H., *EMBO J.* 11:2611-2617 (1992)). Interestingly, the Cysteine-rich domain of DNMT3 proteins shares homology with a similar domain found in the X-linked ATRX gene of the SNF2/SWI family (Picketts, D. J., et al., *Hum. Mol. Genet.* 5:1899-1907 (1996)), raising the interesting possibility that this domain may mediate protein-protein or protein-DNA interactions.

Figure 5C:
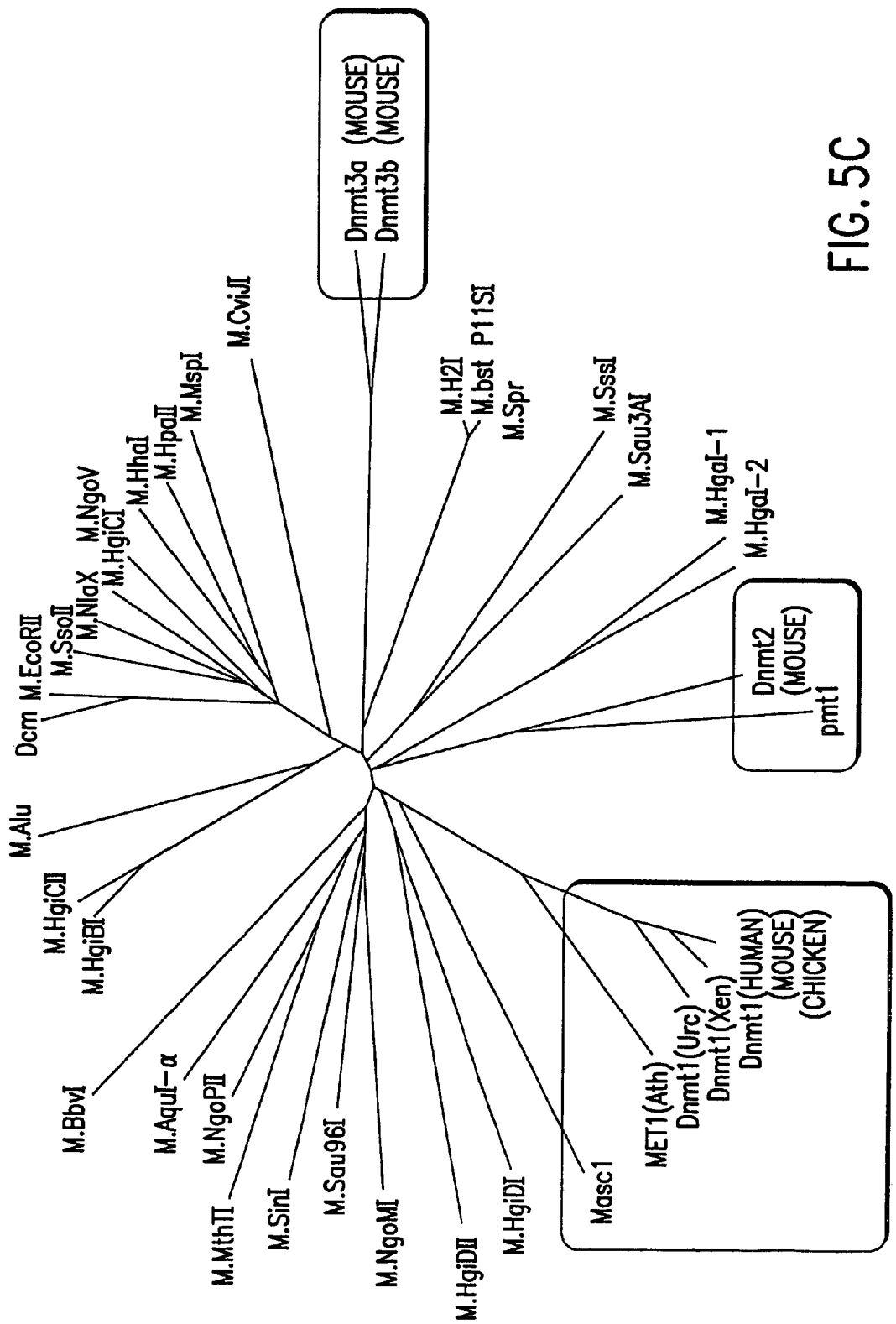
FIG. 5C presents a non-rooted phylogenic tree of methyltransferase proteins.

The evolutionary relatedness of cytosine-5 methyltransferases as shown by a non-rooted phylogenic tree is presented in FIG. 5C. Amino acid sequences from motifI to motifVI of bacterial and eukaryotic cytosine-5 methyltransferases were used for sequence alignment, and the alignment data was analyzed by ClustalW 1.7 under conditions excluding positions with gaps. Results were visualized utilizing Phlip version 3.3. Amino acid sequences from motif IX to motif X were also analyzed and provided similar results (data not shown). (Abbreviation Ath; *Arabidopsis thaliana*, Urc; sea urchin, Xen; *Xenopus laevis*).

Example 2

Baculovirus-Mediated Expression of Dnmt3a and Dnmt3b

To test whether the newly cloned Dnmt3 genes encode active DNA methyltransferases, the cDNAs of Dnmt3a, Dnmt3b1, Dmnt3b2, and Dnmt1 were overexpressed in insect cells using the baculovirus-mediated expression system (Clontech, Calif.).

To construct the Dmnt3a expression vector, pSX134, the Xma I/Eco RI fragment of Dnmt3a cDNA was first cloned into the Nco I/Eco RI sites of pET2 Id with the addition of an Xma I/Nco I adapter (SX165: 5'-CATGGGCAGCAGC-CATCATCATCATCATCATGGGAATTCCATGCCC TCCAGCGGCC (SEQ ID NO:87) and SX166: 5'-GGGCATGGAATT CCCATGATGATGATGATGATG-GCTGCTGCC) (SEQ ID NO:88) that produced pSX132His. pSX134 was obtained by cloning the EcoR I/Xba I fragment of pSX 132His into the EcoR I/Xba I sites of pBacPAK9. The Dnmt3b1 and Dnmt3b2 expression vectors, pSX153 and pSX154, were constructed by cloning Eco RI fragments of Dnmt3b1 and Dnmt3b2 cDNA into the Eco RI site of pBacPAK9, respectively. The Dnmt1 expression vector pSX148 was constructed by cloning the Bgl I/Sac I fragment of Dnmt1 cDNA into the Bgl II/Sac I sites of pBacPAK-His2 with the addition of a Bgl I/Bgl II adapter (SX180: 5'-GATCTATGCCAGCGCGA ACAGCTCCAGC-CCGAGTGCCTGCGCTTGCCTCCC (SEQ ID NO:89) and SX181: 5'-AGGCAAGCGCAGGCACTCGGGCTG-GAGCTGTT CGCGCTGGCATA) (SEQ ID NO:90).

pSX134 (Dnmt3a), pSX153 (Dnmt3b1), pSX153 (Dnmt3b2) and pSX148 (Dnmt1) were used to make the recombinant baculoviruses according to the procedures recommended by the manufacturer. T175 flasks were used for cell culture and virus infection. Sf21 host cells were grown in the SF-900 II SFM medium with 10% of the certified FBS (both from GIBCO, Md.) and infected with the recombinant viruses 12-24 hours after the cells were split when they reached 90-95% affluence. After 3 days, the infected insect cells were harvested and frozen in the liquid nitrogen for future use.

Example 3

RNA Expression Analysis

ES cells were routinely cultured on a feeder layer of mouse embryonic fibroblasts in DMEM medium containing LIF (500 units/ml) and were differentiated as embryoid bodies in suspension culture as described (Lei, H., et al., *Development* 122:3195-3205 (1996)). Ten days after seeding, embryoid bodies were harvested for RNA preparation.

Total RNA was prepared from ES cells, ovary and testis tissue using the GTC-CsCl centrifugation method, fractionated on a formaldehyde denaturing 1% agarose gel by electrophoresis and transferred to a nylon membrane. PolyA+RNA blots (2 µg per lane) of mouse and human tissues were obtained from Clontech, Calif. All blots were hybridized to random-primed cDNA probes in hybridization solution containing 50% formamide at 42° C. and washed with 0.2×SSC, 0.1% SDS at 65° C. and exposed to X-ray film (Kodak).

Figure 6A:
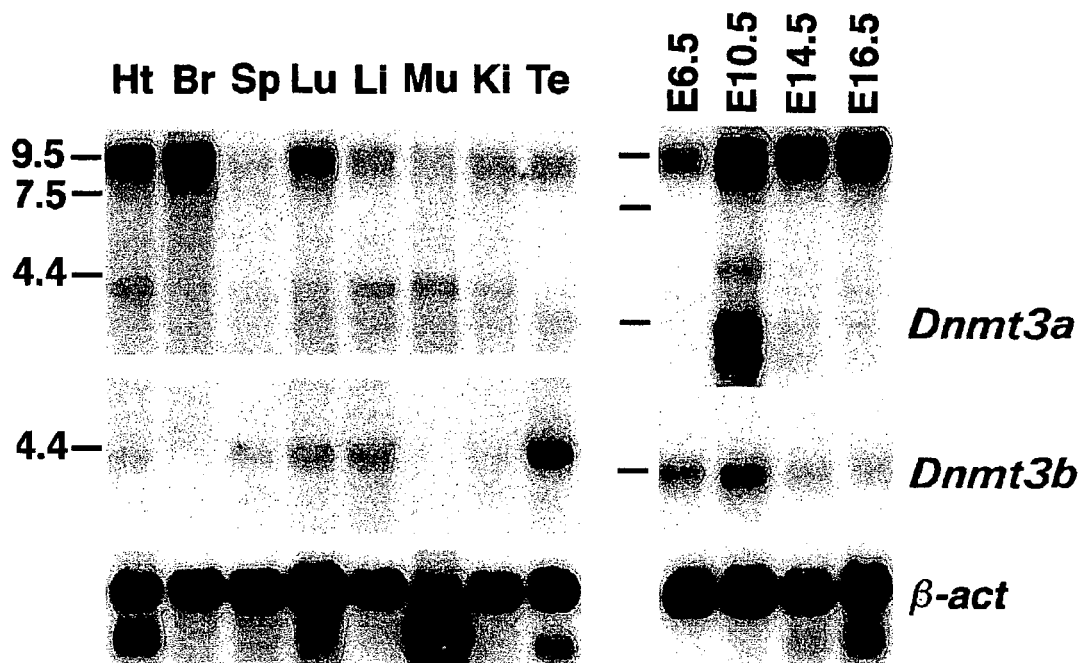
FIGS. 6A-6C demonstrates the expression of Dnmt3a and Dnmt3b in mouse adult tissues, embryos, and ES cells by northern blot.
Figures 6B, 6C:
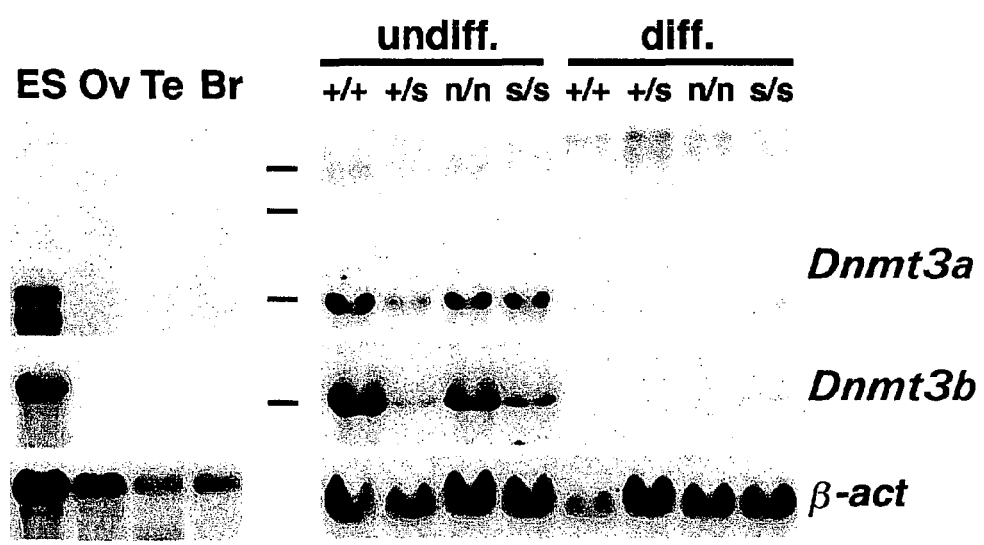

FIG. 6A presents mouse polyA+RNA blots of adult tissues (left) and embryos (right) probed with full length Dnmt3a, Dnmt3b and a control β-actin cDNA probe. Each lane contains 2 µg of polyA+RNA. (Ht, Heart; Br, Brain; Sp, Spleen; Lu, Lung; Li, Liver; Mu, Skeletal Muscle; Ki, Kidney; Te, Testis; and embryos at gestation days 7 (E7), 11 (E11), 15 (E15), and 17 (E17). FIG. 6B is a mouse total RNA blot (10 µg per lane) of ES cell and adult organ RNA samples and FIG. 6C shows a mouse total RNA blot (20 µg per lane) of undifferentiated (Undiff.) and differentiated (Diff.) ES cells RNA hybridized to Dnmt3a, Dnmt3b or β-actin probes.

It has been shown that the maintenance methylation activity is constitutively present in proliferating cells, whereas the de novo methylation activity is highly regulated. Active de novo methylation has been shown to occur primarily in ES cells (or embryonic carcinoma cells), early post implantation embryos and primordial germ cells (Jähaner, D. and Jaenish, R., "DNA Methylation in Early Mammalian Development," In *DNA Methylation: Biochemistry and Biological Significance*, Razin, A. et al., eds., Springer-Verlag (1984) pp. 189-219; Razin, A., and Cedar, H., "DNA Methylation and Embryogenesis," in *DNA Methylation: Molecular Biology and Biological Significance*, Jost., J. P. et al., eds., Birkäuser Verlag, Basel, Switzerland (1993) pp. 343-357; Chaillet, J. R. et al., *Cell* 66:77-83 (1991); and Li, E. "Role of DNA Methylation in Development," in *Genomic Imprinting: Frontiers in Molecular Biology*, Reik, W. and Sorani, A. eds., IRL Press, Oxford (1997) pp. 1-20). The expression of both Dnmt3a and Dnmt3b in mouse embryos, adult tissues and ES cells was examined. The results indicate that two Dnmt3a transcripts, 9.5 kb and 4.2 kb, are present in embryonic and adult tissue RNA. The 4.2 kb transcript, corresponding to the size of the full length cDNA, was expressed at very low levels in most tissues, except for the E11.5 embryo sample (FIG. 6A). A single 4.4 kb Dnmt3b transcript is detected in embryo and adult organ RNAs, with relatively high levels in testes and E11.5 embryo samples (FIG. 6A). Interestingly, both genes are expressed at much higher levels in ES cells than in adult tissues (FIG. 6B), and their expression decreased dramatically upon differentiation of ES cells in culture (FIG. 6C). In addition, Dnmt3a and Dnmt3b expression levels are unaltered in Dnmt1-deficient ES cells (FIG. 6C), suggesting that regulation of Dnmt3a and Dnmt3b expression is independent of Dnmt1.

These results suggest that both Dnmt3a and Dnmt3b are expressed specifically in ES cells and E11.5 embryo and/or testes. The expression in the E11.5 embryo and testes may correlate with the presence of developing or mature germ cells in these tissues. Therefore, the expression pattern of Dnmt3a and Dnmt3b appears to correlate well with de novo methylation activities in development.

Figure 9:
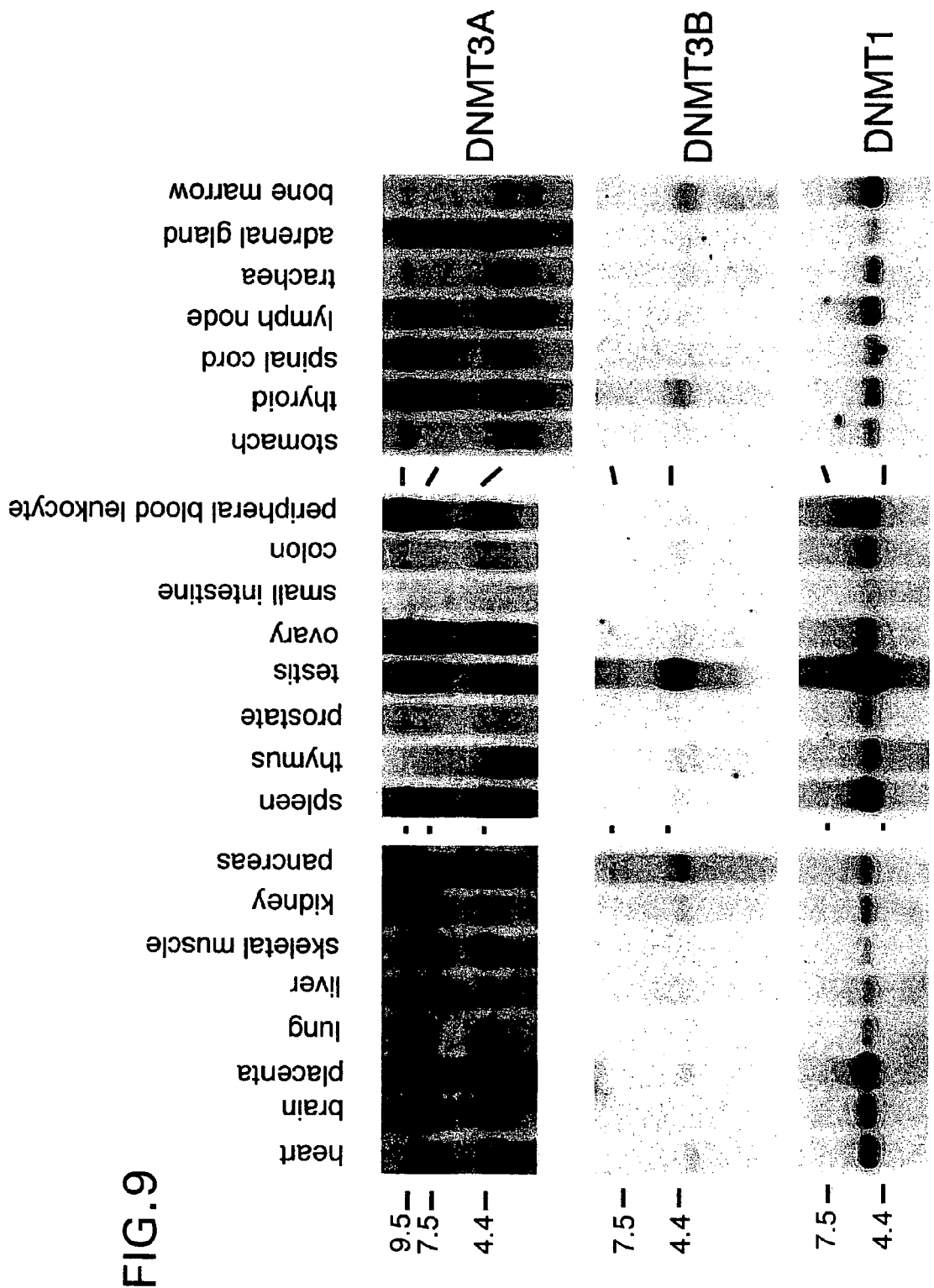
FIG. 9 presents Northern blot expression analysis of DNMT3A and DNMT3B.

For the RNA expression analysis of human DNMT3 genes, polyA+RNA blots were hybridized using DNMT3A and DNMT3B cDNA fragments as probes. Results indicate that DNMT3A RNA was expressed ubiquitously and was readily detected in most tissues examined at levels slightly lower than DNMT1 RNA (FIG. 9). Three major DNMT3A transcripts, approximately 4.0, 4.4, and 9.5 kb, were detected. The relative expression level of the transcripts appeared to vary from tissue to tissue. Transcripts of similar sizes were also detected in mouse tissues. Results utilizing DNMT3B cDNA probes indicate that transcripts of about 4.2 kb were expressed at much lower levels in most tissues, but could be readily detected in the testis, thyroid and bone marrow (FIG. 9). Sequence analyses of different cDNA clones indicate the presence of alternatively spliced transcripts, although the size differences between these transcripts are too small to be detected by Northern analysis.

Figure 10:
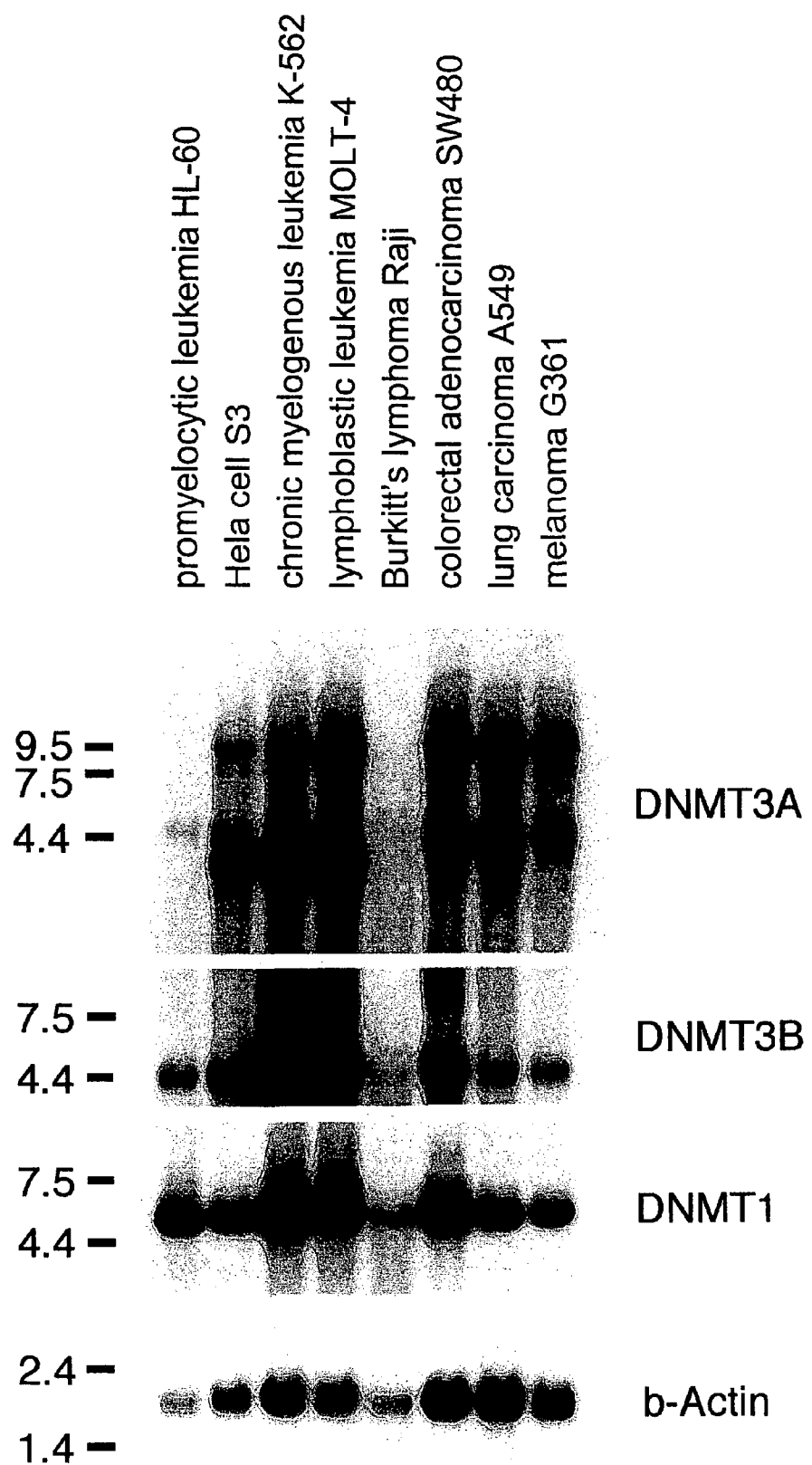
FIG. 10 presents DNMT3 Northern Blot expression analysis of DNMT3A and DNMT3B in human tumor cell lines.

Hypermethylation of tumor suppressor genes is a common epigenetic lesion found in tumor cells (Laird, P. W. & Jaenisch, R., Ann. Rev. Genet. 30:441-464 (1996); Baylin, S. B., Adv. Cancer Res. 72:141-196 (1998)). To investigate whether DNMT3A and DNMT38 am abnormally activated in tumor cells, DNMT3 RNA expression was analyzed in several tumor cell lines by Northern blot hybridization. Results demonstrated that DNMT3A was expressed at higher levels in most tumor cell lines examined. (FIG. 10). As in the normal tissues, three different size transcripts were also detected in tumor cells. The ratio of these transcripts appeared to be variable in different tumor cell lines. DNMT3B expression was dramatically elevated in most tumor cell lines examined though it was expressed at very low levels in normal adult tissues (FIG. 10). The expression levels of both DNMT3A and DNMT3B appear to be comparable and proportional to that of DNMT1.

The murine Dnmt3a and Dnmt3b genes are highly expressed in undifferentiated ES cells, consistent with their potential role in de novo methylation during early embryonic development. Additionally, both genes are highly expressed in early embryos. Differences in their expression patterns in adult tissues in both human and mice suggest that each gene may have a distinct function in somatic tissues and may methylate different genes or genomic sequences. The elevated expression of DNMT3 genes in human tumor cell lines suggests that the DNMT3 enzyme may be responsible for de novo methylation of CpG islands in tumor suppressor genes during tumor formation.

Example 4

Methyltransferase Activity Assay

In order to demonstrate DNA cytosine methyltransferase activity, the polypeptides of the invention were expressed and purified from recombinant host cells for use in in vitro assays.

Infected insect Sf21 cells and NIH3T3 cells were homogenized by ultrasonication in lysis solution (20 mM Tris-HCl, pH7.4, 10 mM EDTA, 500 mM NaCl, 10% glycerol, 1 mM DTT, 1 mM PMSF, 1 ug/ml leupeptin, 10 ug/ml TPCK, 10 ug/ml TLCK) and cleared by centrifugation at 100,000 g for 20 min.

The methyltransferase enzyme assay was carried out as described previously (Lei, H. et al., Development 122:3195-3205 (1996)). DNA substrates used in the assays include: poly (dI-dC), poly (dG-dC) (Pharmacia Biotech), lambda phage DNA (Sigma), pBluescriptIISK (Stratagene, Calif.), pMu3 plasmid, which contains tandem repeats of 535bp RsaI-RsaI fragment of MMLV LTR region in pUC9, and oligonucleotides. The oligonucleotide sequences utilized include:

```
                                          (SEQ ID NO: 91)
1, 5'-AGACMGGTGCCAGMGCAGCTGAGCMGGATC-3', (SEQ ID NO: 92)
2, 5'-GATCMGGCTCAGCTGMGCTGGCACMGGTCT-3', (SEQ ID NO: 93)
3, 5'-AGACCGGTGCCAGCGCAGCTGAGCCGGATC-3' and (SEQ ID NO: 94)
4, 5'-GATCCGGCTCAGCTGCGCTGGCACCGGTCT-3'
(M represents 5-methylcytosine).
```

These sequences are the same as described in a previous study (Pradhan, S. et al., Nucleic Acids Res. 25:4666-4673 (1997)). Oligonucleotides were synthesized and purified by polyacrylamide gel electrophoresis (PAGE). To make double strand oligonucleotides, equimolar amounts of the two complimentary oligonucleotides were heated at 94° C. for 10 min., mixed, incubated at 78° C. for 1 hr and cooled down slowly at room temperature. The annealing products were quantified for the yield of double-stranded oligonucleotides (dsDNA) by PAGE and methylene blue staining. In all cases, the yield of dsDNA was higher than 95%. The dsDNA of #1 and #2 were used as 'fully' methylated substrates, dsDNA of #1 and #4 as the hemi-methylated substrates, and dsDNA of #3 and #4 as unmethylated substrates.

For Southern analysis of the methylation of retrovirus DNA, 2 ug of pMMLV8.3, an 8.3 kb Hind III fragment of Moloney murine leukemia virus cDNA in pBluescriptIISK, was methylated in vitro for 15 hrs under the same reaction conditions described above except that 160 uM of cold SAM was used instead of $^3$H-methyl SAM. Then, an equal volume of the solution containing 1% SDS, 400 mM NaCl, and 0.2 mg/ml Proteinase K was added, and the sample was incubated at 37° C. for 1 hr. After phenol/chloroform extraction, DNA was precipitated with ethanol, dried and dissolved in TE buffer. This procedure was repeated 5 times. An aliquot of DNA was purified after the first, third and fifth reaction, digested with Hpa II or Msp I in combination with Kpn I for 16 hrs, separated on 1% agarose gels, blotted and hybridized to the pMu3 probe.

Figure 7C:
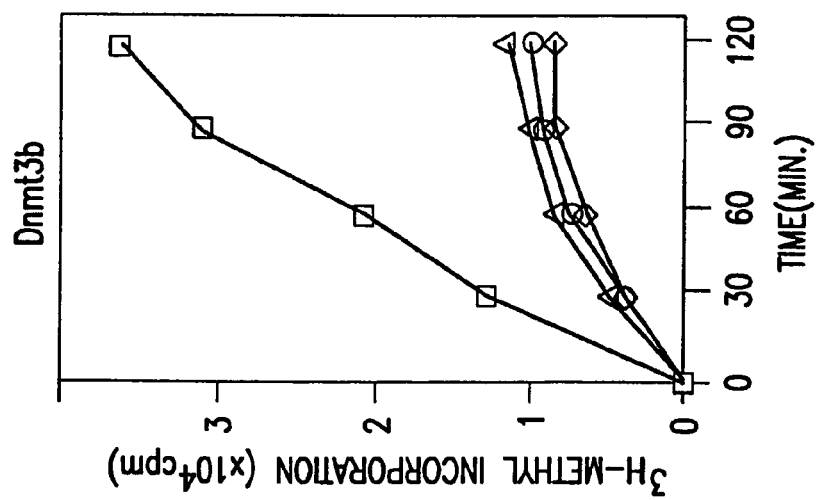
FIGS. 7A-7D demonstrates in vitro methyltransferase activities of mouse Dnmt3a and Dnmt3b proteins.
Figure 7B:
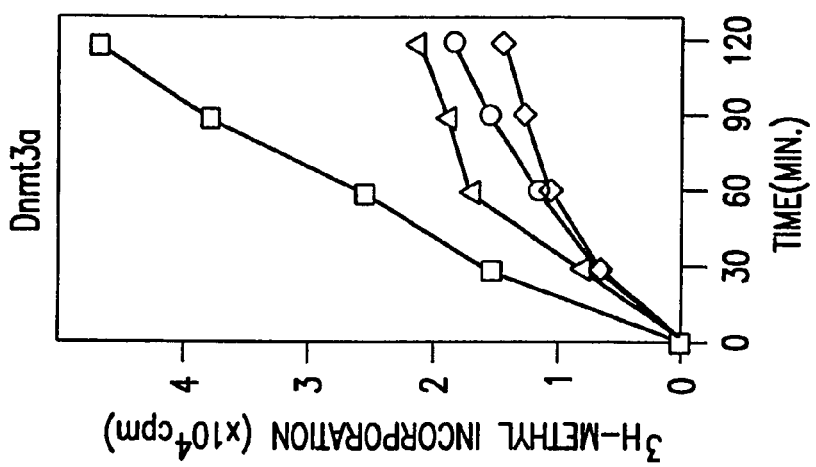
Figure 7A:
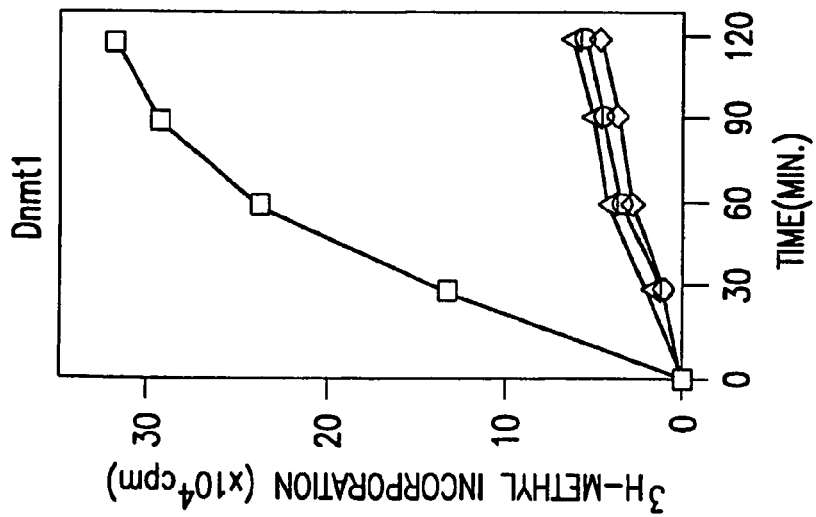
Figure 7D:
Figure 8C:
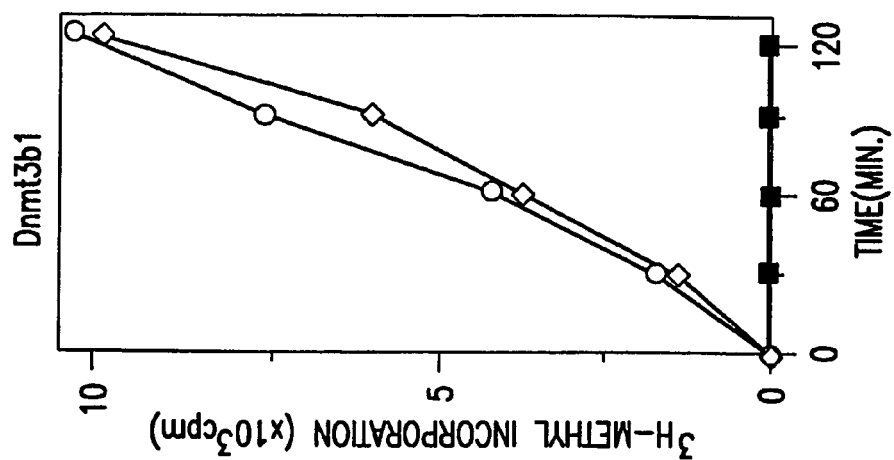
FIG. 8 demonstrates in vitro analysis of de novo and maintenance activities of Dnmt3a, Dnmt3b1 and Dnmt3b2 proteins.
Figure 8B:
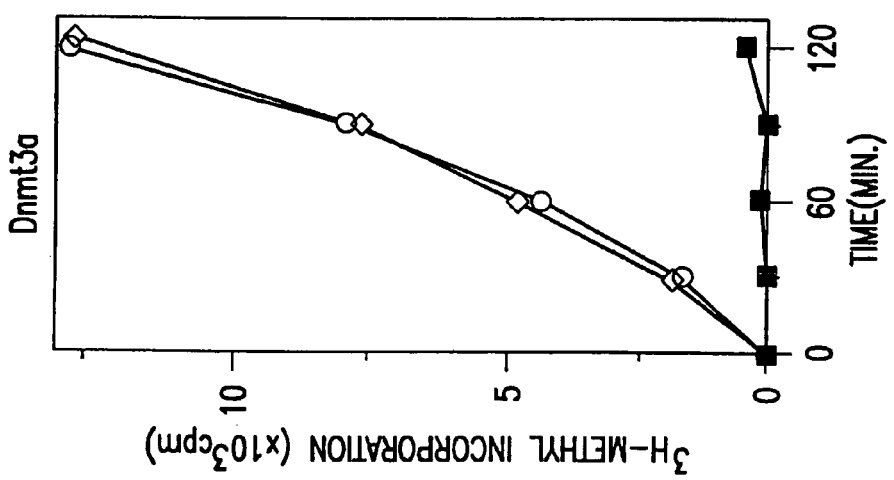
Figure 8A:
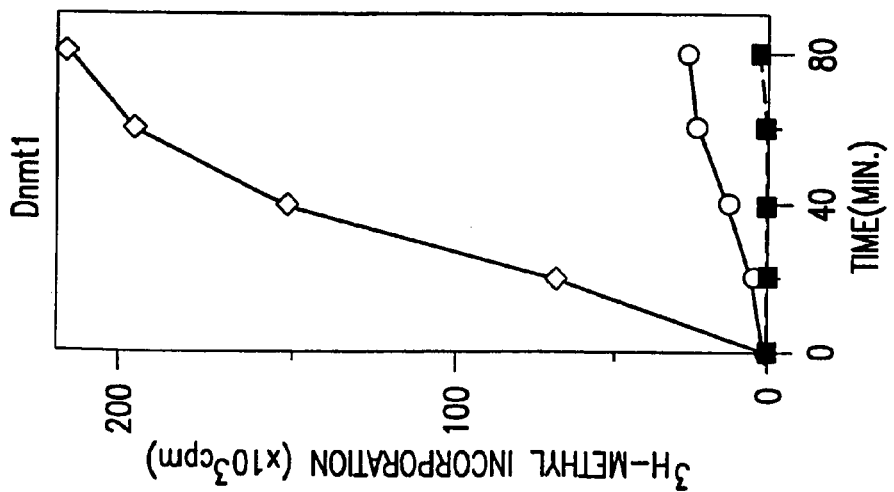
Figure 8E:
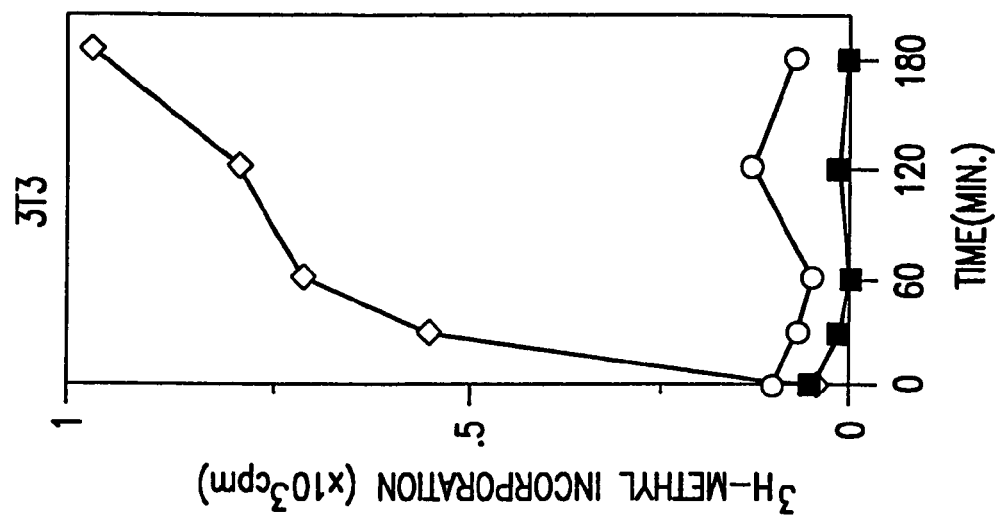
Figure 8D:
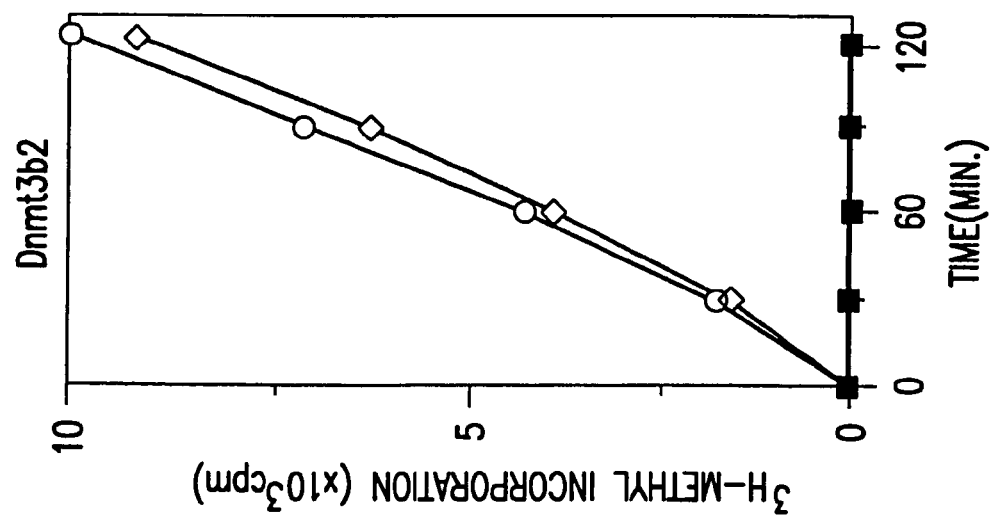

In a standard methyltransferase assay, enzyme activity was detected with protein extracts from Sf21 cells overexpressing Dnmt3a and Dmnt3b polypeptides. Similar to the results obtained with the Dnmt1 polypeptide, the overexpressed Dnmt3 proteins were able to methylate various native and synthetic DNA substrates, among which poly(dI-dC) consistently gave rise to the highest initial velocity (FIG. 7a). An analysis of the methylation of Hpa II sites in retroviral DNA by these enzymes was also performed. An MMLV full length cDNA was methylated for 1-5 times by incubation with protein extract from control Sf21 cells or Sf21 cells infected with baculoviruses expressing Dnmt1, Dnmt3a or Dnmt3b polypeptides. The Hpa II/Msp I target sequence, CCGG, is resistant to the Hpa II restriction enzyme, but sensitive to Msp I digestion when the internal C is methylated, and the restriction site becomes resistant to Msp I digestion when the external C is methylated (Jentsch, S. et al., *Nucleic Acids Res.* 9:2753-2759 (1981)). Both Dnmt3a and Dnmt3b polypeptides could methylate multiple Hpa II sites in the 3' LTR regions of the MMLV DNA, as indicated by the presence of Hpa II-resistant fragments, though less efficiently than Dnmt1 polypeptide (FIG. 7b). Significantly, even after five consecutive rounds of in vitro methylation, the viral DNA was completely digested by Msp I. This result indicates that both Dnmt3a and Dnmt3b polypeptides methylate predominantly the internal cytosine residues, therefore, CpGs. Previously it was shown that the same region of the proviral DNA was efficiently methylated in Dnmt1 null ES cells infected by the MMLV virus (Lei, H. et al., *Development* 122:3195-3205 (1996)).

FIG. 7A shows $^3$H-methyl incorporation into different DNA substrates (poly (dI-dC), poly (dG-dC) (squares), lambda phage DNA (circles), pBluescriptIISK (triangles), and pMu3 (diamonds)) when incubated with protein extracts of Sf21 cells expressing Dnmt1, Dnmt3a, or Dnmt3b1. FIG. 7B shows Southern blot analysis of the in vitro methylation of untreated pMMLV DNA (lanes 1-3) and pMMLV DNA incubated with MT 1 (lane 4-10), MT3a (lanes 11-15), MT3β (lanes 16-20) or control Sf21 (lanes 21-25) extracts that were digested with Kpn I(K), Kpn I and Msp I (K/M) or Kpn I and Hpa II (K/H). Restriction enzyme digested samples were then subjected to Southern blot analysis using the pMu3 probe.

Dnmt1 protein appears to function primarily as a maintenance methyltransferase because of its strong preference for hemimethylated DNA and direct association with newly replicated DNA (Leonhardt, H. et al., *Cell* 71:865-873 (1992)). To determine whether Dnmt3a and Dnmt3b polypeptides show any preference for hemimethylated DNA over unmethylated DNA, a comparison was done to examine the methylation rate of unmethylated versus hemimethylated oligonucleotides. Gel-purified double stranded oligonucleotides were incubated with protein extracts of Sf21 cells expressing Dnmt1, Dnmt3a, Dnmt3b1, Dnmt3b2 or NIH3T3 cell extract (unmethylated substrates (open circles), hemi-methylated substrates (halfblack diamonds) or completely methylated substrates (closed squares)). While baculovirus-expressed Dnmt1 polypeptide or 3T3 cell extract showed much higher activities when hemimethylated DNA was used as a substrate, Dnmt3a, Dmnt3b1 and Dnmt3b2 polypeptides showed no detectable preference for hemimethylated DNA (FIG. 8).

Example 5

Two Dnmt3a Isoforms Produced from Alternative Promoters Show Different Subcellular Localization and Tissue Expression Patterns Materials and Methods Vectors: The GFP-Dnmt3, the Dnmt3-pcDNA, and the His$_6$-tagged Dnmt3a constructs were generated by subcloning the corresponding Dnmt3a or Dmnt3b cDNA into pEGFP-C1 (Clontech), pcDNA6/V5-HisA (Invitrogen), and pET-28b(+) (Novagen), respectively. The P2 targeting vector was constructed by sequentially subcloning Dnmt3a genomic fragments, the hCMV-hygTK cassette, and the PGK-DTA cassette into pBluescript II SK. The Dnmt3a genomic fragments (left arm, 3.7 kb; right arm, 3.0 kb) were generated by PCR using a BAC clone (Genome Systems Inc.) as the template and the following pairs of oligonucleotides as primers: 5'-CTGGAATTCTCCTACCTTTG-3' (SEQ ID NO:95) and 5'-CCTGGATCCCAGCCAGT-GAGCTGG-3' (SEQ ID NO:96) (for left arm), 5'-GTTC-CGCGGCTGCTCATT-3' (SEQ ID NO:97) and 5'-CCAC-CGCGGCCGACTTGCCTCTACTTC-3' (SEQ ID NO:98) (for right arm). (The restriction sites used for cloning are underlined). The identities of the constructs were verified by DNA sequencing.

Antibodies: The Dnmt3 rabbit polyclonal antibodies, 164 and 157, were generated against mouse Dnmt3a amino acids 15-126 and Dnmt3b amino acids 1-181, respectively. The Dnmt3a mAb (clone 64B1446) was purchased from Imgenex. Anti-GFP mAb (a mixture of clones 7.1 and 13.1) was obtained from Roche. Anti-tubulin mAb (Ab-1) was obtained from Oncogene Research Products. Anti-DNMT1 (human) polyclonal AB was purchased from New England Biolabs. Anti-histone H1 (AE-4) and anti-lamin B (M-20) were obtained from Santa Cruz Biotechnology.

Protein expression and analysis: Transient transfection was carried out in COS-7 or NIH 3T3 cells using LIPO-FECTAMINE PLUS reagent (Invitrogen). Immunoprecipitation, immunoblotting, and fluorescence microscopy analyses were performed as previously described (He, D. et al., *J Cell Biol* 110, 569-580 (1990); Chen, T., and Richard, S. *Mol Cell Biol* 18 (8), 4863-71 (1998); Chen, T. et al., *Mol Biol Cell* 10 (9), 3015-33 (1999)).

Luciferase reporter assay: Luciferase reporter constructs as well as pGL-3-Basic (empty vector) were individually co-transfected with pRL-TK (internal control, Promega) into ES cells or NIH 3T3 cells. The cell lysates were analyzed for luciferase activities using the dual-luciferase reporter assay system (Promega).

5' RACE, RT-PCR, and Northern hybridization: 5' RACE was carried out on total RNA prepared from ES cells using the 5' RACE system (Invitrogen)withDnmt3 a-specific primers: 5'-AGCTGCTCGGCTCCG GCC-3' (SEQ ID NO:99) (for reverse transcription), 5'-TCCCCCACAC-CAGCTCTCC-3' (SEQ ID NO:100) (for 1$^{st}$round PCR), and 5'-CTGCAATTACCTTGGCTT-3' (SEQ ID NO:101) (for 2$^{nd}$ round PCR). For RT-PCR analysis, total RNA was reverse transcribed with oligo(dT)$_{12-18}$ and the resulting cDNAs were amplified by PCR. Dnmt3a-specific primers used are 5'-TCCAGCGGCCCCGGGGAC-3' (SEQ ID NO:102) (F1), 5'-CCCAACCTGAGGAAGGGA-3' (SEQ ID NO:103)(F2), 5'-ACCAACATCGAATCCATG-3' (SEQ ID NO:104) (F3), 5'-TCCCGGGGCCGACTGCGA-3' (SEQ ID NO:105) (F4), 5'-AGGGGCTGCACCTGGCCTT-3' (SEQ ID NO:106) (F5), 5'-TCCCCCACAC-CAGCTCTCC-3' (SEQ ID NO:107) (RI), and 5'-CCTCT-GCAGTACAGCTCA-3' (SEQ ID NO:108) (R2). Dnmt3b-specific primers used are 5'-TGGGATCGAGGGCCTCAAAC-3' (SEQ I) NO:109) and 5'-TTCCACAGGACAAACAGCGG-3' (SEQ ID NO:110) (for exon 10), 5'-GCGACAACCGTCCAT-TCTTC-3' (SEQ ID NO:111) and 5'-CTCTGGGCACTG-GCTCTGACC-3' (SEQ ID NO:112) (for exons 21 and 22). Northern hybridization was performed according to standard protocols. Dnmt3a cDNA fragments used as probes were generated by PCR. The primer pairs used were 5'-GCA-GAGCCGCCTGAAGCC-3' (SEQ ID NO:113) and 5'-CCTTTTCCAACGTGCCAG-3' (SEQ ID NO:1 14) (for probe 1), and 5'-GCCAAGGTAATTGCAGTA-3' (SEQ ID NO:115) and 5'-GATGTTTCTGCACTTCTG-3' (SEQ ID NO:116) (for probe 2).

Targeted disruption of Dnmt3a2 in ES cells. The P2 targeting vector was electroporated into Dnmt3a$^{+/-}$ ES cells (Okano, M. et al., *Cell* 99(3):247-257 (1999)), which were subsequently selected in hygromycin-containing medium.

Genomic DNA isolated from hygromycin-resistant colonies was digested with ScaI and analyzed by Southern hybridization using a 0.45 kb KpnI-SpeI fragment as a probe.

DNA methyltransferase assays. For in vitro DNA methyltansferase activity, His$_6$-tagged Dnmt3a proteins were incubated with double-stranded poly(dI-dC) (Pharmacia) in the presence of S-adenosyl-L-methionine [methyl-$^3$H] (NEN), and the incorporation of $^3$H methyl groups into poly(dI-dC) was measured as previously described (Okano, M. et al., *Nat. Genet.* 19(3):219-20 (1998)). For de novo methylation activity, human EC cell lines and breast/ovarian cancer cell lines were infected with Moloney murine leukemia virus, and the methylation status of newly integrated provirus was analyzed as previously described (Lei, H. et al., *Development* 122(10):3195-3205(1996)).

Results

Identification of Dnmt3b6 and Dnmt3a2

Figure 11:
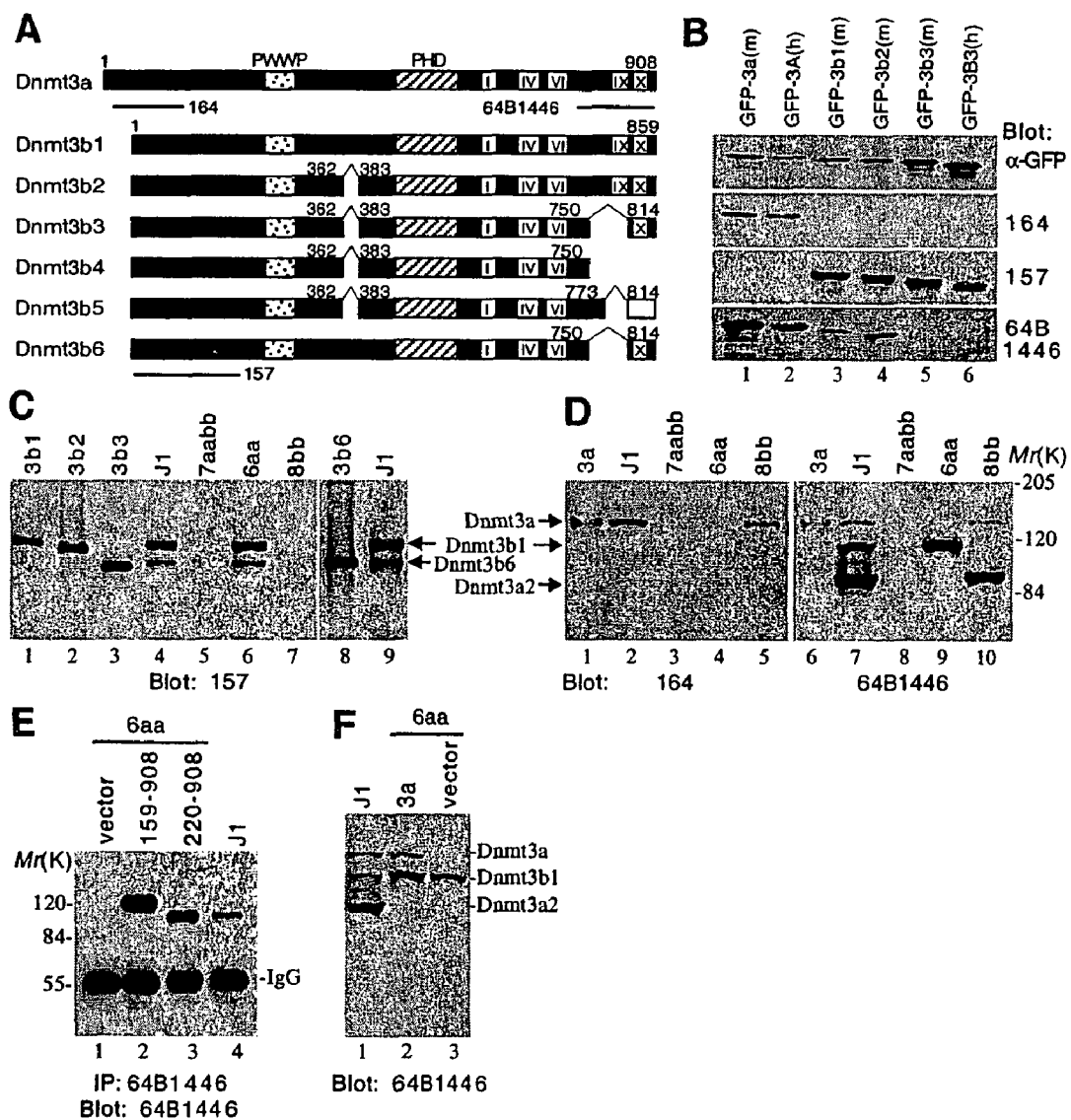
FIGS. 11A-11F present the identification of novel isoforms of Dnmt3a and Dnmt3b proteins.

The Dnmt3a and Dnmt3b proteins show high sequence homology in the C-terminal catalytic domain, but they share little sequence similarity in the N-terminal regulatory region except for the conserved PWWP and PHD domains (FIG. 11A). To characterize the Dnmt3 proteins, rabbit polyclonal antibodies were generated against the N-terminal regions of mouse Dnmt3a (antibody 164) and Dnmt3b (antibody 157), and a commercial monoclonal antibody (64B 1446), which was raised against the full-length mouse Dnmt3a was also obtained. The epitope recognized by 64B1446 was mapped to a region (a.a. 705-908) at the C terminus. The specificity of the Dnmt3 antibodies was examined using GFP fusion proteins expressed in Cos-7 cells (FIG. 11B). Anti-GFP immunoblotting showed the expression of the GFP fusion proteins (1$^{st}$ panel). The polyclonal antibodies, 164 and 157, were specific forDnmt3a and Dnmt3b, respectively (2$^{nd}$ and 3$^{rd}$ panels). The monoclonal antibody, 64B1446, reacted strongly with Dnmt3a proteins and weakly with Dnmt3b1 and Dnmt3b2, but not Dnmt3b3 (4$^{th}$ panel), consistent with the epitope-mapping results.

Figure 16:
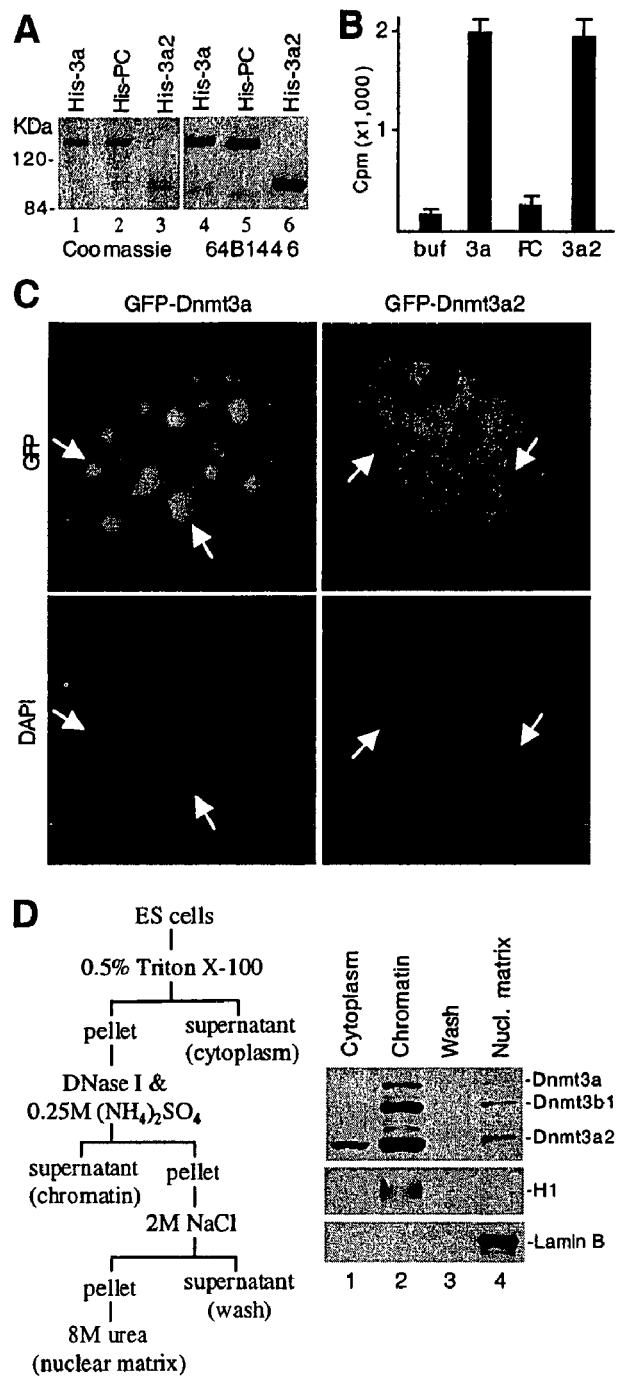
FIGS. 16A-16D demonstrate that Dnmt3a and Dnmt3a2 have similar methyltransferase activity but exhibit different subcellular localization patterns.

Previous studies showed that Dnmt3a and Dnmt3b transcripts were abundant in ES cells (Okano, M. et al., *Nat. Genet.* 19(3):219-220 (1998)), but their protein products had not been analyzed. To address this question, wild-type (J1), Dnmt3a$^{-/-}$ (6aa), Dnmt3b$^{-/-}$ (8bb), and [Dnmt3a$^{-/-}$, Dnmt3b$^{-/-}$] (7aabb) mutant ES cells (Okano, M. et al., *Cell* 99(3):247-257(1999)) were analyzed by immunoblotting with the Dnmt3 antibodies (FIGS. 11C and 11D). Two distinct bands, which migrated at ~120 and ~110 kDa, were detected by antibody 157 in J1 and 6aa cells, but not in 8bb and 7aabb cells (FIG. 11C), indicating that these bands represent Dnmt3b proteins. The more abundant 120-kDa band most likely represents Dnmt3b1 and the 110-kDa band represents an isoform smaller than Dnmt3b2 but slightly larger than Dnmt3b3 (FIG. 11C). RT-PCR analysis confirmed the expression of two major Dnmt3b transcripts in ES cells; one corresponds to Dnmt3b1 and the other is an alternatively spliced variant that lacks exons 21 and 22 (FIG. 16 and data not shown). This new isoform was named Dnmt3b6 (schematically shown in FIG. 11A). Indeed, the 110-kDa band observed in ES cells co-migrated with protein expressed from Dmnt3b6 cDNA (FIG. 11C, lanes 8 and 9). Dnmt3b6 lacks motifIX and thus may not be enzymatically active, like Dnmt3b3 (Aoki, A. et al., *Nucleic Acids Res* 29 (17), 3506-12 (2001)).

Dnmt3a-specific antibody 164 detected a single band of ~130 kDa in J1 and 8bb cells, which co-migrated with the control Dnmt3a protein (FIG. 11D, lanes 1, 2 and 5), but not in 6aa and 7aabb cells (lanes 3 and 4). Surprisingly, when the same blot was reprobed with anti-Dnmt3a monoclonal antibody 64B1446, two more intense bands of ~120 kDa and ~100 kDa were detected in addition to the 130-kDa Dnmt3a protein in J1 cells (FIG. 1D, lane 7). The 120-kDa band represents Dnmt3b 1 as it was also present in 6aa cells but absent in 8bb cells (lanes 9 and 10). Like the 130-kDa Dnmt3a protein, the 100-kDa band could be detected in 8bb cells (lane 10) but not in 6aa and 7aabb cells (lanes 8 and 9), indicating that it is a novel product of the Dnmt3a gene. We named this short form Dnmt3a2. Importantly, the immunoblotting result indicates that Dnmt3a2 is the predominant Dnmt3a gene product in ES cells (FIG. 11D).

The fact that Dmnt3a2 could not be recognized by antibody 164 suggests that Dnmt3a2 lacks the N-terminal region of Dnmt3a. Inspection of the Dnmt3a cDNA sequence revealed that, in addition to the known initiation codon (ATG1), two downstream in-frame ATGs (ATG2 and ATG3), corresponding to Met 159 and Met 220, were found to be within the Kozak consensus sequence. To test the possibility that Dnmt3a2 was produced by translation initiated at one of these ATGs, we expressed in 6aa cells two Dnmt3a proteins with the N-terminal 158 and 219 amino acids truncated and showed that Dnmt3a (220-908) co-migrated with endogenous Dnmt3a2 from J1 cells (FIG. 11E, compare lanes 3 and 4). This suggests that ATG3 might be the initiation codon for Dnmt3a2. To further determine whether Dnmt3a2 is produced from the same mRNA transcript as Dnmt3a, we transfected 6aa cells with an expression vector containing the entire Dnmt3a coding sequence. Immunoblotting analysis using antibody 64B1446 showed that only Dnmt3a was expressed (FIG. 11F, lane 2). These results suggest that Dnmt3a2 does not derive from Dnmt3a transcript by the use of an alternative ATG or from Dnmt3a protein by proteolytic cleavage or degradation.

Dnmt3a2 is Encoded by Transcripts Initiated from a Downstream Promoter

Figure 12:
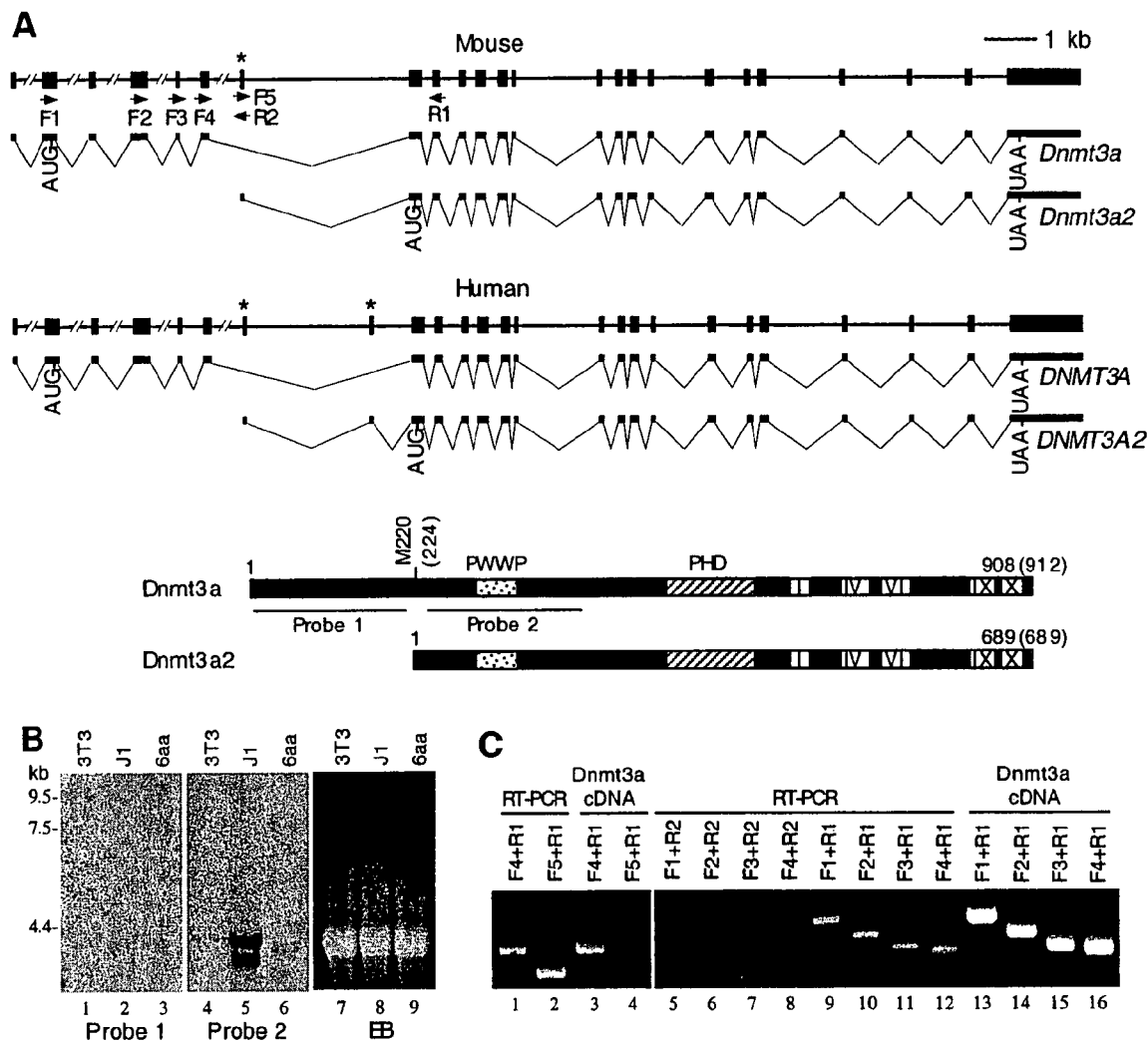
FIGS. 12A-12C demonstrate that Dnmt3a and Dnmt3a2 are encoded by distinct transcripts.
Figure 17:
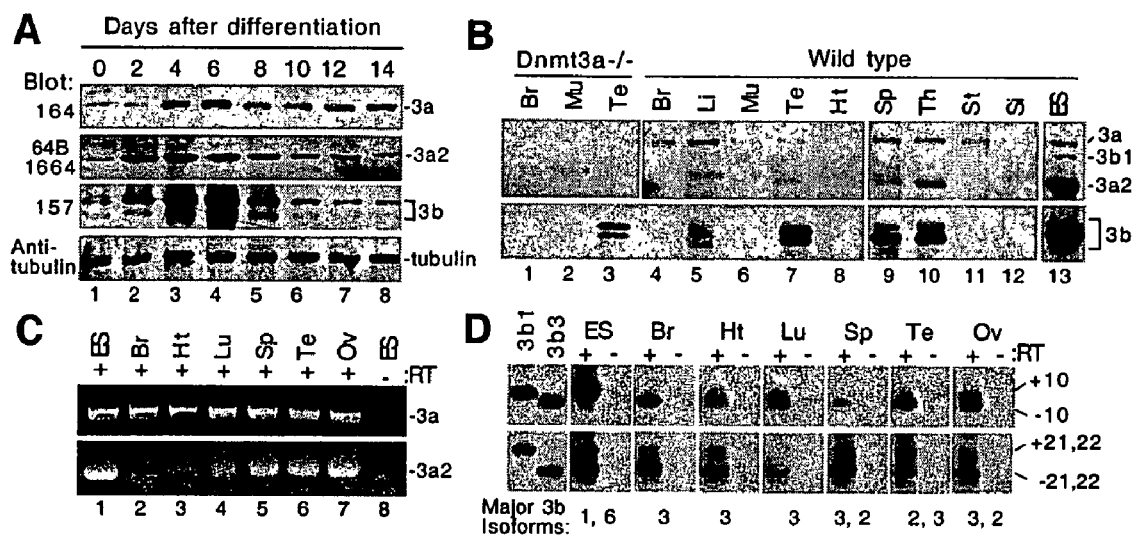
FIGS. 17A-17D present Dmnt3a and Dnmt3b expression in embryoid bodies and mouse tissues.

To determine whether Dnmt3a and Dnmt3a2 are encoded by distinct MRNA transcripts, total RNA from J1, 6aa ES cells, and NIH 3T3 cells (which express only Dnmt3a, see FIG. 17) was analyzed by Northern hybridization with Dnmt3a cDNA probes upstream or downstream of ATG3 (FIG. 12B). The downstream probe (Probe 2, FIG. 12A) detected two major transcripts of 4.2 kb and 4.0 kb and a weak band of 9.5 kb from J1 cells (FIG. 12B, lane 5), consistent with our previous results (Okano, M. et al., *Nat Genet* 19 (3), 219-20 (1998)). All the transcripts were smaller and the intensity of 4.2 kb and 4.0 kb bands was substantially reduced in 6aa cells (lane 6), indicating that truncated transcripts were generated. The 9.5-kb transcript was also present at low level in NIH 3T3 cells, but the 4.2 kb and 4.0 kb transcripts were absent (lane 4). Interestingly, the upstream probe (Probe 1, FIG. 12A) recognized the 9.5 kb transcript in NIH 3T3 and J1 cells and a 7.5 kb truncated form in 6aa cells, but it failed to hybridize to the 4.2 kb and 4.0 kb transcripts in J1 cells (lanes 1-3). Taken together, these observations suggest that Dnmt3a2 is probably encoded by the 4.2 kb and 4.0 kb transcripts. Our previous data indicated that the 4.2 kb and 4.0 kb transcripts differ in their 3'UTR, probablydue to alternative 3' processing (Okano, M. et al., *Nat. Genet.* 19(3):219-220 (1998)).

To determine the identity of the Dnmt3a transcripts, 5' RACE was performed on RNA prepared from J1 ES cells with primers annealing to Dnmt3a sequences downstream of the putative Dnmt3a2 translation start site (ATG3 at M220). Two species of Dnmt3a transcripts were obtained. One of them matched the Dnmt3a cDNA sequence and the other contained a 55-bp sequence at its 5' end that did not match any known Dnmt3a cDNA sequence. Searches of the Celera mouse genome database revealed that the 55-bp sequence was part of an exon located in an intron of the Dnmt3a gene. Using the new exon sequence as query, a mouse EST clone was identified, BE855330, which extended the exon to at least 117 bp. Sequencing analysis revealed that the EST clone shared all the downstream exons with Dnmt3a (FIG. 12A). It is concluded that the newly identified transcript encodes Dnmt3a2 as its open reading frame would predict a protein that lacks the N-terminal 219 amino acids of Dnmt3a (FIG. 12A). As illustrated in FIG. 12A, the murine Dnmt3a gene consists of 24 exons. Exons 8-24 are shared by both Dnmt3a and Dnmt3a2. Exons 1-6 are present only in Dnmt3a whereas exon 7 (indicated by a *) is unique to Dnmt3a2.

The 5' RACE results were confirmed by RT-PCR analysis of total RNA from J1 cells using primers annealing to different Dnmt3a exons (FIG. 12A). Combination of Dnmt3a-specific (F1-F4) or Dnmt3a2-specific (F5) primers with a downstream primer in exon 9 (R1) verified the expression of both Dnmt3a and Dnmt3a2 transcripts in ES cells (FIG. 12C, lanes 1-4 and 9-16). However, combination of the same Dnmt3a primers (F 1-F4) with a primer in the unique Dnmt3a2 exon (R2) failed to generate any PCR products (lanes 5-8). These results indicate that it is unlikely that the Dnmt3a and Dnmt3a2 transcripts are produced via alternative splicing.

The nucleotide and predicted amino acid sequences of Dnmt3a2 are presented in FIG. 13A and B. By RT-PCR analysis and database searches, human DNMT3A2 was also identified (FIG. 12A). The Nucleotide and predicted amino acid sequences of human DNMT3A2 are presented in FIGS. 13C and D. An aligmnent of the human and murine cDNA sequences reveals strong similarity (FIGS. 13E1-E4) except that human DNMT3A2 contains an additional sequence of 68 bp in the 5'UTR, which is encoded by an extra exon located ~2.5 kb downstream of exon 7 (the newly identified exons are indicated by * in FIG. 12A). The predicted mouse Dnmt3a2 and human DNMT3A2 proteins, each consisting of 689 amino acids (FIGS. 13B and D, respectively), show high sequence identity (FIG. 13F; 98.5%).

Figure 14:
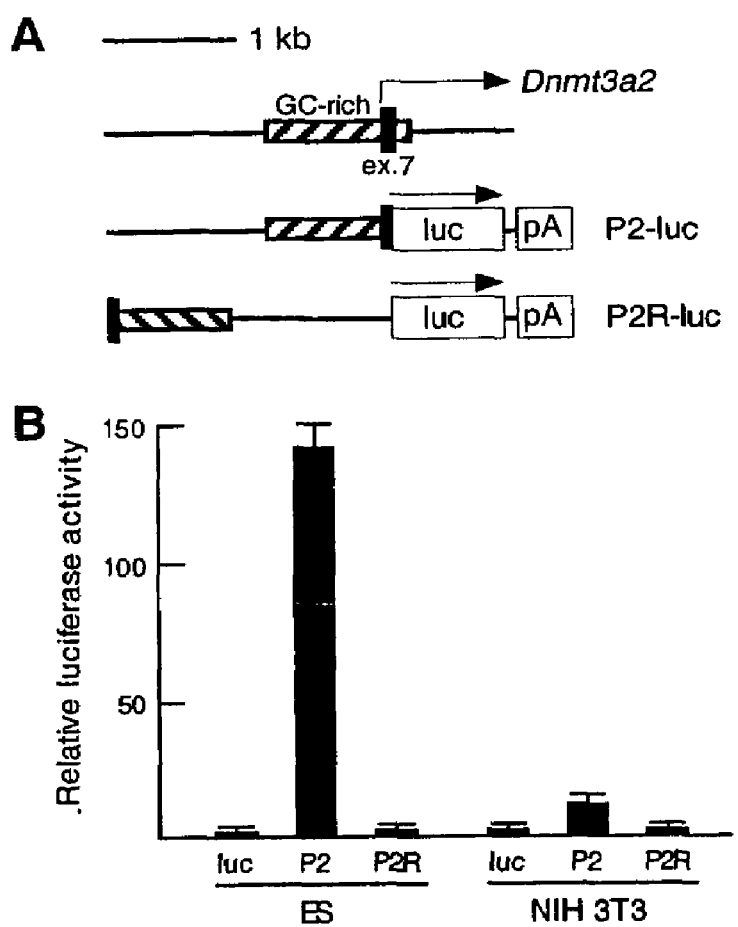
FIGS. 14A-14B demonstrate that a region 5' adjacent to the Dnmt3a2 unique exon has promoter activity.

The observation that the Dnmt3a2-specific exon is located in a region >80 kb downstream of the putative Dnmt3a promoter suggests that Dnmt3a2 transcription maybe driven by a different promoter. Indeed, analysis of the large (~18 kb) "intron" preceding exon 7 with PROSCAN (http://bimas.dcrt.nih.gov/molbio/proscan) predicted that a 1.4-kb region immediately upstream of exon 7 has high probability to function as a promoter. It should also be noted that the unique Dnmt3a2 exon resides in a GC-rich CpG island, which is a hallmark of the promoter region of genes. The transcriptional activity of the putative promoter was tested using a reporter system (FIG. 14). A ~2.0 kb genomic fragment that includes the putative promoter (P2) was inserted, in both orientations, upstream of the cDNA encoding the firefly luciferase followed by the SV40 late poly(A) signal (FIG. 14A; See FIG. 27 for nucleotide sequence of the genomic fragment). Transient transfection experiments demonstrated that the P2 fragment has high promoter activity in ES cells but much lower activity in NIH 3T3 cells (FIG. 14B, P2-luc), consistent with the expression levels of Dnmt3a2 in these cell types (FIG. 12B). The transcriptional activity of the P2 fragment is orientation-dependent, as the same fragment showed no promoter activity when subcloned in reverse orientation (FIG. 14B; P2R-luc). As a positive control, SV40 promoter worked equally well in both cell types. These data strongly suggest that the region 5' adjacent to exon 7 functions as a promoter and drives the expression of Dnmt3a2.

Figure 15:
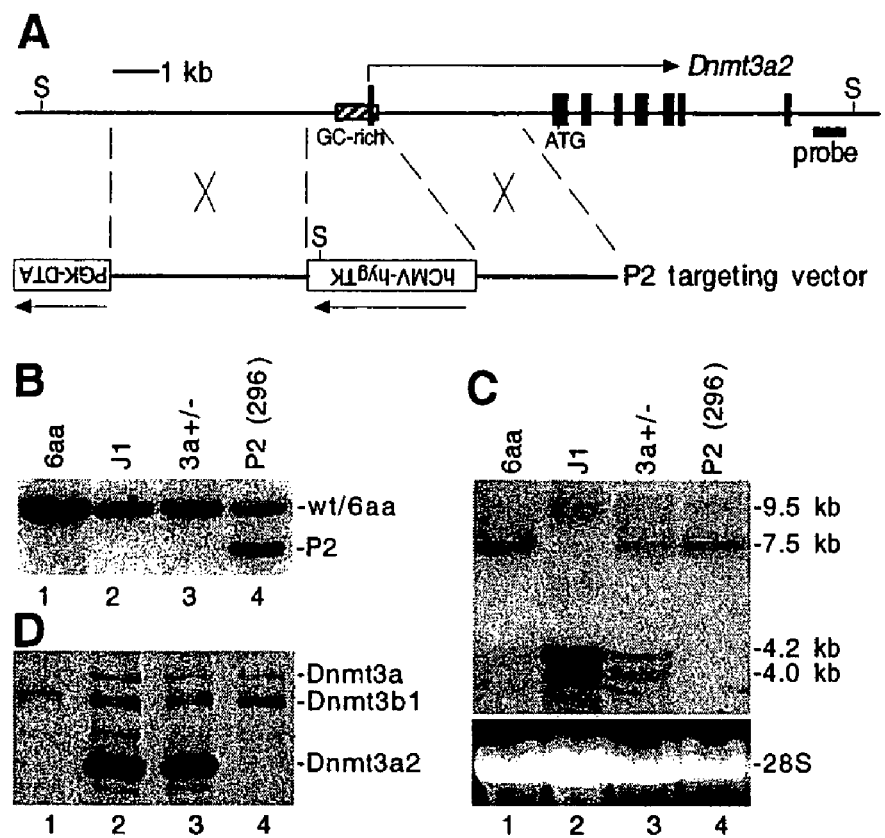
FIGS. 15A-15D demonstrate that deletion of the putative Dnmt3a2 promoter region abolishes Dnmt3a2 transcripts and Dnmt3a2 protein.

To confirm that exon 7 and the adjacent promoter are essential for the expression of Dnmt3a2, we deleted the P2 region from the wild-type allele in Dnmt3a$^{+/-}$ ES cells (Okano, M. et al., Cell 99 (3), 247-57 (1999)) by gene targeting. An hCMV-hygTK cassette was inserted in the opposite orientation of Dnmt3a transcription to avoid disruption of the Dnmt3a transcripts (FIG. 15A). We, therefore, expected that the removal of these sequences would abolish the transcription of Dnmt3a2, but not Dnmt3a. One clone (296) with deletion of the wild type allele was successfully isolated (FIG. 15B). As expected, Northern hybridization showed that the 4.2 kb and 4.0 kb transcripts were completely abolished in clone 296 cells (FIG. 15C). Consistently, immunoprecipitation and immunoblotting analyses demonstrated that Dnmt3a2 protein was abolished whereas Dnmt3a protein was produced in clone 296 cells at similar levels as in Dnmt3a$^{+/-}$ cells (FIG. 15D). These data provide genetic evidence that the newly identified Dnmt3a2 is indeed encoded by MRNA transcribed from a downstream promoter.

Dnmt3a2 and Dnmt3a Show Similar Methyltransferase Activity but Different Subcellular Localization Patterns To test whether Dnmt3a2 has methyltransferase enzyme activity, we generated recombinant Dnmt3a proteins and measured their catalytic activity by a standard in vitro methylation assay. Dnmt3a, Dnmt3a:PC→VD, and Dnmt3a2 were expressed in E. coli as N-terminally His$_6$-tagged fusion proteins and purified by metal chelation chromatography. The proteins were ~90% pure, as estimated by Coomassie blue staining (FIG. 16A, lanes 1-3), and their identity was verified by immunoblotting (lanes 4-6). As shown previously (Okano, M. et al., Nat Genet 19 (3), 219-20 (1998)) Dnmt3a was able to transfer methyl groups to double-stranded poly (dI-dC). Mutation of the PC motif in the catalytic domain (Dnmt3a:PC→VD) abolished the activity. Dmnt3a2 showed similar enzyme activity as Dnmt3a (FIG. 16B), demonstrating that Dnmt3a2 is an active DNA methyltransferase.

It has been recently reported that Dnmt3a localizes to heterochromatin (Bachman, K. E. et al., J Biol Chem 276 (34),32282-7 (2001)). To determine whether Dnmt3a2 localizes differently from Dnmt3a, GFP-Dnmt3a fusion proteins were expressed in NIH 3T3 cells and their localization was analyzed by fluorescence microscopy. Dmnt3a localized exclusively in the nuclei and concentrated in nuclear foci that correspond to DAPI (4,6-diamidino-2-phenylindole) bright spots, consistent with heterochromatin association. In contrast, Dnmt3a2 showed a diffused pattern excluding nucleoli and heterochromatin. Although Dnmt3a2 localized mainly in the nuclei, weak staining was also observed in the cytoplasm (FIG. 16C). Similar results were obtained when the GFP fusion proteins were expressed in ES cells. These data indicate that the N-terminal 219 amino acids of Dnmt3a are required for its exclusive nuclear localization and heterochromatin association.

To confirm the localization data, we investigated the subcellular distribution of endogenous Dnmt3 proteins. ES cells were extracted sequentially to obtain the cytoplasmic, chromatin, and nuclear matrix fractions. Immunoblotting analysis with antibody 64B1446 showed that Dnmt3a and Dnmt3a2 as well as Dnmt3b1 fractionate mainly with chromatin and small proportions of these proteins also associate with the nuclear matrix (FIG. 16D). While Dnmt3a and Dnmt3b1 were exclusively nuclear, a significant proportion of Dnmt3a2 was present in the cytoplasmic fraction (FIG. 16D), consistent with the localization results (FIG. 16C). The efficacy of the fractionation procedure was verified by immunoblotting with control antibodies specific to histone H1 (a component of chromatin) and lamin B (a nuclear matrix-associated protein) (FIG. 16D). Taken together, these results suggest that Dnmt3a associates mainly with heterochromatin and Dnmt3a2 associates primarily with euchromatin.

Expression of Dnmt3a2 and Dnmt3b in Mouse Tissues and Human Cell Lines Correlate with de Novo Methylation Activity Since de novo methylation activity changes during differentiation, the levels of Dnmt3a and Dnmt3b proteins in differentiating ES cells were examined. ES cells were differentiated as embryoid bodies in vitro for 14 days and the change of Dmnt3 protein levels was monitored by immunoblotting (FIG. 17A). Dnmt3a, Dnmt3a2, and Dnmt3b were all upregulated upon differentiation, with the highest level observed in embryoid bodies at 4-6 days. However, after 6 days of differentiation, the level of Dnmt3a2 and Dnmt3b rapidly decreased, whereas the level of Dnmt3a sustained throughout the course of the experiment.

The expression of Dnmt3a and Dnmt3b proteins in somatic tissues from 3-week-old mice was then examined by immunoprecipitation and immunoblot analysis. As shown in FIG. 17B, Dnmt3a was detected in all tissues except for small intestines, whereas Dnmt3a2 and Dnmt3b expression was more restricted. Both Dnmt3a2 and Dnmt3b proteins were detected in testis, spleen, and thymus, tissues known to contain cells that undergo active de novo methylation. Dnmt3b was also present at low levels in liver (FIG. 17B). RT-PCR analysis confirmed the immunoblotting results and also revealed the expression of Dnmt3a2 and Dnmt3b in ovary (FIGS. 17C and 17D). Based on the presence or absence of Dnmt3b exon 10 and/or exons 21/22, we were able to determine the Dnmt3b isoforms (FIG. 17D). Therefore, the Dnmt3b doublets observed in testis, spleen, thymus, and liver (FIG. 17B) most likely represent Dmnt3b2 and Dnmt3b3. Of note is that the relative levels of Dnmt3b2 and Dmnt3b3 are different in these tissues (FIG. 17B). Although Dmnt3b proteins could not be detected in many tissues (FIG. 17B), low levels of Dnmt3b transcripts (mainly Dnmt3b3) were expressed ubiquitously (FIG. 17D). Dnmt3b1 and 16 Dnmt3b6 were detected only in ES cells (FIG. 17D). These observations, along with the dynamic changes during ES cell differentiation, indicate that Dnmt3a2 and Dnmt3b are coordinately regulated and their expression correlates with de novo methylation activity.

Since overexpression of DNMT1, DNMT3A, and DNMT3B transcripts have been reported in various human cancers, the expression of various DNMT proteins was examined in embryonal carcinoma and breast/ovarian cancer cell lines by immunoblotting. We showed that five EC cell lines expressed relatively high levels of DNMT3A2 and low levels of DNMT3A (FIG. 18A). DNMT3B was also highly expressed in these cells but different cells expressed different isoforms (FIG. 18B). In several breast and ovarian cancer cell lines, DNMT1 was expressed at comparable levels, which was similar to the level in an EC cell line, NCCIT (FIG. 18C, $1^{st}$ panel) (note that the antibody does not recognize mouse Dnmt1 in J1 and NIH 3T3 cells). Low levels of DNMT3A1 were detected in most cell lines (FIG. 18C, $2^{nd}$ panel). Although DNMT3A2 and DNMT3B proteins were also detectable in most of the breast/ovarian cancer cell lines, their levels were very low as compared to EC and ES cells (FIG. 18C, $3^{rd}$ and $4^{th}$ panels).

It was then investigated whether the expression levels of DNMT proteins correlate with de novo methylation activity. Human EC and breast and ovarian cancer cell lines were infected with Moloney murine leukemia virus (MMLV, FIG. 18D, lower panel), and the methylation status of proviral DNA was analyzed using the CpG methylation sensitive enzyme Hpa II (FIG. 18D). The proviral DNA was partially or completely methylated in the EC cell lines, as indicated by the presence of Hpa II-resistant bands ranging from 0.8 kb (unmethylated band) to 1.3 kb (fully methylated band), and the level of methylation increased with time (lanes 1-13, compare day 5 and day 20). In contrast, little or no de novo methylation activity was detected in any of the breast and ovarian cancer cell lines examined (lanes 14-21). Since DNMT1 was readily detected in all the cell lines (FIG. 17C), the results provide additional evidence that DNMT1 does not have de novo methyltransferase activity, consistent with the current view that it functions as a maintenance enzyme. It is also unlikely that DNMT3A1 caused the difference in de novo methylation between EC cell lines and breast/ovarian cancer cells, as the expression level of DNMT3A is low but similar in both groups of cell lines (FIG. 18C). The absence of DNMT3B1/3B2 in several EC cell lines (PA-1, NTERA-2, and Tera-2) suggested that the de novo methylation activity observed in these cells can be attributed to the activity of DNMT3A2. The results are therefore most consistent with the notion that DNMT3A2 and DNMT3B1/3B2 are responsible for active de novo methylation of provirus DNA in ES cells and EC cells.

Discussion

In this study it was demonstrated that the Dnmt3a gene encodes at least two isoforms, termed Dnmt3a and Dnmt3a2, of approximately 130 kDa and 100 kDa, respectively. The newly identified Dnmt3a2 protein, which lacks the N-terminal region of Dnmt3a, is encoded by transcripts initiated from a downstream promoter and represents the major isoform in ES cells and EC cells. This conclusion is supported by several lines of evidence from molecular and genetic analyses of wild type and Dnmt3a-deficient ES cells. First, antibodies specific to the N-terminal region of Dnmt3a failed to detect the 100-kDa protein in ES cells and a 5' cDNA probe upstream of the first coding exon of Dnmt3a2 failed to hybridize to the major 4.0 kb and 4.2 kb transcripts. Second, 5' RACE and RT-PCR analysis identified a 5' exon upstream of the Dnmt3a2 coding region, which is located in a large intron of Dnmt3a. Third, a GC-rich "intronic" region upstream of the Dnmt3a2-specific exon showed strong promoter activity for the expression of a reporter gene in ES cells and much lower activity in NIH 3T3 cells, consistent with Dnmt3a2 expression status in these cells. Finally, deletion of the putative promoter region abolished Dnmt3a2 transcripts and Dnmt3b2 protein, whereas transcription and translation of Dnmt3a were unaffected.

Figure 18:
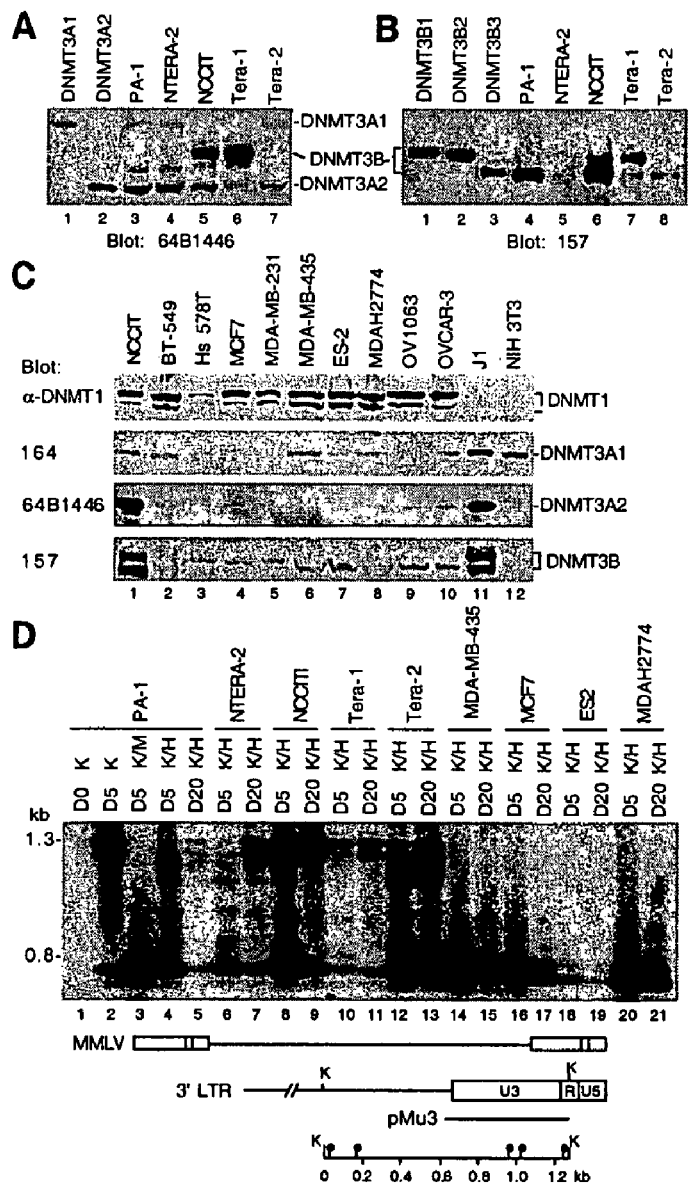
FIGS. 18A-18D demonstrate that expression of DNMT3A2 and DNMT3B in human cell lines correlate with de novo methylation activity.

While both Dnmt3a and Dnmt3a2 are active DNA methyltransferases as shown by in vitro assays, they differ from one another in two main features. First, Dnmt3a2 showed a diffused nuclear staining pattern excluding heterochromatin, in contrast to Dnmt3a, which is concentrated in heterochromatin. It is believed that Dnmt3a and Dmnt3a2 may modify different chromatin domains, with Dnmt3a preferentially methylating heterochromatin and Dnmt3a2 preferentially methylating euchromatin. Given that hypermethylation of single-copy genes, which usually reside in euchromatic regions, contributes to diseases such as cancers, the association of Dnmt3a2 with euchromatin may potentially link Dnmt3a2 action to onto genesis. Notably, Dnmt3a2 is detectable in many breast/ovarian cancer cell lines although the expression level is not sufficient to cause de novo methylation of provirus (FIG. 18). Second, expression of Dnmt3a2 is developmentally regulated, whereas Dnmt3a is ubiquitously expressed. It was observed that Dnmt3a2 is expressed only in tissues, such as testis, ovary, spleen, and thymus, in which de novo methylation is believed to occur during cellular differentiation. Analysis of de novo methylation activity in human cell lines also suggested that DNMT3A2 is capable of methylating newly integrated retroviral DNA. Therefore, Dnmt3a2 may function as a de novo methyltransferase. The absence of Dnmt3a2 in most somatic tissues suggests that expression of Dnmt3a2 must be tightly regulated to avoid abnormal de novo methylation, which could be toxic to cells. Consistent with these results, it was observed that it was difficult to establish stable cell lines with overexpression of Dnmt3a2, but not when Dnmt3a or mutated Dnmt3a2 (mutation of the PC motif) was overexpressed.

In this study, a novel isoform of Dnmt3b, termed Dnmt3b6 was also identified. It was demonstrated that different Dnmt3b isoforms exhibit different tissue distributions. Dnmt3b1 and Dnmt3b6 are the predominant forms in ES cells, while Dnmt3b2 and Dnmt3b3 are expressed at relatively high levels in testis, ovary, spleen, thymus, and liver. It is believed that Dnmt3b1 and Dnmt3b2 function as de novo methyltransferases, whereas Dnmt3b3 and Dnmt3b6 function as regulators of DNA methylation.

Genetic studies have shown that Dnmt3a and Dnmt3b are essential for de novo methylation in ES cells and during embryonic development (Okano, M. et al., *Cell* 99 (3), 247-57 (1999)). Since Dnmt3a and Dnmt3b isoforms show different biochemical properties and expression patterns, they may have distinct functions in development. Dnmt3a2 and Dnmt3b1 are the major isoforms detected in ES cells and likely have redundant functions in carrying out de novo methylation of provirus DNA (Okano, M. et al., *Cell* 99 (3), 247-57 (1999)). Interestingly, the expression level of both Dnmt3a and Dnmt3a2, and different Dnmt3b isoforms is elevated during early stages of ES cell differentiation, but only Dnmt3a expression persists to the late differentiation stage, reminiscent of Dnmt3a and Dnmt3b expression in embryos (Okano, M. et al., *Cell* 99 (3), 247-57 (1999)). It is believed that Dnmt3a2 and Dnmt3b1/3b2 maybe involved in de novo methylation in early post implantation embryos. While these enzymes may have overlapping functions in modifying various genomic sequences, protein targeting may confer specificity to them as well. Lack of access to heterochromatin may explain why Dnmt3a2 can not compensate for Dnmt3b in methylating centromeric minor satellite repeats (Okano, M. et al., *Cell* 99 (3), 247-57(1999)). Dnmt3a2 and Dnmt3b are also expressed at relatively high levels in testis, ovary, spleen and thymus and may play an important role in regulation of genomic imprinting, gametogenesis, and lymphocyte differentiation. It has been shown that disruption of both Dnmt3a and Dnmt3a2 by deleting the conserved motifs in the catalytic domain perturbs de novo methylation of maternally imprinted genes during oocyte maturation and spermatogenesis (Hata, K. et al., *Development* 129, 1983-93). Dnmt3a (and Dnmt3b3) is expressed at low levels in most tissues and cell lines analyzed, suggestive of a housekeeping function.

Example 6

Establishment and Maintenance of Genomic Methylation Patterns in Mouse Embryonic Stem Cells by Dnmt3a and Dnmt3b DNA methyltransferases Dnmt3a and Dnmt3b carry out de novo methylation of the mouse genome during early post implantation development and of maternally imprinted genes in the oocyte. In this study, it is shown that Dnmt3a and Dnmt3b are also essential for the stable inheritance, or 'maintenance' of DNA methylation patterns. Inactivation of both Dnmt3a and Dnmt3b in ES cells results in progressive loss of methylation in various repeats and single copy genes. Interestingly, introduction of various Dnmt3a and Dnmt3b isoforms back into highly demethylated mutant ES cells restores genomic methylation patterns and different isoforms have both common and specific DNA targets, but they all fail to restore the maternal methylation imprints. Evidence is provided shows that Dnmt3b3 (and 3b6 as well) has no enzymatic activity in vivo, but may function as a negative regulator of DNA methylation. It is also shown that hypermethylation of genomic DNA by Dnmt3a and Dnmt3b is necessary for ES cells to form teratomas in nude mice. These results indicate that genomic methylation patterns are determined partly through differential expression of different Dnmt3a and Dnmt3b isoforms.

Introduction

DNA methylation is essential for mammalian development and plays crucial roles in a variety of biological processes such as genomic imprinting and X chromosome inactivation (Li, E. *Nat Rev Genet* 3:662-73 (2002)). DNA methylation patterns are established during embryonic development through a highly orchestrated process that involves demethylation and de novo methylation and can be inherited in a clonal fashion through the action of maintenance methyltransferase activity (Bird, A. P., and A. P. Wolffe. *Cell* 99:451-4 (1999); Li, E. *Nat Rev Genet* 3:662-73 (2002); Reik et al., *Science* 293:1089-93 (2001)). During preimplantation development, both the paternal and maternal genomes undergo a wave of demethylation, which erases most of the methylation patterns inherited from the gametes. Shortly after implantation, the embryo undergoes a wave of de novo methylation, which establishes a new methylation pattern (Howlett, S. K., and W. Reik. *Development* 113:119-27 (1991); Kafri et al., *Genes Dev* 6:705-14 (1992); Monk et al., *Development* 99:371-82 (1987); Sanford et al., *Genes Dev* 1:1039-46 (1987)). De novo methylation also occurs during gametogenesis in both male and female germ cells and is believed to play a critical role in the establishment of genomic imprinting in the gametes. Genomic imprinting is an epigenetic process that marks alleles according to their parental origin during gametogenesis and results in monoallelic expression of a small set of genes, known as imprinted genes, in the offspring (Jaenisch, R. *Trends Genet* 13:323-9 (1997); Li, E. *Nat Rev Genet* 3:662-73 (2002); Reik, W., and J. Walter. *Nat Rev Genet* 2:21-32 (2001)). De novo methylation activity is present mainly in embryonic stem (ES) cells and embryonal carcinoma (EC) cells, early postimplantation embryos, and developing germ cells, whereas it is largely suppressed in differentiated somatic cells (Kafri et al., *Genes Dev* 6:705-14 (1992); Lei et al., *Development* 122:3195-205 (1996); Santos et al., *Dev Biol* 241:172-82 (2002); Stewart et al., *Proc Natl Acad Sci USA* 79:4098-102

(1982)). Therefore, ES cells can be a good model system for studying the mechanisms of de novo methylation.

Three active DNA cytosine methyltransferases, namely Dnmt1, Dnmt3a, and Dnmt3b, have been identified in human and mouse (Bestor et al., *J Mol Biol* 203:971-83 (1988); Okano et al., *Nat Genet* 19:219-20 (1998); Xie et al., *Gene* 236:87-95 (1999)). Dnmt1 is ubiquitously expressed in proliferating cells and localizes to DNA replication foci (Leonhardt et al., *Cell* 71:865-73 (1992)). Purified Dnmt1 protein methylates hemi-methylated DNA substrates more efficiently than unmethylated DNA in vitro (Bestor, T. H. *EMBO J* 11:2611-7 (1992)). Despite its activity in vitro, Dnmt1 has not been convincingly shown to be able to initiate de novo methylation in vivo. Moreover, inactivation of Dnmt1 in ES cells and mice leads to extensive demethylation of all sequences examined (Lei et al., *Development* 122:3195-205 (1996); Li et al., *Cell* 69:915-26 (1992)). All these findings suggest that Dnmt1 functions primarily as a maintenance methyltransferase that is responsible for copying the parental-strand methylation pattern onto the daughter strand after each round of DNA replication. In contrast, Dnmt3a and Dnmt3b are highly expressed in ES cells, early embryos, and developing germ cells, but expressed at low levels in differentiated somatic cells (Chen et al., *J Biol Chem* 277:38746-54 (2002); Okano et al., *Nat Genet* 19:219-20 (1998)). Indeed, genetic studies have demonstrated that Dmnt3a and Dnmt3b are essential for de novo methylation in ES cells and postimplantation embryos as well as for de novo methylation of imprinted genes in the germ cells (Hata et al., Development 129:1983-93 (2002); Okano et al., *Cell* 99:247-57 (1999)). Although Dnmt3a and Dnmt3b function primarily as de novo methyltransferases to establish methylation patterns, they may also play a role in maintaining methylation patterns. We have previously shown that some genomic sequences, such as the differentially methylated region 2 (DMR2) of Igf2 and the 5' region of Xist, are almost completely demethylated and an L1-like repeat is partially demethylated in mutant ES cells that lack Dnmt3a and Dnmt3b (Liang et al., *Mol Cell Biol* 22:480-91 (2002); Okano et al., *Cell* 99:247-57 (1999)).

At least two Dnmt3a and six Dmnt3b isoforms have been identified (FIG. 20A) (Chen et al., *J Biol Chem* 277:38746-54 (2002); Hansen et al., *Proc Natl Acad Sci USA* 96:14412-7 (1999); Okano et al., *Nat Genet* 19:219-20 (1998); Robertson et al., *Nucleic Acids Res* 27:2291-8 (1999); Xie et al., *Gene* 236:87-95 (1999)). Dnmt3a and Dnmt3a2 are encoded by transcripts initiated from two different promoters. Dnmt3a2 lacks the N-terminal region of the full-length Dnmt3a and, as a result, they exhibit different subcellular localization patterns. While Dnmt3a is concentrated in heterochromatic foci, Dnmt3a2 localizes diffusely in the nucleus (Chen et al., *J Biol Chem* 277:38746-54 (2002)). Unlike the Dnmt3a isoforms, all the known Dnmt3b isoforms are derived from alternative splicing. Dnmt3b 1 and Dnmt3b2 are enzymatically active, as shown by in vitro methyltransferase assays, whereas Dnmt3b3, which lacks part of motif IX, appears to be inactive (Aoki et al., *Nucleic Acids Res* 29:3506-12 (2001); Okano et al., *Nat Genet* 19:219-20 (1998)). Dnmt3b4, Dnmt3b5, and Dnmt3b6 are also presumably inactive because they lack either part of motif IX (Dnmt3b6) or both motifs IX and X (Dnmt3b4 and Dnmt3b5) (Chen et al., *J Biol Chem* 277:38746-54 (2002); Hansen et al., *Proc Natl Acad Sci USA* 96:14412-7 (1999); Robertson et al., *Nucleic Acids Res* 27:2291-8 (1999)). Like Dnmt3a, Dnmt3b 1 has been shown to localize to heterochromatin (Bachman et al., *J Biol Chem* 276:32282-7 (2001)). These Dnmt3a/3b isoforms show different expression patterns during development. Dnmt3a2 and Dnmt3b1 are highly expressed in ES cells and germ cells but almost undetectable in most somatic tissues, whereas Dnmt3a and Dnmt3b3 are expressed at low levels in almost all somatic tissues and cell lines examined (Beaulieu et al., *J Biol Chem* 277:28176-81 (2001)).

In this study, we introduced various Dnmt3a/3b isoforms individually back into [Dnmt3a−/−, Dnmt3b−/−] mutant ES cells and showed that these isoforms have both shared and specific genomic targets. In addition, we demonstrated that Dnmt3a and Dnmt3b are required for stable inheritance of global DNA methylation patterns in ES cells and that maintenance of genomic methylation above a threshold level, but not the presence of Dnmt3a and Dnmt3b proteins, is essential for ES cell differentiation and teratoma formation.

Materials and Methods

ES cell culture: Wild-type J1 and mutant ES cells were maintained in Dulbecco's modified Eagle medium (DMEM, Invitrogen) supplemented with 15% fetal bovine serum (HyClone), 0.1 mM non-essential amino acids (Invitrogen), 0.1 mM b-mercaptoethanol, 50 U/ml penicillin, 50 mg/ml streptomycin, and 500 U/ml leukemia inhibitory factor (LIF, Invitrogen). The cells were normally grown on gelatin-coated Petri dishes without feeder cells. For long-term culture, the cells were trypsinized and passaged every other day and the passage numbers were recorded.

DNA constructions: The plasmid vectors expressing Dnmt1, Dnmt3a, Dnmt3a2, Dnmt3b1, Dnmt3b3, and Dnmt3b1:PC (a mutant Dnmt3b1 with the proline-cysteine di-peptide at the active site substituted with glycine-threonine) were generated by subcloning the corresponding cDNAs into pCAG-IRESblast, an expression vector that contains a CAG promoter (a synthetic promoter that includes the chicken b-actin promoter and the human cytomegalovirus immediate early enhancer). pCAG-IRESblast was constructed by replacing the EcoRI-Xho I fragment of pCAGN2-R(H1)-S3H-I-ZF3 (gift from R. Jaenisch) with an IRES-blasticidin cassette.

The Dnmt3b1 targeting vector, in which a 2-kb region containing exons 21 and 22 was replaced by the PGK-puromycin cassette, was generated by sequentially subcloning Dnmt3b genomic fragments (the 8-kb 5' arm and 3.3-kb 3' arm were both obtained from a BAC clone), the PGK-puromycin cassette, and the PGK-DTA cassette into pBluescript II SK. The identities of all constructs were verified by DNA sequencing.

Stable expression of DNA methyltransferases in ES cells: Expression vectors encoding Dnmt3a and Dnmt3b isoforms or Dnmt1 were electroporated into [Dnmt3a−/−. Dnmt3b−/−] or Dnmt1−/− ES cells (Lei et al., *Development* 122:3195-205 (1996); Okano et al., *Cell* 99:247-57 (1999)), which were subsequently selected in blasticidin-containing medium for seven days. Blasticidin-resistant colonies were examined for protein expression by immunoblotting analysis using the following antibodies: monoclonal anti-Dnmt3a (clone 64B1446, Ingenex) (Chen et al., *J Biol Chem* 277: 38746-54 (2002)), polyclonal anti-Dnmt3b (Chen et al., *J Biol Chem* 277:38746-54 (2002)), or polyclonal anti-Dmnt1 (gift from S. Tajima). As loading controls, the levels of a-tubulin in these samples were determined by immunoblotting with monoclonal anti-tubulin antibody (Ab-1, Oncogene Research Products). Expression of the intended Dnmt proteins was observed in ~90% of the colonies, most of which maintained the expression level after four weeks of culture in blasticidin-containing medium.

Targeted disruption of Dnmt3b1 in ES cells: The Dnmt3b1 targeting vector was transfected into Dnmt3b+/− or [Dnmt3a−/−, Dnmt3b+/−] ES cells (Okano, M., et al., *Cell* 99:247-257 (1999)) via electroporation and transfected cells were selected with puromycin. Genomic DNA isolated from puromycin-resistant colonies was digested with EcoRV and analyzed by Southern hybridization using a probe 3' external to the targeting construct. The targeting frequency for the wild-type allele in Dnmt3b+/− and [Dnmt3a−/−, Dnmt3b+/−] cells was 4/150 and 6/200, respectively.

DNA methylation analysis: Genomic DNA isolated from various ES cell lines was digested with methylation-sensitive restriction enzymes, and analyzed by Southern hybridization as previously described (Lei, H. et al., *Development* 122:3195-3205 (1996)). Probes used for methylation analysis include the following: pMO for endogenous C-type retroviruses (Genbank accession NC_001501)(Li, E. et al., *Cell* 69:915-926 (1992)), pMR150 for minor satellite repeats (accession X14469 X07949)(Chapman et al., *Nature* 307: 284-286 (1984)), IAP (accession AF303453)(Walsh etal., *Nat Genet* 20:116-117 (1998)), 3' region of β-globin cDNA (accession J00413 K01748 K03545)(PCR product) (Dennis et al., *Genes Dev* 15:2940-4(2001)), 5' region of Pgk-1 cDNA (accession M18735)(PCR product) (Dennis et al., *Genes Dev* 15:2940-4 (2001)), coding region of Pgk-2 cDNA (PCR product) (Dennis et al., *Genes Dev* 15:2940-4 (2001)), 5' region of Xist cDNA (accession AJ421479, gift from T. Sado), the H19 upstream region (accession U19619) (Tremblay et al., *Nat Genet* 9:407-13 (1995)), DMR2 or "probe 6" for Igf2 (accession NM_010514)(Feil et al., *Development* 120:2933-43 1994)), the Igf2r region 2 probe (accession NM_010515) (Stoger et al., *Cell* 73:61-71 (1993)), Peg1 (accession NM_008590)(Lefebvre et al., *Hum Mol Genet* 6:1907-15(1997)), Snrpn DMR1 (accession NM_013670)(Shemer et al., *Proc Natl Acad Sci USA* 94:10267-72 (1997)), and an oligonucleotide probe (5'-TAT GGC GAG GAA AAC TGA AAA AGG TGG AAA ATT TAG AAA TGT CCA CTG TAG GAC GTG GAA TAT GGC AAG-3' SEQ ID NO:117) specific to major satellite repeats.

Results

Figure 19:
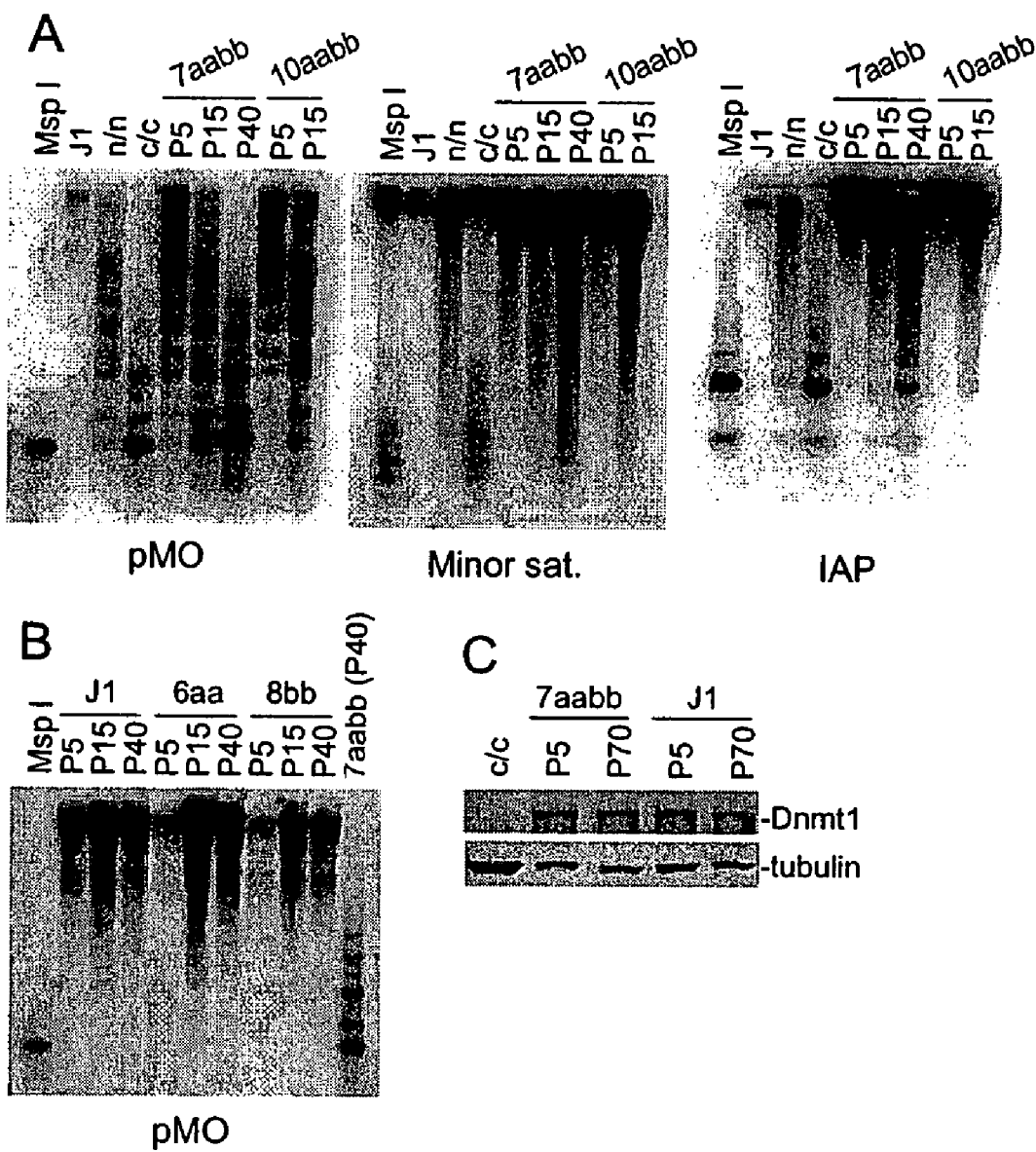
FIGS. 19A-19C demonstrate inactivation of Dnmt3a and Dnmt3b results in progressive loss of DNA methylation in ES cells.

Inactivation of Dnmt3a and Dnmt3b results in progressive loss of DNA methylation in ES cells. Genetic studies have demonstrated that Dnmt3a and Dnmt3b carry out de novo methylation of the mouse genome during early embryonic development (Okano, M. et al., *Cell* 99:247-257 (1999)). To investigate whether these enzymes are also involved in maintaining global DNA methylation patterns, we cultured [Dnmt3a−/−, Dnmt3b−/−] ES cells (Okano, M. et al., *Cell* 99:247-257 (1999)) continuously for various periods of time and examined the methylation status of various genomic sequences using methylation-sensitive restriction enzymes. The endogenous C-type retroviruses and intracisternal A particle (IAP) repeats, which are interspersed in the mouse genome with about 100 and 1000 copies per haploid genome, respectively, are normally highly methylated in ES cells (Li, E. et al., *Cell* 69:915-926 (1992); Okano, M. et al., *Cell* 99:247-257 (1999)). These sequences became progressively demethylated in two independent [Dnmt3a−/−, Dnmt3b−/−] cell lines (7aabb and 10aabb), as indicated by increasing sensitivity to Hpa II digestion (FIG. 19A). Similar results were obtained when DNA methylation of the major and minor satellite repeats was analyzed (FIG. 19A). The major and minor satellite repeats are located in the pericentromeric and centromeric regions at copy numbers of 700,000 and 50,000-100,000, respectively. After prolonged culture of [Dnmt3a−/−, Dnmt3b−/−] ES cells for about 5 months, DNA methylation in both repeats and unique genes examined was almost completely depleted (see below). No significant change in global methylation was observed when wild-type (J1) and Dnmt3a−/− (6aa) or Dmnt3b−/− (8bb) single mutant ES cells were grown in culture for the same periods of time (FIG. 19B, also see below). Loss of methylation in [Dnmt3a−/−, Dnmt3b−/−] ES cells was not due to reduced expression of Dnmt 1 as immunoblotting analysis indicated that early-passage and late-passage cells had similar levels of Dnmt1 protein (FIG. 19C). These results suggested that the Dnmt3 family of methyltransferases are required for stable inheritance of global DNA methylation patterns in ES cells and Dnmt3a and Dnmt3b have largely redundant functions in this respect.

Stable Expression of Dnmt3a and Dnmt3b in [Dnmt3a−/−, Dnmt3b−/−] ES Cells Restores DNA Methylation Dnmt3a and Dnmt3b isoforms show distinct expression profiles and cellular localization patterns (Bachman, K. E. et al., *J Biol Chem* 276:32282-32287 (2001); Chen, T. et al., *J Biol Chem* 277:38746-54 (2002)), raising the possibility that they may methylate different sets of sequences in the genome. To investigate whether the demethylated state of the [Dnmt3a−/−, Dnmt3b−/−] ES cell genome is reversible and whether different Dnmt3a and Dnmt3b isoforms have distinct specificities in re-establishing methylation patterns, we introduced cDNAs encoding Dnmt3a, Dnmt3a2, Dnmt3b1, Dnmt3b3, and Dnmt3b1:PC (Dnmt3b1 with its PC motif mutated) into late-passage 7aabb ES cells (Okano, M. et al., *Cell* 99:247-257 (1999)). DNA methyltransferases Dnmt3a and Dnmt3b are essential for de novo methylation and mammalian development (Okano, M. et al., *Cell* 99:247-257 (1999)) by random integration. Each cDNA was subcloned in a plasmid vector in which a CAG promoter drives the expression of a bicistronic transcript that encodes both the intended Dnmt protein and the selection marker, blasticidin S deaminase (FIG. 20B, top panel). After selection with blasticidin, we were able to obtain individual clones that express various levels of Dnmt3a or Dnmt3b proteins, as determined by immunoblotting analysis (FIG. 20B). The monoclonal Dnmt3a antibody, which recognizes the C-terminal region of Dnmt3a (FIG. 20A), stronglyreacts with Dnmt3a and Dnmt3a2 and weakly reacts with Dnmt3b 1 and Dnmt3b2, but not the other Dnmt3b isoforms Chen, T., et al., (Chen, T. et al., *J Biol Chem* 277:38746-54 (2002)). The polyclonal Dnmt3b antibody, which was raised against the N-terminal region of Dnmt3b (FIG. 20A), is Dnmt3b-specific and recognizes all known Dnmt3b isoforms (Chen, T. et al., *J Biol Chem* 277:38746-54 (2002)). For each construct, we chose two independent clones for methylation analysis. The relative levels of Dnmt3a/3b proteins expressed in these clones, as compared to the levels of the corresponding endogenous Dnmt3a/3b isoforms in wild-type ES cells (J1, 100%), were roughly estimated based on the intensity of the bands: Dnmt3a (clone 1:500%, clone 2:200%), Dnmt3a2 (clone 1:150%, clone 2:200%), Dnmt3b1 (clone 1:150%, clone 2:80%), Dnmt3b3 (clone 1:400%, clone 2:500%, compared with endogenous Dnmt3b6), and Dnmt3b1:PC (clone 1:80%, clone 2:50%, compared with endogenous Dnmt3b1)(FIG. 20B). We also confirmed by immunoblotting analysis that there was no cross-contamination between the control ES cell lines (J1, 6aa, 8bb, and 7aabb) during the course of long-term passage (FIG. 20B, middle and bottom panels, lanes 1-4).

We first examined whether repetitive elements could be re-methylated by the expressed Dnmt3a/3b proteins in 7aabb cells. As shown in FIG. 21A-D, expression of Dnmt3a, Dnmt3a2, or Dnmt3b1 substantially restored the methylation levels of the endogenous C-type retroviral DNA, the IAP repeats, and the major and minor satellite repeats, whereas expression of Dnmt3b3 or Dnmt3b1:PC had no effect. While the two Dnmt3a isoforms showed similar efficiency in methylating these repetitive sequences, Dnmt3a/3a2 and Dnmt3b1 exhibited distinct sequence preferences. As compared to Dnmt3a/3a2, Dnmt3b1 was substantially more efficient in methylating the minor satellite repeats and slightly less efficient in methylating the major satellite repeats and the endogenous C-type retroviral DNA. These enzymes were equally efficient in methylating the IAP repeats and restored the methylation level to normal. To confirm these results, we analyzed genomic DNA from late-passage 6aa and 8bb ES cells and showed that the methylation patterns in these sequences were consistent with those observed in the corresponding Dnmt3a/3b stable clones.

Figure 21:
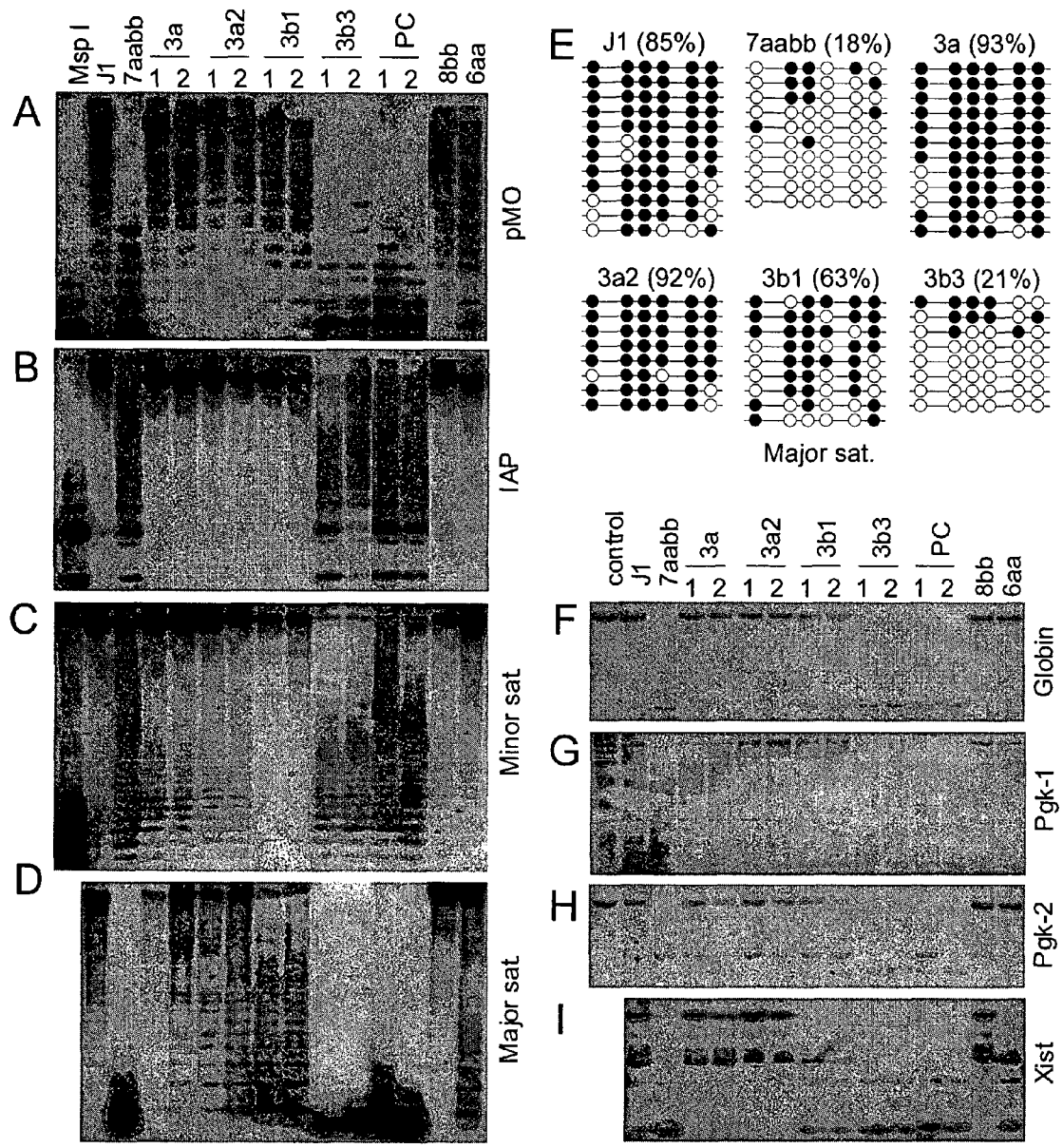

To determine whether expression of Dnmt3a/3b proteins in 7aabb cells also affects methylation of unique genes, a number of specific genomic loci were examined. The b-globin and phosphoglycerate kinase 2 (Pgk-2) genes are highly methylated autosomal genes that show tissue-specific expression patterns. Pgk-1 and Xist, two other highly methylated genes, are located on the X chromosome. The methylation-sensitive sites examined were located in the 5' region (Pgk-1 and Xist), the coding region (Pgk-2), or the 3' region (b-globin) of the genes. All four loci were highly methylated in the wild type ES cells (J1) and became substantially demethylated in late-passage 7aabb cells (FIG. 21E-H). With expression of Dnmt3a, Dnmt3a2, or Dnmt3b 1, but not Dnmt3b3 or Dnmt3b 1:PC, in 7aabb cells, the examined regions in b-globin, Pgk-1, and Pgk-2 genes were completely or partially re-methylated. These results were in agreement with the fact that methylation of these loci was maintained in 8bb and 6aa cells (FIG. 21E-G). Interestingly, Dnmt3a or Dnmt3a2 was able to restore methylation of the Xist promoter region to normal, but Dnmt3b1 was not (FIG. 21H). Consistently, inactivation of Dnmt3a alone in ES cells (6aa) resulted in demethylation of the Xist promoter region, whereas inactivation of Dnmt3b alone (8bb) had no effect (FIG. 21H), suggesting that Dnmt3a, but not Dnmt3b, is capable of establishing and is required for maintaining methylation of this particular region. Taken together, these data demonstrate that methylation of the highly demethylated genome of [Dnmt3a−/−, Dmnt3b−/−] ES cells can be largely re-established by Dnmt3a and Dnmt3b and these enzymes have both shared and specific DNA targets.

Methylation of Imprinted Genes

Figure 22:
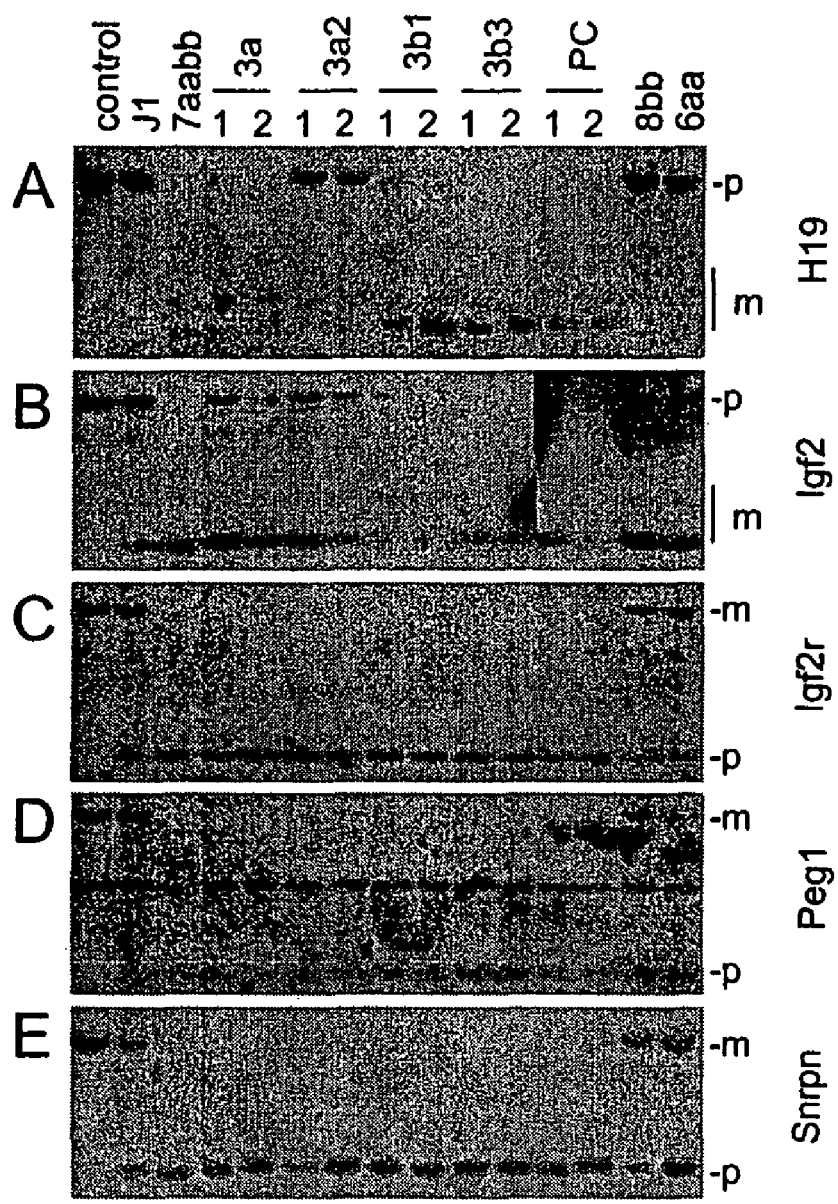

Methylation of some imprinted genes, such as H19 and Igf2 receptor (Igf2r), is maintained in early-passage [Dnmt3a−/−, Dnmt3b−/−] ES cells (Okano, M. et al., *Cell* 99:247-257 (1999)). To determine whether methylation imprints can be stably maintained, the methylation status of a number of imprinted genes was examined at their DMRs using genomic DNA from late-passage 7aabb cells. As shown in FIG. 22, all examined loci, including the 5' upstream region of H19, region 2 of Igf2r, the DMR of Peg1, and DMR1 of Snrpn, became completely demethylated in late-passage 7aabb cells, but not in wild-type (J1), 6aa, or 8bb cells. These observations suggested that Dnmt3a and Dnmt3b not only are involved in de novo methylation of imprinted genes in male and female germ cells, but may also play a role in maintaining-the methylation imprints in the zygote.

We then examined whether expression of Dnmt3a/3b proteins in 7aabb cells could restore methylation imprints. The 5' upstream region of H19, which includes the DMR that regulates expression of Igf2 and H19, is methylated when it is inherited from the father, but unmethylated when it is inherited from the mother. Digestion with the methylation-sensitive enzyme HhaI resulted in a fully methylated paternal band and several weaker undermethylated smaller bands from the maternal allele in wild type (J1) ES cells. Demethylation of this region in 7aabb cells resulted in several lower-molecular-weight bands. We found that Dnmt3a2 almost fully re-methylated this region, whereas Dnmt3a and Dnmt3b1 caused only minimal re-methylation, and Dnmt3b3 and Dnmt3b1:PC showed no activity at all (FIG. 22A). Using similar strategies, we examined several other imprinted genes. DMR2 of Igf2, another paternally methylated region, was fully or partially re-methylated by Dnmt3a, Dnmt3a2, or Dnmt3b1, but not by Dnmt3b3 or Dnmt3b1:PC (FIG. 22B). The intensity of the methylated and unmethylated bands suggested that one allele (presumably the paternal allele) was re-methylated and the other allele remained unmethylated, although we could not rule out the possibility that the methylated band resulted from partial methylation of both alleles. In contrast to H19 and Igf2, none of the maternally methylated genes (Igf2r, Peg1, and Snrpn) could be re-methylated at their DMRs by overexpression of Dnmt3a/3b proteins (FIG. 22C-E). These observations indicate that the maternal methylation imprints, once lost, cannot be restored in ES cells.

Dnmt3b3 Inhibits de novo Methylation by Dnmt3a and Dnmt3b Enzymes

Figure 23:
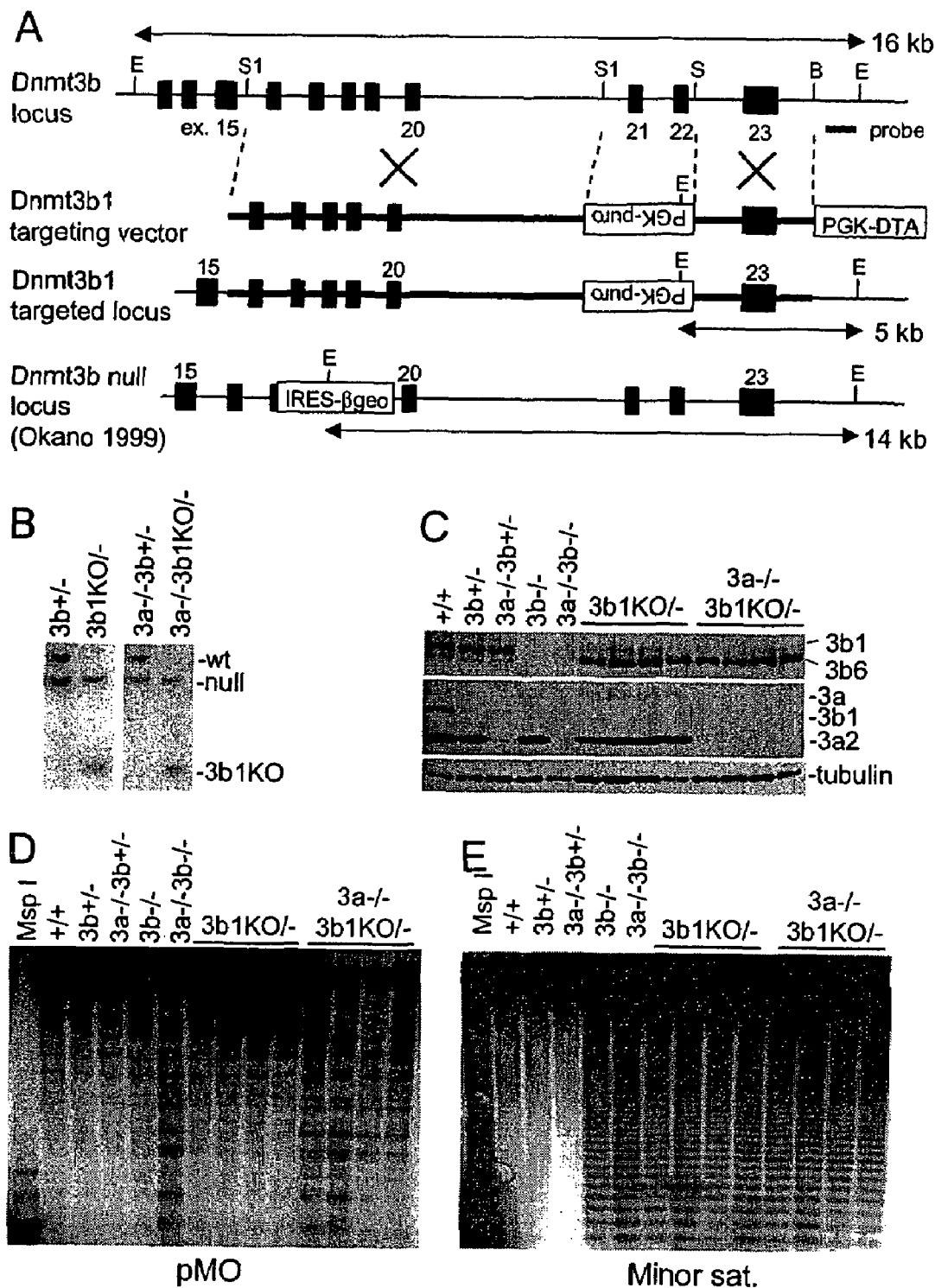

Consistent with previous results from in vitro DNA methyltransferase assays (Aoki, A. et al., *Nucleic Acids Res* 29:3506-3512(2001); Okano, M. et al., *Nat. Genet.* 19:219-220 (1998)), our rescue experiments showed that Dnmt3b3 had no enzymatic activity. It is believed that Dnmt3b4, Dnmt3b5, and Dnmt3b6 are also enzymatically inactive because, like Dnmt3b3, they all lack part of the conserved motif IX, due to alternative splicing of exons 21 and 22 (FIG. 20A). To determine whether these isoforms have any activity in vivo, we deleted exons 21 and 22 from the wild-type allele in Dnmt3b+/− and [Dnmt3a−/−, Dnmt3b+/−] ES cells (Okano, M. et al., *Cell* 99:247-257 (1999)) by gene targeting. A PGK-puromycin (PGK-puro) cassette was inserted in the opposite orientation of Dnmt3b transcription to avoid truncation of the Dnmt3b transcripts (FIG. 23A). Since the major Dnmt3b isoforms expressed in ES cells are Dnmt3b1 and Dnmt3b6 (Chen, T. et al., *J Biol Chem* 277:38746-38754 (2002)), we expected that removal of exons 21 and 22 would eliminate Dnmt3b 1, but not Dnmt3b6. A number of clones with deletion of the wild-type allele were obtained from both Dnmt3b+/− and [Dnmt3a−/−, Dnmt3b+/−] cells and these clones were referred to as Dnmt3b1KO/− and [Dnmt3a−/−, Dnmt3b1KO/−], respectively (FIG. 23B). Immunoblotting analysis confirmed that Dnmt3b1 protein was abolished and, concomitantly, the level of Dnmt3b6 protein increased in these cells (FIG. 23C). We examined the methylation status of various repetitive sequences and unique genes in these cells. Unlike the parental Dnmt3b+/− cell line, Dnmt3b1KO/− cells showed significant demethylation of the minor satellite repeats and the methylation pattern was identical to that in Dnmt3b−/− cells (FIG. 23E). Similarly, all sequences examined showed substantial loss of methylation in [Dnmt3a−/−, 3b1KO/−] cells and exhibited methylation patterns indistinguishable from those observed in [Dnmt3a−/−, Dnmt3b−/−] cells (FIG. 23D-E, and data not shown). In addition, [Dnmt3a−/−, Dnmt3b1KO/−] cells failed to methylate newly integrated proviral DNA after infection with a recombinant retrovirus, MoMuLV$^{sup}$-1, while the parental [Dnmt3a−/−, Dnmt3b+/−] cell line showed efficient de novo methylation activity (data not shown). These data provide genetic evidence that exons 21 and 22 are essential for Dnmt3b activity. We conclude that all Dnmt3b isoforms that lack motif IX have no methyltransferase activity in vivo.

Interestingly, Dnmt3b3 is ubiquitously expressed and often represents the major Dnmt3b isoform in somatic tissues (Beaulieu, N. et al., *J Biol Chem* 277:28176-28181 (2002); Chen, T. et al., *J Biol Chem* 277:38746-38754 (2002); Robertson, K. D. et al., *Nucleic Acids Res* 27:2291-2298 (1999)). To determine whether Dnmt3b3 plays a regulatory role in DNA methylation, we generated 7aabb-derived cell lines that expressed the active Dnmt3a and Dnmt3b isoforms in the presence or absence of Dnmt3b3. As shown in FIG. 24A, the clones we chose to analyze expressed similar levels of Dnmt3a, Dnmt3a2, or Dnmt3b1. Analysis of a number of sequences revealed that the cell lines co-expressing Dnmt3b3 and Dnmt3a, Dnmt3a2, or Dnmt3b1 consistently showed lower methylation levels than their counterparts expressing the corresponding active isoform alone (FIG. 24B). These results suggest that Dnmt3b3 functions as a negative regulator for de novo methylation.

Dnmt3a/3b-Induced Remethylation Rescues the Capacity of[Dnmt3a−/−, Dnmt3b−/−] ES Cells to Form Teratomas in Nude Mice It has been reported that Dnmt1 null ES cells die upon induction of differentiation and cannot form teratomas (Lei, H. et al., *Development* 122:3195-3205 (1996); Tucker, K. L. et al., *Proc. Natl. Acad. Sci USA* 93:12920-5 (1996)). It is not known, however, whether the differentiation defects are caused by loss of methylation or lack of Dnmt1 protein. Unlike Dnmt1 null cells, which lose methylation very quickly, [Dnmt3a−/−, Dnmt3b−/−] ES cells show gradual demethylation during the course of continuous passage, which makes it possible to address the relationship between genomic methylation and cellular differentiation. We injected early-passage (P10) and late-passage (P70) 7aabb cells into nude mice and tested their ability to induce teratomas. While late-passage cells failed to form palpable teratomas (0/3) within 4 weeks, early-passage cells retained the ability to induce teratomas (2/3) despite their much smaller size as compared to those induced by wild type J1 cells (3/3) (FIG. 25A-B). These results indicated that the ability of ES cells to induce teratomas is dependent on the level of genomic methylation, but not the presence of Dnmt3a and Dnmt3b proteins.

We then asked whether expression of Dnmt3a/3b proteins in late-passage 7aabb cells could rescue the capacity of these cells to induce teratomas. Consistent with their methylation level, stable lines expressing Dmnt3a (3/4), Dnmt3a2 (4/4), or Dnmt3b1 (4/4) were able to induce teratomas in nude mice, whereas those expressing Dnmt3b3 (0/4) or Dnmt3b1: PC (0/4) were not (FIG. 25A). Although the teratomas induced by these stable lines did not reach the size of those induced by J1 cells (presumably because expression of any one isoform could not fully restore the methylation level), histological analysis revealed that all these teratomas contained multiple differentiated cell types (epithelial tissue, cartilage, muscle, etc.) with no obvious differences (FIG. 25B).

Overexpression of Dnmt1 Fails to Restore Global DNA Methylation in the Absence of Dnmt3a and Dnmt3b It has been recently reported that overexpression of Dnmt1 in ES cells results in genomic hypermethylation (Biniszkiewicz, D. et al., *Mol Cell Biol* 22:2124-2135. (2002) To determine whether Dnmt1 could induce de novo methylation in the absence of Dnmt3a and Dnmt3b, we overexpressed Dnmt1 in late-passage 7aabb cells and, as a control, in Dnmt1 null (c/c) ES cells (FIG. 26A). As shown in FIGS. 26B and 26C, introduction of Dnmt1 back into Dnmt1 null cells significantly restored methylation of all repetitive sequences and single copy genes examined except for the maternally imprinted gene Igf2r, consistent with a previous study (Biniszkiewicz, D. et al., *Mol Cell Biol* 22:2124-2135 (2002). However, overexpression of Dnmt1 in 7aabb cells had little effect on global methylation as compared to the parental cell line, although a slight increase in methylation of repetitive sequences and in the 5' region of H19 was observed. Likewise, overexpression of Dnmt3a in Dnmt1 null cells could not restore methylation of repetitive elements and unique loci to high levels. These data provide strong evidence that Dnmt1 alone is not capable of methylating genomic DNA de novo and both Dnmt1 and Dnmt3 families of methyltransferases are required for stable maintenance of normal methylation patterns.

Discussion

Maintenance methylation is a key process that ensures stable inheritance of tissues-specific DNA methylation patterns from cell to cell. It was previously thought that Dnmt1 is solely responsible for the maintenance of DNA methylation patterns since Dnmt1 is expressed ubiquitously and inactivation of Dnmt1 by gene targeting in mice results in genome-wide loss of methylation (Lei, H. et al., *Development* 122:3195-3205 (1996); Li, E. et al., *Cell* 69:915-926 (1992)). However, there is no evidence that Dnmt1 alone is sufficient to maintain all methylation in the genome. In contrast, our initial studies of embryonic stem cells lacking the Dnmt3 family methyltransferases suggest that maintenance of methylation of some sequences such as the DMR2 region of Igf2 and the 5' region of Xist requires both Dnmt1 and Dnmt3a/3b (Okano, M. et al., *Cell* 99:247-257 (1999)). In this study, we extended our findings and showed that these enzyrnes are involved in maintaining global DNA methylation patterns. We demonstrated that inactivation of Dnmt3a and Dnmt3b in ES cells resulted in progressive demethylation of all sequences examined, including repetitive elements, imprinted genes, and non-imprinted genes. These results indicate that Dnmt1 alone is not sufficient for stable inheritance of DNA methylation patterns in ES cells.

We propose that Dnmt1 is the major maintenance methyltransferase which, in association with the DNA replication machinery, methylates hemi-methylated CpG sites with high efficiency but not absolute accuracy, while Dnmt3a and Dnmt3b, via their de novo methylation activity, function as "proof-readers" to fill in the gaps of the hemi-methylated CpG sites left over by Dnmt1. Consistent with this model is the observation that Dnmt1−/− and [Dnmt3a−/−, Dnmt3b−/−] ES cells exhibit very different kinetics of demethylation. Complete inactivation of Dnmt1 resulted in a 90% reduction of total methyl CpG in the genome immediately after Dnmt1−/− cell lines were established (at $10^6$ cells or the first passage) (Lei, H. et al., *Development* 122:3195-3205 (1996)). In contrast, inactivation of Dnmt3a and Dnmt3b resulted in gradual loss of methylation in most genomic sequences and it took more than 70 passages to reach a 90% reduction of global methylation.

In this study, we demonstrated that both Dnmt1 and Dnmt3 families of methylatransferases are required for stable maintenance of global methylation patterns in mouse ES cells. Our observation that neither overexpression of Dnmt1 in [Dnmt3a−/−, Dnmt3b−/−] cells nor overexpression of Dnmt3a in Dnmt1−/− cells could restore methylation to normal levels suggests that these two types of enzymes have distinct and non-redundant functions and they act cooperatively to maintain hypermethylation of the genome. It also confirms that Dnmt1 has little or no de novo methylation activity in vivo.

Since the Dnmt1 and Dnmt3 families of methyltransferases do not appear to have any sequence specificity beyond CpG dinucleotides (Dodge, J. et al., *Gene* 289:41-48 (2002); Okano, M. et al., *Nat Genet* 19:219-220 (1998); Yoder, J. A. et al., *J Mol Biol* 270:385-395 (1997)), several chromatin-based mechanisms have been proposed to explain how DNA methyltransferases may find their targets in the genome (Bird, A. *Genes Dev* 16:6-21 (2002)). One explanation is that chromosomal regions are not equally accessible to DNA methyltransferases. Consistent with this notion, recent studies of two SNF2 family helicases, ATRX and Lsh, have shown that proteins with chromatin remodeling and DNA helicase activities can modulate DNA methylation in mammalian cells (Dennis, K. et al., *Genes Dev.* 15:2940-2944 (2001); Gibbons, R. J. et al., *Nat. Genet.* 24:368-371 (2000). Similarly, the SNF2-like protein DDM1 has been shown to be essential for methylation of both CpG and CpNpG sites in the plant *Arabidopsis thaliana* (Jeddeloh, J. A. et al., *Nat. Genet.* 22:94-97 (1999)). Another explanation is that accessory factors (proteins, RNA, etc.) recruit DNA methyltransferases to specific genomic sequences or chromatin structures. A number of proteins, including PCNA, DMAP1, HDAC1, HDAC2, pRB, have been shown to interact with Dnmt1 and may recruit Dnmt1 to highly methylated heterochromatin during the late S phase (Robertson, K. D. and Wolffe. A. P. *Nat Rev Genet* 1:11-19 (2000)). The PML-RAR fusion protein and Dnmt3L have been shown to interact with Dnmt3a or Dnmt3b and may recruit these enzymes to RAR response elements and imprinted genes, respectively (Di Croce, L. et al., *Science* 295:1079-1082 (2002); Hata, K. et al., *Development* 129: 1983-1993 (2002)). In this study, we provide the first evidence that DNA methylation patterns could also be regulated by expressing different isoforms of Dnmt3a and Dnmt3b. We showed that various Dnmt3a and Dnmt3b isoforms appear to have both shared and preferred DNA targets during the process of re-establishing DNA methylation patterns in highly demethylated [Dnmt3a−/−, Dnmt3b−/−] mutant ES cells. Dnmt3a, Dnmt3a2, and Dnmt3b1 exhibited substantial activity toward all the repetitive sequences examined but they clearly had sequence preferences, with Dnmt3b 1 significantly more potent than Dnmt3a proteins in methylating minor satellite repeats. These enzymes also showed notable differences in methylating certain unique genes. Dnmt3a and Dnmt3a2 were able to methylate the 5' region of Xist but Dnmt3b1 was not. Similarly, Dnmt3a2 almost fully restored the methylation status of the 5' region of H19 whereas Dnmt3a and Dnmt3b1 showed little effect. Given that Dnmt3a and Dnmt3b isoforms show distinct cellular localization patterns (Bachman, K. E. et al., *J Biol Chem* 276:32282-32287 (2001); Chen, T. et al., *J Biol Chem* 277:38746-38754 (2902)), their preferences for different genomic sequences may reflect their differences in chromatin accessibility. It is also conceivable that other factors may interact with various Dnmt3a and Dnmt3b isoforms and target them to different genomic regions. It should be noted that the target specificity of different isoforms was determined by overexpression of each isoform in ES cells, although the results are largely consistent with those obtained from Dnmt3a−/− or Dnmt3b−/− single mutant cells. Genetic studies by inactivating specific isoforms in mice will be necessary to confirm their specificity in development.

Previous studies have shown that Dmnt3b3 does not have methyltransferase activity in vitro (Aoki, A. et al., *Nucleic Acids Res.* 29:3506-3512 (2001)). We now confirm that Dnmt3b3, as well as Dnmt3b6, lacks enzymatic activity to chromosomal DNA in vivo. However, these "inactive" isoforms may play an important role in determining the overall methylation level because our co-transfection experiments indicate that Dnmt3b3 may function as a negative regulator for de novo methylation by Dmnt3a and Dnmt3b enzymes. This observation is of potential relevance for understanding regulation of DNA methylation in normal and tumor cells: During development, both the overall level of Dnmt3a/3b proteins and the ratio between different isoforms show dynamic changes. In early embryos, Dnmt3a and Dnmt3b are highly expressed and the major isoforms are Dnmt3a2 and Dnmt3b 1, respectively. In most somatic tissues, Dnmt3a and Dnmt3b are expressed at low levels and the only detectable isoforms are usually Dnmt3a and Dnmt3b3 (Chen, T. et al., *J Biol Chem* 277:38746-38754(2002)). Our data is suggest that Dnmt3a2 and Dnmt3b1 carry out de novo methylation in early postimplantation embryos to establish the initial methylation pattern, and Dnmt3a, in cooperation with Dnmt1, is involved in maintaining tissue-specific methylation patterns. Dnmt3b3 may play a role in preventing Dnmt3a from methylating CpG islands de novo in normal tissues. Generally, the overall level of DNA methylation is lower in cancer cells than in normal cells and hypomethylation has been correlated with elevated mutation rates and thus may contribute to tumorigenesis (Chen, R. Z. et al., *Nature* 395:89-93 (1998)). However, the cause of hypomethylation in cancer cells is not clear. Dnmt3b3 is overexpressed and often represents the only detectable Dnmt3b isoform in many types of human cancer and cancer cell lines (Beaulieu, N. et al., *J Biol Chem* 277:28176-81 (2002); Chen, T. et al., *J Biol Chem* 277:38746-38754 (2002); Robertson, K. D. et al., Nucleic Acids Res 27:2291-2298 (1999)). We propose that overexpression of Dnmt3b3 is a contributing factor for hypomethylation. Other "inactive" Dnmt3b isoforms, such as Dmnt3b4, Dnmt3b5, and Dnmt3b6, may also be overexpressed in certain types of cancers and play a similar role as Dnmt3b3. A recent study has shown that overexpression of Dnmt3b4 may lead to hypomethylation of pericentromeric satellite regions in human hepatocellular carcinoma (Saito, Y. et al., *Proc Natl Acad Sci USA* 99:10060-10065 (2002)).

Genetic studies have shown that Dnmt3a and Dnmt3b are involved in the establishment of methylation imprints during gametogenesis (Hata, K. et al., *Development* 129:1983-93 (2002)). Our finding that late-passage 7aabb cells show complete loss of methylation of DMRs of imprinted genes suggests that these enzymes may also play a role in the maintenance of imprinted methylation patterns during embryogenesis. Compared to repetitive sequences, imprinted genes were more resistant to demethylation caused by inactivation of Dnmt3a and Dnmt3b (data not shown). It is possible that maintenance methylation by Dnmt1 is more accurate for single-copy genes than for repetitive elements. While the paternally imprinted H19 and Igf2 genes are susceptible to re-methylation by ectopically expressed Dnmt1 or Dnmt3 proteins in mutant ES cells, maternally imprinted genes are completely resistant to re-methylation. We speculate that some essential factors required for the establishment of maternal imprints are present in female germ cells but not in ES cells.

An interesting observation is that early-passage [Dnmt3a−/−, Dnmt3b−/−] ES cells, which still contain significant levels of DNA methylation, are capable of inducing teratomas in nude mice, whereas late-passage cells, which are more extensively demethylated, completely lose this capacity. This clearly indicates that the presence of Dnmt3a and Dnmt3b methyltransferases (thus de novo methylation activity) is not required for ES cell differentiation and subsequent cellular proliferation. Rather, these processes are dependent on the level of DNA methylation. In keeping with this notion, expression of enzymatically active Dnmt3 proteins (Dnmt3a, Dnmt3a2, and Dnmt3b1), but not inactive forms (Dnmt3b3 and Dnmt3b1:PC), rescued the capacity of late-passage mutant cells to form teratomas. Our results are consistent with previous studies showing that Dnmt1 mutant ES cells undergo apoptosis upon differentiation (Lei, H. et al., *Development* 122:3195-3205 (1996); Tucker, K. L. et al., *Proc. Natl. Acad. Sci. USA* 93:12920-12925 (1996)). Failure to differentiate and proliferate may account, at least in part, for the early embryonic lethality observed in Dnmt1 and Dnmt3 null mutant embryos. A threshold level of DNA methylation may be required for some essential developmental processes. Interestingly, a recent study showed that inactivation of Lsh, a member of the SNF2/helicase family, results in extensive global demethylation in E13.5 mutant embryos but not embryonic lethality (Dennis, K. et al., *Genes Dev* 15:2940-2944 (2001)). It is possible that embryonic methylation patterns are properly established in Lsh−/− embryos during early development. Further studies are necessary to determine how DNA methylation regulates cell proliferation and differentiation.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. An isolated nucleic acid molecule comprising a polynucleotide selected from the group consisting of:
   a. a polynucleotide sequence encoding a polypeptide comprising amino acids from about 1 to about 689 in SEQ ID NO:85;
   b. a polynucleotide sequence encoding a polypeptide comprising amino acids from about 1 to about 689 in SEQ ID NO:86;
   c. a polynucleotide sequence that is at least 95% identical to the polynucleotide sequence of (a) or (b); and
   d. a polynucleotide sequence complementary to the polynucleotide sequence of (a), (b) or (c) encoding a polypeptide, wherein said polypeptide methylates DNA in an in vitro assay.

2. The nucleic acid molecule of claim 1, wherein said polynucleotide is that of part (a).

3. The nucleic acid molecule of claim 1, wherein said polynucleotide is that of part (b).

4. The nucleic acid molecule of claim 1, wherein said polynucleotide is that of part (c).

5. The nucleic acid molecule of claim 1, wherein said polynucleotide is that of part (d).

6. A method of making a recombinant vector comprising inserting an isolated nucleic acid molecule of claim 1 into a vector selected from a group consisting of:
   a. a DNA vector; and
   b. an RNA vector.

7. A recombinant vector comprising the isolated nucleic acid molecule of claim 1.

8. A method of making an isolated recombinant host cell comprising introducing the recombinant vector of claim 7 into a host cell.

9. An isolated recombinant host cell comprising the vector of claim 7.

10. A method for producing a de novo DNA cytosine methyltransferase polypeptide, comprising culturing the isolated recombinant host cell of claim 9 under conditions such that said polypeptide is expressed and recovering said polypeptide.

11. An isolated nucleic acid molecule comprising a polynucleotide selected from the group consisting of:
   a. a polynucleotide sequence encoding mouse Dnmt3a2 polypeptide contained in ATCC Deposit No. PTA-4611;
   b. a polynucleotide sequence encoding human DNMT3A2 polypeptide contained in ATCC Deposit No. PTA-4610;
   c. a polynucleotide sequence at least 95% identical to the polynucleotide sequence of (a) or (b); and
   d. a polynucleotyide sequence fully complementary to the polynulceotide sequence of (a), (b) or (c) encoding a polypeptide, wherein said polypeptide methylates DNA in an in vitro assay.

12. The nucleic acid molecule of claim 11, wherein said polynucleotide is that of part (a).

13. The nucleic acid molecule of claim 11, wherein said polynucleotide is that of part (b).

14. The nucleic acid molecule of claim 11, wherein said polynucleotide is that of part (c).

15. The nucleic acid molecule of claim 11, wherein said polynucleotide is that of part (d).

16. The nucleic acid molecule of claim 1, wherein said nucleic acid molecule is expressed in embryonic stem cells.

17. The nucleic acid molecule of claim 11, wherein said nucleic acid molecule is expressed in embryonic stem cells.

* * * * *

SEQUENCE LISTING

```
<160> NUMBER OF SEQ ID NOS: 119

<210> SEQ ID NO 1
<211> LENGTH: 4192
<212> TYPE: DNA
<213> ORGANISM: Mus musculus
<220> FEATURE:
<221> NAME/KEY: misc_feature
<222> LOCATION: (4161)..(4161)
<223> OTHER INFORMATION: n is a, c, g, or t

<400> SEQUENCE: 1
gaattccggc ctgctgccgg gccgcccgac ccgccgggcc acacggcaga gccgcctgaa      60
gcccagcgct gaggctgcac tttccgagg gcttgacatc agggtctatg tttaagtctt     120
agctcttgct tacaaagacc acggcaattc cttctctgaa gccctcgcag ccccacagcg     180
ccctcgcagc cccagcctgc cgcctactgc ccagcaatgc cctccagcgg ccccggggac     240
accagcagct cctctctgga gcgggaggat gatcgaaagg aaggagagga acaggaggag     300
aaccgtggca aggaagagcg ccaggagccc agcgccacgg cccggaaggt ggggaggcct     360
ggccggaagc gcaagcaccc accggtggaa agcagtgaca ccccaaggaa cccagcagtg     420
accaccaagt ctcagcccat ggcccaggac tctggcccct cagatctgct acccaatgga     480
gacttggaga agcggagtga accccaacct gaggagggga gcccagctgc agggcagaag     540
ggtggggccc cagctgaagg agagggaact gagacccac cagaagcctc cagagctgtg     600
gagaatggct gctgtgtgac caaggaaggc cgtggagcct ctgcaggaga gggcaaagaa     660
cagaagcaga ccaacatcga atccatgaaa atggagggct cccggggccg actgcgaggt     720
ggcttgggct gggagtccag cctccgtcag cgacccatgc caagactcac cttccaggca     780 ggggaccct actacatcag caaacggaaa cgggatgagt ggctggcacg ttggaaaagg     840
gaggctgaga agaaagccaa ggtaattgca gtaatgaatg ctgtggaaga gaaccaggcc     900
tctggagagt ctcagaaggt ggaggaggcc agccctcctg ctgtgcagca gcccacggac     960
```

```
cctgcttctc cgactgtggc caccacccct gagccagtag gaggggatgc tggggacaag    1020
aatgctacca aagcagccga cgatgagcct gagtatgagg atggccgggg ctttggcatt    1080
ggagagctgg tgtggggaa acttcggggc ttctcctggt ggccaggccg aattgtgtct     1140
tggtggatga caggccggag ccgagcagct gaaggcactc gctgggtcat gtggttcgga    1200
gatggcaagt tctcagtggt gtgtgtggag aagctcatgc cgctgagctc cttctgcagt    1260
gcattccacc aggccaccta caacaagcag cccatgtacc gcaaagccat ctacgaagtc    1320
ctccaggtgg ccagcagccg tgccgggaag ctgtttccag cttgccatga cagtgatgaa    1380
agtgacagtg gcaaggctgt ggaagtgcag aacaagcaga tgattgaatg ggccctcggt    1440
ggcttccagc cctcgggtcc taagggcctg gagccaccag aagaagagaa gaatccttac    1500
aaggaagttt acaccgacat gtgggtggag cctgaagcag ctgcttacgc cccaccccca    1560
ccagccaaga aacccagaaa gagcacaaca gagaaaccta aggtcaagga gatcattgat    1620
gagcgcacaa gggagcggct ggtgtatgag gtgcgccaga agtgcagaaa catcgaggac    1680
atttgtatct catgtgggag cctcaatgtc ccctggagc acccactctt cattggaggc     1740
atgtgccaga actgtaagaa ctgcttcttg gagtgtgctt accagtatga cgacgatggg    1800
taccagtcct attgcaccat ctgctgtggg gggcgtgaag tgctcatgtg tgggaacaac    1860
aactgctgca ggtgcttttg tgtcgagtgt gtggatctct tggtggggcc aggagctgct    1920
caggcagcca ttaaggaaga cccctggaac tgctacatgt gcgggcataa gggcacctat    1980
gggctgctgc gaagacggga agactggcct tctcgactcc agatgttctt tgccaataac    2040
catgaccagg aatttgaccc cccaaaggtt tacccacctg tgccagctga agaggaag     2100 cccatccgcg tgctgtctct ctttgatggg attgctacag gctcctggt gctgaaggac     2160 ctgggcatcc aagtggaccg ctacattgcc tccgaggtgt gtgaggactc catcacggtg    2220
ggcatggtgc ggcaccaggg aaagatcatg tacgtcgggg acgtccgcag cgtcacacag    2280
aagcatatcc aggagtgggg cccattcgac ctggtgattg aggcagtccc ctgcaatgac    2340
ctctccattg tcaaccctgc ccgcaaggga ctttatgagg gtactggccg cctcttcttt    2400
gagttctacc gcctcctgca tgatgcgcgg cccaaggagg gagatgatcg cccttcttc     2460 tggctctttg agaatgtggt ggccatgggc gttagtgaca gagggacat ctcgcgattt      2520 cttgagtcta accccgtgat gattgacgcc aaagaagtgt ctgctgcaca cagggcccgt     2580
tacttctggg gtaaccttcc tggcatgaac aggcctttgg catccactgt gaatgataag    2640
ctggagctgc aagagtgtct ggagcacggc agaatagcca agttcagcaa agtgaggacc    2700
attaccacca ggtcaaactc tataaagcag ggcaaagacc agcatttccc cgtcttcatg    2760
aacgagaagg aggacatcct gtggtgcact gaaatggaaa gggtgtttgg cttccccgtc    2820
cactacacag acgtctccaa catgagccgc ttggcgaggc agagactgct gggccgatcg    2880
tggagcgtgc cggtcatccg ccacctcttc gctccgctga aggaatattt tgcttgtgtg    2940
taagggacat gggggcaaac tgaagtagtg atgataaaaa agttaaacaa acaaacaaac    3000
aaaaaacaaa acaaaacaat aaaacaccaa gaacgagagg acggagaaaa gttcagcacc    3060
cagaagagaa aaaggaattt aaagcaaacc acagaggagg aaaacgccgg agggcttggc    3120
cttgcaaaag ggttggacat catctcctga gttttcaatg ttaaccttca gtcctatcta    3180
aaaagcaaaa taggccctc cccttcttcc cctccggtcc taggaggcga acttttttgtt    3240 ttctactctt tttcagaggg gttttctgtt tgtttgggtt tttgtttctt gctgtgactg    3300
```

```
aaacaagaga gttattgcag caaaatcagt aacaacaaaa agtagaaatg ccttggagag      3360
gaaagggaga gagggaaaat tctataaaaa cttaaaatat tggttttttt ttttttttcct     3420 tttctatata tctctttggt tgtctctagc ctgatcagat aggagcacaa acaggaagag      3480
aatagagacc ctcggaggca gagtctcctc tcccaccccc cgagcagtct caacagcacc      3540
attcctggtc atgcaaaaca gaacccaact agcagcaggg cgctgagaga acaccacacc      3600
agacactttc tacagtattt caggtgccta ccacacagga aaccttgaag aaaaccagtt      3660
tctagaagcc gctgttacct cttgtttaca gtttatatat atatgataga tatgagatat      3720
atatatataa aaggtactgt taactactgt acatcccgac ttcataatgg tgctttcaaa      3780
acagcgagat gagcaaagac atcagcttcc gcctggccct ctgtgcaaag ggtttcagcc      3840
caggatgggg agaggggagc agctggaggg ggttttaaca aactgaagga tgacccatat      3900 cacccccccac ccctgcccca tgcctagctt cacctgccaa aaggggctc agctgaggtg       3960 gtcggaccct ggggaagctg agtgtggaat ttatccagac tcgcgtgcaa taaccttaga      4020
atatgaatct aaaatgactg cctcagaaaa atggcttgag aaaacattgt ccctgatttt      4080
gaattcgtca gccacgttga aggccccttg tgggatcaga aatattccag agtgagggaa      4140
agtgacccgc cattaacccc ncctggagca aataaaaaaa catacaaaat gt              4192
```

<210> SEQ ID NO 2
<211> LENGTH: 4195
<212> TYPE: DNA
<213> ORGANISM: Mus musculus

<400> SEQUENCE: 2

```
gaattccggg cgccgggtt aagcggccca agtaaacgta gcgcagcgat cggcgccgga       60
gattcgcgaa cccgacactc cgcgccgccc gccggccagg acccgcggcg cgatcgcggc      120
gccgcgctac agccagcctc acgacaggcc cgctgaggct tgtgccagac cttggaaacc      180
tcaggtatat acctttccag acgcgggatc tcccctcccc catccatagt gccttgggac      240
caaatccagg gccttcttc aggaaacaat gaagggagac agcagacatc tgaatgaaga       300
agagggtgcc agcgggtatg aggagtgcat tatcgttaat gggaacttca gtgaccagtc      360
ctcagacacg aaggatgctc cctcaccccc agtcttggag gcaatctgca cagagccagt      420
ctgcacacca gagaccagag gccgcaggtc aagctcccgg ctgtctaaga gggaggtctc      480
cagccttctg aattacacgc aggacatgac aggagatgga gacagagatg atgaagtaga      540
tgatgggaat ggctctgata ttctaatgcc aaagctcacc cgtgagacca aggacaccag      600
gacgcgctct gaaagcccgg ctgtccgaac ccgacatagc aatgggacct ccagcttgga      660
gaggcaaaga gcctccccca gaatcacccg aggtcggcag ggccgccacc atgtgcagga      720
gtaccctgtg gagtttccgg ctaccaggtc tcggagacgt cgagcatcgt cttcagcaag      780
cacgccatgg tcatcccctg ccagcgtcga cttcatggaa gaagtgacac ctaagagcgt      840
cagtacccca tcagttgact tgagccagga tggagatcag gagggtatgg ataccacaca      900
ggtggatgca gagagcagag atggagacag cacagagtat caggatgata aagagtttgg      960
aataggtgac ctcgtgtggg gaaagatcaa gggcttctcc tggtggcctg ccatggtggt     1020
gtcctggaaa gccacctcca agcgacaggc catgcccgga atgcgctggg tacagtggtt     1080
tggtgatggc aagttttctg agatctctgc tgacaaactg gtggctctgg ggctgttcag     1140
ccagcacttt aatctggcta ccttcaataa gctggtttct tataggaagg ccatgtacca     1200
cactctggag aaagccaggg ttcgagctgg caagaccttc tccagcagtc ctggagagtc     1260
```

-continued

```
actggaggac cagctgaagc ccatgctgga gtgggcccac ggtggcttca agcctactgg    1320
gatcgagggc tcaaaccca acaagaagca accagtggtt aataagtcga aggtgcgtcg    1380
ttcagacagt aggaacttag aacccaggag acgcagaac aaaagtcgaa gacgcacaac    1440
caatgactct gctgcttctg agtccccccc acccaagcgc tcaagacaa atagctatgg    1500 cgggaaggac cgaggggagg atgaggagag ccgagaacgg atggcttctg aagtcaccaa    1560
caacaagggc aatctggaag accgctgttt gtcctgtgga aagaagaacc ctgtgtcctt    1620 ccacccctc tttgagggtg ggctctgtca gagttgccgg gatcgcttcc tagagctctt    1680
ctacatgtat gatgaggacg gctatcagtc ctactgcacc gtgtgctgtg agggccgtga    1740
actgctgctg tgcagtaaca caagctgctg cagatgcttc tgtgtggagt gtctggaggt    1800
gctggtgggc gcaggcacag ctgaggatgc caagctgcag aaccctggag gctgctatat    1860
gtgcctccct cagcgctgcc atggggtcct ccgacgcagg aaagattgga acatgcgcct    1920
gcaagacttc ttcactactg atcctgacct ggaagaattt gagccaccca agttgtaccc    1980
agcaattcct gcagccaaaa ggaggcccat tagagtcctg tctctgtttg atggaattgc    2040 aacgggtac ttggtgctca aggagttggg tattaaagtg gaaaagtaca ttgcctccga    2100
agtctgtgca gagtccatcg ctgtgggaac tgttaagcat gaaggccaga tcaaatatgt    2160
caatgacgtc cggaaaatca ccaagaaaaa tattgaagag tggggcccgt tcgacttggt    2220
gattggtgga agcccatgca atgatctctc taacgtcaat cctgcccgca aaggtttata    2280
tgagggcaca ggaaggctct tcttcgagtt ttaccacttg ctgaattata cccgccccaa    2340
ggagggcgac aaccgtccat tcttctggat gttcgagaat gttgtggcca tgaaagtgaa    2400
tgacaagaaa gacatctcaa gattcctggc atgtaaccca gtgatgatcg atgccatcaa    2460
ggtgtctgct gctcacaggg cccggtactt ctgggtaac ctacccggaa tgaacaggcc    2520
cgtgatggct tcaaagaatg ataagctcga gctgcaggac tgcctggagt tcagtaggac    2580
agcaaagtta agaaagtgc agacaataac caccaagtcg aactccatca gacagggcaa    2640
aaaccagctt ttccctgtag tcatgaatgg caaggacgac gttttgtggt gcactgagct    2700
cgaaaggatc ttcggcttcc ctgctcacta cacggacgtg tccaacatgg gccgcggcgc    2760
ccgtcagaag ctgctgggca ggtcctggag tgtaccggtc atcagacacc tgtttgcccc    2820
cttgaaggac tactttgcct gtgaatagtt ctacccagga ctggggagct ctcggtcaga    2880
gccagtgccc agagtcaccc ctccctgaag gcacctcacc tgtcccctt ttagctcacc    2940 tgtgtggggc ctcacatcac tgtacctcag cttttctcctg ctcagtggga gcagagcctc    3000
ctggcccttg caggggagcc ccggtgctcc tccgtgtgc acagctcaga cctggctgct    3060
tagagtagcc cggcatggtg ctcatgttct cttaccctga actttaaaa cttgaagtag    3120 gtagtaagat ggctttcttt taccctcctg agtttatcac tcagaagtga tggctaagat    3180
accaaaaaaa caaacaaaaa cagaaacaaa aaacaaaaaa aaacctcaac agctctctta    3240
gtactcaggt tcatgctgca aaatcacttg agattttgtt tttaagtaac ccgtgctcca    3300
catttgctgg aggatgctat tgtgaatgtg ggctcagatg agcaaggtca aggggccaaa    3360
aaaaattccc cctctccccc caggagtatt tgaagatgat gtttatggtt taagtcttcc    3420
tggcaccttc cccttgcttt ggtacaaggg ctgagtcct gttggtcttg tagcatttcc    3480
caggatgatg atgtcagcag ggatgacatc accaccttta gggcttttcc ctggcagggg    3540
cccatgtggc tagtcctcac gaagactgga gtagaatgtt tggagctcag gaagggtggg    3600
```

-continued

| | |
|---|---|
| tggagtggcc ctcttccagg tgtgagggat acgaaggagg aagcttaggg aaatccattc | 3660 |
| cccactccct cttgccaaat gagggcccca gtccccaaca gctcaggtcc ccagaacccc | 3720 |
| ctagttcctc atgagaagct aggaccagaa gcacatcgtt cccttatct gagcagtgtt | 3780 |
| tggggaacta cagtgaaaac cttctggaga tgttaaaagc ttttttacccc acgatagatt | 3840 |
| gtgtttttaa ggggtgcttt ttttagggc atcactggag ataagaaagc tgcatttcag | 3900 |
| aaatgccatc gtaatggttt ttaaacacct tttacctaat tacaggtgct attttataga | 3960 |
| agcagacaac acttctttt atgactctca gacttctatt ttcatgttac cattttttt | 4020 |
| gtaactcgca aggtgtgggc ttttgtaact tcacaggtgt ggggagagac tgccttgttt | 4080 |
| caacagtttg tctccactgg tttctaattt ttaggtgcaa agatgacaga tgcccagagt | 4140 |
| ttaccttct ggttgattaa agttgtattt ctctaaaaaa aaaaaaaaa aaaaa | 4195 |

<210> SEQ ID NO 3
<211> LENGTH: 4293
<212> TYPE: DNA
<213> ORGANISM: Homo sapiens

<400> SEQUENCE: 3

| | |
|---|---|
| gccgcggcac cagggcgcgc agccgggccg gcccgacccc accggccata cggtggagcc | 60 |
| atcgaagccc ccacccacag gctgacagag gcaccgttca ccagagggct caacaccggg | 120 |
| atctatgttt aagttttaac tctcgcctcc aaagaccacg ataattcctt ccccaaagcc | 180 |
| cagcagcccc ccagccccgc gcagcccag cctgcctccc ggcgcccaga tgcccgccat | 240 |
| gccctccagc ggccccgggg acaccagcag ctctgctgcg gagcgggagg aggaccgaaa | 300 |
| ggacggagag gagcaggagg agccgcgtgg caaggaggag cgccaagagc ccagcaccac | 360 |
| ggcacggaag gtggggcggc ctgggaggaa gcgcaagcac ccccggtgg aaagcggtga | 420 |
| cacgccaaag gaccctgcgg tgatctccaa gtccccatcc atgggcccag actcaggcgc | 480 |
| ctcagagcta ttacccaatg gggacttgga gaagcggagt gagccccagc cagaggaggg | 540 |
| gagccctgct gggggcaga agggcggggc cccagcagag ggagagggtg cagctgagac | 600 |
| cctgcctgaa gcctcaagag cagtggaaaa tggctgctgc accccaagg agggccgagg | 660 |
| agccctgca gaagcgggca agaacagaa ggagaccaac atcgaatcca tgaaaatgga | 720 |
| gggctcccgg ggccggctgc ggggtggctt gggctgggag tccagcctcc gtcagcggcc | 780 |
| catgccgagg ctcaccttcc aggcggggga ccctactac atcagcaagc gcaagcggga | 840 |
| cgagtggctg gcacgctgga aagggaggc tgagaagaaa gccaaggtca ttgcaggaat | 900 |
| gaatgctgtg gaagaaaacc aggggcccgg ggagtctcag aaggtggagg aggccagccc | 960 |
| tcctgctgtg cagcagccca ctgaccccgc atccccact gtggctacca cgcctgagcc | 1020 |
| cgtgggtcc gatgctgggg acaagaatgc caccaaagca ggcgatgacg agccagtaa | 1080 |
| cgaggacggc cggggctttg gcattgggga gctggtgtgg gggaaactgc ggggcttctc | 1140 |
| ctggtggcca ggccgcattg tgtcttggtg gatgacgggc cggagccgag cagctgaagg | 1200 |
| cacccgctgg gtcatgtggt tcggagacgg caaattctca gtggtgtgtg ttgagaagct | 1260 |
| gatgccgctg agctcgtttt gcagtgcgtt ccaccaggcc acgtacaaca agcagcccat | 1320 |
| gtaccgcaaa gccatctacg aggtcctgca ggtggccagc agccgcgcgg ggaagctgtt | 1380 |
| cccggtgtgc cacgacagcg atgagagtga cactgccaag gccgtggagg tgcagaacaa | 1440 |
| gcccatgatt gaatgggccc tgggggcttt ccagccttct ggccctaagg gcctggagcc | 1500 |
| accagaagaa gagaagaatc cctacaaaga agtgtacacg gacatgtggg tggaacctga | 1560 |

```
ggcagctgcc tacgcaccac ctccaccagc caaaaagccc cggaagagca cagcggagaa    1620
gcccaaggtc aaggagatta ttgatgagcg cacaagagag cggctggtgt acgaggtgcg    1680
gcagaagtgc cggaacattg aggacatctg catctcctgt gggagcctca atgttaccct    1740
ggaacacccc ctcttcgttg gaggaatgtg ccaaaactgc aagaactgct ttctggagtg    1800
tgcgtaccag tacgacgacg acggctacca gtcctactgc accatctgct gtgggggccg    1860
tgaggtgctc atgtgcggaa acaacaactg ctgcaggtgc ttttgcgtgg agtgtgtgga    1920
cctcttggtg gggccggggg ctgcccaggc agccattaag gaagacccct ggaactgcta    1980
catgtgcggg cacaagggta cctacgggct gctgcggcgg cgagaggact ggccctcccg    2040
gctccagatg ttcttcgcta ataaccacga ccaggaattt gaccctccaa aggtttaccc    2100
acctgtccca gctgagaaga ggaagcccat ccgggtgctg tctctctttg atggaatcgc    2160
tacagggctc ctggtgctga aggacttggg cattcaggtg gaccgctaca ttgcctcgga    2220
ggtgtgtgag gactccatca cggtgggcat ggtgcggcac caggggaaga tcatgtacgt    2280
cggggacgtc cgcagcgtca cacagaagca tatccaggag tggggcccat cgatctggt     2340
gattggggc agtccctgca atgacctctc catcgtcaac cctgctcgca agggcctcta    2400
cgagggcact ggccggctct tctttgagtt ctaccgcctc ctgcatgatg cgcggcccaa    2460
ggagggagat gatcgcccct tcttctggct cttttgagaat gtggtggcca tgggcgttag    2520
tgacaagagg gacatctcgc gatttctcga gtccaaccct gtgatgattg atgccaaaga    2580
agtgtcagct gcacacaggg cccgctactt ctggggtaac cttcccggta tgaacaggcc    2640
gttggcatcc actgtgaatg ataagctgga gctgcaggag tgtctggagc atggcaggat    2700
agccaagttc agcaaagtga ggaccattac tacgaggtca aactccataa agcagggcaa    2760
agaccagcat tttcctgtct tcatgaatga aaagaggac atcttatggt gcactgaaat    2820
ggaaagggta tttggtttcc cagtccacta tactgacgtc tccaacatga gccgcttggc    2880
gaggcagaga ctgctgggcc ggtcatggag cgtgccagtc atccgccacc tcttcgctcc    2940
gctgaaggag tattttgcgt gtgtgtaagg gacatggggg caaactgagg tagcgacaca    3000
aagttaaaca aacaaacaaa aaacacaaaa cataataaaa caccaagaac atgaggatgg    3060
agagaagtat cagcacccag aagagaaaaa ggaatttaaa acaaaaacca cagaggcgga    3120
aataccggag ggctttgcct tgcgaaaagg gttggacatc atctcctgat ttttcaatgt    3180
tattcttcag tcctatttaa aaacaaaacc aagctcccct cccttcctcc cccttccctt    3240
tttttcggt cagacctttt attttctact cttttcagag gggttttctg tttgtttggg    3300
ttttgtttct tgctgtgact gaaacaagaa ggttattgca gcaaaaatca gtaacaaaaa    3360
atagtaacaa taccttgcag aggaaaggtg ggaggagagg aaaaaaggga aattttaaa    3420
gaaatctata tattgggttg ttttttttt tgtttttgt tttttttttt tgggtttttt    3480
tttttacta tatatctttt ttttgttgtc tctagcctga tcagatagga gcacaagcag    3540
gggacggaaa gagagagaca ctcaggcggc agcattccct cccagccact gagctgtcgt    3600
gccagcacca ttcctggtca cgcaaaacag aacccagtta gcagcaggga gacgagaaca    3660
ccacacaaga cattttttcta cagtatttca ggtgcctacc acacaggaaa ccttgaagaa    3720
aatcagtttc tagaagccgc tgttacctct tgtttacagt ttatatatat atgatagata    3780
tgagatatat atataaaagg tactgttaac tactgtacaa cccgacttca taatggtgct    3840
ttcaaacagc gagatgagta aaaacatcag cttccacgtt gccttctgcg caagggtttt    3900
```

```
caccaaggat ggagaaaggg agacagcttg cagatggcgc gttctcacgg tgggctcttc    3960
cccttggttt gtaacgaagt gaaggaggag aacttgggag ccaggttctc cctgccaaaa    4020 aggggctag atgaggtggt cgggcccgtg acagctgag agtgggattc atccagactc      4080
atgcaataac cctttgattg ttttctaaaa ggagactccc tcggcaagat ggcagagggt    4140
acggagtctt caggcccagt ttctcacttt agccaattcg agggctcctt gtggtgggat    4200
cagaactaat ccagagtgtg ggaaagtgac agtcaaaacc ccacctggag caaataaaaa    4260
aacatacaaa acgtaaaaaa aaaaaaaaaa aaa                                 4293

<210> SEQ ID NO 4
<211> LENGTH: 4145
<212> TYPE: DNA
<213> ORGANISM: Homo sapiens

<400> SEQUENCE: 4
ggccgcgaat tcggcacgag ccctgcacgg ccgccagccg gcctcccgcc agccagcccc      60
gacccgcggc tccgccgccc agccgcgccc cagccagccc tgcggcagga aagcatgaag     120
ggagacacca ggcatctcaa tggagaggag gacgccggcg ggaggaaga ctcgatcctc      180 gtcaacgggg cctgcagcga ccagtcctcc gactcgcccc caatcctgga ggctatccgc    240
accccggaga tcagaggccg aagatcaagc tcgcgactct ccaagaggga ggtgtccagt    300
ctgctaagct acacacagga cttgacaggc gatggcgacg gggaagatgg ggatggctct    360
gacaccccag tcatgccaaa gctcttccgg gaaaccagga ctcgttcaga aagcccagct    420
gtccgaactc gaaataacaa cagtgtctcc agccgggaga ggcacaggcc ttccccacgt    480
tccacccgag gccggcaggg ccgcaaccat gtggacgagt ccccgtgga gttcccggct     540 accaggtccc tgagacggcg ggcaacagca tcggcaggaa cgccatggcc gtcccctccc    600
agctcttacc ttaccatcga cctcacagac gacacagagg acacacatgg gacgccccag    660
agcagcagta ccccctacgc ccgcctagcc caggacagcc agcaggggg catggagtcc     720 ccgcaggtgg aggcagacag tggagatgga gacagttcag agtatcagga tgggaaggag    780
tttggaatag gggacctcgt gtggggaaag atcaagggct tctcctggtg gcccgccatg    840
gtggtgtctt ggaaggccac ctccaagcga caggctatgt ctggcatgcg gtgggtccag    900
tggtttggcg atggcaagtt ctccgaggtc tctgcagaca aactggtggc actggggctg    960
ttcagccagc actttaattt ggccaccttc aataagctcg tctcctatcg aaaagccatg    1020
taccatgctc tggagaaagc tagggtgcga gctggcaaga ccttccccag cagccctgga    1080
gactcattgg aggaccagct gaagcccatg ttggagtggg cccacggggg cttcaagccc    1140
actgggatcg agggcctcaa acccaacaac acgcaaccag tggttaataa gtcgaaggtg    1200
cgtcgtgcag gcagtaggaa attagaatca aggaaatacg agaacaagac tcgaagacgc    1260
acagctgacg actcagccac ctctgactac tgccccgcac ccaagcgcct caagacaaat    1320
tgctataaca acggcaaaga ccgaggggat gaagatcaga gccgagaaca aatggcttca    1380
gatgttgcca acaacaagag cagcctggaa gatggctgtt tgtcttgtgg caggaaaaac    1440
cccgtgtcct tccaccctct ctttgagggg gggctctgtc agacatgccg ggatcgcttc    1500
cttgagctgt tttacatgta tgatgacgat ggctatcagt cttactgcac tgtgtgctgc    1560
gagggccgag agctgctgct ttgcagcaac acgagctgct gccggtgttt ctgtgtggag    1620
tgcctggagg tgctggtggg cacaggcaca gcggccgagg ccaagcttca ggagccctgg    1680
agctgctaca tgtgtctccc gcagcgctgt catggcgtcc tgcggcgccg gaaggactgg    1740
```

```
aacgtgcgcc tgcaggcctt cttcaccagt gacacggggc ttgaatacga agcccccaag    1800
ctgtaccctg ccattcccgc agcccgaagg cggcccattc gagtcctgtc attgtttgat    1860
ggcatcgcga caggctacct agtcctcaaa gagttgggca taaaggtagg aaagtacgtc    1920
gcttctgaag tgtgtgagga gtccattgct gttggaaccg tgaagcacga ggggaatatc    1980
aaatacgtga acgacgtgag gaacatcaca aagaaaaata ttgaagaatg ggcccatttt    2040
gacttggtga ttggcggaag cccatgcaac gatctctcaa atgtgaatcc agccaggaaa    2100
ggcctgtatg agggtacagg ccggctcttc ttcgaatttt accacctgct gaattactca    2160
cgccccaagg agggtgatga ccggccgttc ttctggatgt ttgagaatgt tgtagccatg    2220
aaggttggcg acaagaggga catctcacgg ttcctggagt gtaatccagt gatgattgat    2280
gccatcaaag tttctgctgc tcacagggcc cgatacttct ggggcaacct acccgggatg    2340
aacaggcccg tgatagcatc aaagaatgat aaactcgagc tgcaggactg cttggaatac    2400
aataggatag ccaagttaaa gaaagtacag acaataacca ccaagtcgaa ctcgatcaaa    2460
caggggaaaa accaactttt ccctgttgtc atgaatggca agaagatgt tttgtggtgc    2520
actgagctcg aaaggatctt tggctttcct gtgcactaca cagacgtgtc caacatgggc    2580
cgtggtgccc gccagaagct gctgggaagg tcctggagcg tgcctgtcat ccgacacctc    2640
ttcgcccctc tgaaggacta ctttgcatgt gaatagttcc agccaggccc caagcccact    2700
ggggtgtgtg gcagagccag gacccaggag gtgtgattcc tgaaggcatc cccaggccct    2760
gctcttcctc agctgtgtgg gtcataccgt gtacctcagt tccctcttgc tcagtggggg    2820
cagagccacc tgactcttgc aggggtagcc tgaggtgccg cctccttgtg cacaaatcag    2880
acctggctgc ttggagcagc ctaacacggt gctcattttt tcttctccta aaactttaaa    2940
acttgaagta ggtagcaacg tggctttttt ttttttccctt cctgggtcta ccactcagag    3000
aaacaatggc taagatacca aaaccacagt gccgacagct ctccaatact caggttaatg    3060
ctgaaaaatc atccaagaca gttattgcaa gagtttaatt tttgaaaact gggtactgct    3120
atgtgtttac agacgtgtgc agttgtaggc atgtagctac aggacatttt taagggccca    3180
ggatcgtttt ttcccagggc aagcagaaga gaaaatgttg tatatgtctt ttacccggca    3240
cattcccctt gcctaaatac aagggctgga gtctgcacgg gacctattag agtattttcc    3300
acaatgatga tgatttcagc agggatgacg tcatcatcac attcagggct attttttccc    3360
ccacaaaccc aagggcaggg gccactctta gctaaatccc tccccgtgac tgcaatagaa    3420
ccctctgggg agctcaggaa ggggtgtgct gagttctata atataagctg ccatatattt    3480
tgtagacaag tatggctcct ccatatctcc ctcttcccta ggagaggagt gtgaagcaag    3540
gagcttagat aagacacccc ctcaaaccca ttccctctcc aggagaccta ccctccacag    3600
gcacaggtcc ccagatgaga agtctgctac cctcatttct catctttta ctaaactcag    3660
aggcagtgac agcagtcagg gacagacata catttctcat accttcccca catctgagag    3720
atgacaggga aaactgcaaa gctcggtgct ccctttggag attttttaat ccttttttat    3780
tccataagaa gtcgttttta gggagaacgg gaattcagac aagctgcatt tcagaaatgc    3840
tgtcataatg gttttaaca ccttttactc ttccttactgg tgctattttg tagaataagg    3900
aacaacgttg acaagttttg tggggctttt tatacacttt ttaaaatctc aaacttctat    3960
ttttatgttt aacgttttca ttaaaatttt tttgtaactg gagccacgac gtaacaaata    4020
tggggaaaaa actgtgcctt gtttcaacag ttttttgctaa ttttttaggct gaaagatgac    4080
```

```
ggatgcctag agtttacctt atgtttaatt aaaatcagta tttgtctaaa aaaaaaaaaa    4140
aaaaa                                                                4145
```

<210> SEQ ID NO 5
<211> LENGTH: 908
<212> TYPE: PRT
<213> ORGANISM: Mus musculus

<400> SEQUENCE: 5

```
Met Pro Ser Ser Gly Pro Gly Asp Thr Ser Ser Ser Leu Glu Arg
1               5                   10                  15

Glu Asp Asp Arg Lys Glu Gly Glu Gln Glu Glu Asn Arg Gly Lys
                20                  25                  30

Glu Glu Arg Gln Glu Pro Ser Ala Thr Ala Arg Lys Val Gly Arg Pro
            35                  40                  45

Gly Arg Lys Arg Lys His Pro Pro Val Glu Ser Ser Asp Thr Pro Lys
        50                  55                  60

Asp Pro Ala Val Thr Thr Lys Ser Gln Pro Met Ala Gln Asp Ser Gly
65                  70                  75                  80

Pro Ser Asp Leu Leu Pro Asn Gly Asp Leu Glu Lys Arg Ser Glu Pro
                85                  90                  95

Gln Pro Glu Glu Gly Ser Pro Ala Ala Gly Gln Lys Gly Gly Ala Pro
            100                 105                 110

Ala Glu Gly Glu Gly Thr Glu Thr Pro Pro Glu Ala Ser Arg Ala Val
        115                 120                 125

Glu Asn Gly Cys Cys Val Thr Lys Glu Gly Arg Gly Ala Ser Ala Gly
130                 135                 140

Glu Gly Lys Glu Gln Lys Gln Thr Asn Ile Glu Ser Met Lys Met Glu
145                 150                 155                 160

Gly Ser Arg Gly Arg Leu Arg Gly Gly Leu Gly Trp Glu Ser Ser Leu
                165                 170                 175

Arg Gln Arg Pro Met Pro Arg Leu Thr Phe Gln Ala Gly Asp Pro Tyr
            180                 185                 190

Tyr Ile Ser Lys Arg Lys Arg Asp Glu Trp Leu Ala Arg Trp Lys Arg
        195                 200                 205

Glu Ala Glu Lys Lys Ala Lys Val Ile Ala Val Met Asn Ala Val Glu
210                 215                 220

Glu Asn Gln Ala Ser Gly Glu Ser Gln Lys Val Glu Glu Ala Ser Pro
225                 230                 235                 240

Pro Ala Val Gln Gln Pro Thr Asp Pro Ala Ser Pro Thr Val Ala Thr
                245                 250                 255

Thr Pro Glu Pro Val Gly Gly Asp Ala Gly Asp Lys Asn Ala Thr Lys
            260                 265                 270

Ala Ala Asp Asp Glu Pro Glu Tyr Glu Asp Gly Arg Gly Phe Gly Ile
        275                 280                 285

Gly Glu Leu Val Trp Gly Lys Leu Arg Gly Phe Ser Trp Trp Pro Gly
290                 295                 300

Arg Ile Val Ser Trp Trp Met Thr Gly Arg Ser Arg Ala Ala Glu Gly
305                 310                 315                 320

Thr Arg Trp Val Met Trp Phe Gly Asp Gly Lys Phe Ser Val Val Cys
                325                 330                 335

Val Glu Lys Leu Met Pro Leu Ser Ser Phe Cys Ser Ala Phe His Gln
            340                 345                 350

Ala Thr Tyr Asn Lys Gln Pro Met Tyr Arg Lys Ala Ile Tyr Glu Val
```

-continued

```
            355                 360                 365
Leu Gln Val Ala Ser Ser Arg Ala Gly Lys Leu Phe Pro Ala Cys His
    370                 375                 380

Asp Ser Asp Glu Ser Asp Ser Gly Lys Ala Val Glu Val Gln Asn Lys
385                 390                 395                 400

Gln Met Ile Glu Trp Ala Leu Gly Gly Phe Gln Pro Ser Gly Pro Lys
                405                 410                 415

Gly Leu Glu Pro Pro Glu Glu Lys Asn Pro Tyr Lys Glu Val Tyr
            420                 425                 430

Thr Asp Met Trp Val Glu Pro Glu Ala Ala Tyr Ala Pro Pro Pro
        435                 440                 445

Pro Ala Lys Lys Pro Arg Lys Ser Thr Thr Glu Lys Pro Lys Val Lys
    450                 455                 460

Glu Ile Ile Asp Glu Arg Thr Arg Glu Arg Leu Val Tyr Glu Val Arg
465                 470                 475                 480

Gln Lys Cys Arg Asn Ile Glu Asp Ile Cys Ile Ser Cys Gly Ser Leu
                485                 490                 495

Asn Val Thr Leu Glu His Pro Leu Phe Ile Gly Gly Met Cys Gln Asn
            500                 505                 510

Cys Lys Asn Cys Phe Leu Glu Cys Ala Tyr Gln Tyr Asp Asp Asp Gly
        515                 520                 525

Tyr Gln Ser Tyr Cys Thr Ile Cys Cys Gly Gly Arg Glu Val Leu Met
    530                 535                 540

Cys Gly Asn Asn Asn Cys Cys Arg Cys Phe Cys Val Glu Cys Val Asp
545                 550                 555                 560

Leu Leu Val Gly Pro Gly Ala Ala Gln Ala Ala Ile Lys Glu Asp Pro
                565                 570                 575

Trp Asn Cys Tyr Met Cys Gly His Lys Gly Thr Tyr Gly Leu Leu Arg
            580                 585                 590

Arg Arg Glu Asp Trp Pro Ser Arg Leu Gln Met Phe Phe Ala Asn Asn
        595                 600                 605

His Asp Gln Glu Phe Asp Pro Pro Lys Val Tyr Pro Pro Val Pro Ala
    610                 615                 620

Glu Lys Arg Lys Pro Ile Arg Val Leu Ser Leu Phe Asp Gly Ile Ala
625                 630                 635                 640

Thr Gly Leu Leu Val Leu Lys Asp Leu Gly Ile Gln Val Asp Arg Tyr
                645                 650                 655

Ile Ala Ser Glu Val Cys Glu Asp Ser Ile Thr Val Gly Met Val Arg
            660                 665                 670

His Gln Gly Lys Ile Met Tyr Val Gly Asp Val Arg Ser Val Thr Gln
        675                 680                 685

Lys His Ile Gln Glu Trp Gly Pro Phe Asp Leu Val Ile Gly Gly Ser
    690                 695                 700

Pro Cys Asn Asp Leu Ser Ile Val Asn Pro Ala Arg Lys Gly Leu Tyr
705                 710                 715                 720

Glu Gly Thr Gly Arg Leu Phe Phe Glu Phe Tyr Arg Leu Leu His Asp
                725                 730                 735

Ala Arg Pro Lys Glu Gly Asp Asp Arg Pro Phe Phe Trp Leu Phe Glu
            740                 745                 750

Asn Val Val Ala Met Gly Val Ser Asp Lys Arg Asp Ile Ser Arg Phe
        755                 760                 765

Leu Glu Ser Asn Pro Val Met Ile Asp Ala Lys Glu Val Ser Ala Ala
    770                 775                 780
```

```
His Arg Ala Arg Tyr Phe Trp Gly Asn Leu Pro Gly Met Asn Arg Pro
785                 790                 795                 800

Leu Ala Ser Thr Val Asn Asp Lys Leu Glu Leu Gln Glu Cys Leu Glu
            805                 810                 815

His Gly Arg Ile Ala Lys Phe Ser Lys Val Arg Thr Ile Thr Thr Arg
        820                 825                 830

Ser Asn Ser Ile Lys Gln Gly Lys Asp Gln His Phe Pro Val Phe Met
            835                 840                 845

Asn Glu Lys Glu Asp Ile Leu Trp Cys Thr Glu Met Glu Arg Val Phe
850                 855                 860

Gly Phe Pro Val His Tyr Thr Asp Val Ser Asn Met Ser Arg Leu Ala
865                 870                 875                 880

Arg Gln Arg Leu Leu Gly Arg Ser Trp Ser Val Pro Val Ile Arg His
                885                 890                 895

Leu Phe Ala Pro Leu Lys Glu Tyr Phe Ala Cys Val
            900                 905

<210> SEQ ID NO 6
<211> LENGTH: 859
<212> TYPE: PRT
<213> ORGANISM: Mus musculus

<400> SEQUENCE: 6

Met Lys Gly Asp Ser Arg His Leu Asn Glu Glu Gly Ala Ser Gly
1               5                   10                  15

Tyr Glu Glu Cys Ile Ile Val Asn Gly Asn Phe Ser Asp Gln Ser Ser
            20                  25                  30

Asp Thr Lys Asp Ala Pro Ser Pro Val Leu Glu Ala Ile Cys Thr
        35                  40                  45

Glu Pro Val Cys Thr Pro Glu Thr Arg Gly Arg Arg Ser Ser Ser Arg
50                  55                  60

Leu Ser Lys Arg Glu Val Ser Ser Leu Leu Asn Tyr Thr Gln Asp Met
65                  70                  75                  80

Thr Gly Asp Gly Asp Arg Asp Asp Glu Val Asp Gly Asn Gly Ser
                85                  90                  95

Asp Ile Leu Met Pro Lys Leu Thr Arg Glu Thr Lys Asp Thr Arg Thr
            100                 105                 110

Arg Ser Glu Ser Pro Ala Val Arg Thr Arg His Ser Asn Gly Thr Ser
        115                 120                 125

Ser Leu Glu Arg Gln Arg Ala Ser Pro Arg Ile Thr Arg Gly Arg Gln
    130                 135                 140

Gly Arg His His Val Gln Glu Tyr Pro Val Glu Phe Pro Ala Thr Arg
145                 150                 155                 160

Ser Arg Arg Arg Arg Ala Ser Ser Ser Ala Ser Thr Pro Trp Ser Ser
                165                 170                 175

Pro Ala Ser Val Asp Phe Met Glu Glu Val Thr Pro Lys Ser Val Ser
            180                 185                 190

Thr Pro Ser Val Asp Leu Ser Gln Asp Gly Asp Gln Glu Gly Met Asp
        195                 200                 205

Thr Thr Gln Val Asp Ala Glu Ser Arg Asp Gly Asp Ser Thr Glu Tyr
    210                 215                 220

Gln Asp Asp Lys Glu Phe Gly Ile Gly Asp Leu Val Trp Gly Lys Ile
225                 230                 235                 240

Lys Gly Phe Ser Trp Trp Pro Ala Met Val Val Ser Trp Lys Ala Thr
```

-continued

```
                245                 250                 255
Ser Lys Arg Gln Ala Met Pro Gly Met Arg Trp Val Gln Trp Phe Gly
            260                 265                 270
Asp Gly Lys Phe Ser Glu Ile Ser Ala Asp Lys Leu Val Ala Leu Gly
        275                 280                 285
Leu Phe Ser Gln His Phe Asn Leu Ala Thr Phe Asn Lys Leu Val Ser
    290                 295                 300
Tyr Arg Lys Ala Met Tyr His Thr Leu Glu Lys Ala Arg Val Arg Ala
305                 310                 315                 320
Gly Lys Thr Phe Ser Ser Pro Gly Glu Ser Leu Glu Asp Gln Leu
            325                 330                 335
Lys Pro Met Leu Glu Trp Ala His Gly Gly Phe Lys Pro Thr Gly Ile
        340                 345                 350
Glu Gly Leu Lys Pro Asn Lys Lys Gln Pro Val Val Asn Lys Ser Lys
    355                 360                 365
Val Arg Arg Ser Asp Ser Arg Asn Leu Glu Pro Arg Arg Glu Asn
    370                 375                 380
Lys Ser Arg Arg Arg Thr Thr Asn Asp Ser Ala Ala Ser Glu Ser Pro
385                 390                 395                 400
Pro Pro Lys Arg Leu Lys Thr Asn Ser Tyr Gly Gly Lys Asp Arg Gly
            405                 410                 415
Glu Asp Glu Glu Ser Arg Glu Arg Met Ala Ser Glu Val Thr Asn Asn
        420                 425                 430
Lys Gly Asn Leu Glu Asp Arg Cys Leu Ser Cys Gly Lys Lys Asn Pro
    435                 440                 445
Val Ser Phe His Pro Leu Phe Glu Gly Gly Leu Cys Gln Ser Cys Arg
    450                 455                 460
Asp Arg Phe Leu Glu Leu Phe Tyr Met Tyr Asp Glu Asp Gly Tyr Gln
465                 470                 475                 480
Ser Tyr Cys Thr Val Cys Cys Glu Gly Arg Glu Leu Leu Leu Cys Ser
            485                 490                 495
Asn Thr Ser Cys Cys Arg Cys Phe Cys Val Glu Cys Leu Glu Val Leu
        500                 505                 510
Val Gly Ala Gly Thr Ala Glu Asp Ala Lys Leu Gln Glu Pro Trp Ser
    515                 520                 525
Cys Tyr Met Cys Leu Pro Gln Arg Cys His Gly Val Leu Arg Arg Arg
    530                 535                 540
Lys Asp Trp Asn Met Arg Leu Gln Asp Phe Phe Thr Thr Asp Pro Asp
545                 550                 555                 560
Leu Glu Glu Phe Glu Pro Pro Lys Leu Tyr Pro Ala Ile Pro Ala Ala
            565                 570                 575
Lys Arg Arg Pro Ile Arg Val Leu Ser Leu Phe Asp Gly Ile Ala Thr
        580                 585                 590
Gly Tyr Leu Val Leu Lys Glu Leu Gly Ile Lys Val Glu Lys Tyr Ile
    595                 600                 605
Ala Ser Glu Val Cys Ala Glu Ser Ile Ala Val Gly Thr Val Lys His
    610                 615                 620
Glu Gly Gln Ile Lys Tyr Val Asn Asp Val Arg Lys Ile Thr Lys Lys
625                 630                 635                 640
Asn Ile Glu Glu Trp Gly Pro Phe Asp Leu Val Ile Gly Gly Ser Pro
            645                 650                 655
Cys Asn Asp Leu Ser Asn Val Asn Pro Ala Arg Lys Gly Leu Tyr Glu
        660                 665                 670
```

-continued

```
Gly Thr Gly Arg Leu Phe Phe Glu Phe Tyr His Leu Leu Asn Tyr Thr
            675                 680                 685
Arg Pro Lys Glu Gly Asp Asn Arg Pro Phe Phe Trp Met Phe Glu Asn
        690                 695                 700
Val Val Ala Met Lys Val Asn Asp Lys Lys Asp Ile Ser Arg Phe Leu
705                 710                 715                 720
Ala Cys Asn Pro Val Met Ile Asp Ala Ile Lys Val Ser Ala Ala His
                725                 730                 735
Arg Ala Arg Tyr Phe Trp Gly Asn Leu Pro Gly Met Asn Arg Pro Val
            740                 745                 750
Met Ala Ser Lys Asn Asp Lys Leu Glu Leu Gln Asp Cys Leu Glu Phe
        755                 760                 765
Ser Arg Thr Ala Lys Leu Lys Lys Val Gln Thr Ile Thr Thr Lys Ser
    770                 775                 780
Asn Ser Ile Arg Gln Gly Lys Asn Gln Leu Phe Pro Val Val Met Asn
785                 790                 795                 800
Gly Lys Asp Asp Val Leu Trp Cys Thr Glu Leu Glu Arg Ile Phe Gly
                805                 810                 815
Phe Pro Ala His Tyr Thr Asp Val Ser Asn Met Gly Arg Gly Ala Arg
            820                 825                 830
Gln Lys Leu Leu Gly Arg Ser Trp Ser Val Pro Val Ile Arg His Leu
        835                 840                 845
Phe Ala Pro Leu Lys Asp Tyr Phe Ala Cys Glu
    850                 855

<210> SEQ ID NO 7
<211> LENGTH: 912
<212> TYPE: PRT
<213> ORGANISM: Homo sapiens

<400> SEQUENCE: 7

Met Pro Ala Met Pro Ser Ser Gly Pro Gly Asp Thr Ser Ser Ser Ala
1               5                   10                  15
Ala Glu Arg Glu Glu Asp Arg Lys Asp Gly Glu Gln Glu Glu Pro
        20                  25                  30
Arg Gly Lys Glu Glu Arg Gln Glu Pro Ser Thr Thr Ala Arg Lys Val
    35                  40                  45
Gly Arg Pro Gly Arg Lys Arg Lys His Pro Pro Val Glu Ser Gly Asp
50                  55                  60
Thr Pro Lys Asp Pro Ala Val Ile Ser Lys Ser Pro Ser Met Ala Gln
65                  70                  75                  80
Asp Ser Gly Ala Ser Glu Leu Leu Pro Asn Gly Asp Leu Glu Lys Arg
                85                  90                  95
Ser Glu Pro Gln Pro Glu Glu Gly Ser Pro Ala Gly Gly Gln Lys Gly
            100                 105                 110
Gly Ala Pro Ala Glu Gly Glu Gly Ala Ala Glu Thr Leu Pro Glu Ala
        115                 120                 125
Ser Arg Ala Val Glu Asn Gly Cys Cys Thr Pro Lys Glu Gly Arg Gly
    130                 135                 140
Ala Pro Ala Glu Ala Gly Lys Glu Gln Lys Glu Thr Asn Ile Glu Ser
145                 150                 155                 160
Met Lys Met Glu Gly Ser Arg Gly Arg Leu Arg Gly Gly Leu Gly Trp
                165                 170                 175
Glu Ser Ser Leu Arg Gln Arg Pro Met Pro Arg Leu Thr Phe Gln Ala
```

-continued

```
              180                 185                 190
Gly Asp Pro Tyr Tyr Ile Ser Lys Arg Lys Arg Asp Glu Trp Leu Ala
            195                 200                 205
Arg Trp Lys Arg Glu Ala Glu Lys Lys Ala Lys Val Ile Ala Gly Met
210                 215                 220
Asn Ala Val Glu Glu Asn Gln Gly Pro Gly Glu Ser Gln Lys Val Glu
225                 230                 235                 240
Glu Ala Ser Pro Pro Ala Val Gln Gln Pro Thr Asp Pro Ala Ser Pro
                245                 250                 255
Thr Val Ala Thr Thr Pro Glu Pro Val Gly Ser Asp Ala Gly Asp Lys
                260                 265                 270
Asn Ala Thr Lys Ala Gly Asp Asp Glu Pro Glu Tyr Glu Asp Gly Arg
                275                 280                 285
Gly Phe Gly Ile Gly Glu Leu Val Trp Gly Lys Leu Arg Gly Phe Ser
                290                 295                 300
Trp Trp Pro Gly Arg Ile Val Ser Trp Trp Met Thr Gly Arg Ser Arg
305                 310                 315                 320
Ala Ala Glu Gly Thr Arg Trp Val Met Trp Phe Gly Asp Gly Lys Phe
                325                 330                 335
Ser Val Val Cys Val Glu Lys Leu Met Pro Leu Ser Ser Phe Cys Ser
                340                 345                 350
Ala Phe His Gln Ala Thr Tyr Asn Lys Gln Pro Met Tyr Arg Lys Ala
                355                 360                 365
Ile Tyr Glu Val Leu Gln Val Ala Ser Ser Arg Ala Gly Lys Leu Phe
                370                 375                 380
Pro Val Cys His Asp Ser Asp Glu Ser Asp Thr Ala Lys Ala Val Glu
385                 390                 395                 400
Val Gln Asn Lys Pro Met Ile Glu Trp Ala Leu Gly Gly Phe Gln Pro
                405                 410                 415
Ser Gly Pro Lys Gly Leu Glu Pro Pro Glu Glu Glu Lys Asn Pro Tyr
                420                 425                 430
Lys Glu Val Tyr Thr Asp Met Trp Val Glu Pro Glu Ala Ala Ala Tyr
                435                 440                 445
Ala Pro Pro Pro Ala Lys Lys Pro Arg Lys Ser Thr Ala Glu Lys
450                 455                 460
Pro Lys Val Lys Glu Ile Ile Asp Glu Arg Thr Arg Glu Arg Leu Val
465                 470                 475                 480
Tyr Glu Val Arg Gln Lys Cys Arg Asn Ile Glu Asp Ile Cys Ile Ser
                485                 490                 495
Cys Gly Ser Leu Asn Val Thr Leu Glu His Pro Leu Phe Val Gly Gly
                500                 505                 510
Met Cys Gln Asn Cys Lys Asn Cys Phe Leu Glu Cys Ala Tyr Gln Tyr
                515                 520                 525
Asp Asp Asp Gly Tyr Gln Ser Tyr Cys Thr Ile Cys Cys Gly Gly Arg
                530                 535                 540
Glu Val Leu Met Cys Gly Asn Asn Cys Cys Arg Cys Phe Cys Val
545                 550                 555                 560
Glu Cys Val Asp Leu Leu Val Gly Pro Gly Ala Ala Gln Ala Ala Ile
                565                 570                 575
Lys Glu Asp Pro Trp Asn Cys Tyr Met Cys Gly His Lys Gly Thr Tyr
                580                 585                 590
Gly Leu Leu Arg Arg Arg Glu Asp Trp Pro Ser Arg Leu Gln Met Phe
                595                 600                 605
```

-continued

```
Phe Ala Asn Asn His Asp Gln Glu Phe Asp Pro Pro Lys Val Tyr Pro
            610                 615                 620
Pro Val Pro Ala Glu Lys Arg Lys Pro Ile Arg Val Leu Ser Leu Phe
625                 630                 635                 640
Asp Gly Ile Ala Thr Gly Leu Leu Val Leu Lys Asp Leu Gly Ile Gln
                645                 650                 655
Val Asp Arg Tyr Ile Ala Ser Glu Val Cys Glu Asp Ser Ile Thr Val
            660                 665                 670
Gly Met Val Arg His Gln Gly Lys Ile Met Tyr Val Gly Asp Val Arg
        675                 680                 685
Ser Val Thr Gln Lys His Ile Gln Glu Trp Gly Pro Phe Asp Leu Val
690                 695                 700
Ile Gly Gly Ser Pro Cys Asn Asp Leu Ser Ile Val Asn Pro Ala Arg
705                 710                 715                 720
Lys Gly Leu Tyr Glu Gly Thr Gly Arg Leu Phe Phe Glu Phe Tyr Arg
                725                 730                 735
Leu Leu His Asp Ala Arg Pro Lys Glu Gly Asp Asp Arg Pro Phe Phe
            740                 745                 750
Trp Leu Phe Glu Asn Val Val Ala Met Gly Val Ser Asp Lys Arg Asp
        755                 760                 765
Ile Ser Arg Phe Leu Glu Ser Asn Pro Val Met Ile Asp Ala Lys Glu
770                 775                 780
Val Ser Ala Ala His Arg Ala Arg Tyr Phe Trp Gly Asn Leu Pro Gly
785                 790                 795                 800
Met Asn Arg Pro Leu Ala Ser Thr Val Asn Asp Lys Leu Glu Leu Gln
                805                 810                 815
Glu Cys Leu Glu His Gly Arg Ile Ala Lys Phe Ser Lys Val Arg Thr
            820                 825                 830
Ile Thr Thr Arg Ser Asn Ser Ile Lys Gln Gly Lys Asp Gln His Phe
        835                 840                 845
Pro Val Phe Met Asn Glu Lys Glu Asp Ile Leu Trp Cys Thr Glu Met
850                 855                 860
Glu Arg Val Phe Gly Phe Pro Val His Tyr Thr Asp Val Ser Asn Met
865                 870                 875                 880
Ser Arg Leu Ala Arg Gln Arg Leu Leu Gly Arg Ser Trp Ser Val Pro
                885                 890                 895
Val Ile Arg His Leu Phe Ala Pro Leu Lys Glu Tyr Phe Ala Cys Val
            900                 905                 910

<210> SEQ ID NO 8
<211> LENGTH: 853
<212> TYPE: PRT
<213> ORGANISM: Homo sapiens

<400> SEQUENCE: 8

Met Lys Gly Asp Thr Arg His Leu Asn Gly Glu Glu Asp Ala Gly Gly
1               5                   10                  15
Arg Glu Asp Ser Ile Leu Val Asn Gly Ala Cys Ser Asp Gln Ser Ser
            20                  25                  30
Asp Ser Pro Pro Ile Leu Glu Ala Ile Arg Thr Pro Glu Ile Arg Gly
        35                  40                  45
Arg Arg Ser Ser Ser Arg Leu Ser Lys Arg Glu Val Ser Ser Leu Leu
    50                  55                  60
Ser Tyr Thr Gln Asp Leu Thr Gly Asp Gly Asp Gly Glu Asp Gly Asp
```

-continued

```
            65                  70                  75                  80
Gly Ser Asp Thr Pro Val Met Pro Lys Leu Phe Arg Glu Thr Arg Thr
                    85                  90                  95
Arg Ser Glu Ser Pro Ala Val Arg Thr Arg Asn Asn Asn Ser Val Ser
                100                 105                 110
Ser Arg Glu Arg His Arg Pro Ser Pro Arg Ser Thr Arg Gly Arg Gln
                115                 120                 125
Gly Arg Asn His Val Asp Glu Ser Pro Val Glu Phe Pro Ala Thr Arg
            130                 135                 140
Ser Leu Arg Arg Arg Ala Thr Ala Ser Ala Gly Thr Pro Trp Pro Ser
145                 150                 155                 160
Pro Pro Ser Ser Tyr Leu Thr Ile Asp Leu Thr Asp Thr Glu Asp
                165                 170                 175
Thr His Gly Thr Pro Gln Ser Ser Thr Pro Tyr Ala Arg Leu Ala
                180                 185                 190
Gln Asp Ser Gln Gln Gly Gly Met Glu Ser Pro Gln Val Glu Ala Asp
                195                 200                 205
Ser Gly Asp Gly Asp Ser Ser Glu Tyr Gln Asp Gly Lys Glu Phe Gly
            210                 215                 220
Ile Gly Asp Leu Val Trp Gly Lys Ile Lys Gly Phe Ser Trp Trp Pro
225                 230                 235                 240
Ala Met Val Val Ser Trp Lys Ala Thr Ser Lys Arg Gln Ala Met Ser
                    245                 250                 255
Gly Met Arg Trp Val Gln Trp Phe Gly Asp Gly Lys Phe Ser Glu Val
                260                 265                 270
Ser Ala Asp Lys Leu Val Ala Leu Gly Leu Phe Ser Gln His Phe Asn
            275                 280                 285
Leu Ala Thr Phe Asn Lys Leu Val Ser Tyr Arg Lys Ala Met Tyr His
        290                 295                 300
Ala Leu Glu Lys Ala Arg Val Arg Ala Gly Lys Thr Phe Pro Ser Ser
305                 310                 315                 320
Pro Gly Asp Ser Leu Glu Asp Gln Leu Lys Pro Met Leu Glu Trp Ala
                    325                 330                 335
His Gly Gly Phe Lys Pro Thr Gly Ile Glu Gly Leu Lys Pro Asn Asn
                340                 345                 350
Thr Gln Pro Val Val Asn Lys Ser Lys Val Arg Arg Ala Gly Ser Arg
                355                 360                 365
Lys Leu Glu Ser Arg Lys Tyr Glu Asn Lys Thr Arg Arg Thr Ala
        370                 375                 380
Asp Asp Ser Ala Thr Ser Asp Tyr Cys Pro Ala Pro Lys Arg Leu Lys
385                 390                 395                 400
Thr Asn Cys Tyr Asn Asn Gly Lys Asp Arg Gly Asp Glu Asp Gln Ser
                    405                 410                 415
Arg Glu Gln Met Ala Ser Asp Val Ala Asn Asn Lys Ser Ser Leu Glu
                420                 425                 430
Asp Gly Cys Leu Ser Cys Gly Arg Lys Asn Pro Val Ser Phe His Pro
            435                 440                 445
Leu Phe Glu Gly Gly Leu Cys Gln Thr Cys Arg Asp Arg Phe Leu Glu
        450                 455                 460
Leu Phe Tyr Met Tyr Asp Asp Gly Tyr Gln Ser Tyr Cys Thr Val
465                 470                 475                 480
Cys Cys Glu Gly Arg Glu Leu Leu Leu Cys Ser Asn Thr Ser Cys Cys
                    485                 490                 495
```

```
Arg Cys Phe Cys Val Glu Cys Leu Glu Val Leu Gly Thr Gly Thr
            500                 505                 510

Ala Ala Glu Ala Lys Leu Gln Glu Pro Trp Ser Cys Tyr Met Cys Leu
            515                 520                 525

Pro Gln Arg Cys His Gly Val Leu Arg Arg Arg Lys Asp Trp Asn Val
            530                 535                 540

Arg Leu Gln Ala Phe Phe Thr Ser Asp Thr Gly Leu Glu Tyr Glu Ala
545                 550                 555                 560

Pro Lys Leu Tyr Pro Ala Ile Pro Ala Ala Arg Arg Pro Ile Arg
            565                 570                 575

Val Leu Ser Leu Phe Asp Gly Ile Ala Thr Gly Tyr Leu Val Leu Lys
            580                 585                 590

Glu Leu Gly Ile Lys Val Gly Lys Tyr Val Ala Ser Glu Val Cys Glu
            595                 600                 605

Glu Ser Ile Ala Val Gly Thr Val Lys His Glu Gly Asn Ile Lys Tyr
            610                 615                 620

Val Asn Asp Val Arg Asn Ile Thr Lys Lys Asn Ile Glu Glu Trp Gly
625                 630                 635                 640

Pro Phe Asp Leu Val Ile Gly Gly Ser Pro Cys Asn Asp Leu Ser Asn
                    645                 650                 655

Val Asn Pro Ala Arg Lys Gly Leu Tyr Glu Gly Thr Gly Arg Leu Phe
            660                 665                 670

Phe Glu Phe Tyr His Leu Leu Asn Tyr Ser Arg Pro Lys Glu Gly Asp
            675                 680                 685

Asp Arg Pro Phe Phe Trp Met Phe Glu Asn Val Val Ala Met Lys Val
            690                 695                 700

Gly Asp Lys Arg Asp Ile Ser Arg Phe Leu Glu Cys Asn Pro Val Met
705                 710                 715                 720

Ile Asp Ala Ile Lys Val Ser Ala Ala His Arg Ala Arg Tyr Phe Trp
                    725                 730                 735

Gly Asn Leu Pro Gly Met Asn Arg Pro Val Ile Ala Ser Lys Asn Asp
            740                 745                 750

Lys Leu Glu Leu Gln Asp Cys Leu Glu Tyr Asn Arg Ile Ala Lys Leu
            755                 760                 765

Lys Lys Val Gln Thr Ile Thr Thr Lys Ser Asn Ser Ile Lys Gln Gly
            770                 775                 780

Lys Asn Gln Leu Phe Pro Val Val Met Asn Gly Lys Glu Asp Val Leu
785                 790                 795                 800

Trp Cys Thr Glu Leu Glu Arg Ile Phe Gly Phe Pro Val His Tyr Thr
                    805                 810                 815

Asp Val Ser Asn Met Gly Arg Gly Ala Arg Gln Lys Leu Leu Gly Arg
            820                 825                 830

Ser Trp Ser Val Pro Val Ile Arg His Leu Phe Ala Pro Leu Lys Asp
            835                 840                 845

Tyr Phe Ala Cys Glu
    850
```

<210> SEQ ID NO 9
<211> LENGTH: 393
<212> TYPE: DNA
<213> ORGANISM: Mus musculus

<400> SEQUENCE: 9
tttctacagt atttcaggtg cctaccacac aggaaacctt gaagaaaacc agtttctaga    60

```
agccgctgtt acctcttgtt tacagtttat atatatatga tagatatgag atatatatat    120
ataaaaggta ctgttaacta ctgtacatcc cgacttcata atggtgcttt caaaacagcg    180
agatgagcaa agacatcagc ttccgcctgg ccctcgtgtg caaatggcgt ttcatgccca    240
tggatggtgt agaggggagc agctggaggg ggtttcacaa actgaaggat gacccatatc    300 acccccacc cctgccccat gcctagcttc acctgccaaa aggggctca gctgaggtgg      360 tcggaccctg gggaagctga gtgtggaatt tat                                  393

<210> SEQ ID NO 10
<211> LENGTH: 424
<212> TYPE: DNA
<213> ORGANISM: Mus musculus

<400> SEQUENCE: 10
gaagaaaacc agtttctaga agccgctgtt acctcttgtt tacagtttat atatatatga     60
tagatatgag atatatatat ataaaaggta ctgttaacta ctgtacatcc cgacttcata    120
atggtgcttt caaaacagcg agatgagcaa agacatcagc ttccgcctgg ccctctgtgc    180
aaagggtttc agcccaggat ggtgagaggg gagcatctgg aggggttttt aacaaactga    240
aggatgaccc atatcacccc ccaccctgc cccatgccta gcttcacctg ccaaaaggg     300 gctcagctga ggtggtcgga ccctggggaa gctgagtgtg aatttatcc agactcgcgt    360 gcaataacct agaatatga atctaaaatg actgcctcag aaaaatggct tgagaaaaca    420
ttgt                                                                 424

<210> SEQ ID NO 11
<211> LENGTH: 461
<212> TYPE: DNA
<213> ORGANISM: Mus musculus

<400> SEQUENCE: 11
tttaaagcaa accacagagg aggaaaacgc cggaggcttg gccttgcaaa agggttggac     60
atcatctcct gagttttcaa tgttaaccct cagtcctatc taaaaagcaa ataggcccc    120 tccccttcgt tcccctccgg tcctaggagg cgaacttttt gttttctact ctttttcaga    180
ggggttttct gtttgtttgg gttttttgttt cttgctgtga ctgaaacaag agagttattg    240
cagcaaaatc agtaacaaca aaagtagaa atgccttgga gcggaaaggg agagagggaa     300
aattctataa aaacttaaaa tattggtttt tttttttttc cttttctata tatctctttg    360
gttgtctcta gcctgatcag ataggagcac aaacaggaag agaatagaga ccctcggagg    420
cagagtctcc tctcccaccc ccgagcagt ctcaacagca c                         461

<210> SEQ ID NO 12
<211> LENGTH: 465
<212> TYPE: DNA
<213> ORGANISM: Mus musculus

<400> SEQUENCE: 12
tcagaggggt tttctgtttg tttgggtttt tgtttcttgc tgtgactgaa acaagagagt     60
tattgcagca aaatcagtaa caacaaaaag tagaaatgcc ttggagagga aaggagaga    120 gggaaaattc tataaaaact taaaatattg gttttttttt ttttcctttt ctatatatc    180 tctttggttg tctctagcct gatcagatag gagcacaaac aggaagagaa tagagaccct    240
cggaggcaga gtctcctctc ccaccccccg agcagtctca acagccat tcctggtcat     300
```

```
gcaaaacaga acccaactag cagcagggcg ctgagagaac accacaccag acactttcct    360
acagtatttc aggtgcctac cacacaggaa accttgaaga aaaccagttt ctagaagccg    420
ctgttaccct ttgtttacag tttatatata tatgatagat atgag                   465
```

```
<210> SEQ ID NO 13
<211> LENGTH: 393
<212> TYPE: DNA
<213> ORGANISM: Mus musculus

<400> SEQUENCE: 13
aaaacgccgg aggcctttgc cttgcacaag ggttggacat catctcctga gttttcaatg    60
ttaaccttca gtcctatcta aaaagcaaaa taggcccctc cccttcttcc cctccggtcc   120
taggaggcga acttttttgtt ttctactctt tttcagaggg gttttctgtt tgtttgggtt   180
tttgtttctt gctgtgactg aaacaagaga gttattgcag caaaatcagt aacaacaaaa   240
agtagaaatg ccttggagag gaagggaga gagggaaaat tctataaaaa cttaaaatat    300
tggttttttt tttttttcctt ttctatatat cgctttggtt gtctctagcc tgatcagata   360
ggagcacaaa caggaagaga atagagaccc tcg                                393
```

```
<210> SEQ ID NO 14
<211> LENGTH: 309
<212> TYPE: DNA
<213> ORGANISM: Mus musculus

<400> SEQUENCE: 14
gtgatgattg acgccaaaga agtgtctgct gcacacaggg cccgttactt ctaggggtaa    60
ccttcctggc atgaacaggc ctttggatcc actgtgaatg ataagctgga gctgcaagag   120
tgtctggagc acggcagaat agccaagttc agcaaagtga ggaccattac caccaggtca   180
aactctataa agcagggcaa agaccagcat ttccccgtct tcatgaacga aaggaggac    240 atcctgtggt gcactgaaat ggaaagggtc tttggcttcc ccgtccacta cacagacgtc   300
tccaacatg                                                            309
```

```
<210> SEQ ID NO 15
<211> LENGTH: 341
<212> TYPE: DNA
<213> ORGANISM: Mus musculus

<400> SEQUENCE: 15
tgttaacctt cagtcctatc taaaaagcaa ataggcccc tccccttctt cccctccggt     60
cctaggaggc gaacttttg tttttctactc tttttcagag gggttttctg tttgtttggg   120
tttttgtttc ttgctgtgac tgaaacaaga gagttattgc agcaaaatca gtaacaacaa   180
aaagtagaaa tgccttggag aggaaaggga gagagggaaa attctataaa aacttaaaat   240
attggttttt tttttttttcc ttttctatat atctctttgg ttgtctctag cctgatcaga   300
taggagcaca aacaggaaga gaatagagac cctcggaggc a                        341
```

```
<210> SEQ ID NO 16
<211> LENGTH: 240
<212> TYPE: DNA
<213> ORGANISM: Mus musculus
<220> FEATURE:
<221> NAME/KEY: misc_feature
<222> LOCATION: (32)..(32)
<223> OTHER INFORMATION: n is a, c, g, or t

<400> SEQUENCE: 16
```

```
acattttgta tgtttttttta tttgctccag gnggggttaa tggcgggtca ctttccctca    60
ctctggaata tttctgatcc cacaaggggc cttcaacgtg gctgacgaat tcaaaatcag   120
ggacaatgtt ttctcaagcc attttttctga ggcagtcatt ttagattcat attctaaggt  180
tattgcacgc gagtctggat aaattccaca ctcagcttcc ccagggtccg accacctcag   240
```

<210> SEQ ID NO 17  
<211> LENGTH: 256  
<212> TYPE: DNA  
<213> ORGANISM: Mus musculus  
<220> FEATURE:  
<221> NAME/KEY: misc_feature  
<222> LOCATION: (75)..(75)  
<223> OTHER INFORMATION: n is a, c, g, or t

<400> SEQUENCE: 17

```
atcagcttcc gcctggccct ctgtgcaaag ggtttcagcc caggatgggg agagggagc    60 agctggaggg ggttntaaca aactgaagga tgacccatat cacccccac ccctgcccca   120 tgcctagctt cacctgccaa aaggggctc agctgaggtg gtcggaccct ggggaagctg   180
agtgtggaat ttatccagac tcgcgtgcaa taaccttaga atatgaatct aaaatgactg   240
cctcagaaaa atggct                                                  256
```

<210> SEQ ID NO 18  
<211> LENGTH: 435  
<212> TYPE: DNA  
<213> ORGANISM: Mus musculus

<400> SEQUENCE: 18

```
gtggaagccc atgcaatgat ctctctaacg tcaatcctgc ccgcaaaggt ttatatgagg    60
gcacaggaag gctcttcttc gagttttacc acttgctgaa ttatacccgc cccaaggagg   120
gcgacaaccg tccattcttc tggatgttcg agaatgttgt ggccatgaaa gtgaatgaca   180
agaaagacat ctcaagattc ctggcatgta acccagtgat gatcgatgcc atcaaggtgt   240
ctgctgctca cagggcccgg tacttctggg gtaacctacc cggaatgaac aggcccgtga   300
tggcttcaaa gaatgataag ctcgagctgc aggactgcct ggagttcagt aggacagcaa   360
agttaaagaa agtgcagaca ataaccacca gtcgaactc catcagacag gcaaaaacc    420 agcttttccc tgtag                                                   435
```

<210> SEQ ID NO 19  
<211> LENGTH: 522  
<212> TYPE: DNA  
<213> ORGANISM: Mus musculus

<400> SEQUENCE: 19

```
gatgatgtca gcagggatga catcaccacc tttagggctt ttccctggca ggggcccatg    60
tggctagtcc tcacgaagac tggagtagaa tgtttggagc tcaggaaggg tgggtggagt   120
ggagtctctt ccaggtgtga gggatacgaa ggaggaagct tagggaaatc cattccccac   180
tccctcttgc caaatgaggg gcccagtccc caacagctca ggtccccaga accccctagt   240
tcctcatgag aagctaggac cagaagcaca tcgttcccct tatctgagca gtgtttgggg   300
aactacagtg aaaaccttct ggagatgtta aaagcttttt accccacgat agattgtgtt   360
tttaaggggt gctttttttta ggggcatcac tggagataag aaagctgcat ttcagaaatg   420
ccatcgtaat ggttttttaaa caccttttac ctaattacag gtgctatttt atagaagcag   480
```

```
acaacacttc tttttatgac tctcagactt ctattttcat gt                    522
```

<210> SEQ ID NO 20
<211> LENGTH: 348
<212> TYPE: DNA
<213> ORGANISM: Mus musculus

<400> SEQUENCE: 20

```
aaaggaggcc cattagagtc ctgtctctgt ttgatggaat tgcaacgggg tacttggtgc  60
tcaaggagtt gggtattaaa gtggaaaagt acattgcctc cgaagtctgt gcagagtcca  120
tcgctgtggg aactgttaag catgaaggcc agatcaaata tgtcaatgac gtccggaaaa  180
tcaccaagaa aaatattgaa gagtggggcc cgttcgactt ggtgattggt ggaagcccat  240
gcaatgatct ctctaacgtc aatcctgccc gcaaaggttt atatgagggc acaggaaggc  300
tcttcttcga gttttaccac ttgctgaatt atacccgccc caaggagg             348
```

<210> SEQ ID NO 21
<211> LENGTH: 258
<212> TYPE: DNA
<213> ORGANISM: Mus musculus

<400> SEQUENCE: 21

```
gtttatggtt taagtcttcc tggcaccttc cccttgcttt ggtacaaggg ctgaagtcct  60
gttggtcttg tagcatttcc caggatgatg atgtcagcag ggatgacatc atcacctta  120
gggcttttcc ctggcagggg cccatgtggc tagtcctcac gaagactgga gtagaatgtt  180
tggagctcag gaagggtggg tggagtgtgc ctcttccagg tgtgagggat acgaaggagg  240
aagcttaggg aaatccat                                                258
```

<210> SEQ ID NO 22
<211> LENGTH: 334
<212> TYPE: DNA
<213> ORGANISM: Mus musculus

<400> SEQUENCE: 22

```
tggggtaacc tacccggaat gaacagttaa agaaagtgca gacaataacc accaagtcga  60
actccatcag acagggcaaa aaccagcttt tccctgtagt catgaatggc aaggacgacg  120
ttttgtggtg cactgagctc gaaaggatct tcggcttccc tgctcactac acggacgtgt  180
ccaacatggg ccgcggcgcc cgtcagaagc tgctgggcag gtcctggagt gtaccggtca  240
tcagacacct gtttgccccc ttgaaggact actttgcctg tgaatagttc tacccaggac  300
tggggagctc tcggtcagag ccagtgccca gagt                              334
```

<210> SEQ ID NO 23
<211> LENGTH: 299
<212> TYPE: DNA
<213> ORGANISM: Mus musculus
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t

<400> SEQUENCE: 23

```
ctgttttgt ttgttttttt ggtatcttag ccatcacttc tgagtgataa actcaggang  60
gtaaaagaaa gccatcttac tacctacttc aagttttaaa gtttcagggt aagagaacat  120
```

-continued

```
gagcaccatg ccgggctact ctaagcagcc aggtctgagc tgtgcacacg ganggagcac    180
cggggctccc ctgcaaggcc aggaggctct gctcccactg agcaggagaa agctgaggta    240
cagtgatgtg aggccccaca caggtgagct aaaaagggga caggtgaggt gccttcagg     299
```

<210> SEQ ID NO 24
<211> LENGTH: 455
<212> TYPE: DNA
<213> ORGANISM: Mus musculus

<400> SEQUENCE: 24

```
gatcgcttcc tagagctctt ctacatgtat gatgaggacg gctatcagtc ctactgcacc    60
gtgtctgtga gggccgtgaa ctgctgctgt gcagtaacac aagctgctgc agatgcttct   120
gtgtggagtg tctggaggtg ctggtgggcg caggacagct gaggatgcca agctgcagga   180
accctggagc tgctatatgt gcctccctca gcgctgccat ggggtcctcc gacgcaggaa   240
agattggaac atgcgcctgc aagacttctt cactactgat cctgacctgg aagaatttca   300
ggagccaccc aagttgtacc cagcaattcc tgcagccaaa aggaggccca ttagagtcct   360
gtctctgttt gatggaattg caacggggta cttggtgctc aaggagttgg gtattaaagt   420
ggaaaagtac attgcctccg aagtctgtgc agagt                              455
```

<210> SEQ ID NO 25
<211> LENGTH: 368
<212> TYPE: DNA
<213> ORGANISM: Homo sapiens
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t

<400> SEQUENCE: 25

```
acgttttgta tgttttttta tttgctccag gtggggtttt gactgtcact ttcccacact    60
ctggattagt tctgatccca ccacaaggag ccctcgaatt ggctaaagtg agaaactggg   120
cctgaagact ccgtaccctc tgccatcttg ccgagggagt ctccttttag aaaacaatca   180
aagggttatt gcatgagtct ggatgaatcc cactctcagc ttgtccacgg gcccgaccac   240
ctcatctagc cccctttttg gcaagggaga acctggctcc caagttctcc tccttcactt   300
tcgttancaa accaaggggg aagaagccca ccgtngagaa cgcgccatct tgnaaagctn   360
ggtcttcc                                                            368
```

<210> SEQ ID NO 26
<211> LENGTH: 399
<212> TYPE: DNA
<213> ORGANISM: Homo sapiens
<220> FEATURE:
<221> NAME/KEY: misc_feature
<222> LOCATION: (87)..(87)
<223> OTHER INFORMATION: n is a, c, g, or t
<220> FEATURE:

```
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t

<400> SEQUENCE: 26
gaacatgagg atggagagaa gtatcagcac ccagaagaga aaaaggaatt taaaacaaaa      60
accacagagg cggaaatacc ggaggcnttt gcttgcgaaa agggttggac atcatctcct     120 gattttcaa tgttattctt cagtcctatt taaaaacaaa accaagctcc cttcccttcc     180 tccccttcc cttttttttc ggtcagacct tttatttct actcttttca gaggggtttt     240
ctgtttgttt gggttttgtt tcttgctgtg actgaaacaa gaaggttatt gcagcaaaaa     300
tcaggtaaca aaanatangt aacaataccct tgcagaggaa aggtgggagg agaggaaaaa     360
agggaaattn ctatagaaat ctatatattg gggttggtt                           399

<210> SEQ ID NO 27
<211> LENGTH: 318
<212> TYPE: DNA
<213> ORGANISM: Homo sapiens
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t

<400> SEQUENCE: 27
gtacgaggtg cggcagaagt gccggaacat tgaggacatc tgcatctcct gtgggagcct      60
caatgttacc ctggaacacc ccctcttcgt tggaggaatg tgccaaaact gcaagaactg     120
ctttctggag tgtgcgtacc agtacgacga cgacggctac cagtcctact gcaccatctg     180 ctgtggggc cgtgaggtgc tcatntgcgg aaacaacaac tgctgcaggt gcttttgcgt     240
ggagtgtgtg gacctcttgg tggggccggg ggctncccag gcagcagtta aggaagatca     300
tgtacgtcgg ggacgtcc                                                  318

<210> SEQ ID NO 28
<211> LENGTH: 259
<212> TYPE: DNA
<213> ORGANISM: Homo sapiens
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t

<400> SEQUENCE: 28
gagccgagca gctgaaggca cccgctgggt catgtggttc ggagacggca aattctcagt      60
ggtgtgtgtt gagaagctga tgccgctgag ctcgttttgc agtgcgttcc accaggccac     120
gtacaacaag cagcccatgt accgcaaagc catctacgag gtcctgcagg tggccagcag     180
ccgcgcgggg aagctgttcc cggtgtgcca cgacagcgat gagagtnaca ctgncaaggc     240
```

```
cgtgggaggt gcagaacaa                                               259

<210> SEQ ID NO 29
<211> LENGTH: 483
<212> TYPE: DNA
<213> ORGANISM: Homo sapiens

<400> SEQUENCE: 29
tttttttttt ttgtatgttt ttttatttgc tccaggtggg gttttgactg tcactttccc    60
acactctgga ttagttctga tcccaccaca aggagccctc gaattggcta aagtgagaaa   120
ctgggcctga agactccgta ccctctgcca tcttgccgag ggagtctcct tttagaaaac   180
aatcaaaggg ttattgcatg agtctggatg aatcccactc tcagctgtcc acggggccga   240
ccacctcatc taggccccctt tttggcaagg agaacccggg tcccaagttc tcctccttca   300
cttcgttaca aaccagggggg aaaaagccca cgtgaaaacg cggcatctgc aaaatggttc   360
cctttcttca tccctgggga aacctttgcg ccaaggcaac gtggaaactg atggttttac   420
tcaactcgct gttttgaagc gccattatga aatcggggtt gtacgtaggt aaagtcccgt   480
gcc                                                                483

<210> SEQ ID NO 30
<211> LENGTH: 337
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 30
gggcattcag gtggaccgct acattgcctc ggaggtgtgt naggnctcca tcacggtggg    60
catggtgcgg caccagggga agatcatgta cgtcggggac gtccgcagcg tcacacagaa   120
gcatatccag gagtggggcc cattcgatct ggtgattggg ggcagtccct gcaatnacct   180
```

```
ctccatcgtn aaccctgctc gcaaggncct ctacgagggc actggccggc tcttctttaa    240
gttctaccgc ctcctgcatg atgcncggcc caaggagggg agatgatcgn cccttcttct    300
ggctctttaa gaatgtngtg gnccatgggc gtttagt                              337
```

<210> SEQ ID NO 31  
<211> LENGTH: 271  
<212> TYPE: DNA  
<213> ORGANISM: Homo sapiens  
<220> FEATURE:  
<221> NAME/KEY: misc_feature  
<222> LOCATION: (234)..(234)  
<223> OTHER INFORMATION: n is a, c, g, or t

<400> SEQUENCE: 31

```
cttgtttaca gtttatatat atatgataga tatgagatat atatataaaa ggtactgtta     60
actactgtac aacccgactt cataatggtg ctttcaaaca gcgagatgag taaaaacatc    120
agcttccacg ttgccttctg cgcaaagggt ttcaccaagg atggagaaag ggagacagct    180
tgcagatggc gcgttctcac ggtgggctct tccccttggt ttgtaacgaa gtgnaggagg    240
agaacttggg agccaggttc tccctgccaa a                                    271
```

<210> SEQ ID NO 32  
<211> LENGTH: 430  
<212> TYPE: DNA  
<213> ORGANISM: Homo sapiens

<400> SEQUENCE: 32

```
acgttttgta tgttttttta tttgctccag gtggggtttt gactgtcact ttcccacact     60
ctggattagt tctgatccca ccacaaggag ccctcgaatt ggctaaagtg agaaactggg    120
cctgaagact ccgtaccctc tgccatcttg ccagggagt ctcctttaga aaacaatcaa     180
agggttattg catgagtctg gatgaatccc actctcagct gtccacgggc ccgaccacct    240
catctagccc ccttttttggc agggagaacc tggctcccaa gttctcctcc ttcacttcgt   300
tacaaaccaa ggggaagagc ccaccgtgag aacgcgccat ctgcaagctg tctccctttc    360
tccatccttg gtgaaacccc tttgcgcaga aggcaacgtg gaagctgatg tttttactca    420
tctcgctgtt                                                            430
```

<210> SEQ ID NO 33  
<211> LENGTH: 483  
<212> TYPE: DNA  
<213> ORGANISM: Homo sapiens

<400> SEQUENCE: 33

```
tttttttttt ttgtatgttt ttttatttgc tccaggtggg gttttgactg tcactttccc     60
acactctgga ttagttctga tcccaccaca aggagccctc gaattggcta aagtgagaaa    120
ctgggcctga agactccgta ccctctgcca tcttgccgag ggagtctcct tttagaaaac    180
aatcaaaggg ttattgcatg agtctggatg aatcccactc tcagctgtcc acggggccga    240
ccacctcatc taggccccctt tttggcaagg agaacccggg tcccaagttc tcctccttca    300
cttcgttaca aaccaggggg aaaaagccca cgtgaaaacg cggcatctgc aaaatggttc    360
cctttcttca tccctgggga aacctttgcg ccaaggcaac gtggaaactg atggttttac    420
tcaactcgct gttttgaagc gccattatga aatcggggtt gtacgtaggt aaagtcccgt    480
gcc                                                                   483
```

<210> SEQ ID NO 34
<211> LENGTH: 411
<212> TYPE: DNA
<213> ORGANISM: Homo sapiens

<400> SEQUENCE: 34

```
ttttttttta cgttttgtat gttttttat ttgctccagg tggggttttg actgtcactt    60
tcccacactc tggattagtt ctgatcccac cacaaggagc cctcgaattg gctaaagtga   120
gaaactgggc ctgaagactc cgtaccctct gccatcttgc cgagggagtc tccttttaga   180
aaacaatcaa agggttattg catgagtctg gatgaatccc actctcagct gtccacgggc   240
ccgaccacct catctagccc ccttttggca gggagaacct ggctcccaag ttctcctcct   300
tcacttcgtt acaaaccaag gggaagagcc caccgtgaga acgcgccatc tgcaagctgt   360
ctcccttcct ccatccttgg tgaaacccctt tgcgcagaag gcaacgtgga a           411
```

<210> SEQ ID NO 35
<211> LENGTH: 530
<212> TYPE: DNA
<213> ORGANISM: Homo sapiens

<400> SEQUENCE: 35

```
cgcctggacg agcccagact gctgggccgg tcatggagcg cgccagtcat ccgccacctc    60
ttcgctccgc tgaaggcgta ttttgcgtgt gtctaaggga catgggggca aactgaggta   120
gcgacacaaa gttaaacaca caaacacccc acacacaaca taatacaaca ccaagaacat   180
gaggatggag agaagtatca gccacccaga agagaacaag gaatttaaaa ccaaaaccac   240
agaggcggaa ataccggagg actttgcctt gcgaccaggg ttggacatca tctcctgatt   300
tttcaatgtt attcttcagt cctatttaaa aacaaaacca agctcccttc ccttcctgcg   360
gcttcccttt ttttcggtc agacctttta ttttctactc ttttcagagg ggttttctgt    420
ttgtttgggt tttgtttctt gctgtgactg aaacaagaag gttattgcag caaaaatcag   480
taacaaaaaa tagtaacaat accttgcaga ggaaaggtgg gagagaggaa               530
```

<210> SEQ ID NO 36
<211> LENGTH: 535
<212> TYPE: DNA
<213> ORGANISM: Homo sapiens

<400> SEQUENCE: 36

```
tttacgtttt gtatgttttt ttatttgctc caggtggggt tttgactgtc actttcccac    60
actctggatt agttctgatc ccaccacaag gagccctcga attggctaaa gtgagaaact   120
gggcctgaag actccgtacc ctctgccatc ttgccgaggg agtctccttt tagaaaacaa   180
tcaaagggtt attgcatgag tctggatgaa tcccactctc agctgtccac gggcccgacc   240
acctcatcta gccccctttt tggcaggag aacctggctc caagttctc ctccttcact    300 tcgttacaaa ccacggggaa gagcccaccg tgaacgcg ccatctgcaa gctgtctccc    360
tttctccatc cttggtgaaa cccttttgcgc agaaggcaac gtggaagctg atgttttttac   420 tcatctcgct gtttgaaagc accattatga agtcgggttg tacagtagtt aacagtacct   480
tttatatata tatctcatat ctatcatata tatataaact gtaaacaaga ggtaa         535
```

<210> SEQ ID NO 37
<211> LENGTH: 428
<212> TYPE: DNA
<213> ORGANISM: Homo sapiens
<220> FEATURE:

```
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t

<400> SEQUENCE: 37
acgttttgta tntantttta tttgctccag gtggggtttt gactgtcact ttcccacact      60
ctggattagt tctgatccca ccacaaggag ccctcgaatt ggctaaagtg agaaactggg     120
cctgaagact ccgtaccctc tgccatcttg ccgagggagt ctccttttag aaaacaatca    180
aagggttatt gcatgagtct ggatgaatcc cactctcagc tgtccacggg cccgaccacc    240
tcatctagcc ccctttttgg cagggagaac ctgggctccc aagttctcct ccttcacttc    300
gttacaaacc aaggggaagg agcccaccgt gagaacggcg ccatcttgca agctgtctcc    360
ctttctccat ccttgggtga aacccttttg cgcagaaggg caacgtggga agctngatgt    420 tttntaac                                                             428

<210> SEQ ID NO 38
<211> LENGTH: 419
<212> TYPE: DNA
<213> ORGANISM: Homo sapiens
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t

<400> SEQUENCE: 38
atgggcgtta gtgacaagag ggacatctcg cgatttctcg agtccaaccc tgtgatgatt      60
gatgccaaag aagtgtcagc tgcacacagg gcccgctact tctggggtaa ccttcccggt    120
atgaacaggc cgttggatcc actgtgaatg ataagctgga gctgcaggag tgtctggagc    180
atggcaggat agccaagttc agcaaagtga ggaccattac tacgaggtca aactccataa    240
agcagggcaa agaccagcat tttcctgtct tcatgaatga aaagaggac atcttatggt     300 gcactnaaat tggaaagggt atttggggtt tcccagtcca ntatactgac gtctccaaca    360
tgagccncct tggagggca gagantgctg gggccggttc atgggagcgt gcccagttc     419

<210> SEQ ID NO 39
<211> LENGTH: 437
```

```
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t

<400> SEQUENCE: 39 tntttgttg nctctagcct gancagatag gagcacaagc aggggacgga aagagagaga      60
cactcaggcg gcacanttcc ctcccagcca ctgagctgtc gtgccagcac cattcctggt    120
cacgcaaaac agaacccagt tagcagcagg gagacgagaa caccacacaa gacatttttc    180
tacagtattt caggtgccta ccacacagga aaccttgaag aaantcagtt tctaggaagc    240
cgctgttacc tcttgtttac agtttatata tatatgatag atatgagatn tatatataaa    300
aggtactgtt aactactgta caacccgact tcataatggg tgctttcaaa caggcgaggt    360
gngtaaaaac atcagnttcc acgttngcct tttgcgcaaa gggtttcacc aggttgggga    420
aagggngaca gcttttt                                                   437

<210> SEQ ID NO 40
<211> LENGTH: 385
<212> TYPE: DNA
<213> ORGANISM: Homo sapiens
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
```

```
<400> SEQUENCE: 40
tacgttttgt atgttttttt atttgctcca ggtggggttt tgactgtcac tttcccacac    60
tctggattag ttctgatccc accacaagga gccctcgaat tggctaaagt gagaaactgg   120
gcctgaagac tccgtaccct ctgccatctt gccgagggag tctcctttta gaaaacaatc   180
aaagggttat tgcatgagtc tggatgaatc ccactctcag ctgtccacgg gcccgaccac   240
ctcatctagc cccttttttg gcagggagaa cctgggctcc caagttctcc tccttcactt   300
cgttacaaac caaggggaag agcccaccgt gagaacgcgn catctgcaag ctgtctccct   360
ttttncatcc ttggtngaaa ccctt                                         385

<210> SEQ ID NO 41
<211> LENGTH: 294
<212> TYPE: DNA
<213> ORGANISM: Homo sapiens
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t

<400> SEQUENCE: 41
aaaggtggga gagaggaaaa aaggaaattc tatagaaatc tatatattgg gttgtttttt    60
tttttntttt ttnttttttt tttttgggt ttttttttt tactatatat ctttttttg     120 ttgtctctag cctgatcaga taggagcaca agcagggac ggaaagagag agacactcag    180
gcggcacatt tgccctccca gccactgagc tgtcgtgcca gcaccattcc tgggtcacgc   240
aaaacagaac ccagttagca gcagggnaga cgagaacacc acacaagaca tttt         294

<210> SEQ ID NO 42
<211> LENGTH: 610
<212> TYPE: DNA
<213> ORGANISM: Homo sapiens
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 42
tacgttttgt atgttttttt atttgctcca ggtggggttt tgactgtcac tttcccacac    60
tctggattag ttctgatccc accacaagga gccctcgaat tggctaaagt gagaaactgg   120
gcctgaagac tccgtaccct ctgccatctt gccgagggag tctcctttta gaaaacaatc   180
aaagggttat tgcatgagtc tggatgaatc ccactctcag ctgtccacgg gcccgaccac   240
ctcatctagc cccttttttg gcagggagaa cctggctccc aagttctcct ccttcacttc   300
gttacaaacc aaggggaaga gcccaccgtg agaacgcgcc atctgcaagc tgtctccctt   360
tctccatcct ttggtggaaa ccctttttgcg cagaaggcaa cgtggaagct gatgttttta   420
ctcatctcgc tgtttgaaag caccattatg aagtcgggtt gtacagtagt taacagtacc   480
ttttatatat atatctcata tctatcatat atatataaac tggtaaacaa gaggtaacag   540
```
cgggcttcta gaaactgatt ttcttcaagg tttccngtgt ggtaggcacn tgaaatactg    600
gtagaaaatg                                                           610

<210> SEQ ID NO 43
<211> LENGTH: 283
<212> TYPE: DNA
<213> ORGANISM: Homo sapiens
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t

<400> SEQUENCE: 43
taactttgtg tcgctacctc agtttgcccc catgtcccctt acacacacgc aaaatactcc    60
ttcagcggag anacgaggtg gcggatgact ggcacgctcc atgaccggcc cagcagtctc   120
tgcctcgcca agcggctcat gttggagacg tcagtatagt ggactgggaa accaaatacc   180
ctttccattt cagtgcacca taagatgtcc tctttctcat tcatgaagac aggaaaaatg   240
ctggtctttg gcctgcttta tggagttttg anctcgtaag taa                     283

<210> SEQ ID NO 44
<211> LENGTH: 383
<212> TYPE: DNA
<213> ORGANISM: Homo sapiens

<400> SEQUENCE: 44
gcggggacgt ccgcagcgtc acacagaagc atatccagga gtggggccca ttcgatctgg    60
tgattggggg cagtccctgc aatgacctct ccatcgtcaa ccctgctcgc aagggcctct   120 acagggcac tggccggctc ttctttgagt tctaccgcct cctgcatgat gcgcggccca   180
aggagggaga tgatcgcccc ttctctggct ctttgagaat tggtggccca tggcgttagt   240
acacagagag gacacatctc gcgatttctc gagtccaacc ctgtatatga ttgatgccaa   300
agaagtctca tctgcacaga ggcccctcta cttctggggt cacctccccg tattaacagg   360
ccgtaggatc cactgttatt ata                                            383

<210> SEQ ID NO 45
<211> LENGTH: 447
<212> TYPE: DNA
<213> ORGANISM: Homo sapiens
<220> FEATURE:
<221> NAME/KEY: misc_feature
<222> LOCATION: (445)..(445)
<223> OTHER INFORMATION: n is a, c, g, or t

<400> SEQUENCE: 45
acgttttgta tgttttttta tttgctccag gtggggtttt gactgtcact ttcccacact    60
ctggattagt tctgatccca ccacaaggag ccctcgaatt ggctaaagtg agaaactggg   120
cctgaagact ccgtaccctc tgccatcttg ccagggagt ctccttttag aaaacaatca   180
aagggttatt gcatgagtct ggatgaatcc cactctcagc tgtccacggg cccgaccacc   240
tcatctaagc cccctttttg gcagggagaa cctggctccc aagttctcct ccttcacttc   300
gttacaaacc aagggaaga gcccaccgtg agaacgcgcc atctgcaagc tgtctccctt   360
tctccatcct tggtgaaacc tttgcgcaga aggcaacgtg gaaagctgaa ggtttttact   420

```
catctcgctg tttgaaaagc accanta                                      447
```

<210> SEQ ID NO 46
<211> LENGTH: 100
<212> TYPE: DNA
<213> ORGANISM: Homo sapiens
<220> FEATURE:
<221> NAME/KEY: misc_feature
<222> LOCATION: (96)..(96)
<223> OTHER INFORMATION: n is a, c, g, or t

<400> SEQUENCE: 46

```
acaccaagaa catgagggat ggagagaagt atcagcaccc agaagagaaa aaggaattta    60
aaacaaaaac cacagaggcg gaaataccgg tgactnttct                         100
```

<210> SEQ ID NO 47
<211> LENGTH: 150
<212> TYPE: DNA
<213> ORGANISM: Homo sapiens

<400> SEQUENCE: 47

```
tactccttca gcgggtagga ggtggcggat gactggcacg ctccatgacc ggcccagcag    60
tctctgcctc gccaagcgct catgttggag aggtcagtat agtggactgg gaaaccaaat   120
acccttttcca tttcagtgca ccataagatg                                  150
```

<210> SEQ ID NO 48
<211> LENGTH: 237
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 48

```
gctgtcncag gggtgtgtgg gtctaggagc ctggctggag gncancgctg ggtgggagct    60
tgggacaccg atgggcctgc atctgacctg ttgtgctcac tgcttaggac cctccaaagg   120
tttacccacc tgtcccagct gagaagagga agcccatccg ggtgctgtct ctctttgatg   180
gaatcgctac aggtgagggg tgcaggccca agaggtgctg gcctcgtgcg aattcct      237
```

<210> SEQ ID NO 49
<211> LENGTH: 442
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t

<400> SEQUENCE: 49

```
tttttactta tatatcttnt ttttgttgtc tctagcctga tcagatagga gcacaagcag      60
gggacggaaa gagagagaca ctcaggcggc natttccctc ccagccactg agctgtcgtg     120
ccagcaccat tcctggncac gcaaaacaga acccagttag cagcagggag acgagaacac     180
cacacaagac attttctac agtatttcag gtgcctacca cacaggaaac cttgaagaaa      240
atcagtttct aggaagccgc tgttacctct tgtttacagt ttatatatat atggatagga     300
tatgaggata tatatataaa agggtactgt ttaactactg taccaacccg actttcataa     360
tgggtgcttt tcaaacagcc gaggatgngg ttaaaancat cagcttccac gttgccttct     420
gcggcaangg gtttcaccag gg                                              442
```

<210> SEQ ID NO 50
<211> LENGTH: 395
<212> TYPE: DNA
<213> ORGANISM: Homo sapiens
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t

<400> SEQUENCE: 50

```
tacgttttgt atgttttttt atttgctcca ggtggggttt tgactgtcac tttcccacac      60
tctggattag ttctgatccc accacaagga gccctcgaat tggctaaagt gagaaactgg     120
gcctgaagac tccgtaccct ctgccatctt gccgagggag tctccttta gaaaacaatc     180
aaagggttat tgcatgagtc tggatgaatc ccactctcag ctgtccacgg gcccgaccac     240
ctcatctagc ccccttttg ggcagggaga aacctgggct cccaagttct cctccttcac     300
ttcgttaaca aaccaagggg aagagcccac cgtgaggaac ggngccatct ggcaaggttg     360
ttctcccttt tnttccatnc cttnggtgaa aaccc                                395
```

<210> SEQ ID NO 51
<211> LENGTH: 835
<212> TYPE: DNA
<213> ORGANISM: Homo sapiens
<220> FEATURE:
<221> NAME/KEY: misc_feature
<222> LOCATION: (2)..(9)
<223> OTHER INFORMATION: n is a, c, g, or t
<220> FEATURE:
<221> NAME/KEY: misc_feature
<222> LOCATION: (11)..(16)

-continued

```
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
```

-continued

```
<222> LOCATION: (475)..(475)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (536)..(537)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
```

-continued

```
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (695)..(696)
<223> OTHER INFORMATION: n is a, c, g, or t
<220> FEATURE:
<221> NAME/KEY: misc_feature
<222> LOCATION: (699)..(701)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (716)..(719)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (735)..(737)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (743)..(745)
<223> OTHER INFORMATION: n is a, c, g, or t
<220> FEATURE:
<221> NAME/KEY: misc_feature
<222> LOCATION: (754)..(755)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (800)..(801)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (827)..(830)
<223> OTHER INFORMATION: n is a, c, g, or t
```

```
<220> FEATURE:
<221> NAME/KEY: misc_feature
<222> LOCATION: (832)..(832)
<223> OTHER INFORMATION: n is a, c, g, or t

<400> SEQUENCE: 51
cnnnnnnnng nnnnnnttnn nctgccttta tnctcgntgc cgatantnnt atccatcatc    60
annttcttgg tgttnnatta tgttttgtgt tttttgtttg tttgtttaac tttgtgtcgn   120
tacctcagtt tgcccccatn tccctnacac acacgcaaaa tactccttca gcggagcgaa   180
gaggtggcgg atgactggna cgctccatga ccggcccagc agtctctgcc tcgccaagcg   240
gatcatgttg gagacgtcag tatagtggac tgggaaacca ataccctttt ccatttcagn   300
gcaccataag atgtcctctt tctcattcat gaagacaggg aaaatgctgg tctttggcct   360
gctcnatgga gtttgactcc gtagtaangg ccctcanttt ggntgacttg ggctatcctg   420
ncatgctcca gacacttccg nagggtcaca acagaagcat nttccagggg gtggnggcca   480
ttccgacctt tggnggattg gggggggaagc cccnaaaaat aaccccttca aacggnnaaa   540
ccctngttcn gaangggccc cnttncgang ggaaactggn ccgnttnttt ctttngggnt   600 tcctccccc ccccccnaaa ataatgggng gcccaagna ggggaattac ccccccncn     660 ttntttttt tttggaaatt tggggcccg ggggnnaann naaaanggcn acttcnnnnt    720
ttttggnccc nccnnnant ttnnnccaa aaannttaat taaaaaggcc cttttctggg    780 nccccnttn aaccgccccn ngatnggtnc ttggttcccn aacacannnn cncaa        835

<210> SEQ ID NO 52
<211> LENGTH: 479
<212> TYPE: DNA
<213> ORGANISM: Homo sapiens
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t

<400> SEQUENCE: 52
tacgttttgt atgtttttt atttgctcca ggtggggttt tgactgtcac tttcccacac    60
tctggattag ttctgatccc accacaagga gccctcgaat tggctaaagt gagaaactgg   120
gcctgaagac tccgtaccct ctgccatctt gccgagggag tctccttta gaaaacaatc   180 aaagggttat tgcatgagtc tggatgaatc ccactctcag ctgtccacgg gcccgaccac   240
ctcatctagc ccccttttg gcagggagaa cctggctccc aagttctcct ccttcacttc   300
gttacaaacc aaggggaaga gcccaccatg agaacgcgcc atctgcaagc tgtctccctt   360
tctncatcct tggtgaaacc tttgcgcaga aggcaacgtg gaagctgatg tttttntcat   420
ctcgctgttt gaaagcacca ttatgaagtc gggttgtaca gtantaacag tacttttag   479

<210> SEQ ID NO 53
<211> LENGTH: 521
<212> TYPE: DNA
<213> ORGANISM: Homo sapiens
<220> FEATURE:
<221> NAME/KEY: misc_feature
<222> LOCATION: (327)..(327)
```

```
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t

<400> SEQUENCE: 53
agaacaccac acaagacatt tttctacagt atttcaggtg cctaccacac aggaaacctt     60
gaagaaaatc agtttctaga agccgctgtt acctcttgtt tacagtttat atatatatga    120
tagatatgag atatatatat aaaaggtact gttaactact gtacaacccg acttcataat    180
ggtgctttca aacagcgaga tgagtaaaaa catcagcttc cacgttgcct tctgcgcaaa    240
gggtttcacc aaggatggag aaagggagac agcttgcaga tggcgcgttc tcatggtggg    300
ctcttcccct tggtttgtaa cgaagtntag gaggagaact tgggagccag gttctccctg    360
ccaaaaaggg ggctagatga ggtggtcggg cccgtggaca gctgagagtg ggattcatcc    420
agactcatgc aataaccctt tgattgtttc taaaaggaga ctccctcggc aagatggcag    480
agggtacgga gtcttcaggc ccagttntca ctttagccaa t                        521

<210> SEQ ID NO 54
<211> LENGTH: 440
<212> TYPE: DNA
<213> ORGANISM: Homo sapiens

<400> SEQUENCE: 54
ctctctttga tggaatcgct acagggctcc tggtgctgaa ggacttgggc attcaggtgg     60
accgctacat tgcctcggag gtgtgtgagg actccatcac ggtgggcatg gtgcggcacc    120
aggggaagat catgtacgtc ggggacgtcc gcagcgtcac acagaagcat atccaggagt    180
ggggcccatt cgatctggtg attggggggca gtccctgcaa tgacctctcc atcgtcaacc    240
ctgctcgcaa gggcctctac gagggcactg gccggtcttt ctttgagttc taccgcctcc    300
tgcatgatgc gcggcccaag gagggagatg atcgcccctt cttctggctc tttgagaatg    360
tggtggccat gggcgtttag tgacaagagg gacatctcgc gatttctcga gtccaaccct    420
gtgatgattg atgccaaaga                                               440

<210> SEQ ID NO 55
<211> LENGTH: 273
<212> TYPE: DNA
<213> ORGANISM: Homo sapiens

<400> SEQUENCE: 55
acgttttgta tgttttttta tttgctccag gtggggtttt gactgtcact ttcccacact     60
ctggattagt tctgatccca ccacaaggag ccctcgaatt ggctaaagtg agaaactggg    120
cctgaagact ccgtaccctc tgccatcttg ccgagggagt ctccttttag aaaacaatca    180
aagggttatt gcatgagtct ggatgaatcc cactctcagc tgtccacggg cccgaccacc    240
tcatctagcc ccctttttgg cagggagaac ctg                                273

<210> SEQ ID NO 56
<211> LENGTH: 190
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
```

```
<222> LOCATION: (83)..(83)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t

<400> SEQUENCE: 56
aaaaacacaa aacataataa aacaccaaga acatgaggnt ggagagaagt atcagcaccc      60
agaagagaaa aaggaattta aancaaaaac cacagaggcg gaaataccgg agggctttgc     120
cttgcgaaaa gggttggaca tcatctcctg atttttcaat gttattcttc agtcctattt    180 naaaacaaag                                                            190

<210> SEQ ID NO 57
<211> LENGTH: 445
<212> TYPE: DNA
<213> ORGANISM: Homo sapiens
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t

<400> SEQUENCE: 57
ttagacaaat actgatttta attaaacata aggtaaactc taggcatccg tcatctttca      60
gcctaaaaat tagcaaaaac tgttgaaaca aggcacagtt ttttccccat atttgttacg    120
tcgtggctcc agttacaaaa aaattttaat gaaaacgtta aacatanaaa tagaagtttg    180
agattttaaa aagtgtataa aaagccccac aaaacttgtc aacggttgtt ccttattcta    240
caaaatagca ccagtaagaa gagtaaaagg tgttaaaaac catttatgac agcatttctg    300
aaatgcagct tgtctgaatt cccggttctc cctaaaaacg acttctttat ggnattaaaa    360
aagggtttaa aaaatctcc aaaggggagc accgagcttt gcaggttttc cctgtcatct    420
ctcagatgtg ggggaagctc gtggc                                          445

<210> SEQ ID NO 58
<211> LENGTH: 287
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t

<400> SEQUENCE: 58
ttccccacat ctgagagatg acagggaaaa ctgcaaanct cggtgctccc tttggagatt      60
ttttaatcct tttttattcc ataagaagtc gttttttaggg agaacgggaa ttcagacaag   120
ctgcatttca gaaatgctgt cataatggtt tttaacacct tttactcctc nttactggtg    180
```

```
ctattttgt agaataaggg aacnacgttg acaagttttg gtgggggcct ttttatacac    240
cttttttaaa atctccaact tcctaatttt taanggttta accgttt               287
```

<210> SEQ ID NO 59
<211> LENGTH: 535
<212> TYPE: DNA
<213> ORGANISM: Homo sapiens
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t

<400> SEQUENCE: 59

```
tagacaaata ctgattttaa ttaaacataa ggtaaactct aggcatccgt catctttcag    60
cctaaaaatt agcaaaaact gttgaaacaa ggcacagttt tttccccata tttgttacgt   120
cgtggctcca gttacaaaaa aattttaatg aaaacgttaa acataaaaat agaagtttga   180
gattttaaaa agtgtataaa aagccccaca aaacttgtca acgttgttcc ttattctaca   240
aaatagcacc agtaagaaga gtaaaaggtg ttaaaaacca ttatgacagc atttctgaaa   300
tgcagcttgt ctgaattccc gttctcccta aaaacgactt cttatggaat aaaaaaggat   360
taaaaaatct ccaaagggag caccgagctt tgcagttttc cctgtccgtc tctcagatgt   420
ggggaaggta tgagaaatgt atgtctgtcc cngactgctg tcactgcctc tgagttagta   480
aaaggtgaga atgagggtag cagcttccca tctggggcct gtgccngtgg agggt        535
```

<210> SEQ ID NO 60
<211> LENGTH: 449
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t

<400> SEQUENCE: 60

```
atcgcancag gctacctagt cctcaaagag ttgggcataa aggtaggaaa gtacgtcgct    60
tctgaagtgt gtgaggagtc cattgctgtt ggaaccgtga agcacgaggg gaatatcaaa   120
tacgtgaacg acgtgaggaa catcacaaag aaaaatattg aagaatgggg cccatttgac   180
ttggtgattg gcggaaccan tgcaacgatc tctcaaatgt gaatccagcc aggaaaggcc   240
tgtatgaggg tacaggccgg ctcttcttcg aattttacca cctgctgaat tactcacgcc   300
ccaaggaggg tgatgaccgg ccgttcttct ggatgtttga gaatgttgta gccatgaagg   360
ttggcgacaa gagggacatc tcacggttcc tggagtgtaa tccagtgatg attgatgcca   420
tccaaagttt ctgctgctca cagggcccg                                     449
```

<210> SEQ ID NO 61
<211> LENGTH: 522
<212> TYPE: DNA
<213> ORGANISM: Homo sapiens
<220> FEATURE:
<221> NAME/KEY: misc_feature
<222> LOCATION: (146)..(146)
<223> OTHER INFORMATION: n is a, c, g, or t

```
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t

<400> SEQUENCE: 61
aagagggaca tctcacggtt cctggagtgt aatccagtga tgattgatgc catcaaagtt      60
tctgctgctc acagggcccg atacttctgg ggcaacctac ccgggatgaa caggcccgtg     120
atagcatcaa agaatgataa actcgngctg caggactgct tggaatacaa taggatagcc     180
aagttaaaga agtacagac aataaccacc aagtcgaact cgatcaaaca ggggaaaaac      240
caacttttcc ctgttgtcat gaatggcaaa gaagatgttt ngtggtgcac tgagctcgaa     300
aggntctttg gctttcctgt gcactacaca gacgtgtcca acatgggccg tggtgcccgc     360
cagaagctgc tgggaaggtc ctggagcgtg cctgtcatcc gacacctctt cgcccctctg     420
aaggactact tgcatgtga atagttccag ccagggccca agcccactgg ggtgtgtggc      480
agagcaggac ccaggaggtg tgattctgaa ggcatcccca gg                        522

<210> SEQ ID NO 62
<211> LENGTH: 573
<212> TYPE: DNA
<213> ORGANISM: Homo sapiens

<400> SEQUENCE: 62
ctaagatcca ttttctaaac tccaattgag cattctctgt atctgggtgg tttttacttt      60
tttacttaat cttgcttgat caggaactct ggtgtcttct tggccccca cgtgatctcg     120 ttcatggtca ctttttgtt tatctcattt tctctgaggc tggtccttcc tgttaacgtc      180
ttggcatttg tgggaagcac aaaatgttct tgtccctcca actctgcttt tcgctccctg     240
ccctgccatt cctctcccgc gcctgccctc tccttccat cttttcccagg tacttttctc     300 tcccagccct gccactcttc tgccgcacct gcgctctccc ctccatcttt cccaggtact     360
tttgagcctt gactccccag gtcccttcat tctgtgctca ctccatgatg tcattttgtt     420
ctccagttaa agaaagtaca dacaataacc accaagtcga actcgatcaa acaggggaaa     480
aaccaacttt tccctgttgt catgaatggc aaagaagatg ttttgtggtg cactgagctc     540
gaaaggatct ttggctttcc tgtgcactac aca                                 573

<210> SEQ ID NO 63
<211> LENGTH: 559
<212> TYPE: DNA
<213> ORGANISM: Homo sapiens

<400> SEQUENCE: 63
agacaaatac tgattttaat taaacataag gtaaactcta ggcatccgtc atctttcagc      60
ctaaaaatta gcaaaaactg ttgaaacaag gcacagtttt ttccccatat ttgttacgtc     120
gtggctccag ttacaaaaaa attttaatga aaacgttaaa cataaaaata gaagtttgag     180
atttaaaaaa gtgtataaaa agccccacaa aacttgtcaa cgttgttcct tattctacaa     240
aatagcacca gtaagaagag taaaaggtgt taaaaaccat tatgacagca tttctgaaat     300
gcagcttgtc tgaattcccg ttctcccctaa aaacgacttc ttatgaaata aaaaaggatt     360
aaaaaatctc caagggagc accgagcttt gcagtttttc ctgtcatcta tcagatgtgg     420
```

```
ggaaggtatg agaaatgtat gtctgtccct gactgctgtc actgcctctg agtttagtaa    480
aaagatgaga aatgagggta gcagacttct catctgggga cctgtgcctg tggagggtag    540
gtctcctgga gagggaatg                                                 559

<210> SEQ ID NO 64
<211> LENGTH: 391
<212> TYPE: DNA
<213> ORGANISM: Homo sapiens

<400> SEQUENCE: 64
ttttttttta gacaaatact gattttaatt aaacataagg taaactctag gcatccgtca     60
tctttcagcc taaaaattag caaaaactgt tgaaacaagg cacagttttt tccccatatt    120
tgttacgtcg tggctccagt tacaaaaaaa attttaatga aaacgttaaa cataaaaata    180
gaagtttgag attttaaaaa gtgtataaaa agccccacaa aacttgtcaa cgttgttcct    240
tattctacaa aatagcacca gtaagaagag taaaaggtgt taaaaaccat tatgacagca    300
tttctgaaat gcagcttgtc tgaattcccg ttctccctaa aaacgacttc ttatggaata    360
aaaaaggatt aaaaaatctc caagggagc a                                    391

<210> SEQ ID NO 65
<211> LENGTH: 517
<212> TYPE: DNA
<213> ORGANISM: Homo sapiens

<400> SEQUENCE: 65
acaaatactg attttaatta aacataaggt aaactctagg caggggcatc tttcagccta     60
aaaattagca aaaactgttg aaacaaggca cagttttttc ccatatttg ttacgtcgtg     120 gctccagtta cggaaaaatt ttaatgaaaa cgttaaacat aaaaatagaa gtttgagatt    180
ttaaaaagtg tataaaaagc cccacaaaac ttgtcaacgt tgttccttat tctacaaaat    240
agcaccagta agaagagtaa aaggtgttaa aaaccattat gacagcattt ctgaaatgca    300
gcttgtctga attcccgttc tcctaaaaa cgacttctta tggaataaaa aaggattaaa    360
aaatctccaa agggagcacc gagctttgca gttttccctg tcatctctca gatgtgggga    420
aggtatgaga aatgtatgtc tgtccctgac tgctgtcact gcctctgagt ttagtaaaaa    480
gatgagaaat gagggtagca gacttctcat ctgggga                             517

<210> SEQ ID NO 66
<211> LENGTH: 442
<212> TYPE: DNA
<213> ORGANISM: Homo sapiens

<400> SEQUENCE: 66
gacaaatact gattttaatt aaacataagg taaactctag gcatccgtca tctttcagcc     60
taaaaattag caaaaactgt tgaaacaagg cacagttttt tccccatatt tgttacgtcg    120
tggctccagt tacaaaaaaa attttaatga aaacgttaaa cataaaaata gaagtttgag    180
attttaaaaa gtgtataaaa agccccacaa aacttgtcaa cgttgttcct tattctacaa    240
aatagcacca gtaagaagag taaaaggtgt taaaaaccat tatgacagca tttctgaaat    300
gcagcttgtc tgaattcccg ttctccctaa aaacgacttc ttatggaata aaaaaggatt    360
aaaaaatctc caagggagc accgagcttt gcagttttcc ctgtcatctc gcagatgtgg    420
ggaaggtatg agaaatgtat gt                                             442
```

```
<210> SEQ ID NO 67
<211> LENGTH: 396
<212> TYPE: DNA
<213> ORGANISM: Homo sapiens

<400> SEQUENCE: 67
gcagtcaggg acagacatac atttctcata ccttccccac atctgagaga tgacagggaa      60
aactgcaaag ctcggtgctc cctttggaga ttttttaatc ctttttttt ccataagaag     120 tcgtttttag ggagaacggg aattcagaca agctgcattt cagaaatgct gtcataatgg    180
tttttaacac cttttactct tcttactggt gctattttgt agaataagga caacgttga     240 caagttttgt ggggcttttt atacactttt taaaatctca aacttctatt tttatgttta    300
acgttttcat taaaattttt ttgtaactgg agccacgacg taacaaatat ggggaaaaaa    360
ctgtgccttg tttcaacagt ttttgctaat ttttag                              396

<210> SEQ ID NO 68
<211> LENGTH: 287
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t

<400> SEQUENCE: 68
agacaantac tgattttaat taaacataag gtaaactcta ggcatccgtc atctttcagc      60
ctaaaaatta gcaaaaactg ttgaaacaag gcacagtttt tcccccatat ttgttacgtc    120
gtggctccag ttacaaaaaa aatttttaatg aaaacgttaa acataaaant agaagtttga    180
gattttaaaa agtgtataaa aagccccaca aaacttgtca acgttgttcc ttattctaca    240
aaatagcacc agtaagaaga gtaaaaggtg ttaaaaacca ttatgac                   287

<210> SEQ ID NO 69
<211> LENGTH: 356
<212> TYPE: DNA
<213> ORGANISM: Homo sapiens
<220> FEATURE:
<221> NAME/KEY: misc_feature
<222> LOCATION: (193)..(193)
<223> OTHER INFORMATION: n is a, c, g, or t

<400> SEQUENCE: 69
attgaagaat ggggcccatt tgacttggtg attggcggaa ccgatgcaac gatctctcaa      60
atgtgaatcc agccaggaaa ggcctgtatg agggtacagg ccggctcttc ttcgaatttt    120
accacctgct gaattactca cgccccaagg agggtgatga ccggccgttc ttctggatgt    180
ttgagaatgt tgnagccatg aaggttggcg acaagaggga catctcacgg ttcctggagt    240
gtaatccagt gatgattgat gccatcaaag tttctgctgc tcacagggcc cgatacttct    300
ggggcaacct acccgggatg aacaggatct ttggcttttcc tgtgcactac acagac       356

<210> SEQ ID NO 70
<211> LENGTH: 408
<212> TYPE: DNA
<213> ORGANISM: Homo sapiens
<220> FEATURE:
<221> NAME/KEY: misc_feature
<222> LOCATION: (408)..(408)
```

<223> OTHER INFORMATION: n is a, c, g, or t

<400> SEQUENCE: 70

```
tttagacaaa tactgatttt aattaaacat aaggtaaact ctaggcatcc gtcatctttc      60
agcctaaaaa ttagcaaaaa ctgttgaaac aaggcacagt ttttccccca tatttgttac     120
gtcgtggctc cagttacaaa aaaatttta atgaaaacgt taaacataaa aatagaagtt     180
tgagatttta aaagtgtat aaaaagcccc acaaaacttg tcaacgttgt tccttattct     240
acaaaatagc accagtaaga agagtaaaag gtgttaaaaa ccattatgac agcatttctg     300
aaatgcagct tgtctgaatt cccgttctcc ctaaaaacga cttcttatgg aataaaaaag     360
gattaaaaaa tctccaaagg gagcaccgag ctttgcagtt ttccctgn                  408
```

<210> SEQ ID NO 71
<211> LENGTH: 439
<212> TYPE: DNA
<213> ORGANISM: Homo sapiens
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t

<400> SEQUENCE: 71

```
gcatgtagct acaggacatt tttaagggcc caggatcgtt ttttcccagn tgcaagcaga      60
agagaaaatg ttgtatatgt cttttnacccg gcacattccc cttgcctaaa tacaagggct    120
ggagtctgca cgggacctat tagagtattt tccacaatga tgatgatttc agcagggatg    180
acgtcatcat cacattcagg gctatttttt ccccacaaa cccaagggca ggggccactc    240
ttagctaaat ccctcccgt gactgcaata gaaccctctg gggagctcag gaaaggggt      300
gtgctgagtt ctataatata agctgccata tattttgtag acaagtatgg ctcctcccat    360
atctccctct tccctaggag aggagtgtga aagcaaggga gcttngataa gacacccct     420
caaacccatt ccctctcca                                                  439
```

<210> SEQ ID NO 72
<211> LENGTH: 491
<212> TYPE: DNA
<213> ORGANISM: Homo sapiens
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t

```
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t

<400> SEQUENCE: 72
ttaattaaac ataaggtaaa ctctanngca tcngtcatct ttcagcctaa aaattagcaa      60
aaactgttga acaaggcac agttttttcc ccatatttgt tacgtcgtgg ctccagttac      120 aaaaaaatt ttaatgaaaa cgttaaacat aaaaatagaa gtttgagatt ttaaaaagtg      180
tataaaangc cccacaaaac ttgtcaacgt tgttccttat tctacaaaat agcaccagta      240
agaagagtaa aaggtgttaa aaaccattat gacagcattt ctgaaatgca gcttgtctga      300
nttcccgttc tccctaaaaa cgacttctta tgggataana aagggattaa aaaatctccn      360
aaagggaggc accgagcttt gcaggttttc cctggtcatc tctcaggatg tggggggagg      420
gtatggggaa atggtatggt ctggtccctg gactggctgg tcactgcctc tggggtttng      480
gtaaaagggt g                                                           491

<210> SEQ ID NO 73
<211> LENGTH: 443
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
```

<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t

<400> SEQUENCE: 73

```
ttggcggcna ntgcaacgat ctnnaaatgt gaatcagcca ggaaaggctg tatgagggac      60
aggcggctct tcttcgaatt ttccacctgc tgaattactc acgccccaag gagggtgatg     120
accggncgtt cttctggatg tttgagaatg ttgtagncat gaaggttggn gacaagaggg     180
acatctcacg gttcctggag tgtaatccag tgatgattga tgccatcaaa gtttctgctg     240
ctcacagggc ccgatacttc tggggcaacc tacccgggat gaacaggatc tttggctttc     300
ctgtgcacta cacagacgtg tcccaacatg gggccgtggg ngccgcncca ggaagcttgc     360
tggggaaggt nctggggagc gttgccttgt tcatcccgac acctntttcg gnccctattg     420
gaagggattn attttgccca tgt                                            443
```

<210> SEQ ID NO 74
<211> LENGTH: 273
<212> TYPE: DNA
<213> ORGANISM: Homo sapiens

<400> SEQUENCE: 74

```
acgttttgta tgttttttta tttgctccag gtggggtttt gactgtcact ttcccacact      60
ctggattagt tctgatccca ccacaaggag ccctcgaatt ggctaaagtg agaaactggg     120
cctgaagact ccgtaccctc tgccatcttg ccgagggagt ctccttttag aaaacaatca     180
aagggttatt gcatgagtct ggatgaatcc cactctcagc tgtccacggg cccgaccacc     240
tcatctagcc ccctttttgg cagggagaac ctg                                 273
```

<210> SEQ ID NO 75
<211> LENGTH: 250
<212> TYPE: DNA
<213> ORGANISM: Homo sapiens
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 75

```
ttaattaaac ataaggtaaa ctctanngca tcngtcatct ttcagcctaa aaattagcaa      60
aaactgttga acaaggcac agttttttcc ccatatttgt tacgtcgtgg ctccagttac     120
aaaaaaaatt ttaatgaaaa cgttaaacat aaaaatagaa gtttgagatt ttaaaaagtg     180
tataaaangc cccacaaaac ttgtcaacgt tgttccttat tctacaaaat agcaccagta     240
agaagagtaa                                                           250
```

<210> SEQ ID NO 76
<211> LENGTH: 443
<212> TYPE: DNA
<213> ORGANISM: Homo sapiens

```
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t

<400> SEQUENCE: 76
ttggcggcna ntgcaacgat ctnnaaatgt gaatcagcca ggaaaggctg tatgagggac      60
aggcggctct tcttcgaatt ttccacctgc tgaattactc acgccccaag gagggtgatg     120
accggncgtt cttctggatg tttgagaatg ttgtagncat gaaggttggn dacaagaggg     180
acatctcacg gttcctggag tgtaatccag tgatgattga tgccatcaaa gtttctgctg     240
ctcacagggc ccgatacttc tggggcaacc tacccgggat gaacaggatc tttggctttc     300
ctgtgcacta cacagacgtg tcccaacatg gggccgtggg ngccgcncca ggaagcttgc     360
tggggaaggt nctggggagc gttgcccttgt tcatcccgac acctnttttcg gncccctattg     420 gaagggattn attttttgcca tgt                                           443

<210> SEQ ID NO 77
<211> LENGTH: 394
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t

<400> SEQUENCE: 77
```

```
nttttttttt ttttgaaaaa attgtgaaaa aatttaaacc ccaggggact atccaagggg    60
aaaagtgaaa tatggaaaaa ttggcggtat gaccaatttg ggcattgcaa agagccttgc   120
agaattatga agcataaaag gaaattattg gcttttggag agttttcttt tctctcttct   180 tttttgtaa tttcaatcta tatcagtagt ggaaaggtca tagcaaaata tggagaatcc    240
aaatggtaga tacaacctga tatcttgtgg aacaaggcat acaacagcaa agcaacacca   300
gtgaaaccaa ggacaccaaa cagtccccag agaactccag ctgtcatgag gtctcttcta   360
tagccatcag gtcctgagat ggagactggc actg                               394
```

<210> SEQ ID NO 78
<211> LENGTH: 277
<212> TYPE: DNA
<213> ORGANISM: Homo sapiens

<400> SEQUENCE: 78

```
gtcatctttc agcctaaaaa ttagcaaaaa ctgttgaaac aaggcacagt ttttcccca    60 tatttgttac gtcgtggctc cagttaccaa aaaattttaa tgaaaacgtt aaacataaaa   120
atagaagttt gagattttaa aaagtgtata aaaagcccca caaaacttgt caacgttgtt   180
ccttattcta caaaatagca ccagtaagaa gagtaaaagg tgttaaaaac cattatgaca   240
gcatttctga aatgcagctt gtctgaattc ccgttct                            277
```

<210> SEQ ID NO 79
<211> LENGTH: 469
<212> TYPE: DNA
<213> ORGANISM: Homo sapiens

<400> SEQUENCE: 79

```
ttttagacaa atactgattt taattaaaca taaggtaaac tctaggcatc cgtcatcttt    60
cagcctaaaa attagcaaaa actgttgaaa catggcacag ttttttcccc atatttgtta   120
cgtcgtggct ccagttacaa aaaatttta atgaaaacgt taaacataaa aatagaagtt   180
tgagatttta aaaagtgtat aaaaagcccc acaaaacttg tcaacgttgt tccttattct   240
acaaaatagc accagtaaga agagtaaaag gtgttaaaaa ccattatgac agcatttctg   300
aaatgcagct tgtctgaatt cccgttctcc ctaaaaacga cttcttatgg aataaaaaag   360
gattaaaaaa tctccaaagg gagcaccgag ctttgcagtt ttccctgtca tctctcagat   420
gtggggaagg tatgagaaat gtatgtctgt ccctgactgc tgtcactgc                469
```

<210> SEQ ID NO 80
<211> LENGTH: 206
<212> TYPE: DNA
<213> ORGANISM: Homo sapiens

<400> SEQUENCE: 80

```
gacaaatact gatccccct acacataagg taaactctag gcatccgtca tctttcagcc    60
taaaaattag caaaaactgt tgaaacaagg cacagttttt tccccatatt tgttacgtcg   120
tggctccagt tacgaaaaaa attttaatga aaacgttaaa cataaaaata gaagtttgag   180
attttaaaaa gtgtataaaa agcccc                                         206
```

<210> SEQ ID NO 81
<211> LENGTH: 391
<212> TYPE: DNA
<213> ORGANISM: Homo sapiens

<400> SEQUENCE: 81

-continued

```
ttttagacaa atactgattt taattaaaca taaggtaaac tctaggcatc cgtcatcttt    60
cagcctaaaa attagcaaaa actgttgaaa caaggcacag ttttttcccc atatttgtta   120
cgtcgtggct ccagttacaa aaaaaatttt aatgaaaacg ttaaacataa aaatagaagt   180
ttgagatttt aaaaagtgta taaaaagccc cacaaaactt gtcaacgttg ttccttattc   240
tacaaaatag caccagtaag aagagtaaaa ggtgttaaaa accattatga cagcatttct   300
gaaatgcagc ttgtctgaat tcccgttctc cctaaaaacg acttcttatg gaataaaaaa   360
ggattaaaaa atctccaaag ggagcaccga g                                  391
```

<210> SEQ ID NO 82
<211> LENGTH: 755
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (138)..(139)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (157)..(158)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (170)..(172)

```
<223> OTHER INFORMATION: n is a, c, g, or t
<220> FEATURE:
<221> NAME/KEY: misc_feature
<222> LOCATION: (176)..(178)
<223> OTHER INFORMATION: n is a, c, g, or t
<220> FEATURE:
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (191)..(194)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (243)..(244)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
```

```
<222> LOCATION: (338)..(338)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (524)..(524)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (598)..(599)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
```

```
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t

<400> SEQUENCE: 82
tcttcgaagn cgagtcggnc tgtaccctca tacaggcctt tcctggntgg attcacattt      60
gagagatcgt tgcatgggct tccgccaatc accaagtcaa atgggcccca ttcttcnana     120
tttttctttg gggngngnnc ccccnngnc ccccccnngn tntnttttn nntttnnncn     180 ngtccncccg nnnngggtnc tcacncactt cagangngnn gggctntcct nccnttntgg     240
ccnnctcttt gcggatngnt aggctgtcgc gatgncatca aacaatgaca ggactcgnct     300
nggcgccttc gggctgcggg aatgggagga tctttggntt tcctgtgcac tacacagacg     360
tgtccaacat gggncgtggt gnccgccaga agcttgctgg ggaaggtcct tggagnggtg     420
tcttgtcaat cccganaacc tctttccggc ccccttgga aggggcttac ttctgggaat     480
ngttgnattt ggtcccangc cnangggccc caaaaggccc ccantttngg gggttgtttt     540
```

-continued

| | |
|---|---|
| ttggaaagga ggcccaaggg acccccccngg gnggggngnt tgtttcnccc ctgggnanng | 600 |
| ggaattcccc cccangggnc cccngntntt nttcccncc aanttttttgg ggttngggggt | 660 |
| tanaanancc cggggggtttc ccccccaagg ccccccctct ntttgggttc aaaaangggg | 720 |
| gggggggaag gggccccccnc cctgaantttt ttttc | 755 |

<210> SEQ ID NO 83
<211> LENGTH: 2318
<212> TYPE: DNA
<213> ORGANISM: Mus musculus

<400> SEQUENCE: 83

| | |
|---|---|
| ccgcccccaa ccccaacgcc ccctgccccct ccccccagac gggcagctat ttacagagct | 60 |
| tcgggccggg gctcacacct gagctgtact gcagaggggc tgcacctggc cttatgggct | 120 |
| gagaagaaag ccaaggtaat tgcagtaatg aatgctgtgg aagagaaacca ggcctctgga | 180 |
| gagtctcaga aggtggagga ggccagccct cctgctgtgc agcagcccac ggaccctgct | 240 |
| tctccgactg tggccaccac ccctgagcca gtaggagggg atgctgggga caagaatgct | 300 |
| accaaagcag ccgacgatga gcctgagtat gaggatggcc ggggctttgg cattggagag | 360 |
| ctggtgtggg ggaaacttcg gggcttctcc tggtggccag gccgaattgt gtcttggtgg | 420 |
| atgacaggcc ggagccgagc agctgaaggc actcgctggg tcatgtggtt cggagatggc | 480 |
| aagttctcag tggtgtgtgt ggagaagctc atgccgctga gctccttctg cagtgcattc | 540 |
| caccaggcca cctacaacaa gcagcccatg taccgcaaag ccatctacga agtcctccag | 600 |
| gtggccagca gccgtgccgg gaagctgttt ccagcttgcc atgacagtga tgaaagtgac | 660 |
| agtggcaagg ctgtggaagt gcagaacaag cagatgattg aatgggccct cggtggcttc | 720 |
| cagccctcgg gtcctaaggg cctggagcca ccagaagaag agaagaatcc ttacaaggaa | 780 |
| gtttacaccg acatgtgggt ggagcctgaa gcagctgctt acgccccacc cccaccagcc | 840 |
| aagaaaccca gaaagagcac aacagagaaa cctaaggtca aggagatcat tgatgagcgc | 900 |
| acaagggagc ggctggtgta tgaggtgcgc cagaagtgca gaaacatcga ggacatttgt | 960 |
| atctcatgtg ggagcctcaa tgtcaccctg gagcacccac tcttcattgg aggcatgtgc | 1020 |
| cagaactgta gaactgcttc cttggagtgt gcttaccagt atgacgacga tgggtaccag | 1080 |
| tcctattgca ccatctgctg tgggggggcgt gaagtgctca tgtgtgggaa caacaactgc | 1140 |
| tgcaggtgct tttgtgtcga gtgtgtggat ctcttggtgg ggccaggagc tgctcaggca | 1200 |
| gccattaagg aagacccctg gaactgctac atgtgcgggc ataagggcac ctatgggctg | 1260 |
| ctgcgaagac gggaagactg gccttctcga ctccagatgt tctttgccaa taaccatgac | 1320 |
| caggaatttg acccccccaaa ggtttacccca cctgtgccag ctgagaagag gaagcccatc | 1380 |
| cgcgtgctgt ctctctttga tgggattgct acagggctcc tggtgctgaa ggacctgggc | 1440 |
| atccaagtgg accgctacat tgcctccgag gtgtgtgagg actccatcac ggtgggcatg | 1500 |
| gtgcggcacc agggaaagat catgtacgtc ggggacgtcc gcagcgtcac acagaagcat | 1560 |
| atccaggagt ggggcccatt cgacctggtg attggaggca gtcccctgcaa tgacctctcc | 1620 |
| attgtcaacc ctgcccgcaa gggactttat gagggtactg gccgcctctt ctttgagttc | 1680 |
| taccgcctcc tgcatgatgc gcggcccaag gagggagatg atcgcccctt cttctggctc | 1740 |
| tttgagaatg tggtggccat gggcgttagt gacaagaggg acatctcgcg atttcttgag | 1800 |
| tctaaccccg tgatgattga cgccaaagaa gtgtctgctg cacacagggc ccgttacttc | 1860 |

| | |
|---|---|
| tggggtaacc ttcctggcat gaacaggcct ttggcatcca ctgtgaatga taagctggag | 1920 |
| ctgcaagagt gtctggagca cggcagaata gccaagttca gcaaagtgag gaccattacc | 1980 |
| accaggtcaa actctataaa gcagggcaaa gaccagcatt tccccgtctt catgaacgag | 2040 |
| aaggaggaca tcctgtggtg cactgaaatg gaaagggtgt ttggcttccc cgtccactac | 2100 |
| acagacgtct ccaacatgag ccgcttggcg aggcagagac tgctgggccg atcgtggagc | 2160 |
| gtgccggtca tccgccacct cttcgctccg ctgaaggaat attttgcttg tgtgtaaggg | 2220 |
| acatgggggc aaactgaagt agtgatgata aaaagttaa acaaacaaac aaacaaaaaa | 2280 |
| caaaacaaaa caataaaaca ccaagaacga gaaaaaaa | 2318 |

<210> SEQ ID NO 84
<211> LENGTH: 2371
<212> TYPE: DNA
<213> ORGANISM: Homo sapiens

<400> SEQUENCE: 84

| | |
|---|---|
| ccgcccccag ccccatcgcc cccttcccct cccccaagac gggcagctac ttccagagct | 60 |
| tcagggccgc ggctcacacc tgagcgcgac tgcagagggg ctgcacctgg ccttatgggg | 120 |
| atcctggagc gggttgtgag aaggaatggg cgcgtggatc gtagcctgaa agacgagtgt | 180 |
| gatacggctg agaagaaagc caaggtcatt gcaggaatga atgctgtgga agaaaaccag | 240 |
| gggcccgggg agtctcagaa ggtggaggag gccagccctc ctgctgtgca gcagcccact | 300 |
| gaccccgcat cccccactgt ggctaccacg cctgagcccg tggggtccga tgctggggac | 360 |
| aagaatgcca ccaaagcagg cgatgacgag ccagagtacg aggacggccg gggctttggc | 420 |
| attggggagc tggtgtgggg gaaactgcgg ggcttctcct ggtggccagg ccgcattgtg | 480 |
| tcttggtgga tgacgggccg gagccgagca gctgaaggca cccgctgggt catgtggttc | 540 |
| ggagacggca aattctcagt ggtgtgtgtt gagaagctga tgccgctgag ctcgttttgc | 600 |
| agtgcgttcc accaggccac gtacaacaag cagcccatgt accgcaaagc catctacgag | 660 |
| gtcctgcagg tggccagcag ccgcgcgggg aagctgttcc cggtgtgcca cgacagcgat | 720 |
| gagagtgaca ctgccaaggc cgtggaggtg cagaacaagc ccatgattga atgggccctg | 780 |
| gggggcttcc agccttctgg ccctaagggc ctggagccac cagaagaaga gaagaatccc | 840 |
| tacaaagaag tgtacacgga catgtgggtg gaacctgagg cagctgccta cgcaccacct | 900 |
| ccaccagcca aaaagccccg gaagagcaca gcggagaagc ccaaggtcaa ggagattatt | 960 |
| gatgagcgca agagagcg gctggtgtac gaggtgcggc agaagtgccg gaacattgag | 1020 |
| gacatctgca tctcctgtgg gagcctcaat gttaccctgg aacaccccct cttcgttgga | 1080 |
| ggaatgtgcc aaaactgcaa gaactgcttt ctggagtgtg cgtaccagta cgacgacgac | 1140 |
| ggctaccagt cctactgcac catctgctgt ggggccgtg aggtgctcat gtgcggaaac | 1200 |
| aacaactgct gcaggtgctt ttgcgtggag tgtgtggacc tcttggtggg ccgggggct | 1260 |
| gcccaggcag ccattaagga agacccctgg aactgctaca tgtgcgggca aagggtacc | 1320 |
| tacgggctgc tgcggcggcg agaggactgg ccctcccggc tccagatgtt cttcgctaat | 1380 |
| aaccacgacc aggaatttga ccctccaaag gtttaccac ctgtcccagc tgagaagagg | 1440 |
| aagcccatcc gggtgctgtc tctctttgat ggaatcgcta cagggctcct ggtgctgaag | 1500 |
| gacttgggca ttcaggtgga ccgctacatt gcctcggagg tgtgtgagga ctccatcacg | 1560 |
| gtgggcatgg tgcggcacca ggggaagatc atgtacgtcg gggacgtccg cagcgtcaca | 1620 |
| cagaagcata tccaggagtg gggcccattc gatctggtga ttgggggcag tccctgcaat | 1680 |

-continued

```
gacctctcca tcgtcaaccc tgctcgcaag ggcctctacg agggcactgg ccggctcttc    1740
tttgagttct accgcctcct gcatgatgcg cggcccaagg agggagatga tcgccccttc    1800
ttctggctct tgagaatgt ggtggccatg ggcgttagtg acaagaggga catctcgcga    1860
tttctcgagt ccaaccctgt gatgattgat gccaagaag tgtcagctgc acacagggcc    1920
cgctacttct ggggtaacct tcccggtatg aacaggccgt tggcatccac tgtgaatgat    1980
aagctggagc tgcaggagtg tctggagcat ggcaggatag ccaagttcag caaagtgagg    2040
accattacta cgaggtcaaa ctccataaag cagggcaaag accagcattt tcctgtcttc    2100
atgaatgaga agaggacat cttatggtgc actgaaatgg aaagggtatt tggtttccca    2160
gtccactata ctgacgtctc caacatgagc cgcttggcga ggcagagact gctgggccgg    2220
tcatggagcg tgccagtcat ccgccacctc ttcgctccgc tgaaggagta ttttgcgtgt    2280
gtgtaaggga catgggggca aactgaggta gcgacacaaa gttaaacaaa caaacaaaaa    2340
acacaaaaca taataaaaca ccaagaacat g                                  2371
```

<210> SEQ ID NO 85
<211> LENGTH: 689
<212> TYPE: PRT
<213> ORGANISM: Mus musculus

<400> SEQUENCE: 85

| Met | Asn | Ala | Val | Glu | Glu | Asn | Gln | Ala | Ser | Gly | Glu | Ser | Gln | Lys | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Glu Glu Ala Ser Pro Pro Ala Val Gln Gln Pro Thr Asp Pro Ala Ser
                20                  25                  30

Pro Thr Val Ala Thr Thr Pro Glu Pro Val Gly Gly Asp Ala Gly Asp
            35                  40                  45

Lys Asn Ala Thr Lys Ala Ala Asp Asp Glu Pro Glu Tyr Glu Asp Gly
        50                  55                  60

Arg Gly Phe Gly Ile Gly Glu Leu Val Trp Gly Lys Leu Arg Gly Phe
65                  70                  75                  80

Ser Trp Trp Pro Gly Arg Ile Val Ser Trp Trp Met Thr Gly Arg Ser
                85                  90                  95

Arg Ala Ala Glu Gly Thr Arg Trp Val Met Trp Phe Gly Asp Gly Lys
            100                 105                 110

Phe Ser Val Val Cys Val Glu Lys Leu Met Pro Leu Ser Ser Phe Cys
        115                 120                 125

Ser Ala Phe His Gln Ala Thr Tyr Asn Lys Gln Pro Met Tyr Arg Lys
    130                 135                 140

Ala Ile Tyr Glu Val Leu Gln Val Ala Ser Ser Arg Ala Gly Lys Leu
145                 150                 155                 160

Phe Pro Ala Cys His Asp Ser Asp Glu Ser Asp Ser Gly Lys Ala Val
                165                 170                 175

Glu Val Gln Asn Lys Gln Met Ile Glu Trp Ala Leu Gly Gly Phe Gln
            180                 185                 190

Pro Ser Gly Pro Lys Gly Leu Glu Pro Pro Glu Glu Lys Asn Pro
        195                 200                 205

Tyr Lys Glu Val Tyr Thr Asp Met Trp Val Pro Glu Ala Ala Ala
    210                 215                 220

Tyr Ala Pro Pro Pro Ala Lys Lys Pro Arg Lys Ser Thr Thr Glu
225                 230                 235                 240

Lys Pro Lys Val Lys Glu Ile Ile Asp Glu Arg Thr Arg Glu Arg Leu

-continued

```
                245                 250                 255
Val Tyr Glu Val Arg Gln Lys Cys Arg Asn Ile Glu Asp Ile Cys Ile
                260                 265                 270
Ser Cys Gly Ser Leu Asn Val Thr Leu Glu His Pro Leu Phe Ile Gly
                275                 280                 285
Gly Met Cys Gln Asn Cys Lys Asn Cys Phe Leu Glu Cys Ala Tyr Gln
                290                 295                 300
Tyr Asp Asp Asp Gly Tyr Gln Ser Tyr Cys Thr Ile Cys Cys Gly Gly
305                             310                 315                 320
Arg Glu Val Leu Met Cys Gly Asn Asn Cys Cys Arg Cys Phe Cys
                            325                 330                 335
Val Glu Cys Val Asp Leu Leu Val Gly Pro Ala Ala Gln Ala Ala
                340                 345                 350
Ile Lys Glu Asp Pro Trp Asn Cys Tyr Met Cys Gly His Lys Gly Thr
                355                 360                 365
Tyr Gly Leu Leu Arg Arg Glu Asp Trp Pro Ser Arg Leu Gln Met
                370                 375                 380
Phe Phe Ala Asn Asn His Asp Gln Glu Phe Asp Pro Pro Lys Val Tyr
385                             390                 395                 400
Pro Pro Val Pro Ala Glu Lys Arg Lys Pro Ile Arg Val Leu Ser Leu
                            405                 410                 415
Phe Asp Gly Ile Ala Thr Gly Leu Leu Val Leu Lys Asp Leu Gly Ile
                420                 425                 430
Gln Val Asp Arg Tyr Ile Ala Ser Glu Val Cys Glu Asp Ser Ile Thr
                435                 440                 445
Val Gly Met Val Arg His Gln Gly Lys Ile Met Tyr Val Gly Asp Val
                450                 455                 460
Arg Ser Val Thr Gln Lys His Ile Gln Glu Trp Gly Pro Phe Asp Leu
465                             470                 475                 480
Val Ile Gly Gly Ser Pro Cys Asn Asp Leu Ser Ile Val Asn Pro Ala
                            485                 490                 495
Arg Lys Gly Leu Tyr Glu Gly Thr Gly Arg Leu Phe Phe Glu Phe Tyr
                500                 505                 510
Arg Leu Leu His Asp Ala Arg Pro Lys Glu Gly Asp Asp Arg Pro Phe
                515                 520                 525
Phe Trp Leu Phe Glu Asn Val Val Ala Met Gly Val Ser Asp Lys Arg
                530                 535                 540
Asp Ile Ser Arg Phe Leu Glu Ser Asn Pro Val Met Ile Asp Ala Lys
545                             550                 555                 560
Glu Val Ser Ala Ala His Arg Ala Arg Tyr Phe Trp Gly Asn Leu Pro
                            565                 570                 575
Gly Met Asn Arg Pro Leu Ala Ser Thr Val Asn Asp Lys Leu Glu Leu
                580                 585                 590
Gln Glu Cys Leu Glu His Gly Arg Ile Ala Lys Phe Ser Lys Val Arg
                595                 600                 605
Thr Ile Thr Thr Arg Ser Asn Ser Ile Lys Gln Gly Lys Asp Gln His
                610                 615                 620
Phe Pro Val Phe Met Asn Glu Lys Glu Asp Ile Leu Trp Cys Thr Glu
625                             630                 635                 640
Met Glu Arg Val Phe Gly Phe Pro Val His Tyr Thr Asp Val Ser Asn
                            645                 650                 655
Met Ser Arg Leu Ala Arg Gln Arg Leu Leu Gly Arg Ser Trp Ser Val
                660                 665                 670
```

```
Pro Val Ile Arg His Leu Phe Ala Pro Leu Lys Glu Tyr Phe Ala Cys
        675                 680                 685
Val

<210> SEQ ID NO 86
<211> LENGTH: 689
<212> TYPE: PRT
<213> ORGANISM: Homo sapiens

<400> SEQUENCE: 86

Met Asn Ala Val Glu Glu Asn Gln Gly Pro Gly Glu Ser Gln Lys Val
1               5                   10                  15

Glu Glu Ala Ser Pro Pro Ala Val Gln Gln Pro Thr Asp Pro Ala Ser
            20                  25                  30

Pro Thr Val Ala Thr Thr Pro Glu Pro Val Gly Ser Asp Ala Gly Asp
        35                  40                  45

Lys Asn Ala Thr Lys Ala Gly Asp Asp Glu Pro Glu Tyr Glu Asp Gly
    50                  55                  60

Arg Gly Phe Gly Ile Gly Glu Leu Val Trp Gly Lys Leu Arg Gly Phe
65                  70                  75                  80

Ser Trp Trp Pro Gly Arg Ile Val Ser Trp Trp Met Thr Gly Arg Ser
                85                  90                  95

Arg Ala Ala Glu Gly Thr Arg Trp Val Met Trp Phe Gly Asp Gly Lys
            100                 105                 110

Phe Ser Val Val Cys Val Glu Lys Leu Met Pro Leu Ser Ser Phe Cys
        115                 120                 125

Ser Ala Phe His Gln Ala Thr Tyr Asn Lys Gln Pro Met Tyr Arg Lys
    130                 135                 140

Ala Ile Tyr Glu Val Leu Gln Val Ala Ser Ser Arg Ala Gly Lys Leu
145                 150                 155                 160

Phe Pro Val Cys His Asp Ser Asp Glu Ser Asp Thr Ala Lys Ala Val
                165                 170                 175

Glu Val Gln Asn Lys Pro Met Ile Glu Trp Ala Leu Gly Gly Phe Gln
            180                 185                 190

Pro Ser Gly Pro Lys Gly Leu Glu Pro Pro Glu Glu Glu Lys Asn Pro
        195                 200                 205

Tyr Lys Glu Val Tyr Thr Asp Met Trp Val Glu Pro Glu Ala Ala Ala
    210                 215                 220

Tyr Ala Pro Pro Pro Ala Lys Lys Pro Arg Lys Ser Thr Ala Glu
225                 230                 235                 240

Lys Pro Lys Val Lys Glu Ile Ile Asp Glu Arg Thr Arg Glu Arg Leu
                245                 250                 255

Val Tyr Glu Val Arg Gln Lys Cys Arg Asn Ile Glu Asp Ile Cys Ile
            260                 265                 270

Ser Cys Gly Ser Leu Asn Val Thr Leu Glu His Pro Leu Phe Val Gly
        275                 280                 285

Gly Met Cys Gln Asn Cys Lys Asn Cys Phe Leu Glu Cys Ala Tyr Gln
    290                 295                 300

Tyr Asp Asp Asp Gly Tyr Gln Ser Tyr Cys Thr Ile Cys Cys Gly Gly
305                 310                 315                 320

Arg Glu Val Leu Met Cys Gly Asn Asn Asn Cys Cys Arg Cys Phe Cys
                325                 330                 335

Val Glu Cys Val Asp Leu Leu Val Gly Pro Gly Ala Ala Gln Ala Ala
            340                 345                 350
```

```
Ile Lys Glu Asp Pro Trp Asn Cys Tyr Met Cys Gly His Lys Gly Thr
        355                 360                 365

Tyr Gly Leu Leu Arg Arg Arg Glu Asp Trp Pro Ser Arg Leu Gln Met
    370                 375                 380

Phe Phe Ala Asn Asn His Asp Gln Glu Phe Asp Pro Pro Lys Val Tyr
385                 390                 395                 400

Pro Pro Val Pro Ala Glu Lys Arg Lys Pro Ile Arg Val Leu Ser Leu
                405                 410                 415

Phe Asp Gly Ile Ala Thr Gly Leu Leu Val Leu Lys Asp Leu Gly Ile
                420                 425                 430

Gln Val Asp Arg Tyr Ile Ala Ser Glu Val Cys Glu Asp Ser Ile Thr
                435                 440                 445

Val Gly Met Val Arg His Gln Gly Lys Ile Met Tyr Val Gly Asp Val
                450                 455                 460

Arg Ser Val Thr Gln Lys His Ile Gln Glu Trp Gly Pro Phe Asp Leu
465                 470                 475                 480

Val Ile Gly Gly Ser Pro Cys Asn Asp Leu Ser Ile Val Asn Pro Ala
                485                 490                 495

Arg Lys Gly Leu Tyr Glu Gly Thr Gly Arg Leu Phe Phe Glu Phe Tyr
                500                 505                 510

Arg Leu Leu His Asp Ala Arg Pro Lys Glu Gly Asp Asp Arg Pro Phe
                515                 520                 525

Phe Trp Leu Phe Glu Asn Val Val Ala Met Gly Val Ser Asp Lys Arg
                530                 535                 540

Asp Ile Ser Arg Phe Leu Glu Ser Asn Pro Val Met Ile Asp Ala Lys
545                 550                 555                 560

Glu Val Ser Ala Ala His Arg Ala Arg Tyr Phe Trp Gly Asn Leu Pro
                565                 570                 575

Gly Met Asn Arg Pro Leu Ala Ser Thr Val Asn Asp Lys Leu Glu Leu
                580                 585                 590

Gln Glu Cys Leu Glu His Gly Arg Ile Ala Lys Phe Ser Lys Val Arg
                595                 600                 605

Thr Ile Thr Thr Arg Ser Asn Ser Ile Lys Gln Gly Lys Asp Gln His
                610                 615                 620

Phe Pro Val Phe Met Asn Glu Lys Glu Asp Ile Leu Trp Cys Thr Glu
625                 630                 635                 640

Met Glu Arg Val Phe Gly Phe Pro Val His Tyr Thr Asp Val Ser Asn
                645                 650                 655

Met Ser Arg Leu Ala Arg Gln Arg Leu Leu Gly Arg Ser Trp Ser Val
                660                 665                 670

Pro Val Ile Arg His Leu Phe Ala Pro Leu Lys Glu Tyr Phe Ala Cys
                675                 680                 685

Val

<210> SEQ ID NO 87
<211> LENGTH: 56
<212> TYPE: DNA
<213> ORGANISM: Artificial
<220> FEATURE:
<223> OTHER INFORMATION: oligonucleotide primer

<400> SEQUENCE: 87
catgggcagc agccatcatc atcatcatca tgggaattcc atgccctcca gcggcc      56
```

<210> SEQ ID NO 88
<211> LENGTH: 56
<212> TYPE: DNA
<213> ORGANISM: Artificial
<220> FEATURE:
<223> OTHER INFORMATION: oligonucleotide primer

<400> SEQUENCE: 88
ccggggccgc tggagggcat ggaattccca tgatgatgat gatgatggct gctgcc        56

<210> SEQ ID NO 89
<211> LENGTH: 51
<212> TYPE: DNA
<213> ORGANISM: Artificial
<220> FEATURE:
<223> OTHER INFORMATION: oligonucleotide primer

<400> SEQUENCE: 89
gatctatgcc agcgcgaaca gctccagccc gagtgcctgc gcttgcctcc c        51

<210> SEQ ID NO 90
<211> LENGTH: 44
<212> TYPE: DNA
<213> ORGANISM: Artificial
<220> FEATURE:
<223> OTHER INFORMATION: oligonucleotide primer

<400> SEQUENCE: 90
aggcaagcgc aggcactcgg gctggagctg ttcgcgctgg cata        44

<210> SEQ ID NO 91
<211> LENGTH: 30
<212> TYPE: DNA
<213> ORGANISM: Artificial
<220> FEATURE:
<223> OTHER INFORMATION: oligonucleotide sequence
<220> FEATURE:
<221> NAME/KEY: misc_feature
<222> LOCATION: (5)..(5)
<223> OTHER INFORMATION: n represents 5-methylcytosine
<220> FEATURE:
<221> NAME/KEY: misc_feature
<222> LOCATION: (14)..(14)
<223> OTHER INFORMATION: n represents 5-methylcytosine
<220> FEATURE:
<221> NAME/KEY: misc_feature
<222> LOCATION: (25)..(25)
<223> OTHER INFORMATION: n represents 5-methylcytosine

<400> SEQUENCE: 91
agacnggtgc cagngcagct gagcnggatc        30

<210> SEQ ID NO 92
<211> LENGTH: 30
<212> TYPE: DNA
<213> ORGANISM: Artificial
<220> FEATURE:
<223> OTHER INFORMATION: Artificial sequence
<220> FEATURE:
<221> NAME/KEY: misc_feature
<222> LOCATION: (5)..(5)
<223> OTHER INFORMATION: n represents 5-methylcytosine
<220> FEATURE:
<221> NAME/KEY: misc_feature
<222> LOCATION: (16)..(16)
<223> OTHER INFORMATION: n represents 5-methylcytosine
<220> FEATURE:
<221> NAME/KEY: misc_feature
<222> LOCATION: (25)..(25)
<223> OTHER INFORMATION: n represents 5-methylcytosine

```
<400> SEQUENCE: 92
gatcnggctc agctgngctg gcacnggtct                                        30

<210> SEQ ID NO 93
<211> LENGTH: 30
<212> TYPE: DNA
<213> ORGANISM: Artificial
<220> FEATURE:
<223> OTHER INFORMATION: oligonucleotide sequence

<400> SEQUENCE: 93
agaccggtgc cagcgcagct gagccggatc                                        30

<210> SEQ ID NO 94
<211> LENGTH: 30
<212> TYPE: DNA
<213> ORGANISM: Artificial
<220> FEATURE:
<223> OTHER INFORMATION: oligonucleotide sequence

<400> SEQUENCE: 94
gatccggctc agctgcgctg gcaccggtct                                        30

<210> SEQ ID NO 95
<211> LENGTH: 20
<212> TYPE: DNA
<213> ORGANISM: Artificial
<220> FEATURE:
<223> OTHER INFORMATION: oligonucleotide primer

<400> SEQUENCE: 95
ctggaattct cctacctttg                                                   20

<210> SEQ ID NO 96
<211> LENGTH: 24
<212> TYPE: DNA
<213> ORGANISM: Artificial
<220> FEATURE:
<223> OTHER INFORMATION: oligonucleotide primer

<400> SEQUENCE: 96
cctggatccc agccagtgag ctgg                                              24

<210> SEQ ID NO 97
<211> LENGTH: 18
<212> TYPE: DNA
<213> ORGANISM: Artificial
<220> FEATURE:
<223> OTHER INFORMATION: oligonucleotide primer

<400> SEQUENCE: 97
gttccgcggc tgctcatt                                                     18

<210> SEQ ID NO 98
<211> LENGTH: 27
<212> TYPE: DNA
<213> ORGANISM: Artificial
<220> FEATURE:
<223> OTHER INFORMATION: oligonucleotide primer

<400> SEQUENCE: 98
ccaccgcggc cgacttgcct ctacttc                                           27

<210> SEQ ID NO 99
<211> LENGTH: 18
```

```
<212> TYPE: DNA
<213> ORGANISM: Artificial
<220> FEATURE:
<223> OTHER INFORMATION: oligonucleotide primer

<400> SEQUENCE: 99
agctgctcgg ctccggcc                                                18

<210> SEQ ID NO 100
<211> LENGTH: 19
<212> TYPE: DNA
<213> ORGANISM: Artificial
<220> FEATURE:
<223> OTHER INFORMATION: oligonucleotide primer

<400> SEQUENCE: 100
tcccccacac cagctctcc                                               19

<210> SEQ ID NO 101
<211> LENGTH: 18
<212> TYPE: DNA
<213> ORGANISM: Artificial
<220> FEATURE:
<223> OTHER INFORMATION: oligonucleotide primer

<400> SEQUENCE: 101
ctgcaattac cttggctt                                                18

<210> SEQ ID NO 102
<211> LENGTH: 18
<212> TYPE: DNA
<213> ORGANISM: Artificial
<220> FEATURE:
<223> OTHER INFORMATION: oligonucleotide primer

<400> SEQUENCE: 102
tccagcggcc ccggggac                                                18

<210> SEQ ID NO 103
<211> LENGTH: 18
<212> TYPE: DNA
<213> ORGANISM: Artificial
<220> FEATURE:
<223> OTHER INFORMATION: oligonucleotide primer

<400> SEQUENCE: 103
cccaacctga ggaaggga                                                18

<210> SEQ ID NO 104
<211> LENGTH: 18
<212> TYPE: DNA
<213> ORGANISM: Artificial
<220> FEATURE:
<223> OTHER INFORMATION: oligonucleotide primer

<400> SEQUENCE: 104
accaacatcg aatccatg                                                18

<210> SEQ ID NO 105
<211> LENGTH: 18
<212> TYPE: DNA
<213> ORGANISM: Artificial
<220> FEATURE:
<223> OTHER INFORMATION: oligonucleotide primer

<400> SEQUENCE: 105
```

```
tcccggggcc gactgcga                                             18

<210> SEQ ID NO 106
<211> LENGTH: 19
<212> TYPE: DNA
<213> ORGANISM: Artificial
<220> FEATURE:
<223> OTHER INFORMATION: oligonucleotide primer

<400> SEQUENCE: 106
aggggctgca cctggcctt                                            19

<210> SEQ ID NO 107
<211> LENGTH: 19
<212> TYPE: DNA
<213> ORGANISM: Artificial
<220> FEATURE:
<223> OTHER INFORMATION: oligonucleotide primer

<400> SEQUENCE: 107
tcccccacac cagctctcc                                            19

<210> SEQ ID NO 108
<211> LENGTH: 18
<212> TYPE: DNA
<213> ORGANISM: Artificial
<220> FEATURE:
<223> OTHER INFORMATION: oligonucleotide primer

<400> SEQUENCE: 108
cctctgcagt acagctca                                             18

<210> SEQ ID NO 109
<211> LENGTH: 20
<212> TYPE: DNA
<213> ORGANISM: Artificial
<220> FEATURE:
<223> OTHER INFORMATION: oligonucleotide primer

<400> SEQUENCE: 109
tgggatcgag ggcctcaaac                                           20

<210> SEQ ID NO 110
<211> LENGTH: 20
<212> TYPE: DNA
<213> ORGANISM: Artificial
<220> FEATURE:
<223> OTHER INFORMATION: oligonucleotide primer

<400> SEQUENCE: 110
ttccacagga caaacagcgg                                           20

<210> SEQ ID NO 111
<211> LENGTH: 20
<212> TYPE: DNA
<213> ORGANISM: Artificial
<220> FEATURE:
<223> OTHER INFORMATION: oligonucleotide primer

<400> SEQUENCE: 111
gcgacaaccg tccattcttc                                           20

<210> SEQ ID NO 112
<211> LENGTH: 21
<212> TYPE: DNA
<213> ORGANISM: Artificial
```

```
<220> FEATURE:
<223> OTHER INFORMATION: oligonucleotide primer

<400> SEQUENCE: 112
ctctgggcac tggctctgac c                                              21

<210> SEQ ID NO 113
<211> LENGTH: 18
<212> TYPE: DNA
<213> ORGANISM: Artificial
<220> FEATURE:
<223> OTHER INFORMATION: oligonucleotide primer

<400> SEQUENCE: 113
gcagagccgc ctgaagcc                                                  18

<210> SEQ ID NO 114
<211> LENGTH: 18
<212> TYPE: DNA
<213> ORGANISM: Artificial
<220> FEATURE:
<223> OTHER INFORMATION: oligonucleotide primer

<400> SEQUENCE: 114 cctttccaa cgtgccag                                                   18

<210> SEQ ID NO 115
<211> LENGTH: 18
<212> TYPE: DNA
<213> ORGANISM: Artificial
<220> FEATURE:
<223> OTHER INFORMATION: oligonucleotide primer

<400> SEQUENCE: 115
gccaaggtaa ttgcagta                                                  18

<210> SEQ ID NO 116
<211> LENGTH: 18
<212> TYPE: DNA
<213> ORGANISM: Artificial
<220> FEATURE:
<223> OTHER INFORMATION: oligonucleotide primer

<400> SEQUENCE: 116
gatgtttctg cacttctg                                                  18

<210> SEQ ID NO 117
<211> LENGTH: 69
<212> TYPE: DNA
<213> ORGANISM: Artificial
<220> FEATURE:
<223> OTHER INFORMATION: oligonucleotide probe

<400> SEQUENCE: 117
tatggcgagg aaaactgaaa aaggtggaaa atttagaaat gtccactgta ggacgtggaa    60
tatggcaag                                                            69

<210> SEQ ID NO 118
<211> LENGTH: 2108
<212> TYPE: DNA
<213> ORGANISM: Mus sp.
<220> FEATURE:
<221> NAME/KEY: misc_feature
<222> LOCATION: (723)..(972)
<223> OTHER INFORMATION: Length of region can vary from 75 to 250
      nucleotides
```

<220> FEATURE:
<221> NAME/KEY: misc_feature
<222> LOCATION: (723)..(972)
<223> OTHER INFORMATION: N can represent any nucleotide: a, t, g, c

<400> SEQUENCE: 118

```
ggagccaggc acctggggtg ttacctcagt gcctttagga tattggttttt cctagctcta      60
gagggctgat gtcatcaccc ctattttgca gatgagaaaa cagacatctt ggggttaagt     120
ggtctgtgtc aaggtcaccg caatgggatc aggtcttccc caagcgttcc agccagatag     180
cggcggctcc ctgctgggc attctccttc agttctttgt tctaattcat cttgcaaact      240
taatcctggc taatctttgt aaaatactca ttcaccttgt ttttccagaa catctgccat     300
gttacagaat atctccattc agtgcttgac cccagtccca ctactcagcc atttagcttt     360
agtcaaaatt gagagggtgg gtggaagagt tctttcttcc ttctacctgc ttgccacctc     420
caaatcgtgg ttatcttctg atctctactg tcctatctct cacccacacc cttcatttga     480
tgcagccttc tgctatctgc ttggtggttt gggtagttat ccacacagga gtttgctttt     540
cagtgattcc cccttccccc acccatctc cccaagtcta gtggaatcta tcaacttcct      600
gagagcagga ccaagtgtcc atttctgtat ccgatgatgc tccagtcctc taatgggggg     660
gggggcgggg cgccaggagt ggcgtgtgtg cttcttcaaa cccaacttta gtcctctact     720
gtnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnacacacct tggggtacta tgtctttgct caggaatggc atgaaatggc    1020
ctacacttta cctggtggtt ctaggagaga gacactagca cgtgcgtggg agtgtgtcta    1080
ttactattac ataattgctg agacagggtt tcgtgatgtt caggctggcc ttgaacttgt    1140
gttagtcaag aatgatctta aatttctgat ctctggtttc ccaagttcta ggattacagg    1200
tgtacttcac caccaaaagt ttgaacagct gcagatgcct tggcattgct cttaacgaac    1260
agaaaatgaa acaagcaagc aagacccatt gtgacccggg ggactcgggg actggacggg    1320
gaagttttca aagtctactt gtgaaccacg ctttttaaag caccccctcc attcacctgt    1380
agcgtggcgg tgaagttatt gtcctggggc gccctcaacc tgcgtgggac acctcctatc    1440
cactcacatc tgtcttctga ctttgcctaa actacgtttc cgtaaactcc gagcctcatc    1500
tctaatctgt aaacttgcta gcgcgctctc gcacgcgctc tttttttttt ttttttttccc    1560
ggaaactcac tttctacaac tttctccccg gactctcagg ctgtctgaag ccagcgctcc    1620
tgtcccacca ccgctgctct gggtgccccg cggcccgcac gcaccctgcc tccctcaagg    1680
tccccaactt ccctatgtac cccccatcc ccagagttgg gggaagggag cagagcgggc     1740
tgtcccataa acctggctgg aggggcgggg ccctgggaac ggactggcca gcctctcccc    1800
caggcccccc gcgcccctcg ggcccgggtg aggggctggc ccagcgccag cgtaggaggc    1860
cggccccctc ccccggccc gcgcttagcc aaccagaaac tccagtgggg cccacgtgac     1920
ctggagttct agacaaagaa aatgttccct ccctccccc cggcgccccc tccccctccc     1980
tctggccccc tccgccccca accccaacgc ccctgccc tccccccaga cgggcagcta      2040
tttacagagc ttcgggccgg ggctcacacc tgagctgtac tgcagagggg ctgcacctgg    2100
ccttatgg                                                             2108
```

<210> SEQ ID NO 119
<211> LENGTH: 2065
<212> TYPE: DNA
<213> ORGANISM: Homo sapiens

<400> SEQUENCE: 119

```
ggagccaggc acctagagaa ttgtctcatt gtcattagga gatggtggcg ttccatggcc      60
aaagagggct gatgtcatca ctcgttttgc agatgagaca acagatttct tgggggttaa     120
gtgacttgtt taaggtcatg gtggtggaaa cagaactgaa gtccagatct tttttttttt     180
ttttttgag acggagtctc gctctgttgc ccaggctgga gtgcagtggc atgatctcgg      240
ctcactgcaa catccgcctc ctaagttgaa gcgattctct tgcctcagcc tcccaagtag     300
ctgggattac tggcgcacgc caccacgcct ggctaatttt tgtatttta gtagagacaa      360
ggtttcacca tgttagtcag gccggtctca aactcctgac ctcatgatcc gcctgcctca     420
gccttccaaa gtgctgggat tataggcgtg agccaccgcg ctcggccaag tccagatctt     480
ctaacaagtg ccgctgccca atagccctc tgctgtgggg tgcattttcc tccatttcct      540
cagttcttcc ttctaattca tcttgccaac ggcaactagg ctgattttc caaaatactc      600
attcatcttg tcagaaaacc tgcggttatt cttccctgct acagaatata cccaaggacg     660
cacctgaagg cttgccatta ccttgccctg tcgtgtactg ggagggtgga ggtgggcgag     720
ggtctcctcc ctccccagcc cggcagctct tgctcatcct acccatctca cctcattcca     780
agtccgatcc agcctccagg cccagtcggc tcacctggaa ctgacctctg acctcttttg     840
tcatccatgc cgcccatttt tttctacttg gtatttgtgg catagttacc tttacatatg     900
tttgttttac agtgatcctt tcatatttct ccaagtctag tggaatcttc aacccctcga     960
gggcagagcc aacagggtct atttctttat ctgatcctac agccaacgta atggagggct    1020
gtgggtgggg actgcgtctg ccttgggggt aggtgccttt gttcaggagg aggaagcttg    1080
aaatggcgga ggctgcacct ggaggccgca cctggaggcc caggagagg agtcaggtct     1140
tctcgatctg cagatgtttg agcctgggaa tgaaggaatt gctgaacttt ctgaaggagc    1200
gccctcgccg cgaccaacct tgcaaacagg aaaatgagaa atccagggaa ggcccagagt    1260
gacgcagggg ccctgggact cgaagcctga cctcctcacg ccgcgctttt tgaggccccc    1320
ccgcttctct attcacctgt agtgtggagg cgggagaccc cccaaacaat ccccgatctg    1380
gagcgctccc aatgcctgcg cgcgcctgct gtcactctcc gtctgtgtgc tgagttttcc    1440
tacagcttcc tgggcctcct atctgtaagc ttttctttt ttttttttg gttgtgcttc     1500
agagaaactc acttttcaca actttctccc ggctctccca ggccgtccga agctccggc      1560
ttgctttcgc ccgacccccc ggctccctcc gggcaggcgg ctcgggagca gccccttccc    1620
tccctccccg gcccccggc cccgcgctaa tctcttccag agctggggga ggggccaggc     1680
ggtcttcccg aaggcgggc gctccctgca gccggcctg gcgggccct gggaacgggc       1740
ggggaacggc ctcgcccccc ggccccgcgc ccctcggacc ggagaagagg ggctggccca    1800
gcgccagcgt cggagcgccg gcccctcccc cgggccgctc gcagccaacc aggccctcca    1860
gcggggccca cgtgacctgg agtcctagac aaagaaaatg ttccctccct ccccccgcc     1920
gcccccctcc cctcccagtg gccccctccg ccccagccc catcgccccc ttccctccc      1980
ccaagacggg cagctacttc cagagcttca gggccgcgc tcacacctga gcgcgactgc    2040
agagggcctg cacctggcct tatgg                                          2065
```